United States Patent
Naoi et al.

(10) Patent No.: US 11,274,151 B2
(45) Date of Patent: Mar. 15, 2022

(54) CD3-TARGETING AND DLL3-TARGETING MULTISPECIFIC ANTIGEN-BINDING MOLECULES AND USES THEREOF

(71) Applicant: Chugai Seiyaku Kabushiki Kaisha, Tokyo (JP)

(72) Inventors: Sotaro Naoi, Shizuoka (JP); Shu Feng, Singapore (SG); Tomoyuki Igawa, Singapore (SG); Shu Wen Samantha Ho, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/216,981

(22) Filed: Mar. 30, 2021

(65) Prior Publication Data

US 2021/0301016 A1 Sep. 30, 2021

(30) Foreign Application Priority Data

Mar. 31, 2020 (JP) .............................. JP2020-062326

(51) Int. Cl.
*C07K 16/28* (2006.01)
*A61K 39/00* (2006.01)

(52) U.S. Cl.
CPC .......... *C07K 16/2809* (2013.01); *C07K 16/28* (2013.01); *C07K 16/2878* (2013.01);
(Continued)

(58) Field of Classification Search
None
See application file for complete search history.

(56) References Cited

U.S. PATENT DOCUMENTS 6,344,443 B1 2/2002 Liu et al.
9,127,021 B2 9/2015 Yoshida et al.
(Continued)

FOREIGN PATENT DOCUMENTS

CN 1069124 2/1993
CN 101123983 2/2008
(Continued)

OTHER PUBLICATIONS

U.S. Appl. No. 15/035,098, Igawa et al., filed May 6, 2016 (abandoned).
(Continued)

*Primary Examiner* — Claire Kaufman
(74) *Attorney, Agent, or Firm* — Fish & Richardson P.C.

(57) ABSTRACT

The disclosure provides multispecific antigen-binding molecules that comprise a first antigen-binding moiety and a second antigen-binding moiety, each of which is capable of binding to CD3 and CD137, but does not bind to CD3 and CD137 at the same time; and a third antigen-binding moiety that is capable of binding to DLL3, preferably human DLL3, which induce T-cell dependent cytotoxicity more efficiently whilst circumventing adverse toxicity concerns or side effects that other multispecific antigen-binding molecules may have. The present invention provides multispecific antigen-binding molecules and pharmaceutical compositions that can treat various cancers, especially those associated with DLL3, by comprising the antigen-binding molecule as an active ingredient.

28 Claims, 6 Drawing Sheets

Specification includes a Sequence Listing.

(52) U.S. Cl.
CPC .... *A61K 2039/505* (2013.01); *C07K 2317/31* (2013.01); *C07K 2317/35* (2013.01); *C07K 2317/52* (2013.01); *C07K 2317/522* (2013.01); *C07K 2317/55* (2013.01); *C07K 2317/565* (2013.01); *C07K 2317/73* (2013.01); *C07K 2317/92* (2013.01)

(56) References Cited

U.S. PATENT DOCUMENTS

| | | |
|---|---|---|
| 11,154,615 B2 | 10/2021 | Igawa et al. |
| 2006/0121042 A1 | 6/2006 | Dallacqua et al. |
| 2006/0140934 A1 | 6/2006 | Gegg et al. |
| 2007/0141066 A1 | 6/2007 | Phillips et al. |
| 2007/0237767 A1 | 10/2007 | Lazar et al. |
| 2007/0286859 A1 | 12/2007 | Lazar et al. |
| 2008/0014205 A1 | 1/2008 | Horowitz et al. |
| 2010/0150918 A1 | 6/2010 | Kufer et al. |
| 2010/0316641 A1 | 12/2010 | Dimitrov |
| 2010/0322946 A1 | 12/2010 | Bostrom et al. |
| 2012/0149876 A1 | 6/2012 | Kreudenstein et al. |
| 2012/0328624 A1 | 12/2012 | Yoshida et al. |
| 2013/0101581 A1 | 4/2013 | Kuramochi et al. |
| 2014/0112914 A1 | 4/2014 | Nezu et al. |
| 2014/0199294 A1 | 7/2014 | Mimoto et al. |
| 2014/0242077 A1 | 8/2014 | Choi et al. |
| 2015/0344570 A1 | 12/2015 | Igawa et al. |
| 2015/0368355 A1 | 12/2015 | Yosida et al. |
| 2016/0244530 A2 | 8/2016 | Yoshida et al. |
| 2016/0280787 A1 | 9/2016 | Igawa et al. |
| 2017/0037130 A1* | 2/2017 | Raum .............. A61K 39/00113 |
| 2017/0274072 A1 | 9/2017 | Kumagai et al. |
| 2017/0306036 A1* | 10/2017 | Vu ..................... C07K 16/2809 |
| 2018/0296668 A1 | 10/2018 | Igawa et al. |
| 2020/0332001 A1 | 10/2020 | Igawa et al. |
| 2020/0377595 A1 | 12/2020 | Shimizu et al. |

FOREIGN PATENT DOCUMENTS

| | | |
|---|---|---|
| EP | 1 293 514 A | 3/2003 |
| EP | 1 752 471 A | 2/2007 |
| EP | 2 078 731 A | 7/2009 |
| EP | 2 647 707 A | 10/2013 |
| EP | 2731 970 A | 5/2014 |
| EP | 3 070 168 A | 9/2016 |
| EP | 3 130 606 A | 2/2017 |
| EP | 2 817 338 B | 7/2017 |
| EP | 3 219 724 A | 9/2017 |
| EP | 2 530 091 B | 4/2018 |
| JP | H11-299493 | 11/1999 |
| JP | 2007-536912 | 12/2007 |
| JP | 2008-514201 | 5/2008 |
| JP | 2008-518023 | 5/2008 |
| JP | 2008-526809 | 7/2008 |
| JP | 2008-273973 | 11/2008 |
| JP | 2009/511587 | 3/2009 |
| JP | 2009-523709 | 6/2009 |
| JP | 2009-538273 | 11/2009 |
| JP | 2009-540837 | 11/2009 |
| JP | 2010-524851 | 7/2010 |
| JP | 2012-501648 | 1/2012 |
| JP | 6628966 | 1/2020 |
| WO | WO 92/19973 | 11/1992 |
| WO | WO 94/18221 | 8/1994 |
| WO | WO 95/14714 | 6/1995 |
| WO | WO 00/42072 | 7/2000 |
| WO | WO 00/47602 | 8/2000 |
| WO | WO 01/012664 | 2/2001 |
| WO | WO 01/075067 | 10/2001 |
| WO | WO 02/014358 | 2/2002 |
| WO | WO 03/025138 | 3/2003 |
| WO | WO 2004/030615 | 4/2004 |
| WO | WO 2004/053102 | 6/2004 |
| WO | WO 2005/070966 | 8/2005 |
| WO | WO 2005/077090 | 8/2005 |
| WO | WO 2006/019447 | 2/2006 |
| WO | WO 2006/036834 | 4/2006 |
| WO | WO 2006/047639 | 5/2006 |
| WO | WO 2006/072620 | 7/2006 |
| WO | WO 2006/083706 | 8/2006 |
| WO | WO 2006/106905 | 10/2006 |
| WO | WO 2007/047291 | 4/2007 |
| WO | WO 2007/080597 | 7/2007 |
| WO | WO 2007/111733 | 10/2007 |
| WO | WO 2007/121354 | 10/2007 |
| WO | WO 2008/003103 | 1/2008 |
| WO | WO 2008/047925 | 4/2008 |
| WO | WO 2008/119567 | 10/2008 |
| WO | WO 2008/157379 | 12/2008 |
| WO | WO 2009/025846 | 2/2009 |
| WO | WO 2009/124931 | 10/2009 |
| WO | WO 2010/027981 | 3/2010 |
| WO | WO 2010/035012 | 4/2010 |
| WO | WO 2010/080538 | 7/2010 |
| WO | WO 2011/093097 | 8/2011 |
| WO | WO 2011/108714 | 9/2011 |
| WO | WO 2011/133886 | 10/2011 |
| WO | WO 2012/064792 | 5/2012 |
| WO | WO 2012/073985 | 6/2012 |
| WO | WO 2012/096994 | 7/2012 |
| WO | WO 2012/143524 | 10/2012 |
| WO | WO 2012/162067 | 11/2012 |
| WO | WO 2013/026833 | 2/2013 |
| WO | WO 2013/059593 | 4/2013 |
| WO | WO 2013/126746 | 8/2013 |
| WO | WO 2013/180200 | 12/2013 |
| WO | WO 2013/187495 | 12/2013 |
| WO | WO 2014/116846 | 7/2014 |
| WO | WO 2014/125273 | 8/2014 |
| WO | WO 2015/068847 | 5/2015 |
| WO | WO 2015/127407 | 8/2015 |
| WO | WO 2015/156268 | 10/2015 |
| WO | WO 2016/016415 | 2/2016 |
| WO | WO 2016/016859 | 2/2016 |
| WO | WO 2016/040856 | 3/2016 |
| WO | WO 2016/076345 | 5/2016 |
| WO | WO 2017/010874 | 1/2017 |
| WO | WO 2017/021349 | 2/2017 |
| WO | WO 2017/191101 | 11/2017 |
| WO | WO 2018/027204 | 2/2018 |
| WO | WO 2018/204907 | 11/2018 |
| WO | WO 2019/111871 | 6/2019 |
| WO | WO 2019/131988 | 7/2019 |
| WO | WO-2019131988 A1 * | 7/2019 .............. C07K 16/28 |
| WO | WO 2020/027330 | 2/2020 |
| WO | WO 2020/067399 | 4/2020 |
| WO | WO 2020/067419 | 4/2020 |

OTHER PUBLICATIONS

U.S. Appl. No. 16/704,464, Igawa et al., filed Dec. 5, 2019.
U.S. Appl. No. 15/525,603, Igawa et al., filed May 10, 2017.
U.S. Appl. No. 16/769,299, Shimizu et al., filed Jun. 3, 2020.
U.S. Appl. No. 17/272,972, Ho et al., filed Mar. 3, 2021.
U.S. Appl. No. 17/280,239, Igawa et al., filed Mar. 26, 2021.
U.S. Appl. No. 17/264,388, Shiraiwa et al., filed Jan. 29, 2021.
U.S. Appl. No. 14/846,135, Yoshida et al., filed Sep. 4, 2015.
Adams et al., "Monoclonal antibody therapy of cancer," Nature Biotechnology, Sep. 2005, 23(9):1147-1157.
Ayyanan et al., "Increased Wnt signaling triggers oncogenic conversion of human breast epithelial cells by a Notch-dependent mechanism," Proc Nat Acad Sci USA, Mar. 7, 2006, 103(10):3799-3804.
Amann et al., "Therapeutic window of an EpCAM/CD3-specific BiTE antibody in mice is determined by a subpopulation of EpCAM-expressing lymphocytes that is absent in humans," Cancer Immunol Immunother, Jan. 2009, 58(1):95-109, Epub Jul. 2, 2008.
Ashkenazi, "Directing cancer cells to self-destruct with pro-apoptotic receptor agonists," Nat Rev Drug Discov, Dec. 2008, 7(12):1001-1012.

(56) References Cited

OTHER PUBLICATIONS

Baeuerle et al., "Bispecific T-Cell Engaging Antibodies for Cancer Therapy," Cancer Res, Jun. 15, 2009, 69(12):4941-4944, doi:10.1158/0008-5472.CAN-09-0547. Epub Jun. 9, 2009.
Ball, "Achaete-scute homolog-1 and Notch in lung neuroendocrine development and cancer," Cancer Letters, Feb. 20, 2004, 204:159-169.
Beljaars et al., "The preferential homing of a platelet derived growth factor receptor-recognizing macromolecule to fibroblast-like cells in fibrotic tissue," Biochemical Pharmacology, Oct. 2003, 66(7):1307-1317.
Berntzen et al., "Identification of a High Affinity FcγRIIA-binding Peptide that Distinguishes FcγRIIA from FcγRIIB and Exploits FcγRIIA-mediated Phagocytosis and Degradation" J Biol Chem, Jan. 2009, 284(2): 1126-1135, doi: 10.1074/jbc.M803584200. Epub Oct. 28, 2008.
Binetruy-Tournaire et al., "Identification of a peptide blocking vascular endothelial growth factor (VEGF)-mediated angiogenesis," EMBO J, Apr. 3, 2000, 19(7):1525-1533.
Boder et al., "Directed evolution of antibody fragments with monovalent femtomolar antigen binding affinity," Proc Natl Acad Sci USA, Sep. 26, 2000, 97(20):10701-10705.
Bostrom et al., "Variants of the Antibody Herceptin That Interact with HER2 and VEGF at the Antigen Binding Site," Science, Mar. 20, 2009, 323(5921):1610-1614.
Brennand et al., "A cyclic peptide analogue of loop III of PDGF-BB causes an apoptosis in human fibroblasts," FEBS Lett, Dec. 15, 1997, 419(2-3):166-170.
Brinkmann et al., "The making of bispecific antibodies," mAbs, Feb./Mar. 2017, 9(2):82-212.
Bulman et al., "Mutations in the human Delta homologue, DLL3, cause axial skeletal defects in spondylocostal dysostosis," Nat Genet, Apr. 2000, 24:43 8-441.
Campoli et al., "Immunotherapy of Malignant Disease with Tumor Antigen-Specific Monoclonal Antibodies," Clin Cancer Res, Jan. 1, 2010, 16(1):11-20. Epub Dec. 22, 2009.
Carter et al., "Next generation antibody drugs: pursuit of the 'high-hanging fruit'," Nat Rev Drug Discov, Mar. 2018, 17(3):197-223. doi:10.1038/nrd.2017.227.
Carter et al., "Identification and validation of cell surface antigens for antibody targeting in oncology," Endocrine-Related Cancer, Dec. 2004, 11:659-687.
Carter et al., "Antibody-Drug Conjugates for Cancer Therapy," The Cancer Journal, May-Jun. 2008, 14(3):154-169.
Chamarthy et al., "Gene delivery to dendritic cells facilitated by a tumor necrosis factor alpha-competing peptide," Mol Immunol, Jul. 2004, 41(8):741-749.
Chan et al., "Therapeutic antibodies for autoimmunity and inflammation," Nat Rev Immunol, May 2010, 10(5):301-316.doi: 10.1038/nri2761.
Chen et al., "Characterization of human IgG repertoires in an acute HIV-1 infection," Exp Mol Pathol, Dec. 2012, 93(3):399-407. doi: 10.1016/j.yexmp.2012.09.022. Epub Oct. 1, 2012.
Chen et al., "Enhancement and destruction of antibody function by somatic mutation: unequal occurrence is controlled by V gene combinatorial associations," The EMBO Journal, Jun. 1995, 14(12):2784-2794.
Chen et al., "Antibody-cytotoxic agent conjugates for cancer therapy," Expert Opinion in Drug Delivery, Sep. 2005, 2(5):873-890.
Choi et al., "Distinct Biological Roles for the Notch Ligands Jagged-1 and Jagged-2," The Journal of Biological Chemistiy, Jun. 26, 2009, 284(26):17766-17774.
Chung et al., "Characterization of in vitro antibody-dependent cell-mediated cytotoxicity activity of therapeutic antibodies—Impact of effector cells," Journal of Immunological Methods, May 2014, 407:63-75.
Clackson et al., "Making antibody fragments using phage display libraries," Nature, Aug. 15, 1991, 352(6336):624-628.
Clark, "IgG effector mechanisms," Chem Immunol, 1997, 65:88-110.
Communication of Notices of Oppositions against EP 2 530 091, dated Jan. 30, 2019.
COMPUGEN Press Releases, "Compugen Announces Discovery of Blood Based Biomarker Diagnosis of Lung Cancer," Apr. 29, 2008, 2 pages.
Conrad et al., "TCR and CD3 antibody cross-reactivity in 44 species," Cytometry A, Nov. 2007, 71(11):925-933.
Collu et al., "Cooperation between Wnt and Notch signaling in human breast cancer," Breast Cancer Research, May 11, 2007, 9(3):105, 3 pages.
D'Souza et al., "The many facets of Notch ligands," Oncogene, Sep. 1, 2008, 27:5148-5167.
D'Souza et al., Chapter 3 "Canonical and Non-Canonical Notch Ligands," Current Topics in Developmental Biology, 2010, 92:73-129.
Dall'Acqua et al., "Modulation of the Effector Functions of a Human IgG1 through Engineering of Its Hinge Region," J Immunol, Jul. 15, 2006, 177(2):1129-1138.
De La Lastra et al., "Epitope mapping of 10 monoclonal antibodies against the pig analogue of human membrane cofactor protein (MCP)," Immunology, Apr. 1999, 96:663-670.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-3084.
Deambrosis et al., "Inhibition of CD40-CD154 costimulatory pathway by a cyclic peptide targeting CD154," J Mol Med, Feb. 2009, 87(2): 181-197.
Decision Revoking the European Patent in opposition against EP 2 990 420, dated Mar. 22, 2019, 31 pages.
Declaration of Dr. William Decker, dated Dec. 2, 20201, and accompanying CV, 23 pages (document submitted in opposition against EP 2 530 091 and posted by the EPO on Dec. 23, 2020).
Declaration of Professor Mark Gerstein, dated Feb. 28, 2020, and accompanying Abridged CV, 5 pages (document submitted in opposition against EP 2 530 091 and posted by the EPO on Mar. 6, 2020).
Dermer et al., "Another Anniversary for the War on Cancer," Bio/Technology, Mar. 12, 1994, 12:320.
Dillon et al., "Structural and Functional Characterization of Disulfide Isoforms of the Human IgG2 Subclass," J Biol Chern, Jun. 6, 2008, 283(23):16206-16215, Epub Mar. 12, 2008.
Dreier et al., "Extremely Potent, Rapid and Costimulation-Independent Cytotoxic T-Cell Response Against Lymphoma Cells Catalyzed by a Single-Chain Bispecific Antibody," Int J Cancer, Aug. 20, 2002, 100(6):690-697.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233.
Dufner, "Harnessing phage and ribosome display for antibody optimization," Trends Biotechnol, Nov. 2006, 24(11):523-529.
Dunwoodie, "The role of Notch in patterning the human vertebral column," Current Opinion in Genetics & Development, Aug. 2009, 19:329-337.
Edelman et al., "A Covalent Structure of an Entire γG Immunoglobulin Molecule," Proc Natl Acad Sci USA, May 1969, 63(1): 78-85.
Edwards et al., "The Remarkable Flexibility of the Human Antibody Repertoire; Isolation of Over One Thousand Different Antibodies to a Single Protein, BLyS," J Mol Biol, Nov. 14, 2003, 334:103-118.
Eigenbrot et al., "Two-in-One antibodies with dual action Fabs," Curr Opin Chem Biol, Jun. 2013, 17(3):400-405, doi: 0.1016/j.cbpa.2013.04.015. Epub May 14, 2013.
EPO Communication dated Oct. 27, 2016 in EP Appn. No. 11736812.6, 5 pages.
EPO Communication dated Oct. 19, 2015 in EP Appn. No. 11736812.6, 5 pages.
Ercan et al., "Mammary development and breast cancer: the role of stem cells," Curr Mol Med, Jun. 2011, 11(4):270-285.
Espinoza et al., "Notch inhibitors for cancer treatment," Pharmacology & Therapeutics, Aug. 2013, 139:95-110.

(56) References Cited

OTHER PUBLICATIONS

Faham et al., "Antigen-Containing Liposomes Engrafted with Flagellin-Related Peptides Are Effective Vaccines That Can Induce Potent Antitumor Immunity and Immunotherapeutic Effect," J Immunol, Jul. 7, 2010, 185, 1744-1754.

Form posted on EPO website and dated Mar. 4, 2021, disclosing that EP 2 530 091 was revoked, 1 page.

Fukuda et al., "In vitro evolution of single-chain antibodies using mRNA display," Nucleic Acids Res, Nov. 2006, 34(19):e127, 8 pages.

Gad et al., "Nonclinical Vehicle Use in Studies by Multiple Routes in Multiple Species," International Journal of Toxicology, Nov.-Dec. 2006 25:499-521.

Geffers et al., "Divergent functions and distinct localization of the Notch ligands DLL1 and Dll3 in vivo," J Cell Biol, Jul. 30, 2007, 178(3):465-76.

Gershoni et al., "Epitope Mapping—The First Step in Developing Epitope-Based Vaccines," Biodrugs, 2007, 21(3):145-156.

Goding, "Introduction to Monoclonal Antibodies," Monoclonal Antibodies: Principles and Practice, 3rd edition, 1996, pp. 134-135.

Golay et al., "Design and Validation of a Novel Generic Platform for the Production of Tetravalent IgG1-like Bispecific Antibodies," J Immunol, Apr. 1, 2016, 196(7):3199-3211.

Grant et al., "Targeting of small-cell lung cancer using the anti-GD2 ganglioside monoclonal antibody 3F8: a pilot trial," European Journal of Nuclear Medicine, Feb. 1996, 23(2):145-149.

Greenbaum et al., "Comparing protein abundance and mRNA expression levels on a genomic scale," Genome Biology, Aug. 29, 2003, 4:117, 8 pages.

Greenwood et al., "Structural motifs involved in human IgG antibody effector functions," Eur J Immunol, May 1993, 23(5):1098-1104.

Guo et al., "Role of Notch and its oncogenic signaling crosstalk in breast cancer," Biochim Biophys Acta, Apr. 2011, 1815(2):197-213.

Gura et al., "Systems for Identifying New Drugs Are Often Faulty," Science, Nov. 7, 1997, 278:1041-1042.

Hanes et al., "Picomolar affinity antibodies from a fully synthetic naive library selected and evolved by ribosome display," Nat Biotechnol, Dec. 2000, 18(12):1287-1292.

Harvey et al., "Anchored periplasmic expression, a versatile technology for the isolation of high-affinity antibodies from *Escherichia coli*-expressed libraries," Proc Natl Acad Sci USA, Jun. 22, 2004, 101(25):9193-9198.

Hawkins et al., "Selection of Phage Antibodies by Binding Affinity—Mimicking Affinity Maturation," J Mol Biol, Aug. 5, 1992, 226(3):889-896.

Henke et al., "Ascl1 and Neurog2 Form Novel Complexes and Regulate Delta-like3 (Dll3) Expression in the Neural Tube," Dev Biology, Apr. 15, 2009, 328(2):529-540.

Hess et al., "Cancer therapy with trifunctional antibodies: linking innate and adaptive immunity," Future Oncol, Jan. 2012, 8(1):73-85. doi: 10.2217/fon.11.138.

Hetian et al., "A Novel Peptide Isolated from a Phage Display Library Inhibits Tumor Growth and Metastasis by Blocking the Binding of Vascular Endothelial Growth Factor to Its Kinase Domain Receptor," J Biol Chem, Nov. 8, 2002, 277(45):43137-43142.

Hezareh et al., "Effector Function Activities of a Panel of Mutants of a Broadly Neutralizing Antibody against Human Immunodeficiency Vims Type 1," J Virol, Dec. 2001, 75(24):12161-12168.

Hill et al., "Human antibody-based chemically induced dimerizers for cell therapeutic applications," Nat Chem Biol, Feb. 2018, 14(2):112-117. doi:10.1038/nchembio.2529.

Holen et al., "Activation of EphA receptors on CD47CD45R07 memory cells stimulates migration," J Leukoc Biol, Jun. 2010, 87(6):1059-1068, doi: 10.1189/jlb.0709497. Epub Feb. 16, 2010.

Houot et al., "Therapeutic effect of CD137 immunomodulation in lymphoma and its enhancement by $T_{reg}$ depletion," Blood, Oct. 15, 2009, 114(16):3431-3438.

Huet et al., "Multivalent nanobodies targeting death receptor 5 elicit superior tumor cell killing through efficient caspase induction," mAbs, Nov./Dec. 2014, 6(6)1560-1570.

Igawa et al., "Antibody recycling by engineered pH-dependent antigen binding improves the duration of antigen neutralization," Nat Biotechnol, Nov. 2010, 28(11):1203-1207, Epub Oct. 17, 2010.

Ikuta et al., "Expression of human immunodeficiency virus type 1 (HIV-1) gag antigens on the surface of a cell line persistently infected with HIV-1 that highly expresses HIV-1 antigens," Virology, Jun. 1989, 170(2):408-417.

Ishiguro et al., "An anti-glypican 3/CD3 bispecific T cell-redirecting antibody for treatment of solid tumors," Sci Transl Med, Oct. 4, 2017, 9(410), pii: eaal4291. doi: 10.1126/scitranslmed.aal4291.

Jefferis et al., "Interaction sites on human IgG—Fc for Fc gamma R: current models," Immunol Lett, Jun. 3, 2002, 82(1-2):57-65.

Jiang et al., "Achaete-Scute Complex Homologue 1 regulates Tumor-Initiating Capacity in Human Small Cell Lung Cancer," Cancer Research, Feb. 1, 2009, 69(3):845-854.

Jo et al., "Engineering therapeutic antibodies targeting G-protein-coupled receptors," Exp Mol Med, Feb. 5, 2016, 48(2):e207, 9 pages.

Jones et al., "Growth factor receptor interplay and resistance in cancer," Endocr Relat Cancer, Dec. 2006, 13 Suppl 1:S45-51.

De Jong et al., "A Novel Platform for the Potentiation of Therapeutic Antibodies Based on Antigen-Dependent Formation of IgG Hexamers at the Cell Surface," PLoS Biol, Jan. 6, 2016, 14(1):e1002344, 24 pages.

Katoh et al., "Precision medicine for human cancers with Notch signaling dysregulation (Review)," International Journal of Molecular Medicine, Feb. 2020, 45:279-297.

Knowles et al., "Advances in Immuno—Positron Emission Tomography: Antibodies for Molecular Imaging in Oncology," Journal of Clinical Oncology, Nov. 1, 2012, 30(31):3884-3892.

Kontermann, "Dual targeting strategies with bispecific antibodies," mAbs, Mar.Apr. 2012, 4(2):182-197. doi: 10.4161/mabs.4.2.19000. Epub Mar. 1, 2012.

Kraft et al., "Definition of an Unexpected Ligand Recognition Motif for αvβ6 Integrin," J Biol Chem, Jan. 22, 1999, 274:1979-1985.

Kramer et al., "Molecular basis for the binding promiscuity of an anti-p24 (HIV-1) monoclonal antibody" Cell, Dec. 12, 1997, 91(6):799-809.

Kronqvist et al., "A novel affinity protein selection system based on staphylococcal cell surface display and flow cytometiy," Protein Eng Des Sei, Apr. 2008, 21(4):247-255.

Kussie et al., "A Single Engineered Amino Acid Substitution Changes Antibody Fine Specificity," J Immunol, Jan. 1, 1994, 152(1):146-152.

Ladi et al., "The divergent DSL ligand Dll3 does not activate Notch signaling but cell autonomously attenuates signaling induced by other DSL ligands," J Cell Biol, Sep. 12, 2005, 170(6):983-992.

Lazar et al., "Engineered antibody Fc variants with enhanced effector function," Proc Natl Acad Sci USA, Mar. 2006, 103(11):4005-4010. Epub Mar. 6, 2006.

Lederman et al., "A Single Amino Acid Substitution in a Common African Allele of the CD4 Molecule Ablates Binding of the Monoclonal Antibody, OKT4," Molecular Immunology, Nov. 1991, 28(11):1171-1181.

Lee et al., "Cell-type specific potent Wnt signaling blockade by bispecific antibody," Sci Rep, Jan. 15, 2018, 8(1):766, 16 pages.

Li et al., "β-Endorphin omission analogs: Dissociation of immunoreactivity from other biological activities," Proc Natl Acad Sci USA, Jun. 1980, 77:3211-3214.

Li et al., "Activation of the Proapoptotic Death Receptor DR5 by Oligomeric Peptide and Antibody Agonists," J Mol Biol, Aug. 18, 2006, 361(3):522-536.

Li et al., "Antitumor activities of agonistic anti-TNFR antibodies require differential FcγRIIB coengagement in vivo," Proc Natl Acad Sci USA, Nov. 26, 2013, 110(48):19501-19506. doi: 10.1073/pnas. 1319502110, Epub Nov. 11, 2013.

Lightfield D et al., "Critical function for Naip5 in inflammasome activation by a conserved carboxy-terminal domain of flagellin," Nature Immunology, Oct. 2008, 9(10): 1171-1178. doi: 10.1038/ni. 1646. Epub Aug. 24, 2008.

(56) References Cited

OTHER PUBLICATIONS

Livingston et al., "Selection of GM2, fucosyl GM1, globo H and polysialic acid as targets on small cell lung cancers for antibody mediated immunotherapy," Cancer Immunol Immunother, Oct. 1, 2005, 54(10):1018-1025.
Lloyd et al., "Modelling the human immune response: performance of a $10^{11}$ human antibody repertoire against a broad panel of therapeutically relevant antigens," Protein Engineering, Mar. 2009, 22:159-168.
Lum et al., "Targeting T Cells with Bispecific Antibodies for Cancer Therapy," BioDrugs, Dec. 1, 2011, 25(6):365-379. doi: 10.2165/11595950-000000000-00000.
Lutterbuese et al., "T cell-engaging BiTE antibodies specific for EGFR potently eliminate KRAS- and BRAF-mutated colorectal cancer cells," Pro Natl Acad Sci USA, Jul. 13, 2010, 107(28):12605-12610, doi: 10.1073/pnas.1000976107, Epub Jun. 28, 2010.
MacCallum et al., "Antibody-antigen Interactions: Contact Analysis and Binding Site Topography," J Mol Biol, Oct. 11, 1996, 262(5):732-745.
Mack et al., "A small bispecific antibody construct expressed as a functional single-chain molecule with high tumor cell cytotoxicity," Proc Natl Acad Sci USA, Jul. 18, 1995, 92(15):7021-7025.
Maier et al., "Correlation of mRNA and protein in complex biological samples," FEBS letters, Dec. 17, 2009, 583(24):3966-3973.
Marks et al., "By-passing Immunization—Human Antibodies from V-gene Libraries Displayed on Phage," J Mol Biol, Dec. 5, 1991, 222(3):581-597.
Meerten et al., "Complement-induced cell death by rituximab depends on CD20 expression level and acts complementary to antibody-dependent cellular cytotoxicity," Clin Cancer Res, Jul. 1, 2006, 12(13):4027-4035.
Mezzanzanica et al., "Human Ovarian Carcinoma Lysis by Cytotoxic T Cells Targeted by Bispecific Monoclonal Antibodies: Analysis of the Antibody," Int J Cancer, Apr. 15, 1988, 41(4):609-615.
Millipore, Anti-Delta3, clone 1E7.2, Jul. 15, 2008, pp. 1-3.
Mimoto et al., "Fc Engineering to Improve the Function of Therapeutic Antibodies," Curr Pharm Biotechnol, 2016, 17(15):1298-1314. doi: 10.2174/1389201017666160824161854.
Morgan et al., "The N-terminal end of the CH2 domain of chimeric human IgG1 anti-HLA-DR is necessary for C1q, Fc gamma RI and Fc gamma RIII binding," Immunology, Oct. 1995, 86(2):319-324.
Mukai et al., "Codon reassignment in the *Escherichia coli* genetic code," Nucleic Acids Res, Dec. 2010, 38(22):8188-8195.
Mullendore et al., "Ligand-dependent Notch Signaling is Involved in Tumor Initiation and Tumor Maintenance in Pancreatic Cancer," Clin Cancer Res, Apr. 1, 2009, 15(7):2291-2301.
Nakamura et al., "Peptide mimics of epidermal growth factor (EGF) with antagonistic activity," Journal of Biotechnology, Mar. 30, 2005, 116(3): 211-219.
Nimmerjahn et al., "Fcgamma receptors as regulators of immune responses," Nat Rev Immunol, Jan. 2008, 8(1):34-47.
Nimmerjahn et al., "Fcgamma receptors: old friends and new family members," Immunity, Jan. 2006, 24:19-28.
Odegrip et al., "CIS display: In vitro selection of peptides from libraries of protein-DNA complexes," Proc Natl Acad Sci USA, Mar. 2, 2004, 101(9):2806-2810.
Opposition 1 (Boehringer Ingelheim RCV GmbH & Co KG/Boehringer Ingelheim International GmbH) against EP 2 530 091, dated Jan. 8, 2019.
Opposition 2 (Schiweck Weinzierl Koch Patentanwalte Partnerschaft mbB) against EP 2 530 091, dated Jan. 8, 2019.
Opposition 3 (AbbVie Inc.) against EP 2 530 091, dated Jan. 15, 2019.
Orita et al., "A novel therapeutic approach for thrombocytopenia by minibody agonist of the thrombopoietin receptor," Blood, Jan. 15, 2005, 105(2):562-566, Epub Sep. 16, 2004.
Owonikoko et al., "Two Novel Immunotherapy Agents Targeting DLL3 in SCLC: Trials in Progress of AMG 757 and AMG 119," J Thorac Oncol, Sep. 26, 2018, 13(10S):S351-S353.
Patentee Submission dated Jan. 19, 2016 in EP Appn. No. 11736812.6, 10 pages.
Pavlou et al., "The therapeutic antibodies market to 2008," Eur J Pharm Biopharm, Apr. 2005, 59(3):389-396.
Peggs et al., "Cancer immunotherapy: co-stimulatory agonists and co-inhibitory antagonists," Clin Exp Immunol, Jul. 2009, 157(1):9-19. doi: 10.1111/j.1365-2249.2009.03912.x. Epub Feb. 18, 2009.
Phillips et al., "Molecular subclasses of high-grade glioma predict prognosis, delineate a pattern of disease progression, and resemble stages in neurogenesis," Cancer Cell, Mar. 2006, 9(3)157-173.
Porter et al., "Chimeric Antigen Receptor-Modified T Cells in Chronic Lymphoid Leukemia," N Engl J Med, Aug. 25, 2011, 365(8):725-733, doi: 10.1056/NEJMoa1103849, Epub Aug. 10, 2011.
R&D Systems, Inc., Human DLL3 Antibody, Catalog No. MAB4315, May 20, 2010, 1 page.
R&D Systems, Inc., Product sheet for Monoclonal Anti-human DLL3 Antibody, Catalog No. MAB4315, May 17, 2007, 1 page.
Rader, "DARTs take aim at BiTEs," Blood, Apr. 28, 2011, 117(17):4403-4404.
Ranjan et al., "Masking mRNA from translation in somatic cells," Genes and Development, Sep. 1993, 7:1725-1736.
Rao et al., "Novel cyclic and linear oligopeptides that bind to integrin β1 chain and either inhibit or costimulate T lymphocytes," Int Immunopharmacol, Mar. 2003, 3(3): 435-443.
Reichert et al., "Monoclonal antibody successes in the clinic," Nat Biotechnol, Sep. 2005, 23(9):1073-1078.
Review InvivoGen, Immunoglobulin G, 2011, 1 page.
Richards et al., "A peptide containing a novel FPGN CD40-binding sequence enhances adenoviral infection of murine and human dendritic cells," Eur J Biochem, May 2003, 270(10):2287-2294.
Riechelmann et al., "Adoptive therapy of head and neck squamous cell carcinoma with antibody coated immune cells: a pilot clinical trial," Cancer Immunol Immunother, Sep. 2007, 56(9):1397-1406, Epub Feb. 2, 2007.
Rothe et al., "Recombinant proteins in rheumatology—recent advances," N Biotechnol, Sep. 2011, 28(5):502-510, doi: 10.1016/j.nbt.2011,03.019. Epub Apr. 5, 2011.
Saunders et al., "A DLL3-targeted antibody-drug conjugate eradicates high-grade pulmonary neuroendocrine tumor-initiating cells in vivo," Science Translational Medicine, Aug. 26, 2015, 7(302):1-13.
Schaefer et al., "A two-in-one antibody against HER3 and EGFR has superior inhibitory activity compared with monospecific antibodies," Cancer Cell, Oct. 18, 2011, 20(4):472-486. doi: 10.1016/j.ccr.2011.09.003.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-522, doi: 10.1016/j.vaccine.2009.09.127. Epub Oct. 29, 2009.
Scheer et al., "Reorienting the Fab Domains of Trastuzumab Results in Potent HER2 Activators," PLoS One, Dec. 2012, 7(12):e51817, 13 pages.
Schlereth et al., "T-cell activation and B-cell depletion in chimpanzees treated with a bispecific anti-CD19/anti-CD3 single-chain antibody construct," Cancer Immunol Immunother, May 2006, 55(5):503-514, Epub Jul. 20, 2005.
Schraa et al., "RGD-Modified Anti-CD3 Antibodies Redirect Cytolytic Capacity of Cytotoxic T Lymphocytes Toward αvβ3-Expressing Endothelial Cells," Int J Cancer, Nov. 1, 2004, 112(2):279-285.
Sebastian et al., "Treatment of non-small cell lung cancer patients with the trifunctional monoclonal antibody catumaxomab (anti-EpCAM x anti-CD3): a phase I study," Cancer Immunol Immunother, Oct. 2007, 56(10):1637-1644, Epub Apr. 5, 2007.
Seimetz et al., "Development and approval of the trifunctional antibody catumaxomab (anti-EpCAM x anti-CD3) as a targeted cancer immunotherapy," Cancer Treat Rev, Oct. 2010, 36(6):458-467. doi: 10.1016/j.ctrv.2010.03.001. Epub Mar. 27, 2010.
Sepp et al., "Cell-Free Selection of Domain Antibodies by in vitro Compartmentalization," Methods Mol Biol, Jul. 2012, 911:183-198.
Sequence Alignments, 2 pages (document submitted in opposition against EP 2 530 091 and posted by the EPO on Mar. 6, 2020).

(56) References Cited

OTHER PUBLICATIONS

Shanmugam et al., "Synthetic Toll Like Receptor-4 (TLR-4) Agonist Peptides as a Novel Class of Adjuvants," PLoS ONE, Feb. 2012, 7(2):e30839.
Shields et al., "High Resolution Mapping of the Binding Site on Human IgG1 for FcKRI, FcyRII, FcyRIII, and FcRn and Design of IgG1 Variants with Improved Binding to the FcyR," The Journal of Biological Chemistiy, Mar. 2, 2001, 276(9):6591-6604.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-3473. Epub Nov. 8, 2002.
Shitara, "Potelligent Antibodies as Next Generation Therapeutic Antibodies," Yakugaku Zasshi, The Pharmaceutical Society of Japan, 2009, 129(1):3-9 (with Partial English translation).
Spirin, "Storage of messenger RNA in eukaryotes: Envelopment with protein, translational barrier at 5' side, or conformational masking by 3' side?," Molecular Reproduction and Development, May 1994, 38:107-117.
Staerz et al., "Hybrid antibodies can target sites for attack by T cells," Nature, Apr. 18-24, 1985, 314(6012):628-631.
Staerz et al., "Hybrid hybridoma producing a bispecific monoclonal antibody that can focus effector T-cell activity," Proc Natl Acad Sci USA, Mar. 1986, 83(5):1453-1457.
Stancovski et al., "Mechanistic Aspects of the Opposing Effects of Monoclonal Antibodies to the ERBB2 Receptor on Tumor Growth," Proc Nat Acad Sci USA, Oct. 1, 1991, 88(19):8691-8695.
Stevenson et al., "A chimeric antibody with dual Fc regions (bisFabFc) prepared by manipulations at the IgG hinge," Anticancer Drug Des, Mar. 1989, 3(4):219-230.
Stockwin et al., "Antibodies as therapeutic agents: vive la renaissance!," Expert Opinion on Biological Therapy, Oct. 2003, 3(7):1133-1152.
Summons to Attend Oral Proceedings in opposition against EP 2 530 091, dated Oct. 10, 2019.
Summons to Attend Oral Proceedings in opposition against EP 18156974.0, dated Jun. 10, 2020.
Sun et al., "Antibody-drug conjugates as targeted cancer therapeutics," Acta Pharmaceutica Sinica, Sep. 2009, 44(9):943-952.
Taneja et al., "Markers of small cell lung cancer," World Journal of Surgical Oncology, May 5, 2004, 2(10)1-5.
Traxlmayr et al., "Integrin binding human antibody constant domains—Probing the C-termmal structural loops for grafting the RGD motif," J Biotechnol, Sep. 10, 2011, 155(2):193-202. doi: 10.1016/j.jbiotec.201L06.042. Epub Jul. 8, 2011.
Turnpenny et al., "Novel mutations in *DLL3*, a somitogenesis gene encoding a ligand for the Notch signalling pathway, cause a consistent pattern of abnormal vertebral segmentation in spondylocostal dysostosis," J Med Genet, May 2003, 40(5):333-339.
Tutt et al., "Trispecific F(ab')3 derivatives that use cooperative signaling via the TCR/CD3 complex and CD2 to activate and redirect resting cytotoxic T cells," J Immunol, Jul. 1, 1991, 147(1):60-69.
Unkeless et al., "Structure and function of human and murine receptors for IgG," Annu Rev Immunol, Apr. 1988, 6:251-281.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-428.
Vaughan et al., "Human Antibodies with Sub-nanomolar Affinities Isolated from a Large Non-immunized Phage Display Libraiy," Nat Biotechnol, Mar. 1996, 14(3):309-314.
Vinay et al., "4-1BB signaling beyond T Cells," Cell Mol Immunol, Jul. 2011, 8(4):281-284. doi: 10.1038/cmi.2010.82. Epub Jan. 10, 2011.
Wang et al., "Epithelial-mesenchymal transition in breast cancer progression and metastasis," Chin J Cancer, Sep. 2011, 30(9):603-611.
Weng et al., "Two Immunoglobulin G Fragment C Receptor Polymorphisms Independently Predict Response to Rituximab in Patients With Follicular Lymphoma," Journal of Clinical Oncology, Nov. 1, 2003, 21(21):3940-3947.
Witte et al., "Monoclonal antibodies targeting the VEGF receptor-2 (Flk1/KDR) as an anti-angiogenic therapeutic strategy," Cancer and Metastasis Reviews, Jun. 1998, 17(2):155-161.
Wolf et al., "BiTEs: bispecific antibody constmcts with unique anti-tumor activity," Drug Discov Today, Sep. 15, 2005, 10(18):1237-1244.
Wozniak-Knopp et al., "Introducing antigen-binding sites in structural loops of immunoglobulin constant domains: Fc fragments with engineered HER2/neu-binding sites and antibody properties," Protein Eng Des Sel, Apr. 2010, 23(4):289-297, doi: 10.1093/protein/gzq005. Epub Feb. 11, 2010.
Written Submissions by Patentee (Chugai Seiyaku Kabushiki Kaisha et al.) in opposition against EP 2 530 091, dated Mar. 6, 2020, 33 pages.
Wu et al., "Humanization of a Murine Monoclonal Antibody by Simultaneous Optimization of Framework and CDR Residues," J Mol Biol, Nov. 19, 1999, 294(1):151-162.
Wu et al., "Structures of the CXCR4 Chemokine GPCR with Small-Molecule and Cyclic Peptide Antagonists," Science, Nov. 19, 2010, 330:1066-1071.
Xiao et al., "A large library based on a novel (CH2) scaffold: Identification of HIV-1 inhibitors," Biochem Biophys Res Commun, Sep. 18, 2009, 387(2):387-392. doi: 10.1016/j.bbrc.2009.07.044. Epub Jul. 15, 2009.
Yu et al., "Interaction between Bevacizumab and Murine VEGF-A: A Reassessment," Investigative Ophthalmology and Visual Science, Feb. 2008, 49(2):522-527.
Zanetti et al., "Mechanisms of Antibody-Based Tumor Immunity," The Antibodies, 2000, 6:36-37.
Zeidler et al., "Simultaneous activation of T cells and accessory cells by a new class of intact bispecific antibody results in efficient tumor cell killing," J Immunol, Aug. 1, 1999, 163(3):1246-1252.
Zhang et al., "Selection of antibodies that regulate phenotype from intracellular combinatorial antibody libraries," Proc Natl Acad Sci USA, Sep. 25, 2012, 109(39):15728-15733.
Zhou et al., "Development of a novel mammalian cell surface antibody display platform," mAbs, Sep.-Oct. 2010, 2(5):508-518.
Ferran et al., "Cytokine-related syndrome following injection of anti-CD3 monoclonal antibody: Further evidence for transient in vivo T cell activation," Eur J Immunol, Mar. 1990, 20(3):509-515.
Frey et al., "Cytokine release syndrome with novel therapeutics for acute lymphoblastic leukemia," Hematology Am Soc Hematol Educ Program, Dec. 2, 2016, 2016(1):567-572.
U.S. Appl. No. 16/957,072, filed Jun. 25, 2020, Kamikawaji.
U.S. Appl. No. 17/506,733, filed Oct. 21, 2021, Igawa et al.
Bardwell et al., "Potent and conditional redirected T cell killing of tumor cells using Half DVD-Ig," Protein Cell, Jan. 2018, 9(1):121-129.
Dickopf et al., "Format and geometries matter: Structure-based design defines the functionality of bispecific antibodies," Comput Struct Biotechnol J, May 14, 2020, 18:1221-1227.
Ellmark et al., "Selective FcγR engagement by human agonistic anti-CD40 antibodies," Transl Cancer Res, 2016, 5(Suppl 4):S839-S841.

* cited by examiner

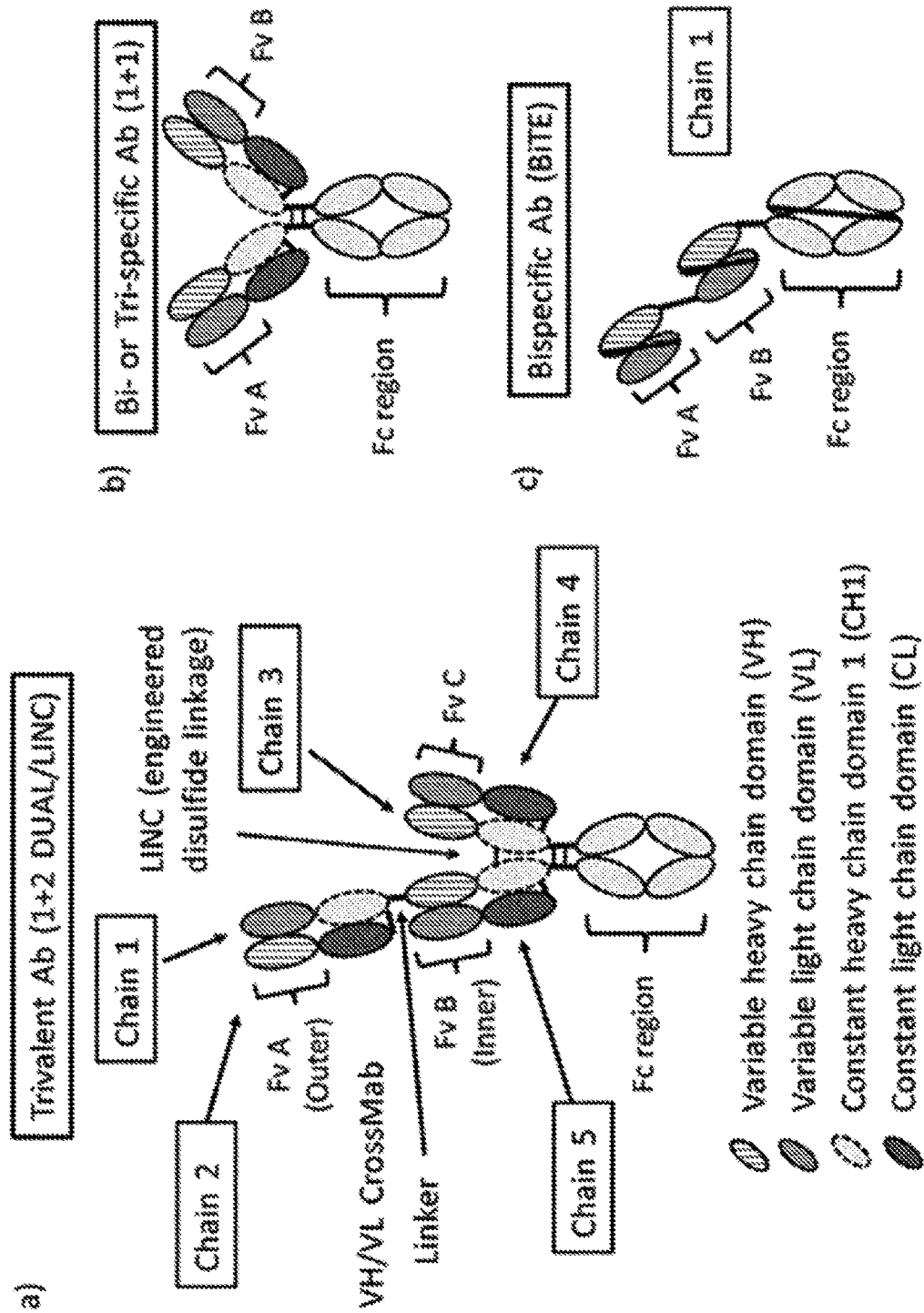

[Fig. 2]
a)
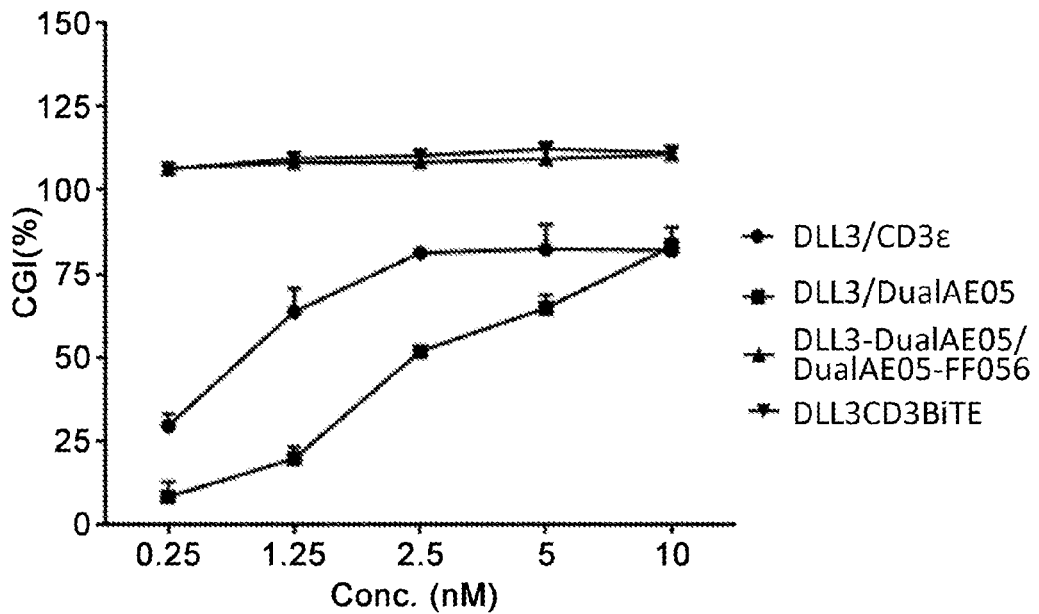
b)
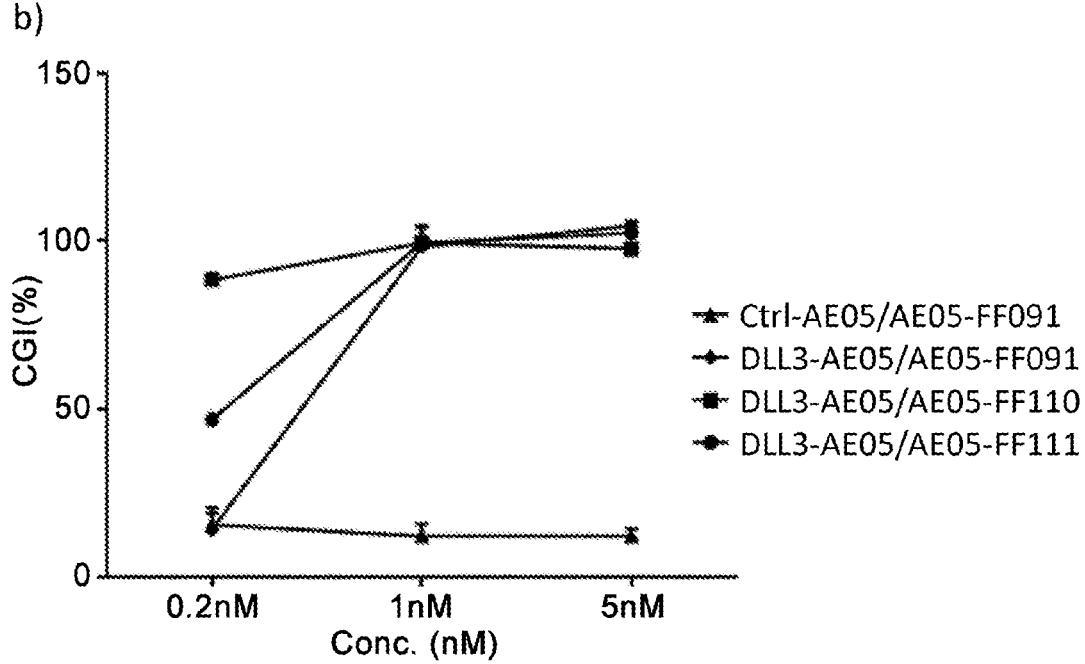

[Fig. 3]
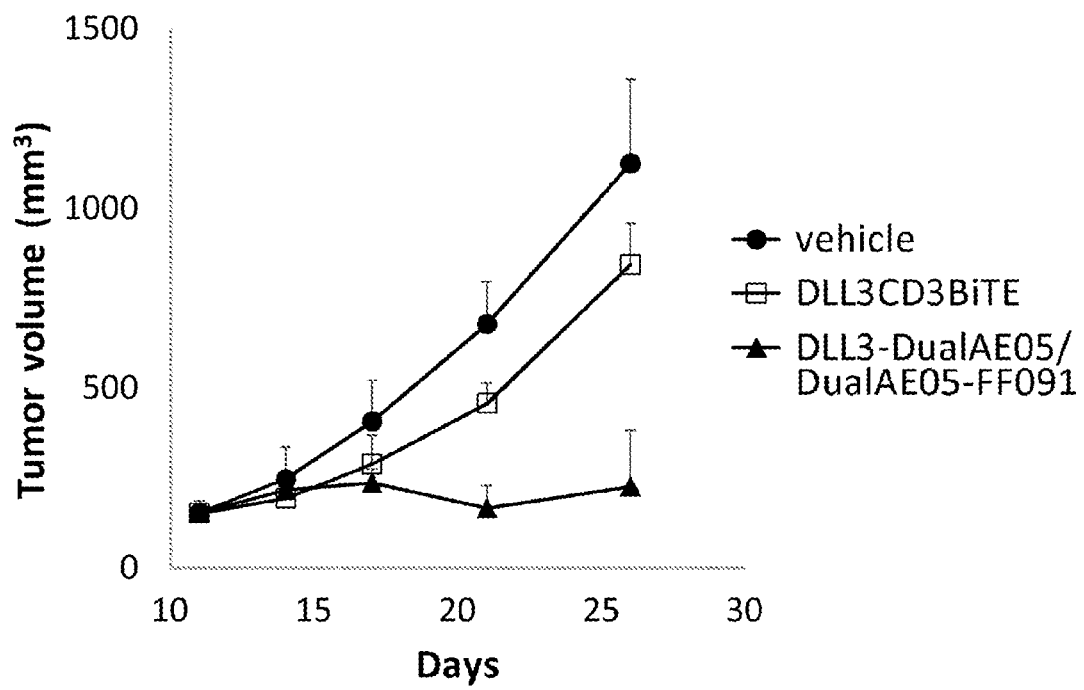

[Fig. 4]
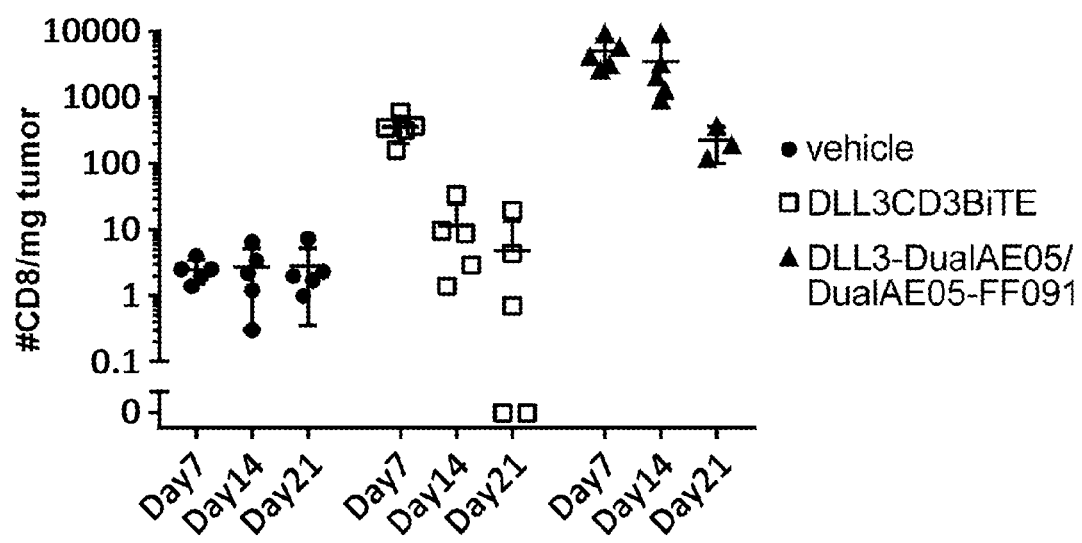

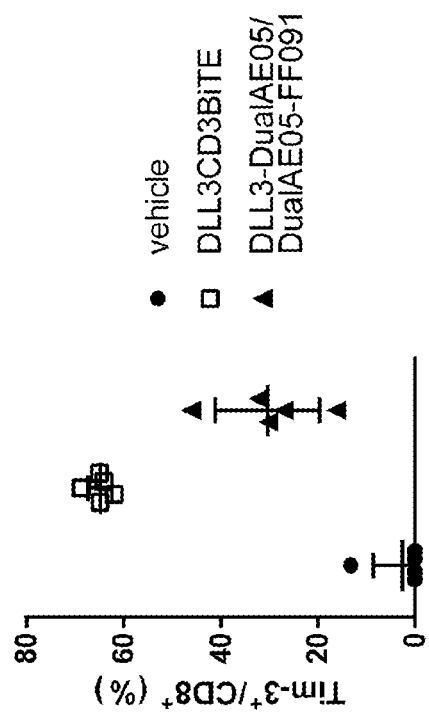
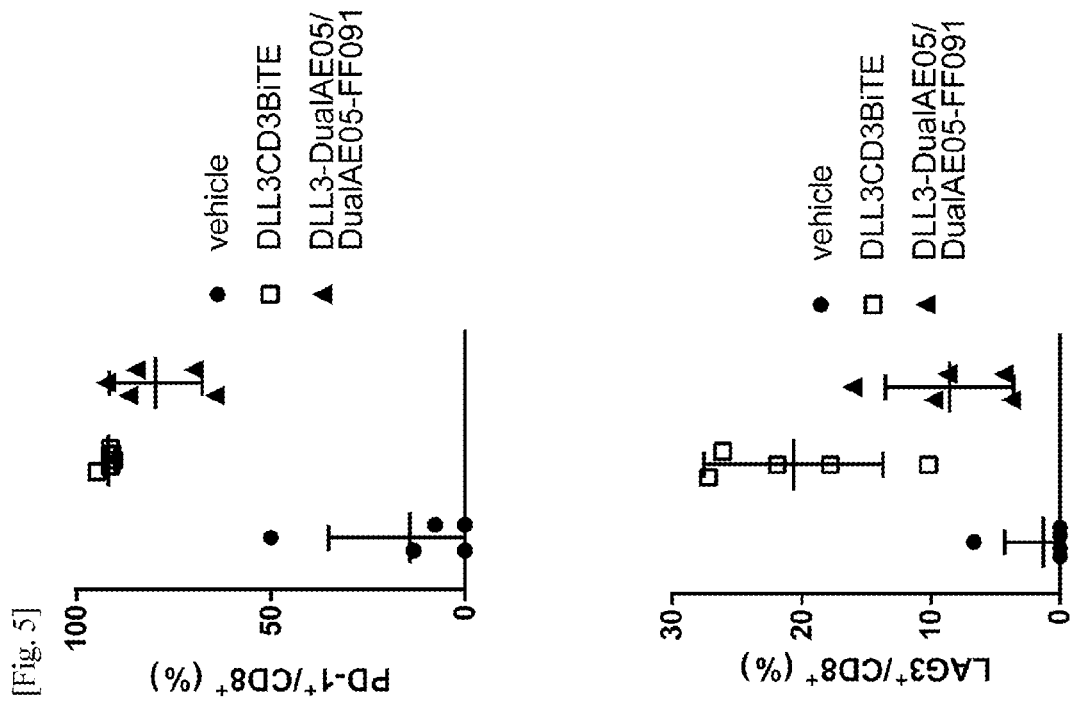
[Fig. 5]

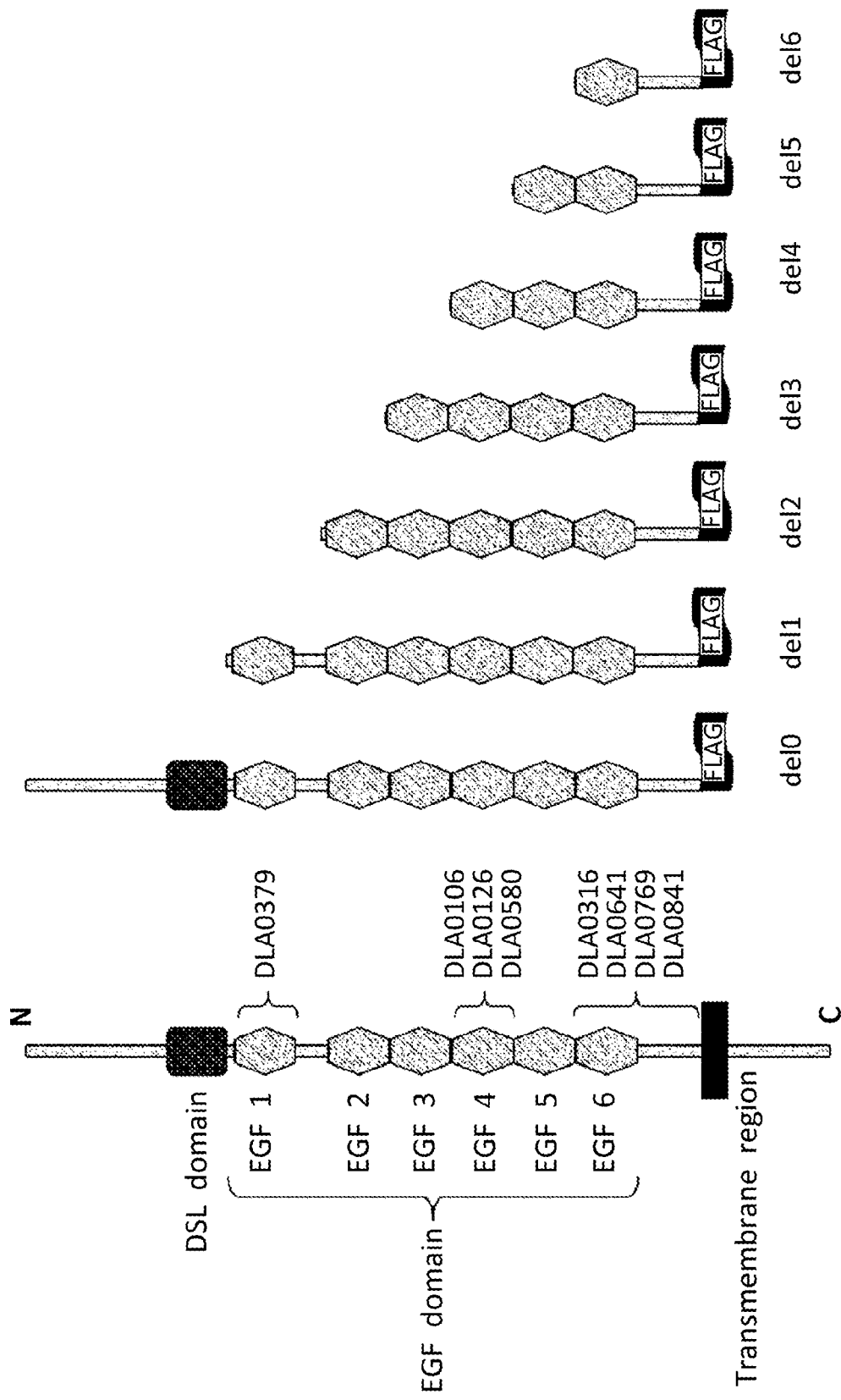
[Fig. 6]

SEQUENCE LISTING

```
<160> NUMBER OF SEQ ID NOS: 320

<210> SEQ ID NO 1
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 1

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Val Leu Pro Ala
            100                 105                 110
```

```
Phe Gly Val Asp Ala Trp Gly Gln Gly Thr Thr Val Thr Val Ser Ser
        115                 120                 125
```

<210> SEQ ID NO 2
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 2

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Met His Trp Val Arg Gln Ala Pro Gly Lys Gly Leu Glu Trp Val
        35                  40                  45

Ala Gln Ile Lys Asp Lys Tyr Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Phe Gly Val Asp Ala Trp Gly Gln Gly Thr Thr Val Thr Val Ser Ser
        115                 120                 125
```

<210> SEQ ID NO 3
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 3

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Met His Trp Val Arg Gln Ala Pro Gly Lys Gly Leu Glu Trp Val
        35                  40                  45

Ala Gln Ile Lys Asp Lys Tyr Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Ile His Tyr Ala Ser Ala Ser Thr Leu Leu Pro Ala
            100                 105                 110

Phe Gly Val Asp Ala Trp Gly Gln Gly Thr Thr Val Thr Val Ser Ser
        115                 120                 125
```

<210> SEQ ID NO 4
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 4

```
Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Lys Phe Ser Asn Val
            20                  25                  30
Trp Phe His Trp Val Arg Gln Ala Pro Gly Lys Gly Leu Glu Trp Val
        35                  40                  45
Ala Gln Ile Lys Asp Lys Tyr Asn Ala Tyr Ala Thr Tyr Tyr Ala Pro
    50                  55                  60
Ser Val Lys Gly Arg Phe Thr Ile Ser Arg Asp Asp Ser Lys Asn Ser
65                  70                  75                  80
Ile Tyr Leu Gln Met Asn Ser Leu Lys Thr Glu Asp Thr Ala Val Tyr
                85                  90                  95
Tyr Cys His Tyr Val His Tyr Ala Ser Ala Ser Thr Leu Leu Pro Ala
            100                 105                 110
Phe Gly Val Asp Ala Trp Gly Gln Gly Thr Thr Val Thr Val Ser Ser
        115                 120                 125
```

<210> SEQ ID NO 5
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 5

```
Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Val Phe Ser Asn Val
            20                  25                  30
Trp Met His Trp Val Arg Gln Ala Pro Gly Lys Gly Leu Glu Trp Val
        35                  40                  45
Ala Gln Ile Lys Asp Lys Trp Asn Ala Tyr Ala Ala Tyr Tyr Ala Pro
    50                  55                  60
Ser Val Lys Gly Arg Phe Thr Ile Ser Arg Asp Asp Ser Lys Asn Ser
65                  70                  75                  80
Ile Tyr Leu Gln Met Asn Ser Leu Lys Thr Glu Asp Thr Ala Val Tyr
                85                  90                  95
Tyr Cys His Tyr Ile His Tyr Ala Ser Ala Ser Thr Leu Leu Pro Ala
            100                 105                 110
Glu Gly Ile Asp Ala Trp Gly Gln Gly Thr Thr Val Thr Val Ser Ser
        115                 120                 125
```

<210> SEQ ID NO 6
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 6

```
Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Lys Phe Ser Asn Val
            20                  25                  30
Trp Phe His Trp Val Arg Gln Ala Pro Gly Lys Gly Leu Glu Trp Val
        35                  40                  45
```

```
Ala Gln Ile Lys Asp Tyr Tyr Asn Ala Tyr Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Glu Gly Val Asp Ala Trp Gly Gln Gly Thr Thr Val Thr Val Ser Ser
            115                 120                 125
```

<210> SEQ ID NO 7
<211> LENGTH: 207
<212> TYPE: PRT
<213> ORGANISM: Artificial Sequence
<220> FEATURE:
<223> OTHER INFORMATION: an artificially synthesized sequence

<400> SEQUENCE: 7

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 8
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 8

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Thr
            20                  25                  30
```

Trp Phe His Trp Val Arg Gln Ala Pro Gly Lys Gly Leu Glu Trp Val
            35                  40                  45

Ala Gln Ile Lys Asp Tyr Tyr Asn Asp Tyr Ala Ala Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
                100                 105                 110

Glu Gly Val Asp Ala Trp Gly Gln Gly Thr Thr Val Thr Val Ser Ser
            115                 120                 125

<210> SEQ ID NO 9
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 9

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
            35                  40                  45

Ala Gln Ile Lys Asp Lys Tyr Asn Ala Tyr Ala Asp Tyr Tyr Ala Pro
        50                  55                  60

Ser Val Lys Glu Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
                100                 105                 110

Glu Gly Val Asp Ala Trp Gly Gln Gly Thr Thr Val Thr Val Ser Ser
            115                 120                 125

<210> SEQ ID NO 10
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
            35                  40                  45

Ala Gln Ile Lys Asp Lys Tyr Asn Ala Tyr Ala Asp Tyr Tyr Ala Pro
        50                  55                  60

Ser Val Glu Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr 85                  90                  95

Tyr Cys His Tyr Val His Tyr Ala Ser Ala Ser Thr Leu Leu Pro Ala
                100                 105                 110

Glu Gly Val Asp Ala Trp Gly Gln Gly Thr Thr Val Thr Val Ser Ser
            115                 120                 125

<210> SEQ ID NO 11
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 11

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Asp Tyr Tyr Ala Pro
    50                  55                  60

Ser Val Glu Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
                100                 105                 110

Glu Gly Val Asp Ala Trp Gly Gln Gly Thr Thr Val Thr Val Ser Ser
            115                 120                 125

<210> SEQ ID NO 12
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 12

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Lys Trp Asn Ala Tyr Ala Asp Tyr Tyr Ala Pro
    50                  55                  60

Ser Val Lys Glu Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Ile His Tyr Ala Ser Ala Ser Thr Leu Leu Pro Ala
                100                 105                 110

Glu Gly Ile Asp Ala Trp Gly Gln Gly Thr Thr Val Thr Val Ser Ser
            115                 120                 125

<210> SEQ ID NO 13
<211> LENGTH: 128

-continued

```
<212> TYPE: PRT
<213> ORGANISM: Artificial Sequence
<220> FEATURE:
<223> OTHER INFORMATION: an artificially synthesized sequence

<400> SEQUENCE: 13

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Gly Tyr Tyr His Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ala Ala Ser Thr Leu Leu Pro Ala
            100                 105                 110

Glu Gly Val Asp Ala Trp Gly Gln Gly Thr Thr Val Thr Val Ser Ser
        115                 120                 125

<210> SEQ ID NO 14
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 14

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Gly Tyr Tyr His Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ala Ala Ser Gln Leu Leu Pro Ala
            100                 105                 110

Glu Gly Val Asp Ala Trp Gly Gln Gly Thr Thr Val Thr Val Ser Ser
        115                 120                 125

<210> SEQ ID NO 15
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 15

Asn Ala Trp Met His
1               5
```

-continued

```
<210> SEQ ID NO 16
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 16

Asn Val Trp Met His
1               5

<210> SEQ ID NO 17
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 17

Asn Val Trp Met His
1               5

<210> SEQ ID NO 18
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 18

Asn Val Trp Phe His
1               5

<210> SEQ ID NO 19
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 19

Asn Val Trp Met His
1               5

<210> SEQ ID NO 20
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 20

Asn Val Trp Phe His
1               5

<210> SEQ ID NO 21
<211> LENGTH: 72
<212> TYPE: PRT
<213> ORGANISM: Artificial Sequence
<220> FEATURE:
<223> OTHER INFORMATION: an artificially synthesized sequence

<400> SEQUENCE: 21

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
                20                  25                  30
```

Cys Ser Ser Thr Ser Asn Ala Glu Cys Asp Cys Thr Pro Gly Phe His
            35                  40                  45

Cys Leu Gly Ala Gly Cys Ser Met Cys Glu Gln Asp Cys Lys Gln Gly
     50                  55                  60

Gln Glu Leu Thr Lys Lys Gly Cys
65                  70

<210> SEQ ID NO 22
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 22

Asn Thr Trp Phe His
1               5

<210> SEQ ID NO 23
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 23

Asn Val Trp Phe His
1               5

<210> SEQ ID NO 24
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 24

Asn Val Trp Phe His
1               5

<210> SEQ ID NO 25
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 25

Asn Val Trp Phe His
1               5

<210> SEQ ID NO 26
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 26

Asn Val Trp Phe His
1               5

<210> SEQ ID NO 27
<211> LENGTH: 5
<212> TYPE: PRT

```
<213> ORGANISM: Artificial Sequence
<220> FEATURE:
<223> OTHER INFORMATION: an artificially synthesized sequence

<400> SEQUENCE: 27

Asn Val Trp Phe His
1               5

<210> SEQ ID NO 28
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 28

Asn Val Trp Phe His
1               5

<210> SEQ ID NO 29
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 29

Gln Ile Lys Asp Lys Gly Asn Ala Tyr Ala Ala Tyr Tyr Ala Pro Ser
1               5                   10                  15

Val Lys Gly

<210> SEQ ID NO 30
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 30

Gln Ile Lys Asp Lys Tyr Asn Ala Tyr Ala Ala Tyr Tyr Ala Pro Ser
1               5                   10                  15

Val Lys Gly

<210> SEQ ID NO 31
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 31

Gln Ile Lys Asp Lys Tyr Asn Ala Tyr Ala Ala Tyr Tyr Ala Pro Ser
1               5                   10                  15

Val Lys Gly

<210> SEQ ID NO 32
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 32

Gln Ile Lys Asp Lys Tyr Asn Ala Tyr Ala Thr Tyr Tyr Ala Pro Ser
1               5                   10                  15
```

Val Lys Gly

<210> SEQ ID NO 33
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 33

Gln Ile Lys Asp Lys Trp Asn Ala Tyr Ala Ala Tyr Tyr Ala Pro Ser
1               5                   10                  15

Val Lys Gly

<210> SEQ ID NO 34
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 34

Gln Ile Lys Asp Tyr Tyr Asn Ala Tyr Ala Ala Tyr Tyr Ala Pro Ser
1               5                   10                  15

Val Lys Gly

<210> SEQ ID NO 35
<211> LENGTH: 31
<212> TYPE: PRT
<213> ORGANISM: Artificial Sequence
<220> FEATURE:
<223> OTHER INFORMATION: an artificially synthesized sequence

<400> SEQUENCE: 35

Asp Cys Thr Pro Gly Phe His Cys Leu Gly Ala Gly Cys Ser Met Cys
1               5                   10                  15

Glu Gln Asp Cys Lys Gln Gly Gln Glu Leu Thr Lys Lys Gly Cys
            20                  25                  30

<210> SEQ ID NO 36
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 36

Gln Ile Lys Asp Tyr Tyr Asn Asp Tyr Ala Ala Tyr Tyr Ala Pro Ser
1               5                   10                  15

Val Lys Gly

<210> SEQ ID NO 37
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 37

Gln Ile Lys Asp Lys Tyr Asn Ala Tyr Ala Asp Tyr Tyr Ala Pro Ser
1               5                   10                  15

Val Lys Glu

```
<210> SEQ ID NO 38
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 38

Gln Ile Lys Asp Lys Tyr Asn Ala Tyr Ala Asp Tyr Tyr Ala Pro Ser
1               5                   10                  15

Val Glu Gly

<210> SEQ ID NO 39
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 39

Gln Ile Lys Asp Tyr Tyr Asn Ala Tyr Ala Asp Tyr Tyr Ala Pro Ser
1               5                   10                  15

Val Glu Gly

<210> SEQ ID NO 40
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 40

Gln Ile Lys Asp Lys Trp Asn Ala Tyr Ala Asp Tyr Tyr Ala Pro Ser
1               5                   10                  15

Val Lys Glu

<210> SEQ ID NO 41
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 41

Gln Ile Lys Asp Tyr Tyr Asn Ala Tyr Ala Gly Tyr Tyr His Pro Ser
1               5                   10                  15

Val Lys Gly

<210> SEQ ID NO 42
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 42

Gln Ile Lys Asp Tyr Tyr Asn Ala Tyr Ala Gly Tyr Tyr His Pro Ser
1               5                   10                  15

Val Lys Gly

<210> SEQ ID NO 43
<211> LENGTH: 17
<212> TYPE: PRT
```

<213> ORGANISM: Artificial Sequence
<220> FEATURE:
<223> OTHER INFORMATION: an artificially synthesized sequence

<400> SEQUENCE: 43

Val His Tyr Ala Ser Ala Ser Thr Val Leu Pro Ala Phe Gly Val Asp
1               5                   10                  15
Ala

<210> SEQ ID NO 44
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 44

Val His Tyr Ala Ser Ala Ser Thr Leu Leu Pro Ala Phe Gly Val Asp
1               5                   10                  15
Ala

<210> SEQ ID NO 45
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 45

Ile His Tyr Ala Ser Ala Ser Thr Leu Leu Pro Ala Phe Gly Val Asp
1               5                   10                  15
Ala

<210> SEQ ID NO 46
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 46

Val His Tyr Ala Ser Ala Ser Thr Leu Leu Pro Ala Phe Gly Val Asp
1               5                   10                  15
Ala

<210> SEQ ID NO 47
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 47

Ile His Tyr Ala Ser Ala Ser Thr Leu Leu Pro Ala Glu Gly Ile Asp
1               5                   10                  15
Ala

<210> SEQ ID NO 48
<211> LENGTH: 17
<212> TYPE: PRT
<213> ORGANISM: Artificial Sequence
<220> FEATURE:
<223> OTHER INFORMATION: an artificially synthesized sequence

```
<400> SEQUENCE: 48

Val His Tyr Ala Ser Ala Ser Thr Leu Leu Pro Ala Glu Gly Val Asp
1               5                   10                  15

Ala

<210> SEQ ID NO 49
<211> LENGTH: 63
<212> TYPE: PRT
<213> ORGANISM: Artificial Sequence
<220> FEATURE:
<223> OTHER INFORMATION: an artificially synthesized sequence

<400> SEQUENCE: 49

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys
    50                  55                  60

<210> SEQ ID NO 50
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 50

Val His Tyr Ala Ser Ala Ser Thr Leu Leu Pro Ala Glu Gly Val Asp
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 51

Val His Tyr Ala Ser Ala Ser Thr Leu Leu Pro Ala Glu Gly Val Asp
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 52

Val His Tyr Ala Ser Ala Ser Thr Leu Leu Pro Ala Glu Gly Val Asp
1               5                   10                  15

Ala

<210> SEQ ID NO 53
<211> LENGTH: 17
<212> TYPE: PRT
<213> ORGANISM: Artificial Sequence
```

<220> FEATURE:
<223> OTHER INFORMATION: an artificially synthesized sequence

<400> SEQUENCE: 53

Val His Tyr Ala Ser Ala Ser Thr Leu Leu Pro Ala Glu Gly Val Asp
1               5                   10                  15

Ala

<210> SEQ ID NO 54
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 54

Ile His Tyr Ala Ser Ala Ser Thr Leu Leu Pro Ala Glu Gly Ile Asp
1               5                   10                  15

Ala

<210> SEQ ID NO 55
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 55

Val His Tyr Ala Ala Ala Ser Thr Leu Leu Pro Ala Glu Gly Val Asp
1               5                   10                  15

Ala

<210> SEQ ID NO 56
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 56

Val His Tyr Ala Ala Ala Ser Gln Leu Leu Pro Ala Glu Gly Val Asp
1               5                   10                  15

Ala

<210> SEQ ID NO 57
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Gln Ala Ser Gln Glu Leu Val His Met
            20                  25                  30

Asn Arg Asn Thr Tyr Leu His Trp Tyr Gln Lys Pro Gly Gln Ala
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
            85                  90                  95

Thr Ser Val Pro Phe Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Gln Pro Ser Gln Glu Val Val His Met
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
            85                  90                  95

Thr Ser His Pro Phe Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Gln Pro Ser Gln Glu Val Val His Met
            20                  25                  30

Asn Asn Val Val Tyr Leu His Trp Tyr Gln Gln Lys Pro Gly Gln Ala
        35                  40                  45

Pro Arg Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
            85                  90                  95

Thr Ser His Pro Phe Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 60

```
Asp Ile Val Met Thr Gln Ser Pro Leu Ser Leu Pro Val Thr Pro Gly
1               5                   10                  15

Glu Pro Ala Ser Ile Ser Cys Gln Pro Ser Gln Glu Val Val His Met
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Val Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr His His Pro Phe Thr Phe Gly Gln Gly Thr Lys Leu Glu Ile Lys
            100                 105                 110
```

<210> SEQ ID NO 61
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 61

```
Asp Ile Val Met Thr Gln Ser Pro Leu Ser Leu Pro Val Thr Pro Gly
1               5                   10                  15

Glu Pro Ala Ser Ile Ser Cys Gln Pro Ser Glu Glu Val Val His Met
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Leu Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Gly
                85                  90                  95

Thr His His Pro Phe Thr Phe Gly Gln Gly Thr Lys Leu Glu Ile Lys
            100                 105                 110
```

<210> SEQ ID NO 62
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 62

```
Gln Ala Ser Gln Glu Leu Val His Met Asn Arg Asn Thr Tyr Leu His
1               5                   10                  15
```

<210> SEQ ID NO 63
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 63

```
Gln Pro Ser Gln Glu Val Val His Met Asn Arg Asn Thr Tyr Leu His
1               5                   10                  15
```

```
<210> SEQ ID NO 64
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 64

Gln Pro Ser Gln Glu Val Val His Met Asn Asn Val Val Tyr Leu His
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 65

Gln Pro Ser Gln Glu Val Val His Met Asn Arg Asn Thr Tyr Leu His
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 66

Gln Pro Ser Glu Glu Val Val His Met Asn Arg Asn Thr Tyr Leu His
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 67

Lys Val Ser Asn Arg Phe Pro
1               5

<210> SEQ ID NO 68
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 68

Lys Val Ser Asn Arg Phe Pro
1               5

<210> SEQ ID NO 69
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 69

Lys Val Ser Asn Arg Phe Pro
1               5

<210> SEQ ID NO 70
```

```
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 70

Lys Val Ser Asn Val Phe Pro
1               5

<210> SEQ ID NO 71
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 71

Lys Val Ser Asn Leu Phe Pro
1               5

<210> SEQ ID NO 72
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 72

Ala Gln Gly Thr Ser Val Pro Phe Thr
1               5

<210> SEQ ID NO 73
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 73

Ala Gln Gly Thr Ser His Pro Phe Thr
1               5

<210> SEQ ID NO 74
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 74

Ala Gln Gly Thr Ser His Pro Phe Thr
1               5

<210> SEQ ID NO 75
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 75

Ala Gln Gly Thr His His Pro Phe Thr
1               5

<210> SEQ ID NO 76
<211> LENGTH: 9
```

```
<212> TYPE: PRT
<213> ORGANISM: Artificial Sequence
<220> FEATURE:
<223> OTHER INFORMATION: an artificially synthesized sequence

<400> SEQUENCE: 76

Ala Gln Gly Thr His His Pro Phe Thr
1               5

<210> SEQ ID NO 77
<211> LENGTH: 122
<212> TYPE: PRT
<213> ORGANISM: Artificial Sequence
<220> FEATURE:
<223> OTHER INFORMATION: an artificially synthesized sequence

<400> SEQUENCE: 77

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Asn Ala
                20                  25                  30

Trp Met His Trp Val Arg Gln Ala Pro Gly Lys Gly Leu Glu Trp Val
            35                  40                  45

Ala Gln Ile Lys Asp Lys Ser Gln Asn Tyr Ala Thr Tyr Val Ala Glu
        50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp
            100                 105                 110

Gly Gln Gly Thr Thr Val Thr Val Ser Ser
        115                 120

<210> SEQ ID NO 78
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 78

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 79
<211> LENGTH: 121
<212> TYPE: PRT
```

<213> ORGANISM: Artificial Sequence
<220> FEATURE:
<223> OTHER INFORMATION: an artificially synthesized sequence

<400> SEQUENCE: 79

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120
```

<210> SEQ ID NO 80
<211> LENGTH: 109
<212> TYPE: PRT
<213> ORGANISM: Artificial Sequence
<220> FEATURE:
<223> OTHER INFORMATION: an artificially synthesized sequence

<400> SEQUENCE: 80

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105
```

<210> SEQ ID NO 81
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 81

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
        35                  40                  45
```

```
Ala Gln Ile Lys Asp Tyr Tyr Asn Ala Tyr Ala Ala Tyr Tyr Ala Pro
    50                  55                  60
Ser Val Lys Gly Arg Phe Thr Ile Ser Arg Asp Asp Ser Lys Asn Ser
65                  70                  75                  80
Ile Tyr Leu Gln Met Asn Ser Leu Lys Thr Glu Asp Thr Ala Val Tyr
                85                  90                  95
Tyr Cys His Tyr Val His Tyr Ala Ser Ala Ser Thr Leu Leu Pro Ala
            100                 105                 110
Glu Gly Val Asp Ala Trp Gly Gln Gly Thr Thr Val Thr Val Ser Ser
                115                 120                 125
```

<210> SEQ ID NO 82
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 82

```
Asn Val Trp Phe His
1               5
```

<210> SEQ ID NO 83
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 83

```
Gln Ile Lys Asp Tyr Tyr Asn Ala Tyr Ala Ala Tyr Tyr Ala Pro Ser
1               5                   10                  15

Val Lys Gly
```

<210> SEQ ID NO 84
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 84

```
Val His Tyr Ala Ser Ala Ser Thr Leu Leu Pro Ala Glu Gly Val Asp
1               5                   10                  15

Ala
```

<210> SEQ ID NO 85
<211> LENGTH: 330
<212> TYPE: PRT
<213> ORGANISM: Artificial Sequence
<220> FEATURE:
<223> OTHER INFORMATION: an artificially synthesized sequence

<400> SEQUENCE: 85

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
                50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 326
<212> TYPE: PRT
<213> ORGANISM: Artificial Sequence
<220> FEATURE:
<223> OTHER INFORMATION: an artificially synthesized sequence

<400> SEQUENCE: 86

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
                 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
            85                  90                  95
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 87
<211> LENGTH: 377
<212> TYPE: PRT
<213> ORGANISM: Artificial Sequence
<220> FEATURE:
<223> OTHER INFORMATION: an artificially synthesized sequence

<400> SEQUENCE: 87

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
            85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
```

```
            115                 120                 125
Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
                355                 360                 365

Lys Ser Leu Ser Leu Ser Pro Gly Lys
            370                 375

<210> SEQ ID NO 88
<211> LENGTH: 327
<212> TYPE: PRT
<213> ORGANISM: Artificial Sequence
<220> FEATURE:
<223> OTHER INFORMATION: an artificially synthesized sequence

<400> SEQUENCE: 88

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
```

```
            100                 105                 110
Glu Phe Leu Gly Gly Pro Ser Val Phe Leu Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 88
<212> TYPE: PRT
<213> ORGANISM: Artificial Sequence
<220> FEATURE:
<223> OTHER INFORMATION: an artificially synthesized sequence

<400> SEQUENCE: 89

Met Val Leu Ala Ser Ser Thr Thr Ser Ile His Thr Met Leu Leu Leu
1               5                   10                  15

Leu Leu Met Leu Ala Gln Pro Ala Met Ala Arg Ala Asp Pro Cys Ala
                20                  25                  30

Ala Arg Pro Cys Ala His Gly Gly Arg Cys Tyr Ala His Phe Ser Gly
                35                  40                  45

Leu Val Cys Ala Cys Ala Pro Gly Tyr Met Gly Ala Arg Cys Glu Phe
                50                  55                  60

Pro Val His Pro Asp Gly Ala Ser Ala Leu Pro Ala Ala Pro Pro Gly
65                  70                  75                  80

Leu Arg Pro Gly Asp Pro Gln Arg
                85

<210> SEQ ID NO 90
<211> LENGTH: 618
<212> TYPE: PRT
<213> ORGANISM: Artificial Sequence
<220> FEATURE:
<223> OTHER INFORMATION: an artificially synthesized sequence
```

<400> SEQUENCE: 90

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
            115                 120                 125

Glu Glu Leu Gly Asp Gln Ile Gly Gly Pro Ala Trp Ser Leu Leu Ala
            130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
            195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
            245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
            275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
                340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
            370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Gly Ala His Arg Cys Ser
```

-continued

```
                405                 410                 415
Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
        435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
            485                 490                 495

Leu Gly Leu Leu Val Ala Ala Gly Val Ala Gly Ala Ala Leu Leu Leu
            500                 505                 510

Val His Val Arg Arg Gly His Ser Gln Asp Ala Gly Ser Arg Leu
            515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
            595                 600                 605

Pro Tyr Pro Ser Ser Ile Leu Ser Val Lys
            610                 615

<210> SEQ ID NO 91
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 91

Gly Gly Gly Ser
1

<210> SEQ ID NO 92
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 92

Ser Gly Gly Gly
1

<210> SEQ ID NO 93
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 93

Gly Gly Gly Gly Ser
1               5
```

<210> SEQ ID NO 94
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 94

Ser Gly Gly Gly Gly
1               5

<210> SEQ ID NO 95
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 95

Gly Gly Gly Gly Gly Ser
1               5

<210> SEQ ID NO 96
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 96

Ser Gly Gly Gly Gly Gly
1               5

<210> SEQ ID NO 97
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 97

Gly Gly Gly Gly Gly Gly Ser
1               5

<210> SEQ ID NO 98
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 98

Ser Gly Gly Gly Gly Gly Gly
1               5

<210> SEQ ID NO 99
<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 99

Cys Pro Pro Cys Pro Ala Pro Glu Ala Ala Gly Gly Pro Ser Val Phe
1               5                   10                  15

```
Leu Phe Pro Pro Lys Pro Lys Asp Thr Leu Met Ile Ser Arg Thr Pro
             20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
 50                      55                  60

Lys Pro Arg Glu Glu Gln Tyr Ala Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Cys Arg Asp Glu Leu Thr Lys Asn Gln Val Ser Leu Trp Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Glu Gly Asn Val Phe Ser Cys Ser Val Leu His Glu Ala Leu His
        195                 200                 205

Ala His Tyr Thr Arg Lys Glu Leu Ser Leu Ser Pro
    210                 215                 220

<210> SEQ ID NO 100
<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 100

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
             20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
 50                      55                  60

Lys Pro Arg Glu Glu Gln Tyr Ala Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Cys Arg Asp Glu Leu Thr Lys Asn Gln Val Ser Leu Trp Cys Leu Val
        130                 135                 140

Lys Gly Phe Tyr Pro Ser Asp Ile Ala Val Glu Trp Glu Ser Asn Gly
145                 150                 155                 160
```

```
Gln Pro Glu Asn Asn Tyr Lys Thr Thr Pro Pro Val Leu Asp Ser Asp
                    165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Leu His Glu Ala Leu His
            195                 200                 205

Ala His Tyr Thr Arg Lys Glu Leu Ser Leu Ser Pro
        210                 215                 220

<210> SEQ ID NO 101
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 101

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Met His Trp Val Arg Gln Ala Pro Gly Lys Gly Leu Glu Trp Val
        35                  40                  45

Ala Gln Ile Lys Asp Lys Trp Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Ile His Tyr Ala Ser Ala Ser Thr Leu Leu Pro Ala
            100                 105                 110

Phe Gly Ile Asp Ala Trp Gly Gln Gly Thr Thr Val Thr Val Ser Ser
        115                 120                 125

<210> SEQ ID NO 102
<211> LENGTH: 212
<212> TYPE: PRT
<213> ORGANISM: Artificial Sequence
<220> FEATURE:
<223> OTHER INFORMATION: an artificially synthesized sequence

<400> SEQUENCE: 102

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Gly Ser Ala Asp Asp Ala Lys Lys Asp Ala Ala Lys Lys Asp Asp
            100                 105                 110

Ala Lys Lys Asp Asp Ala Lys Lys Asp Gly Ser Gln Ser Ile Lys Gly
        115                 120                 125
```

```
Asn His Leu Val Lys Val Tyr Asp Tyr Gln Glu Asp Gly Ser Val Leu
        130                 135                 140

Leu Thr Cys Asp Ala Glu Ala Lys Asn Ile Thr Trp Phe Lys Asp Gly
145                 150                 155                 160

Lys Met Ile Gly Phe Leu Thr Glu Asp Lys Lys Trp Asn Leu Gly
                165                 170                 175

Ser Asn Ala Lys Asp Pro Arg Gly Met Tyr Gln Cys Lys Gly Ser Gln
            180                 185                 190

Asn Lys Ser Lys Pro Leu Gln Val Tyr Tyr Arg Met Asp Tyr Lys Asp
        195                 200                 205

Asp Asp Asp Lys
    210

<210> SEQ ID NO 103
<211> LENGTH: 189
<212> TYPE: PRT
<213> ORGANISM: Artificial Sequence
<220> FEATURE:
<223> OTHER INFORMATION: an artificially synthesized sequence

<400> SEQUENCE: 103

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln His His His His His Gly Gly Gly Ser Gly Leu
                165                 170                 175

Asn Asp Ile Phe Glu Ala Gln Lys Ile Glu Trp His Glu
        180                 185

<210> SEQ ID NO 104
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 104

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Thr
```

```
                20                  25                  30
Trp Met His Trp Val Arg Gln Ala Pro Gly Lys Gly Leu Glu Trp Val
         35                  40                  45

Ala Gln Ile Lys Asp Lys Tyr Asn Ala Tyr Ala Tyr Tyr Ala Pro
     50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys His Tyr Ile His Tyr Ala Ser Ala Ser Thr Leu Leu Pro Ala
                100                 105                 110

Phe Gly Val Asp Ala Trp Gly Gln Gly Thr Thr Val Thr Val Ser Ser
                115                 120                 125

<210> SEQ ID NO 105
<211> LENGTH: 22
<212> TYPE: PRT
<213> ORGANISM: Artificial Sequence
<220> FEATURE:
<223> OTHER INFORMATION: an artificially synthesized sequence

<400> SEQUENCE: 105

Leu Gln Asp Pro Cys Ser Asn Cys Pro Ala Gly Thr Phe Cys Asp Asn
 1               5                  10                  15

Asn Arg Asn Gln Ile Cys
             20

<210> SEQ ID NO 106
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 106

Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Lys Phe Ser Asn Val
             20                  25                  30

Trp Phe His Trp Val Arg Gln Ala Pro Gly Lys Gly Leu Glu Trp Val
         35                  40                  45

Ala Gln Ile Lys Asp Tyr Tyr Asn Ala Tyr Ala Ala Tyr Tyr Ala Pro
     50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys His Tyr Val His Tyr Ala Ser Ala Ser Thr Leu Leu Pro Ala
                100                 105                 110

Phe Gly Val Asp Ala Trp Gly Gln Gly Thr Thr Val Thr Val Ser Ser
                115                 120                 125

<210> SEQ ID NO 107
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 107
```

Gln Val Gln Leu Val Glu Ser Gly Gly Leu Val Gln Pro Gly Arg
1               5                   10                  15

Ser Leu Arg Leu Ser Cys Ala Ala Ser Gly Phe Lys Phe Ser His Val
            20                  25                  30

Trp Phe His Trp Val Arg Gln Ala Pro Gly Lys Gly Leu Glu Trp Val
            35                  40                  45

Ala Gln Ile Lys Asp Lys Tyr Asn Ala Tyr Ala Ala Tyr Tyr Ala Pro
50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Phe Gly Val Asp Ala Trp Gly Gln Gly Thr Val Thr Val Ser Ser
            115                 120                 125

<210> SEQ ID NO 108
<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 108

Cys Pro Pro Cys Pro Ala Pro Glu Leu Arg Gly Gly Pro Lys Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
50                  55                  60

Lys Pro Arg Glu Glu Gln Tyr Ala Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
            115                 120                 125

Cys Arg Glu Glu Met Thr Lys Asn Gln Val Ser Leu Trp Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Glu Gly Asn Val Phe Ser Cys Ser Val Met His Glu Ala Leu His
            195                 200                 205

Asn His Tyr Thr Gln Lys Ser Leu Ser Leu Ser Pro
210                 215                 220

<210> SEQ ID NO 109

<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 109

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Ala Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Glu Gly Asn Val Phe Ser Cys Ser Val Leu His Glu Ala Leu His
        195                 200                 205

Ala His Tyr Thr Arg Lys Glu Leu Ser Leu Ser Pro
    210                 215                 220

<210> SEQ ID NO 110
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 110

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Lys Tyr Asn Ala Tyr Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala

```
                100                 105                 110

Glu Gly Val Asp Ala Trp Gly Gln Gly Thr Thr Val Thr Val Ser Ser
            115                 120                 125

<210> SEQ ID NO 111
<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 111

Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Ala Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125

Ser Arg Asp Glu Leu Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Leu His Glu Ala Leu His
        195                 200                 205

Ala His Tyr Thr Arg Lys Glu Leu Ser Leu Ser Pro
    210                 215                 220

<210> SEQ ID NO 112
<211> LENGTH: 220
<212> TYPE: PRT
<213> ORGANISM: Artificial Sequence
<220> FEATURE:
<223> OTHER INFORMATION: an artificially synthesized sequence

<400> SEQUENCE: 112

Cys Pro Pro Cys Pro Ala Pro Glu Leu Arg Gly Gly Pro Lys Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60
```

-continued

```
Lys Pro Arg Glu Glu Gln Tyr Ala Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Cys Thr Leu Pro Pro
        115                 120                 125

Ser Arg Glu Glu Met Thr Lys Asn Gln Val Ser Leu Ser Cys Ala Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Glu Gly Asn Val Phe Ser Cys Ser Val Met His Glu Ala Leu His
        195                 200                 205

Asn His Tyr Thr Gln Lys Ser Leu Ser Leu Ser Pro
    210                 215                 220
```

<210> SEQ ID NO 113
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 113

```
Gln Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Ser Asn Ala
             20                  25                  30

Trp Met His Trp Val Arg Gln Ala Pro Gly Lys Gly Leu Glu Trp Val
         35                  40                  45

Ala Gln Ile Lys Asp Lys Gly Asn Ala Tyr Ala Ala Tyr Tyr Ala Pro
     50                  55                  60

Ser Val Lys Gly Arg Phe Thr Ile Ser Arg Asp Asp Ser Lys Asn Ser
 65                  70                  75                  80

Ile Tyr Leu Gln Met Asn Ser Leu Lys Thr Glu Asp Thr Ala Val Tyr
                 85                  90                  95

Tyr Cys Arg Tyr Val His Tyr Ala Ser Ala Ser Thr Leu Leu Pro Ala
            100                 105                 110

Phe Gly Val Asp Ala Trp Gly Gln Gly Thr Thr Val Thr Val Ser Ser
        115                 120                 125
```

<210> SEQ ID NO 114
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 114

```
Asn Val Trp Met His
  1               5
```

<210> SEQ ID NO 115

<400> SEQUENCE: 115

000

<210> SEQ ID NO 116

<400> SEQUENCE: 116

000

<210> SEQ ID NO 117
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 117

Asn Thr Trp Met His
1               5

<210> SEQ ID NO 118

<400> SEQUENCE: 118

000

<210> SEQ ID NO 119
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 119

Asn Val Trp Phe His
1               5

<210> SEQ ID NO 120
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 120

His Val Trp Phe His
1               5

<210> SEQ ID NO 121

<400> SEQUENCE: 121

000

<210> SEQ ID NO 122

<400> SEQUENCE: 122

000

<210> SEQ ID NO 123
<211> LENGTH: 5
<212> TYPE: PRT
<213> ORGANISM: Artificial Sequence
<220> FEATURE:
<223> OTHER INFORMATION: an artificially synthesized sequence

```
<400> SEQUENCE: 123

Asn Val Trp Phe His
1               5

<210> SEQ ID NO 124

<400> SEQUENCE: 124

000

<210> SEQ ID NO 125

<400> SEQUENCE: 125

000

<210> SEQ ID NO 126
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 126

Asn Ala Trp Met His
1               5

<210> SEQ ID NO 127
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 127

Gln Ile Lys Asp Lys Trp Asn Ala Tyr Ala Ala Tyr Tyr Ala Pro Ser
1               5                   10                  15

Val Lys Gly

<210> SEQ ID NO 128

<400> SEQUENCE: 128

000

<210> SEQ ID NO 129

<400> SEQUENCE: 129

000

<210> SEQ ID NO 130
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 130

Gln Ile Lys Asp Lys Tyr Asn Ala Tyr Ala Ala Tyr Tyr Ala Pro Ser
1               5                   10                  15

Val Lys Gly

<210> SEQ ID NO 131
```

```
<400> SEQUENCE: 131

000

<210> SEQ ID NO 132
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 132

Gln Ile Lys Asp Tyr Tyr Asn Ala Tyr Ala Ala Tyr Tyr Ala Pro Ser
 1               5                  10                  15

Val Lys Gly

<210> SEQ ID NO 133
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 133

Gln Ile Lys Asp Lys Tyr Asn Ala Tyr Ala Ala Tyr Tyr Ala Pro Ser
 1               5                  10                  15

Val Lys Gly

<210> SEQ ID NO 134

<400> SEQUENCE: 134

000

<210> SEQ ID NO 135

<400> SEQUENCE: 135

000

<210> SEQ ID NO 136
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 136

Gln Ile Lys Asp Lys Tyr Asn Ala Tyr Ala Ala Tyr Tyr Ala Pro Ser
 1               5                  10                  15

Val Lys Gly

<210> SEQ ID NO 137

<400> SEQUENCE: 137

000

<210> SEQ ID NO 138

<400> SEQUENCE: 138

000
```

```
<210> SEQ ID NO 139
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 139

Gln Ile Lys Asp Lys Gly Asn Ala Tyr Ala Ala Tyr Tyr Ala Pro Ser
1               5                   10                  15

Val Lys Gly

<210> SEQ ID NO 140
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 140

Ile His Tyr Ala Ser Ala Ser Thr Leu Leu Pro Ala Phe Gly Ile Asp
1               5                   10                  15

Ala

<210> SEQ ID NO 141

<400> SEQUENCE: 141

000

<210> SEQ ID NO 142

<400> SEQUENCE: 142

000

<210> SEQ ID NO 143
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 143

Ile His Tyr Ala Ser Ala Ser Thr Leu Leu Pro Ala Phe Gly Val Asp
1               5                   10                  15

Ala

<210> SEQ ID NO 144

<400> SEQUENCE: 144

000

<210> SEQ ID NO 145
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 145

Val His Tyr Ala Ser Ala Ser Thr Leu Leu Pro Ala Phe Gly Val Asp
1               5                   10                  15

Ala
```

<210> SEQ ID NO 146
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 146

Val His Tyr Ala Ser Ala Ser Thr Leu Leu Pro Ala Phe Gly Val Asp
1               5                   10                  15

Ala

<210> SEQ ID NO 147

<400> SEQUENCE: 147

000

<210> SEQ ID NO 148

<400> SEQUENCE: 148

000

<210> SEQ ID NO 149
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 149

Val His Tyr Ala Ser Ala Ser Thr Leu Leu Pro Ala Glu Gly Val Asp
1               5                   10                  15

Ala

<210> SEQ ID NO 150

<400> SEQUENCE: 150

000

<210> SEQ ID NO 151

<400> SEQUENCE: 151

000

<210> SEQ ID NO 152
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 152

Val His Tyr Ala Ser Ala Ser Thr Leu Leu Pro Ala Phe Gly Val Asp
1               5                   10                  15

Ala

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 201

```
Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gly Gly Gly Gly
    210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Lys Phe Ser Asn
                245                 250                 255

Val Trp Phe His Trp Val Arg Gln Ala Pro Gly Lys Gly Leu Glu Trp
            260                 265                 270

Val Ala Gln Ile Lys Asp Tyr Tyr Asn Ala Tyr Ala Ala Tyr Tyr Ala
        275                 280                 285
```

Pro Ser Val Lys Gly Arg Phe Thr Ile Ser Arg Asp Ser Lys Asn
    290                 295                 300

Ser Ile Tyr Leu Gln Met Asn Ser Leu Lys Thr Glu Asp Thr Ala Val
305                 310                 315                 320

Tyr Tyr Cys His Tyr Val His Tyr Ala Ser Ala Ser Thr Leu Leu Pro
                325                 330                 335

Ala Glu Gly Val Asp Ala Trp Gly Gln Gly Thr Thr Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Glu Asp
370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Cys Ser Leu Gly Thr Gln
            420                 425                 430

Thr Tyr Ile Cys Asn Val Asn His Lys Pro Ser Asn Thr Lys Val Asp
        435                 440                 445

Glu Lys Val Glu Pro Lys Ser Cys Asp Lys Thr His Thr Cys Pro Pro
450                 455                 460

Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
                645                 650                 655

Asn Val Phe Ser Cys Ser Val Leu His Glu Ala Leu His Ala His Tyr
            660                 665                 670

Thr Arg Lys Glu Leu Ser Leu Ser Pro
        675                 680

<210> SEQ ID NO 202
<211> LENGTH: 678
<212> TYPE: PRT

<213> ORGANISM: Artificial Sequence
<220> FEATURE:
<223> OTHER INFORMATION: an artificially synthesized sequence

<400> SEQUENCE: 202

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys Ser Ser Ala Ser Thr
            100                 105                 110

Lys Gly Pro Ser Val Phe Pro Leu Ala Pro Ser Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
            180                 185                 190

Asn Val Asp His Lys Pro Ser Asn Thr Lys Val Asp Lys Arg Val Glu
        195                 200                 205

Pro Lys Ser Cys Gly Gly Gly Ser Gly Gly Gly Gly Ser Gln Val
    210                 215                 220

Gln Leu Val Glu Ser Gly Gly Gly Leu Val Gln Pro Gly Arg Ser Leu
225                 230                 235                 240

Arg Leu Ser Cys Ala Ala Ser Gly Phe Lys Phe Ser Asn Val Trp Phe
                245                 250                 255

His Trp Val Arg Gln Ala Pro Gly Lys Gly Leu Glu Trp Val Ala Gln
            260                 265                 270

Ile Lys Asp Tyr Tyr Asn Ala Tyr Ala Ala Tyr Ala Pro Ser Val
        275                 280                 285

Lys Gly Arg Phe Thr Ile Ser Arg Asp Asp Ser Lys Asn Ser Ile Tyr
    290                 295                 300

Leu Gln Met Asn Ser Leu Lys Thr Glu Asp Thr Ala Val Tyr Tyr Cys
305                 310                 315                 320

His Tyr Val His Tyr Ala Ser Ala Ser Thr Leu Leu Pro Ala Glu Gly
                325                 330                 335

Val Asp Ala Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Glu Asp Tyr Phe Pro
    370                 375                 380

Glu Pro Val Thr Val Ser Trp Asn Ser Gly Ala Leu Thr Ser Gly Val
```

```
385                 390                 395                 400
His Thr Phe Pro Ala Val Leu Gln Ser Ser Gly Leu Tyr Ser Leu Ser
            405                 410                 415
Ser Val Val Thr Val Pro Ser Cys Ser Leu Gly Thr Gln Thr Tyr Ile
            420                 425                 430
Cys Asn Val Asn His Lys Pro Ser Asn Thr Lys Val Asp Glu Lys Val
            435                 440                 445
Glu Pro Lys Ser Cys Asp Lys Thr His Thr Cys Pro Pro Cys Pro Ala
450                 455                 460
Pro Glu Ala Ala Gly Gly Pro Ser Val Phe Leu Phe Pro Pro Lys Pro
465                 470                 475                 480
Lys Asp Thr Leu Met Ile Ser Arg Thr Pro Glu Val Thr Cys Val Val
                485                 490                 495
Val Asp Val Ser His Glu Asp Pro Glu Val Lys Phe Asn Trp Tyr Val
                500                 505                 510
Asp Gly Val Glu Val His Asn Ala Lys Thr Lys Pro Arg Glu Glu Gln
            515                 520                 525
Tyr Ala Ser Thr Tyr Arg Val Val Ser Val Leu Thr Val Leu His Gln
530                 535                 540
Asp Trp Leu Asn Gly Lys Glu Tyr Lys Cys Lys Val Ser Asn Lys Ala
545                 550                 555                 560
Leu Pro Ala Pro Ile Glu Lys Thr Ile Ser Lys Ala Lys Gly Gln Pro
                565                 570                 575
Arg Glu Pro Gln Val Tyr Thr Leu Pro Pro Cys Arg Asp Glu Leu Thr
            580                 585                 590
Lys Asn Gln Val Ser Leu Trp Cys Leu Val Lys Gly Phe Tyr Pro Ser
            595                 600                 605
Asp Ile Ala Val Glu Trp Glu Ser Asn Gly Gln Pro Glu Asn Asn Tyr
610                 615                 620
Lys Thr Thr Pro Pro Val Leu Asp Ser Asp Gly Ser Phe Phe Leu Tyr
625                 630                 635                 640
Ser Lys Leu Thr Val Asp Lys Ser Arg Trp Gln Glu Gly Asn Val Phe
                645                 650                 655
Ser Cys Ser Val Leu His Glu Ala Leu His Ala His Tyr Thr Arg Lys
                660                 665                 670
Glu Leu Ser Leu Ser Pro
            675

<210> SEQ ID NO 203
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 203

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
```

```
                65                  70                  75                  80
        Glu Ala Glu Asp Ala Ala Thr Tyr Tyr Cys Gln Gly Tyr Tyr Ser Gly
                            85                  90                  95
        Tyr Ile Tyr Ala Phe Gly Gly Gly Thr Lys Val Glu Ile Lys Ser Ser
                           100                 105                 110
        Ala Ser Thr Lys Gly Pro Ser Val Phe Pro Leu Ala Pro Ser Ser Arg
                           115                 120                 125
        Ser Thr Ser Glu Ser Thr Ala Ala Leu Gly Cys Leu Val Lys Asp Tyr
                           130                 135                 140
        Phe Pro Glu Pro Val Thr Val Ser Trp Asn Ser Gly Ala Leu Thr Ser
        145                 150                 155                 160
        Gly Val His Thr Phe Pro Ala Val Leu Gln Ser Ser Gly Leu Tyr Ser
                           165                 170                 175
        Leu Ser Ser Val Val Thr Val Pro Ser Ser Ser Leu Gly Thr Lys Thr
                           180                 185                 190
        Tyr Thr Cys Asn Val Asp His Lys Pro Ser Asn Thr Lys Val Asp Lys
                           195                 200                 205
        Arg Val Glu Pro Lys Ser Cys Gly Gly Gly Ser Gly Gly Gly Gly
                           210                 215                 220
        Ser Gln Val Gln Leu Val Glu Ser Gly Gly Gly Leu Val Gln Pro Gly
        225                 230                 235                 240
        Arg Ser Leu Arg Leu Ser Cys Ala Ala Ser Gly Phe Lys Phe Ser Asn
                           245                 250                 255
        Val Trp Phe His Trp Val Arg Gln Ala Pro Gly Lys Gly Leu Glu Trp
                           260                 265                 270
        Val Ala Gln Ile Lys Asp Tyr Tyr Asn Ala Tyr Ala Ala Tyr Tyr Ala
                           275                 280                 285
        Pro Ser Val Lys Gly Arg Phe Thr Ile Ser Arg Asp Asp Ser Lys Asn
                           290                 295                 300
        Ser Ile Tyr Leu Gln Met Asn Ser Leu Lys Thr Glu Asp Thr Ala Val
        305                 310                 315                 320
        Tyr Tyr Cys His Tyr Val His Tyr Ala Ser Ala Ser Thr Leu Leu Pro
                           325                 330                 335
        Ala Glu Gly Val Asp Ala Trp Gly Gln Gly Thr Thr Val Thr Val Ser
                           340                 345                 350
        Ser Ala Ser Thr Lys Gly Pro Ser Val Phe Pro Leu Ala Pro Ser Ser
                           355                 360                 365
        Lys Ser Thr Ser Gly Gly Thr Ala Ala Leu Gly Cys Leu Val Glu Asp
                           370                 375                 380
        Tyr Phe Pro Glu Pro Val Thr Val Ser Trp Asn Ser Gly Ala Leu Thr
        385                 390                 395                 400
        Ser Gly Val His Thr Phe Pro Ala Val Leu Gln Ser Ser Gly Leu Tyr
                           405                 410                 415
        Ser Leu Ser Ser Val Val Thr Val Pro Ser Cys Ser Leu Gly Thr Gln
                           420                 425                 430
        Thr Tyr Ile Cys Asn Val Asn His Lys Pro Ser Asn Thr Lys Val Asp
                           435                 440                 445
        Glu Lys Val Glu Pro Lys Ser Cys Asp Lys Thr His Thr Cys Pro Pro
                           450                 455                 460
        Cys Pro Ala Pro Glu Ala Ala Gly Gly Pro Ser Val Phe Leu Phe Pro
        465                 470                 475                 480
        Pro Lys Pro Lys Asp Thr Leu Met Ile Ser Arg Thr Pro Glu Val Thr
                           485                 490                 495
```

```
Cys Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
        530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Leu His Glu Ala Leu His Ala His Tyr
            660                 665                 670

Thr Arg Lys Glu Leu Ser Leu Ser Pro
        675                 680

<210> SEQ ID NO 204
<211> LENGTH: 676
<212> TYPE: PRT
<213> ORGANISM: Artificial Sequence
<220> FEATURE:
<223> OTHER INFORMATION: an artificially synthesized sequence

<400> SEQUENCE: 204

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175
```

```
Leu Ser Ser Val Val Thr Val Pro Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gln Val Gln Leu
210                 215                 220

Val Glu Ser Gly Gly Gly Leu Val Gln Pro Gly Arg Ser Leu Arg Leu
225                 230                 235                 240

Ser Cys Ala Ala Ser Gly Phe Lys Phe Ser Asn Val Trp Phe His Trp
                245                 250                 255

Val Arg Gln Ala Pro Gly Lys Gly Leu Glu Trp Val Ala Gln Ile Lys
            260                 265                 270

Asp Tyr Tyr Asn Ala Tyr Ala Ala Tyr Ala Pro Ser Val Lys Gly
        275                 280                 285

Arg Phe Thr Ile Ser Arg Asp Asp Ser Lys Asn Ser Ile Tyr Leu Gln
290                 295                 300

Met Asn Ser Leu Lys Thr Glu Asp Thr Ala Val Tyr Tyr Cys His Tyr
305                 310                 315                 320

Val His Tyr Ala Ser Ala Ser Thr Leu Leu Pro Ala Glu Gly Val Asp
            325                 330                 335

Ala Trp Gly Gln Gly Thr Thr Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Glu Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
            405                 410                 415

Val Thr Val Pro Ser Cys Ser Leu Gly Thr Gln Thr Tyr Ile Cys Asn
            420                 425                 430

Val Asn His Lys Pro Ser Asn Thr Lys Val Asp Glu Lys Val Glu Pro
        435                 440                 445

Lys Ser Cys Asp Lys Thr His Thr Cys Pro Pro Cys Pro Ala Pro Glu
450                 455                 460

Ala Ala Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
        500                 505                 510

Val Glu Val His Asn Ala Lys Thr Lys Pro Arg Glu Glu Gln Tyr Ala
        515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
            565                 570                 575

Pro Gln Val Tyr Thr Leu Pro Pro Cys Arg Asp Glu Leu Thr Lys Asn
        580                 585                 590
```

```
Gln Val Ser Leu Trp Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Leu His Glu Ala Leu His Ala His Tyr Thr Arg Lys Glu Leu
            660                 665                 670

Ser Leu Ser Pro
            675

<210> SEQ ID NO 205
<211> LENGTH: 671
<212> TYPE: PRT
<213> ORGANISM: Artificial Sequence
<220> FEATURE:
<223> OTHER INFORMATION: an artificially synthesized sequence

<400> SEQUENCE: 205

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gln Val Gln Leu Val Glu Ser Gly Gly
    210                 215                 220

Gly Leu Val Gln Pro Gly Arg Ser Leu Arg Leu Ser Cys Ala Ala Ser
225                 230                 235                 240

Gly Phe Lys Phe Ser Asn Val Trp Phe His Trp Val Arg Gln Ala Pro
                245                 250                 255

Gly Lys Gly Leu Glu Trp Val Ala Gln Ile Lys Asp Tyr Tyr Asn Ala
            260                 265                 270
```

```
Tyr Ala Ala Tyr Tyr Ala Pro Ser Val Lys Gly Arg Phe Thr Ile Ser
            275                 280                 285

Arg Asp Asp Ser Lys Asn Ser Ile Tyr Leu Gln Met Asn Ser Leu Lys
290                 295                 300

Thr Glu Asp Thr Ala Val Tyr Tyr Cys His Tyr Val His Tyr Ala Ser
305                 310                 315                 320

Ala Ser Thr Leu Leu Pro Ala Glu Gly Val Asp Ala Trp Gly Gln Gly
                325                 330                 335

Thr Thr Val Thr Val Ser Ser Ala Ser Thr Lys Gly Pro Ser Val Phe
            340                 345                 350

Pro Leu Ala Pro Ser Ser Lys Ser Thr Ser Gly Gly Thr Ala Ala Leu
            355                 360                 365

Gly Cys Leu Val Glu Asp Tyr Phe Pro Glu Pro Val Thr Val Ser Trp
370                 375                 380

Asn Ser Gly Ala Leu Thr Ser Gly Val His Thr Phe Pro Ala Val Leu
385                 390                 395                 400

Gln Ser Ser Gly Leu Tyr Ser Leu Ser Ser Val Val Thr Val Pro Ser
                405                 410                 415

Cys Ser Leu Gly Thr Gln Thr Tyr Ile Cys Asn Val Asn His Lys Pro
            420                 425                 430

Ser Asn Thr Lys Val Asp Glu Lys Val Glu Pro Lys Ser Cys Asp Lys
            435                 440                 445

Thr His Thr Cys Pro Pro Cys Pro Ala Pro Glu Ala Ala Gly Gly Pro
450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Ala Ser Thr Tyr Arg Val
            515                 520                 525

Val Ser Val Leu Thr Val Leu His Gln Asp Trp Leu Asn Gly Lys Glu
530                 535                 540

Tyr Lys Cys Lys Val Ser Asn Lys Ala Leu Pro Ala Pro Ile Glu Lys
545                 550                 555                 560

Thr Ile Ser Lys Ala Lys Gly Gln Pro Arg Glu Pro Gln Val Tyr Thr
                565                 570                 575

Leu Pro Pro Cys Arg Asp Glu Leu Thr Lys Asn Gln Val Ser Leu Trp
            580                 585                 590

Cys Leu Val Lys Gly Phe Tyr Pro Ser Asp Ile Ala Val Glu Trp Glu
            595                 600                 605

Ser Asn Gly Gln Pro Glu Asn Asn Tyr Lys Thr Thr Pro Pro Val Leu
610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Leu His Glu
                645                 650                 655

Ala Leu His Ala His Tyr Thr Arg Lys Glu Leu Ser Leu Ser Pro
            660                 665                 670

<210> SEQ ID NO 206
<211> LENGTH: 226
<212> TYPE: PRT
```

<213> ORGANISM: Artificial Sequence
<220> FEATURE:
<223> OTHER INFORMATION: an artificially synthesized sequence

<400> SEQUENCE: 206

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
50                  55                  60

Ala Lys Gly Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser Ala Ser Val Ala Ala Pro Ser Val Phe
        115                 120                 125

Ile Phe Pro Pro Ser Asp Glu Gln Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225

<210> SEQ ID NO 207
<211> LENGTH: 223
<212> TYPE: PRT
<213> ORGANISM: Artificial Sequence
<220> FEATURE:
<223> OTHER INFORMATION: an artificially synthesized sequence

<400> SEQUENCE: 207

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

```
Ala Leu Tyr Gly Asn Tyr Phe Asp Tyr Trp Gly Gln Gly Thr Thr Leu
                100                 105                 110

Thr Val Ser Ser Ala Ser Val Ala Ala Pro Ser Val Phe Ile Phe Pro
            115                 120                 125

Pro Ser Asp Glu Gln Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220
```

<210> SEQ ID NO 208
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 208

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Glu Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
        195                 200                 205

Tyr Ile Cys Asn Val Asn His Lys Pro Ser Asn Thr Lys Val Asp Glu
    210                 215                 220

Lys Val Glu Pro Lys Ser Cys Asp Lys Thr His Thr Cys Pro Pro Cys
225                 230                 235                 240
```

```
Pro Ala Pro Glu Ala Ala Gly Gly Pro Ser Val Phe Leu Phe Pro Pro
            245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Cys Thr Leu Pro Pro Ser Arg Asp Glu
            355                 360                 365

Leu Thr Lys Asn Gln Val Ser Leu Ser Cys Ala Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Val Ser Lys Leu Thr Val Asp Lys Ser Arg Trp Gln Glu Gly Asn
        420                 425                 430

Val Phe Ser Cys Ser Val Leu His Glu Ala Leu His Ala His Tyr Thr
            435                 440                 445

Arg Lys Glu Leu Ser Leu Ser Pro
    450                 455

<210> SEQ ID NO 209
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 209

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
            85                  90                  95

Tyr Cys His Tyr Val His Tyr Ala Ser Ala Ser Thr Leu Leu Pro Ala
        100                 105                 110

Glu Gly Val Asp Ala Trp Gly Gln Gly Thr Thr Val Thr Val Ser Ser
    115                 120                 125

Ala Ser Thr Lys Gly Pro Ser Val Phe Pro Leu Ala Pro Ser Ser Lys
130                 135                 140
```

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
            195                 200                 205

Tyr Ile Cys Asn Val Asn His Lys Pro Ser Asn Thr Lys Val Asp Glu
            210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
            245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
            355                 360                 365

Leu Thr Lys Asn Gln Val Ser Leu Ser Cys Ala Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Val Ser Lys Leu Thr Val Asp Lys Ser Arg Trp Gln Gln Gly Asn
            420                 425                 430

Val Phe Ser Cys Ser Val Leu His Glu Ala Leu His Ala His Tyr Thr
            435                 440                 445

Arg Lys Glu Leu Ser Leu Ser Pro
450                 455

<210> SEQ ID NO 210
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 210

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
            35                  40                  45

```
Ala Gln Ile Lys Asp Tyr Tyr Asn Ala Tyr Ala Gly Tyr Tyr His Pro
 50                  55                  60
Ser Val Lys Gly Arg Phe Thr Ile Ser Arg Asp Asp Ser Lys Asn Ser
 65                  70                  75                  80
Ile Tyr Leu Gln Met Asn Ser Leu Lys Thr Glu Asp Thr Ala Val Tyr
                     85                  90                  95
Tyr Cys His Tyr Val His Tyr Ala Ala Ala Ser Gln Leu Leu Pro Ala
                    100                 105                 110
Glu Gly Val Asp Ala Trp Gly Gln Gly Thr Thr Val Thr Val Ser Ser
                115                 120                 125
Ala Ser Thr Lys Gly Pro Ser Val Phe Pro Leu Ala Pro Ser Ser Lys
            130                 135                 140
Ser Thr Ser Gly Gly Thr Ala Ala Leu Gly Cys Leu Val Glu Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
                180                 185                 190
Leu Ser Ser Val Val Thr Val Pro Ser Cys Ser Leu Gly Thr Gln Thr
            195                 200                 205
Tyr Ile Cys Asn Val Asn His Lys Pro Ser Asn Thr Lys Val Asp Glu
        210                 215                 220
Lys Val Glu Pro Lys Ser Cys Asp Lys Thr His Thr Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
                260                 265                 270
Val Val Val Asp Val Ser His Glu Asp Pro Glu Val Lys Phe Asn Trp
            275                 280                 285
Tyr Val Asp Gly Val Glu Val His Asn Ala Lys Thr Lys Pro Arg Glu
        290                 295                 300
Glu Gln Tyr Ala Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
                340                 345                 350
Gln Pro Arg Glu Pro Gln Val Cys Thr Leu Pro Pro Ser Arg Asp Glu
            355                 360                 365
Leu Thr Lys Asn Gln Val Ser Leu Ser Cys Ala Val Lys Gly Phe Tyr
        370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Val Ser Lys Leu Thr Val Asp Lys Ser Arg Trp Gln Glu Gly Asn
            420                 425                 430
Val Phe Ser Cys Ser Val Leu His Glu Ala Leu His Ala His Tyr Thr
        435                 440                 445
Arg Lys Glu Leu Ser Leu Ser Pro
450                 455
```

<210> SEQ ID NO 211
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 211

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Gly Tyr Tyr His Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ala Ala Ser Gln Leu Leu Pro Ala
            100                 105                 110

Glu Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
        195                 200                 205

Tyr Ile Cys Asn Val Asn His Lys Pro Ser Asn Thr Lys Val Asp Glu
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Cys Thr Leu Pro Pro Ser Arg Asp Glu
        355                 360                 365

Leu Thr Lys Asn Gln Val Ser Leu Ser Cys Ala Val Lys Gly Phe Tyr
```

```
                370                 375                 380
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
                420                 425                 430

Val Phe Ser Cys Ser Val Leu His Glu Ala Leu His Ala His Tyr Thr
                435                 440                 445

Arg Lys Glu Leu Ser Leu Ser Pro
    450                 455

<210> SEQ ID NO 212
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 212

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
                20                  25                  30

Trp Phe His Trp Val Arg Gln Ala Pro Gly Lys Gly Leu Glu Trp Val
            35                  40                  45

Ala Gln Ile Lys Asp Tyr Tyr Asn Ala Tyr Ala Ala Tyr Tyr Ala Pro
        50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Glu Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
        195                 200                 205

Tyr Ile Cys Asn Val Asn His Lys Pro Ser Asn Thr Lys Val Asp Glu
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
```

```
            275                 280                 285
Tyr Val Asp Gly Val Glu Val His Asn Ala Lys Thr Lys Pro Arg Glu
        290                 295                 300
Glu Gln Tyr Ala Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
                340                 345                 350
Gln Pro Arg Glu Pro Gln Val Cys Thr Leu Pro Pro Ser Arg Asp Glu
                355                 360                 365
Leu Thr Lys Asn Gln Val Ser Leu Ser Cys Ala Val Lys Gly Phe Tyr
        370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Val Ser Lys Leu Thr Val Asp Lys Ser Arg Trp Gln Gln Gly Asn
                420                 425                 430
Val Phe Ser Cys Ser Val Leu His Glu Ala Leu His Ala His Tyr Thr
                435                 440                 445
Arg Lys Glu Leu Ser Leu Ser Pro
        450                 455

<210> SEQ ID NO 213
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 213

Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Val Phe Ser Asn Val
                20                  25                  30
Trp Phe His Trp Val Arg Gln Ala Pro Gly Lys Gly Leu Glu Trp Val
            35                  40                  45
Ala Gln Ile Lys Asp Tyr Tyr Asn Ala Tyr Ala Tyr Tyr Ala Pro
        50                  55                  60
Ser Val Lys Gly Arg Phe Thr Ile Ser Arg Asp Asp Ser Lys Asn Ser
65              70                  75                  80
Ile Tyr Leu Gln Met Asn Ser Leu Lys Thr Glu Asp Thr Ala Val Tyr
                85                  90                  95
Tyr Cys His Tyr Val His Tyr Ala Ser Ala Ser Thr Leu Leu Pro Ala
                100                 105                 110
Glu Gly Val Asp Ala Trp Gly Gln Gly Thr Thr Val Thr Val Ser Ser
            115                 120                 125
Ala Ser Thr Lys Gly Pro Ser Val Phe Pro Leu Ala Pro Ser Ser Lys
        130                 135                 140
Ser Thr Ser Gly Gly Thr Ala Ala Leu Gly Cys Leu Val Glu Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
```

```
            180                 185                 190
Leu Ser Ser Val Val Thr Val Pro Cys Ser Leu Gly Thr Gln Thr
        195                 200                 205
Tyr Ile Cys Asn Val Asn His Lys Pro Ser Asn Thr Lys Val Asp Glu
    210                 215                 220
Lys Val Glu Pro Lys Ser Cys Asp Lys Thr His Thr Cys Pro Pro Cys
225                 230                 235                 240
Pro Ala Pro Glu Ala Ala Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Ala Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Cys Thr Leu Pro Pro Ser Arg Asp Glu
        355                 360                 365
Leu Thr Lys Asn Gln Val Ser Leu Ser Cys Ala Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Val Ser Lys Leu Thr Val Asp Lys Ser Arg Trp Gln Gln Gly Asn
            420                 425                 430
Val Phe Ser Cys Ser Val Leu His Glu Ala Leu His Ala His Tyr Thr
        435                 440                 445
Arg Lys Glu Leu Ser Leu Ser Pro
    450                 455

<210> SEQ ID NO 214
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 214

Asp Ile Val Met Thr Gln Ser Pro Leu Ser Leu Pro Val Thr Pro Gly
1               5                   10                  15
Glu Pro Ala Ser Ile Ser Cys Gln Pro Ser Gln Glu Val His Met
            20                  25                  30
Asn Arg Asn Thr Tyr Leu His Trp Tyr Gln Gln Lys Pro Gly Gln Ala
        35                  40                  45
Pro Arg Leu Leu Ile Tyr Lys Val Ser Asn Arg Phe Pro Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Gly
```

```
                    85                  90                  95
Thr Ser His Pro Phe Thr Phe Gly Gln Gly Thr Lys Leu Glu Ile Lys
                100                 105                 110
Arg Thr Val Ala Ala Pro Ser Val Phe Ile Phe Pro Pro Ser Asp Arg
                115                 120                 125
Lys Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
                210                 215

<210> SEQ ID NO 215
<211> LENGTH: 219
<212> TYPE: PRT
<213> ORGANISM: Artificial Sequence
<220> FEATURE:
<223> OTHER INFORMATION: an artificially synthesized sequence

<400> SEQUENCE: 215

Asp Ile Val Met Thr Gln Ser Pro Leu Ser Leu Pro Val Thr Pro Gly
1               5                   10                  15
Glu Pro Ala Ser Ile Ser Cys Gln Pro Ser Gln Glu Val Val His Met
                20                  25                  30
Asn Arg Asn Thr Tyr Leu His Trp Tyr Gln Gln Lys Pro Gly Gln Ala
            35                  40                  45
Pro Arg Leu Leu Ile Tyr Lys Val Ser Asn Val Phe Pro Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Gly
                85                  90                  95
Thr His His Pro Phe Thr Phe Gly Gln Gly Thr Lys Leu Glu Ile Lys
                100                 105                 110
Arg Thr Val Ala Ala Pro Ser Val Phe Ile Phe Pro Pro Ser Asp Arg
                115                 120                 125
Lys Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
                210                 215
```

<210> SEQ ID NO 216
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 216

```
Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Gly Ser Gly Gly Gly Gly
    210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Lys Phe Ser Asn
                245                 250                 255

Val Trp Phe His Trp Val Arg Gln Ala Pro Gly Lys Gly Leu Glu Trp
            260                 265                 270

Val Ala Gln Ile Lys Asp Tyr Tyr Asn Ala Tyr Ala Ala Tyr Tyr Ala
        275                 280                 285

Pro Ser Val Lys Gly Arg Phe Thr Ile Ser Arg Asp Asp Ser Lys Asn
    290                 295                 300

Ser Ile Tyr Leu Gln Met Asn Ser Leu Lys Thr Glu Asp Thr Ala Val
305                 310                 315                 320

Tyr Tyr Cys His Tyr Val His Tyr Ala Ser Ala Ser Thr Leu Leu Pro
                325                 330                 335

Ala Glu Gly Val Asp Ala Trp Gly Gln Gly Thr Thr Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Glu Asp
```

```
                370                 375                 380
Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Cys Ser Leu Gly Thr Gln
            420                 425                 430

Thr Tyr Ile Cys Asn Val Asn His Lys Pro Ser Asn Thr Lys Val Asp
        435                 440                 445

Glu Lys Val Glu Pro Lys Ser Cys Asp Lys Thr His Thr Cys Pro Pro
    450                 455                 460

Cys Pro Ala Pro Glu Leu Arg Gly Gly Pro Lys Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Glu
            580                 585                 590

Glu Met Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro
        675                 680

<210> SEQ ID NO 217
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 217

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
```

```
            50                  55                  60
Ser Gly Ser Gly Ser Gly Thr Asp Phe Thr Leu Thr Ile Asn Ser Leu
65                      70                  75                  80
Glu Ala Glu Asp Ala Ala Thr Tyr Tyr Cys Gln Gly Tyr Tyr Ser Gly
                    85                  90                  95
Tyr Ile Tyr Ala Phe Gly Gly Gly Thr Lys Val Glu Ile Lys Ser Ser
                100                 105                 110
Ala Ser Thr Lys Gly Pro Ser Val Phe Pro Leu Ala Pro Ser Ser Arg
            115                 120                 125
Ser Thr Ser Glu Ser Thr Ala Ala Leu Gly Cys Leu Val Lys Asp Tyr
        130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Lys Thr
                180                 185                 190
Tyr Thr Cys Asn Val Asp His Lys Pro Ser Asn Thr Lys Val Asp Lys
            195                 200                 205
Arg Val Glu Pro Lys Ser Cys Gly Gly Gly Ser Gly Gly Gly Gly
        210                 215                 220
Ser Gln Val Gln Leu Val Glu Ser Gly Gly Leu Val Gln Pro Gly
225                 230                 235                 240
Arg Ser Leu Arg Leu Ser Cys Ala Ala Ser Gly Phe Lys Phe Ser Asn
                245                 250                 255
Val Trp Phe His Trp Val Arg Gln Ala Pro Gly Lys Gly Leu Glu Trp
                260                 265                 270
Val Ala Gln Ile Lys Asp Tyr Tyr Asn Ala Tyr Ala Gly Tyr Tyr His
            275                 280                 285
Pro Ser Val Lys Gly Arg Phe Thr Ile Ser Arg Asp Asp Ser Lys Asn
        290                 295                 300
Ser Ile Tyr Leu Gln Met Asn Ser Leu Lys Thr Glu Asp Thr Ala Val
305                 310                 315                 320
Tyr Tyr Cys His Tyr Val His Tyr Ala Ala Ala Ser Gln Leu Leu Pro
                325                 330                 335
Ala Glu Gly Val Asp Ala Trp Gly Gln Gly Thr Thr Val Thr Val Ser
            340                 345                 350
Ser Ala Ser Thr Lys Gly Pro Ser Val Phe Pro Leu Ala Pro Ser Ser
        355                 360                 365
Lys Ser Thr Ser Gly Gly Thr Ala Ala Leu Gly Cys Leu Val Glu Asp
    370                 375                 380
Tyr Phe Pro Glu Pro Val Thr Val Ser Trp Asn Ser Gly Ala Leu Thr
385                 390                 395                 400
Ser Gly Val His Thr Phe Pro Ala Val Leu Gln Ser Ser Gly Leu Tyr
                405                 410                 415
Ser Leu Ser Ser Val Val Thr Val Pro Ser Cys Ser Leu Gly Thr Gln
                420                 425                 430
Thr Tyr Ile Cys Asn Val Asn His Lys Pro Ser Asn Thr Lys Val Asp
            435                 440                 445
Glu Lys Val Glu Pro Lys Ser Cys Asp Lys Thr His Thr Cys Pro Pro
        450                 455                 460
Cys Pro Ala Pro Glu Ala Ala Gly Gly Pro Ser Val Phe Leu Phe Pro
465                 470                 475                 480
```

```
Pro Lys Pro Lys Asp Thr Leu Met Ile Ser Arg Thr Pro Glu Val Thr
            485                 490                 495

Cys Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
            515                 520                 525

Glu Glu Gln Tyr Ala Ser Thr Tyr Arg Val Val Ser Val Leu Thr Val
            530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
            565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
            595                 600                 605

Tyr Pro Ser Asp Ile Ala Val Glu Trp Glu Ser Asn Gly Gln Pro Glu
            610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
            645                 650                 655

Asn Val Phe Ser Cys Ser Val Leu His Glu Ala Leu His Ala His Tyr
            660                 665                 670

Thr Arg Lys Glu Leu Ser Leu Ser Pro
            675                 680

<210> SEQ ID NO 218
<211> LENGTH: 678
<212> TYPE: PRT
<213> ORGANISM: Artificial Sequence
<220> FEATURE:
<223> OTHER INFORMATION: an artificially synthesized sequence

<400> SEQUENCE: 218

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
            85                  90                  95

Thr Phe Gly Gly Gly Thr Lys Leu Glu Val Lys Ser Ser Ala Ser Thr
            100                 105                 110

Lys Gly Pro Ser Val Phe Pro Leu Ala Pro Ser Ser Arg Ser Thr Ser
            115                 120                 125

Glu Ser Thr Ala Ala Leu Gly Cys Leu Val Lys Asp Tyr Phe Pro Glu
            130                 135                 140

Pro Val Thr Val Ser Trp Asn Ser Gly Ala Leu Thr Ser Gly Val His
145                 150                 155                 160
```

```
Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
                180                 185                 190

Asn Val Asp His Lys Pro Ser Asn Thr Lys Val Asp Lys Arg Val Glu
                195                 200                 205

Pro Lys Ser Cys Gly Gly Gly Ser Gly Gly Gly Ser Gln Val
            210                 215                 220

Gln Leu Val Glu Ser Gly Gly Leu Val Gln Pro Gly Arg Ser Leu
225                 230                 235                 240

Arg Leu Ser Cys Ala Ala Ser Gly Phe Lys Phe Ser Asn Val Trp Phe
                245                 250                 255

His Trp Val Arg Gln Ala Pro Gly Lys Gly Leu Glu Trp Val Ala Gln
                260                 265                 270

Ile Lys Asp Tyr Tyr Asn Ala Tyr Ala Gly Tyr Tyr His Pro Ser Val
                275                 280                 285

Lys Gly Arg Phe Thr Ile Ser Arg Asp Asp Ser Lys Asn Ser Ile Tyr
            290                 295                 300

Leu Gln Met Asn Ser Leu Lys Thr Glu Asp Thr Ala Val Tyr Tyr Cys
305                 310                 315                 320

His Tyr Val His Tyr Ala Ala Ala Ser Gln Leu Leu Pro Ala Glu Gly
                325                 330                 335

Val Asp Ala Trp Gly Gln Gly Thr Thr Val Thr Val Ser Ser Ala Ser
                340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Glu Asp Tyr Phe Pro
        370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Cys Ser Leu Gly Thr Gln Thr Tyr Ile
                420                 425                 430

Cys Asn Val Asn His Lys Pro Ser Asn Thr Lys Val Asp Glu Lys Val
            435                 440                 445

Glu Pro Lys Ser Cys Asp Lys Thr His Thr Cys Pro Pro Cys Pro Ala
        450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Ala Ser Thr Tyr Arg Val Val Ser Val Leu Thr Val Leu His Gln
        530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575
```

```
Arg Glu Pro Gln Val Tyr Thr Leu Pro Pro Cys Arg Asp Glu Leu Thr
                580                 585                 590

Lys Asn Gln Val Ser Leu Trp Cys Leu Val Lys Gly Phe Tyr Pro Ser
        595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Glu Gly Asn Val Phe
                645                 650                 655

Ser Cys Ser Val Leu His Glu Ala Leu His Ala His Tyr Thr Arg Lys
            660                 665                 670

Glu Leu Ser Leu Ser Pro
            675

<210> SEQ ID NO 219
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 219

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gly Gly Gly Gly
    210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Lys Phe Ser Asn
                245                 250                 255
```

-continued

```
Val Trp Phe His Trp Val Arg Gln Ala Pro Gly Lys Gly Leu Glu Trp
                260                 265                 270
Val Ala Gln Ile Lys Asp Tyr Tyr Asn Ala Tyr Ala Gly Tyr Tyr His
                275                 280                 285
Pro Ser Val Lys Gly Arg Phe Thr Ile Ser Arg Asp Asp Ser Lys Asn
290                 295                 300
Ser Ile Tyr Leu Gln Met Asn Ser Leu Lys Thr Glu Asp Thr Ala Val
305                 310                 315                 320
Tyr Tyr Cys His Tyr Val His Tyr Ala Ala Ser Gln Leu Leu Pro
                325                 330                 335
Ala Glu Gly Val Asp Ala Trp Gly Gln Gly Thr Thr Val Thr Val Ser
                340                 345                 350
Ser Ala Ser Thr Lys Gly Pro Ser Val Phe Pro Leu Ala Pro Ser Ser
                355                 360                 365
Lys Ser Thr Ser Gly Gly Thr Ala Ala Leu Gly Cys Leu Val Glu Asp
                370                 375                 380
Tyr Phe Pro Glu Pro Val Thr Val Ser Trp Asn Ser Gly Ala Leu Thr
385                 390                 395                 400
Ser Gly Val His Thr Phe Pro Ala Val Leu Gln Ser Ser Gly Leu Tyr
                405                 410                 415
Ser Leu Ser Ser Val Val Thr Val Pro Ser Cys Ser Leu Gly Thr Gln
                420                 425                 430
Thr Tyr Ile Cys Asn Val Asn His Lys Pro Ser Asn Thr Lys Val Asp
                435                 440                 445
Glu Lys Val Glu Pro Lys Ser Cys Asp Lys Thr His Thr Cys Pro Pro
                450                 455                 460
Cys Pro Ala Pro Glu Ala Ala Gly Gly Pro Ser Val Phe Leu Phe Pro
465                 470                 475                 480
Pro Lys Pro Lys Asp Thr Leu Met Ile Ser Arg Thr Pro Glu Val Thr
                485                 490                 495
Cys Val Val Val Asp Val Ser His Glu Asp Pro Glu Val Lys Phe Asn
                500                 505                 510
Trp Tyr Val Asp Gly Val Glu Val His Asn Ala Lys Thr Lys Pro Arg
                515                 520                 525
Glu Glu Gln Tyr Ala Ser Thr Tyr Arg Val Val Ser Val Leu Thr Val
                530                 535                 540
Leu His Gln Asp Trp Leu Asn Gly Lys Glu Tyr Lys Cys Lys Val Ser
545                 550                 555                 560
Asn Lys Ala Leu Pro Ala Pro Ile Glu Lys Thr Ile Ser Lys Ala Lys
                565                 570                 575
Gly Gln Pro Arg Glu Pro Gln Val Tyr Thr Leu Pro Pro Cys Arg Asp
                580                 585                 590
Glu Leu Thr Lys Asn Gln Val Ser Leu Trp Cys Leu Val Lys Gly Phe
                595                 600                 605
Tyr Pro Ser Asp Ile Ala Val Glu Trp Glu Ser Asn Gly Gln Pro Glu
                610                 615                 620
Asn Asn Tyr Lys Thr Thr Pro Pro Val Leu Asp Ser Asp Gly Ser Phe
625                 630                 635                 640
Phe Leu Tyr Ser Lys Leu Thr Val Asp Lys Ser Arg Trp Gln Gln Gly
                645                 650                 655
Asn Val Phe Ser Cys Ser Val Leu His Glu Ala Leu His Ala His Tyr
                660                 665                 670
Thr Arg Lys Glu Leu Ser Leu Ser Pro
```

```
                    675                 680

<210> SEQ ID NO 220
<211> LENGTH: 676
<212> TYPE: PRT
<213> ORGANISM: Artificial Sequence
<220> FEATURE:
<223> OTHER INFORMATION: an artificially synthesized sequence

<400> SEQUENCE: 220

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gln Val Gln Leu
    210                 215                 220

Val Glu Ser Gly Gly Gly Leu Val Gln Pro Gly Arg Ser Leu Arg Leu
225                 230                 235                 240

Ser Cys Ala Ala Ser Gly Phe Lys Phe Ser Asn Val Trp Phe His Trp
                245                 250                 255

Val Arg Gln Ala Pro Gly Lys Gly Leu Glu Trp Val Ala Gln Ile Lys
            260                 265                 270

Asp Tyr Tyr Asn Ala Tyr Ala Gly Tyr Tyr His Pro Ser Val Lys Gly
        275                 280                 285

Arg Phe Thr Ile Ser Arg Asp Asp Ser Lys Asn Ser Ile Tyr Leu Gln
    290                 295                 300

Met Asn Ser Leu Lys Thr Glu Asp Thr Ala Val Tyr Tyr Cys His Tyr
305                 310                 315                 320

Val His Tyr Ala Ala Ala Ser Gln Leu Leu Pro Ala Glu Gly Val Asp
                325                 330                 335

Ala Trp Gly Gln Gly Thr Thr Val Thr Val Ser Ser Ala Ser Thr Lys
            340                 345                 350

Gly Pro Ser Val Phe Pro Leu Ala Pro Ser Ser Lys Ser Thr Ser Gly
```

```
                    355                 360                 365
Gly Thr Ala Ala Leu Gly Cys Leu Val Glu Asp Tyr Phe Pro Glu Pro
            370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Cys Ser Leu Gly Thr Gln Thr Tyr Ile Cys Asn
            420                 425                 430

Val Asn His Lys Pro Ser Asn Thr Lys Val Asp Glu Lys Val Glu Pro
        435                 440                 445

Lys Ser Cys Asp Lys Thr His Thr Cys Pro Pro Cys Pro Ala Pro Glu
    450                 455                 460

Ala Ala Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Ala
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Cys Arg Asp Glu Leu Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Leu His Glu Ala Leu His Ala His Tyr Thr Arg Lys Glu Leu
            660                 665                 670

Ser Leu Ser Pro
        675

<210> SEQ ID NO 221
<211> LENGTH: 671
<212> TYPE: PRT
<213> ORGANISM: Artificial Sequence
<220> FEATURE:
<223> OTHER INFORMATION: an artificially synthesized sequence

<400> SEQUENCE: 221

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
```

```
                35                  40                  45
Leu Ile Tyr Gln Ala Ser Asn Leu Glu Ile Gly Val Pro Ser Arg Phe
 50                  55                  60
Ser Gly Ser Gly Ser Gly Thr Asp Phe Thr Leu Thr Ile Asn Ser Leu
 65                  70                  75                  80
Glu Ala Glu Asp Ala Ala Thr Tyr Tyr Cys Gln Gly Tyr Tyr Ser Gly
                 85                  90                  95
Tyr Ile Tyr Ala Phe Gly Gly Gly Thr Lys Val Glu Ile Lys Ser Ser
                100                 105                 110
Ala Ser Thr Lys Gly Pro Ser Val Phe Pro Leu Ala Pro Ser Ser Arg
            115                 120                 125
Ser Thr Ser Glu Ser Thr Ala Ala Leu Gly Cys Leu Val Lys Asp Tyr
            130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Lys Thr
            180                 185                 190
Tyr Thr Cys Asn Val Asp His Lys Pro Ser Asn Thr Lys Val Asp Lys
            195                 200                 205
Arg Val Glu Pro Lys Ser Cys Gln Val Gln Leu Val Glu Ser Gly Gly
210                 215                 220
Gly Leu Val Gln Pro Gly Arg Ser Leu Arg Leu Ser Cys Ala Ala Ser
225                 230                 235                 240
Gly Phe Lys Phe Ser Asn Val Trp Phe His Trp Val Arg Gln Ala Pro
                245                 250                 255
Gly Lys Gly Leu Glu Trp Val Ala Gln Ile Lys Asp Tyr Tyr Asn Ala
            260                 265                 270
Tyr Ala Gly Tyr Tyr His Pro Ser Val Lys Gly Arg Phe Thr Ile Ser
            275                 280                 285
Arg Asp Asp Ser Lys Asn Ser Ile Tyr Leu Gln Met Asn Ser Leu Lys
290                 295                 300
Thr Glu Asp Thr Ala Val Tyr Tyr Cys His Tyr Val His Tyr Ala Ala
305                 310                 315                 320
Ala Ser Gln Leu Leu Pro Ala Glu Gly Val Asp Ala Trp Gly Gln Gly
                325                 330                 335
Thr Thr Val Thr Val Ser Ser Ala Ser Thr Lys Gly Pro Ser Val Phe
            340                 345                 350
Pro Leu Ala Pro Ser Ser Lys Ser Thr Ser Gly Gly Thr Ala Ala Leu
            355                 360                 365
Gly Cys Leu Val Glu Asp Tyr Phe Pro Glu Pro Val Thr Val Ser Trp
            370                 375                 380
Asn Ser Gly Ala Leu Thr Ser Gly Val His Thr Phe Pro Ala Val Leu
385                 390                 395                 400
Gln Ser Ser Gly Leu Tyr Ser Leu Ser Ser Val Val Thr Val Pro Ser
                405                 410                 415
Cys Ser Leu Gly Thr Gln Thr Tyr Ile Cys Asn Val Asn His Lys Pro
            420                 425                 430
Ser Asn Thr Lys Val Asp Glu Lys Val Glu Pro Lys Ser Cys Asp Lys
            435                 440                 445
Thr His Thr Cys Pro Pro Cys Pro Ala Pro Glu Ala Ala Gly Gly Pro
            450                 455                 460
```

```
Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Ala Ser Thr Tyr Arg Val
            515                 520                 525

Val Ser Val Leu Thr Val Leu His Gln Asp Trp Leu Asn Gly Lys Glu
530                 535                 540

Tyr Lys Cys Lys Val Ser Asn Lys Ala Leu Pro Ala Pro Ile Glu Lys
545                 550                 555                 560

Thr Ile Ser Lys Ala Lys Gly Gln Pro Arg Glu Pro Gln Val Tyr Thr
                565                 570                 575

Leu Pro Pro Cys Arg Asp Glu Leu Thr Lys Asn Gln Val Ser Leu Trp
            580                 585                 590

Cys Leu Val Lys Gly Phe Tyr Pro Ser Asp Ile Ala Val Glu Trp Glu
            595                 600                 605

Ser Asn Gly Gln Pro Glu Asn Asn Tyr Lys Thr Thr Pro Pro Val Leu
610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Leu His Glu
                645                 650                 655

Ala Leu His Ala His Tyr Thr Arg Lys Glu Leu Ser Leu Ser Pro
            660                 665                 670

<210> SEQ ID NO 222
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 222

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
                20                  25                  30

Asp Trp Leu Ser Trp Tyr Gln Gln Lys Pro Gly Gln Pro Pro Lys Leu
            35                  40                  45

Leu Ile Tyr Gln Ala Ser Asn Leu Glu Ile Gly Val Pro Ser Arg Phe
        50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
                100                 105                 110

Ala Ser Thr Lys Gly Pro Ser Val Phe Pro Leu Ala Pro Ser Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160
```

-continued

Gly Val His Thr Phe Pro Ala Val Leu Gln Ser Ser Gly Leu Tyr Ser
                165                 170                 175
Leu Ser Ser Val Val Thr Val Pro Ser Ser Leu Gly Thr Lys Thr
                180                 185                 190
Tyr Thr Cys Asn Val Asp His Lys Pro Ser Asn Thr Lys Val Asp Lys
                195                 200                 205
Arg Val Glu Pro Lys Ser Cys Gly Gly Gly Ser Gly Gly Gly Gly
        210                 215                 220
Ser Gln Val Gln Leu Val Glu Ser Gly Gly Leu Val Gln Pro Gly
225                 230                 235                 240
Arg Ser Leu Arg Leu Ser Cys Ala Ala Ser Gly Phe Lys Phe Ser Asn
                245                 250                 255
Val Trp Phe His Trp Val Arg Gln Ala Pro Gly Lys Gly Leu Glu Trp
                260                 265                 270
Val Ala Gln Ile Lys Asp Tyr Tyr Asn Ala Tyr Ala Gly Tyr Tyr His
                275                 280                 285
Pro Ser Val Lys Gly Arg Phe Thr Ile Ser Arg Asp Asp Ser Lys Asn
        290                 295                 300
Ser Ile Tyr Leu Gln Met Asn Ser Leu Lys Thr Glu Asp Thr Ala Val
305                 310                 315                 320
Tyr Tyr Cys His Tyr Val His Tyr Ala Ala Ser Gln Leu Leu Pro
                325                 330                 335
Ala Glu Gly Val Asp Ala Trp Gly Gln Gly Thr Thr Val Thr Val Ser
                340                 345                 350
Ser Ala Ser Thr Lys Gly Pro Ser Val Phe Pro Leu Ala Pro Ser Ser
                355                 360                 365
Lys Ser Thr Ser Gly Gly Thr Ala Ala Leu Gly Cys Leu Val Glu Asp
        370                 375                 380
Tyr Phe Pro Glu Pro Val Thr Val Ser Trp Asn Ser Gly Ala Leu Thr
385                 390                 395                 400
Ser Gly Val His Thr Phe Pro Ala Val Leu Gln Ser Ser Gly Leu Tyr
                405                 410                 415
Ser Leu Ser Ser Val Val Thr Val Pro Ser Cys Ser Leu Gly Thr Gln
                420                 425                 430
Thr Tyr Ile Cys Asn Val Asn His Lys Pro Ser Asn Thr Lys Val Asp
                435                 440                 445
Glu Lys Val Glu Pro Lys Ser Cys Asp Lys Thr His Thr Cys Pro Pro
        450                 455                 460
Cys Pro Ala Pro Glu Leu Arg Gly Gly Pro Lys Val Phe Leu Phe Pro
465                 470                 475                 480
Pro Lys Pro Lys Asp Thr Leu Met Ile Ser Arg Thr Pro Glu Val Thr
                485                 490                 495
Cys Val Val Val Asp Val Ser His Glu Asp Pro Glu Val Lys Phe Asn
                500                 505                 510
Trp Tyr Val Asp Gly Val Glu Val His Asn Ala Lys Thr Lys Pro Arg
        515                 520                 525
Glu Glu Gln Tyr Ala Ser Thr Tyr Arg Val Val Ser Val Leu Thr Val
530                 535                 540
Leu His Gln Asp Trp Leu Asn Gly Lys Glu Tyr Lys Cys Lys Val Ser
545                 550                 555                 560
Asn Lys Ala Leu Pro Ala Pro Ile Glu Lys Thr Ile Ser Lys Ala Lys
                565                 570                 575

-continued

```
Gly Gln Pro Arg Glu Pro Gln Val Tyr Thr Leu Pro Pro Cys Arg Glu
            580                 585                 590

Glu Met Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro
        675                 680

<210> SEQ ID NO 223
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 223

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gly Gly Gly Gly
    210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Val Phe Ser Asn
                245                 250                 255
```

```
Val Trp Phe His Trp Val Arg Gln Ala Pro Gly Lys Gly Leu Glu Trp
            260                 265                 270

Val Ala Gln Ile Lys Asp Tyr Tyr Asn Ala Tyr Ala Tyr Tyr Ala
        275                 280                 285

Pro Ser Val Lys Gly Arg Phe Thr Ile Ser Arg Asp Asp Ser Lys Asn
290                 295                 300

Ser Ile Tyr Leu Gln Met Asn Ser Leu Lys Thr Glu Asp Thr Ala Val
305                 310                 315                 320

Tyr Tyr Cys His Tyr Val His Tyr Ala Ser Ala Ser Thr Leu Leu Pro
                325                 330                 335

Ala Glu Gly Val Asp Ala Trp Gly Gln Gly Thr Thr Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Glu Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Cys Ser Leu Gly Thr Gln
            420                 425                 430

Thr Tyr Ile Cys Asn Val Asn His Lys Pro Ser Asn Thr Lys Val Asp
        435                 440                 445

Glu Lys Val Glu Pro Lys Ser Cys Asp Lys Thr His Thr Cys Pro Pro
450                 455                 460

Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
                645                 650                 655

Asn Val Phe Ser Cys Ser Val Leu His Glu Ala Leu His Ala His Tyr
            660                 665                 670

Thr Arg Lys Glu Leu Ser Leu Ser Pro
```

<210> SEQ ID NO 224
<211> LENGTH: 678
<212> TYPE: PRT
<213> ORGANISM: Artificial Sequence
<220> FEATURE:
<223> OTHER INFORMATION: an artificially synthesized sequence

<400> SEQUENCE: 224

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys Ser Ser Ala Ser Thr
            100                 105                 110

Lys Gly Pro Ser Val Phe Pro Leu Ala Pro Ser Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
            180                 185                 190

Asn Val Asp His Lys Pro Ser Asn Thr Lys Val Asp Lys Arg Val Glu
        195                 200                 205

Pro Lys Ser Cys Gly Gly Gly Ser Gly Gly Gly Gly Ser Gln Val
    210                 215                 220

Gln Leu Val Glu Ser Gly Gly Gly Leu Val Gln Pro Gly Arg Ser Leu
225                 230                 235                 240

Arg Leu Ser Cys Ala Ala Ser Gly Phe Val Phe Ser Asn Val Trp Phe
                245                 250                 255

His Trp Val Arg Gln Ala Pro Gly Lys Gly Leu Glu Trp Val Ala Gln
            260                 265                 270

Ile Lys Asp Tyr Tyr Asn Ala Tyr Ala Ala Tyr Tyr Ala Pro Ser Val
        275                 280                 285

Lys Gly Arg Phe Thr Ile Ser Arg Asp Asp Ser Lys Asn Ser Ile Tyr
    290                 295                 300

Leu Gln Met Asn Ser Leu Lys Thr Glu Asp Thr Ala Val Tyr Tyr Cys
305                 310                 315                 320

His Tyr Val His Tyr Ala Ser Ala Ser Thr Leu Leu Pro Ala Glu Gly
                325                 330                 335

Val Asp Ala Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
```

```
                    355                 360                 365
Ser Gly Gly Thr Ala Ala Leu Gly Cys Leu Val Glu Asp Tyr Phe Pro
            370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Cys Ser Leu Gly Thr Gln Thr Tyr Ile
            420                 425                 430

Cys Asn Val Asn His Lys Pro Ser Asn Thr Lys Val Asp Glu Lys Val
            435                 440                 445

Glu Pro Lys Ser Cys Asp Lys Thr His Thr Cys Pro Pro Cys Pro Ala
        450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Ala Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Cys Arg Asp Glu Leu Thr
            580                 585                 590

Lys Asn Gln Val Ser Leu Trp Cys Leu Val Lys Gly Phe Tyr Pro Ser
            595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Glu Gly Asn Val Phe
                645                 650                 655

Ser Cys Ser Val Leu His Glu Ala Leu His Ala His Tyr Thr Arg Lys
            660                 665                 670

Glu Leu Ser Leu Ser Pro
        675

<210> SEQ ID NO 225
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 225

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
```

```
                35                  40                  45
Leu Ile Tyr Gln Ala Ser Asn Leu Glu Ile Gly Val Pro Ser Arg Phe
 50                  55                  60

Ser Gly Ser Gly Ser Gly Thr Asp Phe Thr Leu Thr Ile Asn Ser Leu
 65                  70                  75                  80

Glu Ala Glu Asp Ala Ala Thr Tyr Tyr Cys Gln Gly Tyr Tyr Ser Gly
                 85                  90                  95

Tyr Ile Tyr Ala Phe Gly Gly Gly Thr Lys Val Glu Ile Lys Ser Ser
                100                 105                 110

Ala Ser Thr Lys Gly Pro Ser Val Phe Pro Leu Ala Pro Ser Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gly Gly Gly Gly
210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Val Phe Ser Asn
                245                 250                 255

Val Trp Phe His Trp Val Arg Gln Ala Pro Gly Lys Gly Leu Glu Trp
            260                 265                 270

Val Ala Gln Ile Lys Asp Tyr Tyr Asn Ala Tyr Ala Ala Tyr Tyr Ala
        275                 280                 285

Pro Ser Val Lys Gly Arg Phe Thr Ile Ser Arg Asp Asp Ser Lys Asn
290                 295                 300

Ser Ile Tyr Leu Gln Met Asn Ser Leu Lys Thr Glu Asp Thr Ala Val
305                 310                 315                 320

Tyr Tyr Cys His Tyr Val His Tyr Ala Ser Ala Ser Thr Leu Leu Pro
                325                 330                 335

Ala Glu Gly Val Asp Ala Trp Gly Gln Gly Thr Thr Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Glu Asp
370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Cys Ser Leu Gly Thr Gln
            420                 425                 430

Thr Tyr Ile Cys Asn Val Asn His Lys Pro Ser Asn Thr Lys Val Asp
        435                 440                 445

Glu Lys Val Glu Pro Lys Ser Cys Asp Lys Thr His Thr Cys Pro Pro
450                 455                 460
```

```
Cys Pro Ala Pro Glu Ala Ala Gly Gly Pro Ser Val Phe Leu Phe Pro
465                 470                 475                 480

Pro Lys Pro Lys Asp Thr Leu Met Ile Ser Arg Thr Pro Glu Val Thr
            485                 490                 495

Cys Val Val Asp Val Ser His Glu Asp Pro Glu Val Lys Phe Asn
        500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Asp
            580                 585                 590

Glu Leu Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
        610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Leu His Glu Ala Leu His Ala His Tyr
            660                 665                 670

Thr Arg Lys Glu Leu Ser Leu Ser Pro
            675                 680

<210> SEQ ID NO 226
<211> LENGTH: 676
<212> TYPE: PRT
<213> ORGANISM: Artificial Sequence
<220> FEATURE:
<223> OTHER INFORMATION: an artificially synthesized sequence

<400> SEQUENCE: 226

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140
```

```
Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Lys Thr
        180                 185                 190

Tyr Thr Cys Asn Val Asp His Lys Pro Ser Asn Thr Lys Val Asp Lys
    195                 200                 205

Arg Val Glu Pro Lys Ser Cys Gly Gly Gly Ser Gln Val Gln Leu
210                 215                 220

Val Glu Ser Gly Gly Gly Leu Val Gln Pro Gly Arg Ser Leu Arg Leu
225                 230                 235                 240

Ser Cys Ala Ala Ser Gly Phe Val Phe Ser Asn Val Trp Phe His Trp
                245                 250                 255

Val Arg Gln Ala Pro Gly Lys Gly Leu Glu Trp Val Ala Gln Ile Lys
            260                 265                 270

Asp Tyr Tyr Asn Ala Tyr Ala Ala Tyr Tyr Ala Pro Ser Val Lys Gly
        275                 280                 285

Arg Phe Thr Ile Ser Arg Asp Asp Ser Lys Asn Ser Ile Tyr Leu Gln
290                 295                 300

Met Asn Ser Leu Lys Thr Glu Asp Thr Ala Val Tyr Tyr Cys His Tyr
305                 310                 315                 320

Val His Tyr Ala Ser Ala Ser Thr Leu Leu Pro Ala Glu Gly Val Asp
                325                 330                 335

Ala Trp Gly Gln Gly Thr Thr Val Thr Val Ser Ser Ala Ser Thr Lys
            340                 345                 350

Gly Pro Ser Val Phe Pro Leu Ala Pro Ser Ser Lys Ser Thr Ser Gly
        355                 360                 365

Gly Thr Ala Ala Leu Gly Cys Leu Val Glu Asp Tyr Phe Pro Glu Pro
370                 375                 380

Val Thr Val Ser Trp Asn Ser Gly Ala Leu Thr Ser Gly Val His Thr
385                 390                 395                 400

Phe Pro Ala Val Leu Gln Ser Ser Gly Leu Tyr Ser Leu Ser Ser Val
                405                 410                 415

Val Thr Val Pro Ser Cys Ser Leu Gly Thr Gln Thr Tyr Ile Cys Asn
            420                 425                 430

Val Asn His Lys Pro Ser Asn Thr Lys Val Asp Glu Lys Val Glu Pro
        435                 440                 445

Lys Ser Cys Asp Lys Thr His Thr Cys Pro Pro Cys Pro Ala Pro Glu
450                 455                 460

Ala Ala Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Ala
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560
```

```
Ala Pro Ile Glu Lys Thr Ile Ser Lys Ala Lys Gly Gln Pro Arg Glu
                565                 570                 575

Pro Gln Val Tyr Thr Leu Pro Pro Cys Arg Asp Glu Leu Thr Lys Asn
            580                 585                 590

Gln Val Ser Leu Trp Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Leu His Glu Ala Leu His Ala His Tyr Thr Arg Lys Glu Leu
            660                 665                 670

Ser Leu Ser Pro
        675

<210> SEQ ID NO 227
<211> LENGTH: 671
<212> TYPE: PRT
<213> ORGANISM: Artificial Sequence
<220> FEATURE:
<223> OTHER INFORMATION: an artificially synthesized sequence

<400> SEQUENCE: 227

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gln Val Gln Leu Val Glu Ser Gly Gly
    210                 215                 220

Gly Leu Val Gln Pro Gly Arg Ser Leu Arg Leu Ser Cys Ala Ala Ser
225                 230                 235                 240
```

-continued

```
Gly Phe Val Phe Ser Asn Val Trp Phe His Trp Val Arg Gln Ala Pro
                245                 250                 255
Gly Lys Gly Leu Glu Trp Val Ala Gln Ile Lys Asp Tyr Tyr Asn Ala
            260                 265                 270
Tyr Ala Ala Tyr Tyr Ala Pro Ser Val Lys Gly Arg Phe Thr Ile Ser
        275                 280                 285
Arg Asp Asp Ser Lys Asn Ser Ile Tyr Leu Gln Met Asn Ser Leu Lys
    290                 295                 300
Thr Glu Asp Thr Ala Val Tyr Tyr Cys His Tyr Val His Tyr Ala Ser
305                 310                 315                 320
Ala Ser Thr Leu Leu Pro Ala Glu Gly Val Asp Ala Trp Gly Gln Gly
                325                 330                 335
Thr Thr Val Thr Val Ser Ser Ala Ser Thr Lys Gly Pro Ser Val Phe
            340                 345                 350
Pro Leu Ala Pro Ser Ser Lys Ser Thr Ser Gly Gly Thr Ala Ala Leu
        355                 360                 365
Gly Cys Leu Val Glu Asp Tyr Phe Pro Glu Pro Val Thr Val Ser Trp
    370                 375                 380
Asn Ser Gly Ala Leu Thr Ser Gly Val His Thr Phe Pro Ala Val Leu
385                 390                 395                 400
Gln Ser Ser Gly Leu Tyr Ser Leu Ser Ser Val Val Thr Val Pro Ser
                405                 410                 415
Cys Ser Leu Gly Thr Gln Thr Tyr Ile Cys Asn Val Asn His Lys Pro
            420                 425                 430
Ser Asn Thr Lys Val Asp Glu Lys Val Glu Pro Lys Ser Cys Asp Lys
        435                 440                 445
Thr His Thr Cys Pro Pro Cys Pro Ala Pro Glu Ala Ala Gly Gly Pro
    450                 455                 460
Ser Val Phe Leu Phe Pro Pro Lys Pro Lys Asp Thr Leu Met Ile Ser
465                 470                 475                 480
Arg Thr Pro Glu Val Thr Cys Val Val Val Asp Val Ser His Glu Asp
                485                 490                 495
Pro Glu Val Lys Phe Asn Trp Tyr Val Asp Gly Val Glu Val His Asn
            500                 505                 510
Ala Lys Thr Lys Pro Arg Glu Glu Gln Tyr Ala Ser Thr Tyr Arg Val
        515                 520                 525
Val Ser Val Leu Thr Val Leu His Gln Asp Trp Leu Asn Gly Lys Glu
    530                 535                 540
Tyr Lys Cys Lys Val Ser Asn Lys Ala Leu Pro Ala Pro Ile Glu Lys
545                 550                 555                 560
Thr Ile Ser Lys Ala Lys Gly Gln Pro Arg Glu Pro Gln Val Tyr Thr
                565                 570                 575
Leu Pro Pro Cys Arg Asp Glu Leu Thr Lys Asn Gln Val Ser Leu Trp
            580                 585                 590
Cys Leu Val Lys Gly Phe Tyr Pro Ser Asp Ile Ala Val Glu Trp Glu
        595                 600                 605
Ser Asn Gly Gln Pro Glu Asn Asn Tyr Lys Thr Thr Pro Pro Val Leu
    610                 615                 620
Asp Ser Asp Gly Ser Phe Phe Leu Tyr Ser Lys Leu Thr Val Asp Lys
625                 630                 635                 640
Ser Arg Trp Gln Gln Gly Asn Val Phe Ser Cys Ser Val Leu His Glu
                645                 650                 655
Ala Leu His Ala His Tyr Thr Arg Lys Glu Leu Ser Leu Ser Pro
```

```
                    660             665             670
```

<210> SEQ ID NO 228
<211> LENGTH: 681
<212> TYPE: PRT
<213> ORGANISM: Artificial Sequence
<220> FEATURE:
<223> OTHER INFORMATION: an artificially synthesized sequence

<400> SEQUENCE: 228

```
Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ile Tyr Ala Phe Gly Gly Gly Thr Lys Val Glu Ile Lys Ser Ser
            100                 105                 110

Ala Ser Thr Lys Gly Pro Ser Val Phe Pro Leu Ala Pro Ser Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Pro Lys Ser Cys Gly Gly Gly Ser Gly Gly Gly Gly
    210                 215                 220

Ser Gln Val Gln Leu Val Glu Ser Gly Gly Gly Leu Val Gln Pro Gly
225                 230                 235                 240

Arg Ser Leu Arg Leu Ser Cys Ala Ala Ser Gly Phe Val Phe Ser Asn
                245                 250                 255

Val Trp Phe His Trp Val Arg Gln Ala Pro Gly Lys Gly Leu Glu Trp
            260                 265                 270

Val Ala Gln Ile Lys Asp Tyr Tyr Asn Ala Tyr Ala Ala Tyr Tyr Ala
        275                 280                 285

Pro Ser Val Lys Gly Arg Phe Thr Ile Ser Arg Asp Asp Ser Lys Asn
    290                 295                 300

Ser Ile Tyr Leu Gln Met Asn Ser Leu Lys Thr Glu Asp Thr Ala Val
305                 310                 315                 320

Tyr Tyr Cys His Tyr Val His Tyr Ala Ser Ala Ser Thr Leu Leu Pro
                325                 330                 335

Ala Glu Gly Val Asp Ala Trp Gly Gln Gly Thr Thr Val Thr Val Ser
            340                 345                 350

Ser Ala Ser Thr Lys Gly Pro Ser Val Phe Pro Leu Ala Pro Ser Ser
```

```
            355                 360                 365
Lys Ser Thr Ser Gly Gly Thr Ala Ala Leu Gly Cys Leu Val Glu Asp
    370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Cys Ser Leu Gly Thr Gln
            420                 425                 430

Thr Tyr Ile Cys Asn Val Asn His Lys Pro Ser Asn Thr Lys Val Asp
        435                 440                 445

Glu Lys Val Glu Pro Lys Ser Cys Asp Lys Thr His Thr Cys Pro Pro
    450                 455                 460

Cys Pro Ala Pro Glu Leu Arg Gly Gly Pro Lys Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Ala Ser Thr Tyr Arg Val Val Ser Val Leu Thr Val
    530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Cys Arg Glu
            580                 585                 590

Glu Met Thr Lys Asn Gln Val Ser Leu Trp Cys Leu Val Lys Gly Phe
        595                 600                 605

Tyr Pro Ser Asp Ile Ala Val Glu Trp Glu Ser Asn Gly Gln Pro Glu
    610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Glu Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro
        675                 680

<210> SEQ ID NO 229
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 229

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
```

```
                35                  40                  45
Ala Gln Ile Lys Asp Tyr Tyr Asn Ala Tyr Ala Tyr Tyr Ala Pro
 50                  55                  60
Ser Val Lys Gly Arg Phe Thr Ile Ser Arg Asp Asp Ser Lys Asn Ser
 65                  70                  75                  80
Ile Tyr Leu Gln Met Asn Ser Leu Lys Thr Glu Asp Thr Ala Val Tyr
                 85                  90                  95
Tyr Cys His Tyr Val His Tyr Ala Ser Ala Ser Thr Leu Leu Pro Ala
                100                 105                 110
Glu Gly Val Asp Ala Trp Gly Gln Gly Thr Thr Val Thr Val Ser Ser
                115                 120                 125
Ala Ser Thr Lys Gly Pro Ser Val Phe Pro Leu Ala Pro Ser Ser Lys
                130                 135                 140
Ser Thr Ser Gly Gly Thr Ala Ala Leu Gly Cys Leu Val Glu Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
                180                 185                 190
Leu Ser Ser Val Val Thr Val Pro Ser Cys Ser Leu Gly Thr Gln Thr
                195                 200                 205
Tyr Ile Cys Asn Val Asn His Lys Pro Ser Asn Thr Lys Val Asp Glu
210                 215                 220
Lys Val Glu Pro Lys Ser Cys Asp Lys Thr His Thr Cys Pro Pro Cys
225                 230                 235                 240
Pro Ala Pro Glu Leu Arg Gly Gly Pro Lys Val Phe Leu Phe Pro Pro
                245                 250                 255
Lys Pro Lys Asp Thr Leu Met Ile Ser Arg Thr Pro Glu Val Thr Cys
                260                 265                 270
Val Val Val Asp Val Ser His Glu Asp Pro Glu Val Lys Phe Asn Trp
                275                 280                 285
Tyr Val Asp Gly Val Glu Val His Asn Ala Lys Thr Lys Pro Arg Glu
                290                 295                 300
Glu Gln Tyr Ala Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
                340                 345                 350
Gln Pro Arg Glu Pro Gln Val Cys Thr Leu Pro Pro Ser Arg Glu Glu
                355                 360                 365
Met Thr Lys Asn Gln Val Ser Leu Ser Cys Ala Val Lys Gly Phe Tyr
                370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Val Ser Lys Leu Thr Val Asp Lys Ser Arg Trp Gln Glu Gly Asn
                420                 425                 430
Val Phe Ser Cys Ser Val Met His Glu Ala Leu His Asn His Tyr Thr
                435                 440                 445
Gln Lys Ser Leu Ser Leu Ser Pro
450                 455
```

<210> SEQ ID NO 230
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 230

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Lys Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Gly Tyr Tyr His Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ala Ala Ser Gln Leu Leu Pro Ala
            100                 105                 110

Glu Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
        195                 200                 205

Tyr Ile Cys Asn Val Asn His Lys Pro Ser Asn Thr Lys Val Asp Glu
    210                 215                 220

Lys Val Glu Pro Lys Ser Cys Asp Lys Thr His Thr Cys Pro Pro Cys
225                 230                 235                 240

Pro Ala Pro Glu Leu Arg Gly Gly Pro Lys Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Cys Thr Leu Pro Pro Ser Arg Glu Glu
        355                 360                 365

```
Met Thr Lys Asn Gln Val Ser Leu Ser Cys Ala Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Val Ser Lys Leu Thr Val Asp Lys Ser Arg Trp Gln Glu Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro
            450                 455

<210> SEQ ID NO 231
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 231

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Val Phe Ser Asn Val
            20                  25                  30

Trp Phe His Trp Val Arg Gln Ala Pro Gly Lys Gly Leu Glu Trp Val
        35                  40                  45

Ala Gln Ile Lys Asp Tyr Tyr Asn Ala Tyr Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys His Tyr Val His Tyr Ala Ser Ala Ser Thr Leu Leu Pro Ala
            100                 105                 110

Glu Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Glu Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Cys Ser Leu Gly Thr Gln Thr
        195                 200                 205

Tyr Ile Cys Asn Val Asn His Lys Pro Ser Asn Thr Lys Val Asp Glu
    210                 215                 220

Lys Val Glu Pro Lys Ser Cys Asp Lys Thr His Thr Cys Pro Pro Cys
225                 230                 235                 240

Pro Ala Pro Glu Leu Arg Gly Gly Pro Lys Val Phe Leu Phe Pro Pro
                245                 250                 255

Lys Pro Lys Asp Thr Leu Met Ile Ser Arg Thr Pro Glu Val Thr Cys
            260                 265                 270
```

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Cys Thr Leu Pro Pro Ser Arg Glu Glu
                355                 360                 365

Met Thr Lys Asn Gln Val Ser Leu Ser Cys Ala Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Glu Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro
450                 455

<210> SEQ ID NO 232
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 232

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
                100                 105                 110

Thr Leu Val Thr Val Ser Ser
        115

<210> SEQ ID NO 233
<211> LENGTH: 6
<212> TYPE: PRT
<213> ORGANISM: Artificial Sequence
<220> FEATURE:
<223> OTHER INFORMATION: an artificially synthesized sequence

```
<400> SEQUENCE: 233

Ser Ser Tyr Asp Met Gly
1               5

<210> SEQ ID NO 234
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 234

Thr Ile Tyr Thr Gly Asp Tyr Ser Thr Asp Tyr Ala Ser Trp Ala Lys
1               5                   10                  15

Gly

<210> SEQ ID NO 235
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 235

His Thr Gly Tyr Gly Tyr Phe Gly Leu
1               5

<210> SEQ ID NO 236
<211> LENGTH: 110
<212> TYPE: PRT
<213> ORGANISM: Artificial Sequence
<220> FEATURE:
<223> OTHER INFORMATION: an artificially synthesized sequence

<400> SEQUENCE: 236

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
            20                  25                  30

Asp Trp Leu Ser Trp Tyr Gln Gln Lys Pro Gly Gln Pro Pro Lys Leu
        35                  40                  45

Leu Ile Tyr Gln Ala Ser Asn Leu Glu Ile Gly Val Pro Ser Arg Phe
    50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Ser Gly
                85                  90                  95

Tyr Ile Tyr Ala Phe Gly Gly Gly Thr Lys Val Glu Ile Lys
            100                 105                 110

<210> SEQ ID NO 237
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 237

Gln Ser Thr Glu Ser Val Tyr Gly Ser Asp Trp Leu Ser
1               5                   10

<210> SEQ ID NO 238
```

```
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 238

Gln Ala Ser Asn Leu Glu Ile
1               5

<210> SEQ ID NO 239
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 239

Gln Gly Tyr Tyr Ser Gly Tyr Ile Tyr Ala
1               5                   10

<210> SEQ ID NO 240
<211> LENGTH: 116
<212> TYPE: PRT
<213> ORGANISM: Artificial Sequence
<220> FEATURE:
<223> OTHER INFORMATION: an artificially synthesized sequence

<400> SEQUENCE: 240

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
            100                 105                 110

Thr Val Ser Ser
        115

<210> SEQ ID NO 241
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 241

Ser Tyr Trp Met His
1               5

<210> SEQ ID NO 242
<211> LENGTH: 17
<212> TYPE: PRT
<213> ORGANISM: Artificial Sequence
<220> FEATURE:
<223> OTHER INFORMATION: an artificially synthesized sequence
```

```
<400> SEQUENCE: 242

Met Ile Asp Pro Ser Tyr Ser Glu Thr Arg Leu Asn Gln Lys Phe Lys
1               5                   10                  15

Asp

<210> SEQ ID NO 243
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 243

Tyr Gly Asn Tyr Phe Asp Tyr
1               5

<210> SEQ ID NO 244
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 244

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys
            100                 105

<210> SEQ ID NO 245
<211> LENGTH: 11
<212> TYPE: PRT
<213> ORGANISM: Artificial Sequence
<220> FEATURE:
<223> OTHER INFORMATION: an artificially synthesized sequence

<400> SEQUENCE: 245

Lys Ala Ser Glu Asp Ile Tyr Asn Arg Leu Ala
1               5                   10

<210> SEQ ID NO 246
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 246

Gly Ala Thr Ser Leu Glu Thr
1               5

<210> SEQ ID NO 247
```

```
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 247

Gln Gln Tyr Trp Ser Thr Pro Tyr Thr
1               5

<210> SEQ ID NO 248
<211> LENGTH: 11
<212> TYPE: PRT
<213> ORGANISM: Artificial Sequence
<220> FEATURE:
<223> OTHER INFORMATION: an artificially synthesized sequence

<400> SEQUENCE: 248

Val Glu Pro Lys Ser Cys Gly Gly Gly Gly Ser
1               5                   10

<210> SEQ ID NO 249
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 249

Val Glu Pro Lys Ser Cys Gly Gly Gly Ser Gly Gly Gly Gly Ser
1               5                   10                  15

<210> SEQ ID NO 250
<211> LENGTH: 984
<212> TYPE: PRT
<213> ORGANISM: Artificial Sequence
<220> FEATURE:
<223> OTHER INFORMATION: an artificially synthesized sequence

<400> SEQUENCE: 250

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Val Tyr Tyr Ser Gly Thr Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175
```

```
Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Asp Arg Ser Pro Leu Thr Phe Gly Gly Gly Thr Lys Leu Glu Ile
225                 230                 235                 240

Lys Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

Gly Gly Gly Gly Asp Lys Thr His Thr Cys Pro Pro Cys Pro Ala Pro
            500                 505                 510

Glu Leu Leu Gly Gly Pro Ser Val Phe Leu Phe Pro Pro Lys Pro Lys
        515                 520                 525

Asp Thr Leu Met Ile Ser Arg Thr Pro Glu Val Thr Cys Val Val Val
    530                 535                 540

Asp Val Ser His Glu Asp Pro Glu Val Lys Phe Asn Trp Tyr Val Asp
545                 550                 555                 560

Gly Val Glu Val His Asn Ala Lys Thr Lys Pro Cys Glu Glu Gln Tyr
                565                 570                 575

Gly Ser Thr Tyr Arg Cys Val Ser Val Leu Thr Val Leu His Gln Asp
            580                 585                 590
```

```
Trp Leu Asn Gly Lys Glu Tyr Lys Cys Lys Val Ser Asn Lys Ala Leu
            595                 600                 605

Pro Ala Pro Ile Glu Lys Thr Ile Ser Lys Ala Lys Gly Gln Pro Arg
610                 615                 620

Glu Pro Gln Val Tyr Thr Leu Pro Pro Ser Arg Glu Glu Met Thr Lys
625                 630                 635                 640

Asn Gln Val Ser Leu Thr Cys Leu Val Lys Gly Phe Tyr Pro Ser Asp
                645                 650                 655

Ile Ala Val Glu Trp Glu Ser Asn Gly Gln Pro Glu Asn Asn Tyr Lys
            660                 665                 670

Thr Thr Pro Pro Val Leu Asp Ser Asp Gly Ser Phe Phe Leu Tyr Ser
        675                 680                 685

Lys Leu Thr Val Asp Lys Ser Arg Trp Gln Gln Gly Asn Val Phe Ser
690                 695                 700

Cys Ser Val Met His Glu Ala Leu His Asn His Tyr Thr Gln Lys Ser
705                 710                 715                 720

Leu Ser Leu Ser Pro Gly Lys Gly Gly Gly Ser Gly Gly Gly Gly
                725                 730                 735

Ser Gly Gly Gly Gly Ser Gly Gly Gly Gly Ser Gly Gly Gly Ser
            740                 745                 750

Gly Gly Gly Gly Ser Asp Lys Thr His Thr Cys Pro Pro Cys Pro Ala
        755                 760                 765

Pro Glu Leu Leu Gly Gly Pro Ser Val Phe Leu Phe Pro Pro Lys Pro
    770                 775                 780

Lys Asp Thr Leu Met Ile Ser Arg Thr Pro Glu Val Thr Cys Val Val
785                 790                 795                 800

Val Asp Val Ser His Glu Asp Pro Glu Val Lys Phe Asn Trp Tyr Val
                805                 810                 815

Asp Gly Val Glu Val His Asn Ala Lys Thr Lys Pro Cys Glu Glu Gln
            820                 825                 830

Tyr Gly Ser Thr Tyr Arg Cys Val Ser Val Leu Thr Val Leu His Gln
        835                 840                 845

Asp Trp Leu Asn Gly Lys Glu Tyr Lys Cys Lys Val Ser Asn Lys Ala
850                 855                 860

Leu Pro Ala Pro Ile Glu Lys Thr Ile Ser Lys Ala Lys Gly Gln Pro
865                 870                 875                 880

Arg Glu Pro Gln Val Tyr Thr Leu Pro Pro Ser Arg Glu Glu Met Thr
                885                 890                 895

Lys Asn Gln Val Ser Leu Thr Cys Leu Val Lys Gly Phe Tyr Pro Ser
            900                 905                 910

Asp Ile Ala Val Glu Trp Glu Ser Asn Gly Gln Pro Glu Asn Asn Tyr
        915                 920                 925

Lys Thr Thr Pro Pro Val Leu Asp Ser Asp Gly Ser Phe Phe Leu Tyr
930                 935                 940

Ser Lys Leu Thr Val Asp Lys Ser Arg Trp Gln Gln Gly Asn Val Phe
945                 950                 955                 960

Ser Cys Ser Val Met His Glu Ala Leu His Asn His Tyr Thr Gln Lys
                965                 970                 975

Ser Leu Ser Leu Ser Pro Gly Lys
            980

<210> SEQ ID NO 251
<211> LENGTH: 122
<212> TYPE: PRT
```

<213> ORGANISM: Artificial Sequence
<220> FEATURE:
<223> OTHER INFORMATION: an artificially synthesized sequence

<400> SEQUENCE: 251

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp
            100                 105                 110

Gly Gln Gly Thr Thr Val Thr Val Ser Ser
        115                 120

<210> SEQ ID NO 252
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 252

Asn Ala Trp Met His
1               5

<210> SEQ ID NO 253
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 253

Gln Ile Lys Asp Lys Ser Gln Asn Tyr Ala Thr Tyr Val Ala Glu Ser
1               5                   10                  15

Val Lys Gly

<210> SEQ ID NO 254
<211> LENGTH: 11
<212> TYPE: PRT
<213> ORGANISM: Artificial Sequence
<220> FEATURE:
<223> OTHER INFORMATION: an artificially synthesized sequence

<400> SEQUENCE: 254

Val His Tyr Ala Ala Gly Tyr Gly Val Asp Ile
1               5                   10

<210> SEQ ID NO 255
<211> LENGTH: 112
<212> TYPE: PRT
<213> ORGANISM: Artificial Sequence
<220> FEATURE:
<223> OTHER INFORMATION: an artificially synthesized sequence -continued

<400> SEQUENCE: 255

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

<210> SEQ ID NO 256
<211> LENGTH: 16
<212> TYPE: PRT
<213> ORGANISM: Artificial Sequence
<220> FEATURE:
<223> OTHER INFORMATION: an artificially synthesized sequence

<400> SEQUENCE: 256

Arg Ser Ser Gln Pro Leu Val His Ser Asn Arg Asn Thr Tyr Leu His
1               5                   10                  15

<210> SEQ ID NO 257
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 257

Lys Val Ser Asn Arg Phe Ser
1               5

<210> SEQ ID NO 258
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 258

Gly Gln Gly Thr Gln Val Pro Tyr Thr
1               5

<210> SEQ ID NO 259
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 259

Val Glu Pro Lys Ser Cys
1               5

<210> SEQ ID NO 260
<211> LENGTH: 122
<212> TYPE: PRT

-continued

<213> ORGANISM: Artificial Sequence
<220> FEATURE:
<223> OTHER INFORMATION: an artificially synthesized sequence

<400> SEQUENCE: 260

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Ile Ile Ser Asn Ser Gly Ser Gly Phe Tyr Ala Asn Trp Ala Lys Gly
50                  55                  60

Arg Phe Thr Ile Ser Lys Thr Ser Thr Thr Val Asp Val Lys Ile
65                  70                  75                  80

Ser Ser Pro Thr Thr Glu Asp Thr Ala Thr Tyr Phe Cys Ala Arg Val
                85                  90                  95

Phe Asp Ala Asp Ser Ser Gly Tyr Tyr Tyr Tyr Gly Met Asp Pro Trp
            100                 105                 110

Gly Pro Gly Thr Leu Val Thr Val Ser Ser
        115                 120

<210> SEQ ID NO 261
<211> LENGTH: 111
<212> TYPE: PRT
<213> ORGANISM: Artificial Sequence
<220> FEATURE:
<223> OTHER INFORMATION: an artificially synthesized sequence

<400> SEQUENCE: 261

Asp Val Val Met Thr Gln Thr Pro Ser Ser Val Ser Glu Pro Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Thr Leu Ala Ser Gly Val Ser Ser Arg Phe Arg Gly
50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Thr Tyr Tyr Asp Ser Ser
                85                  90                  95

Gly Val Asp Trp Ala Phe Gly Gly Gly Thr Glu Val Val Val Lys
            100                 105                 110

<210> SEQ ID NO 262
<211> LENGTH: 123
<212> TYPE: PRT
<213> ORGANISM: Artificial Sequence
<220> FEATURE:
<223> OTHER INFORMATION: an artificially synthesized sequence

<400> SEQUENCE: 262

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Tyr Ala
            20                  25                  30

Met Ser Trp Val Arg Gln Ala Pro Gly Lys Gly Leu Glu Trp Ile Gly
        35                  40                  45

```
Ile Ile Thr Gly Gly Asp Pro Tyr Tyr Ala Ser Trp Ala Lys Gly
 50                  55                  60

Arg Phe Thr Ile Ser Lys Thr Ser Thr Thr Met Asp Leu Lys Ile Thr
 65                  70                  75                  80

Ser Pro Thr Thr Glu Asp Thr Ala Thr Tyr Phe Cys Ala Arg Met Ile
                 85                  90                  95

Gly Ser Glu Tyr Ala Ser Ser Ser Glu Tyr Tyr Asp Ala Phe Asp Pro
                100                 105                 110

Trp Gly Pro Gly Thr Leu Val Thr Val Ser Ser
            115                 120

<210> SEQ ID NO 263
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 263

Ala Leu Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
                 20                  25                  30

Leu Ala Trp Tyr Gln Gln Lys Pro Gly Gln Arg Pro Lys Leu Leu Ile
             35                  40                  45

Tyr Gly Ala Ser Asn Leu Glu Ser Gly Val Pro Ser Arg Phe Lys Gly
 50                  55                  60

Ser Gly Ser Gly Thr Glu Tyr Thr Leu Thr Ile Ser Asp Leu Glu Cys
 65                  70                  75                  80

Asp Asp Ala Ala Ile Tyr Tyr Cys Gln Ser Ala Tyr Tyr Thr Thr Ser
                 85                  90                  95

Val Asp Val Leu Tyr Pro Phe Gly Gly Gly Thr Glu Val Val Val Lys
                100                 105                 110

<210> SEQ ID NO 264
<211> LENGTH: 124
<212> TYPE: PRT
<213> ORGANISM: Artificial Sequence
<220> FEATURE:
<223> OTHER INFORMATION: an artificially synthesized sequence

<400> SEQUENCE: 264

Gln Glu Gln Leu Val Glu Ser Gly Gly Gly Leu Val Gln Pro Gly Gly
 1               5                  10                  15

Ser Leu Lys Leu Ser Cys Lys Val Ser Gly Phe Asp Phe Ser Asn Tyr
                 20                  25                  30

Gly Val Ser Trp Val Arg Gln Ala Pro Gly Lys Gly Leu Glu Trp Ile
             35                  40                  45

Gly Tyr Ile Asp Pro Ala Phe Gly Arg Thr Tyr Tyr Ala Ser Trp Val
 50                  55                  60

Asn Gly Arg Phe Thr Ile Ser Ser His Asn Ala Gln Asn Thr Leu Tyr
 65                  70                  75                  80

Leu Gln Leu Asn Ser Leu Thr Ala Ala Asp Thr Ala Thr Tyr Phe Cys
                 85                  90                  95

Val Arg Val Ala Leu Val Val Ala Gly Val Ala Tyr Tyr Gly Met Asp
                100                 105                 110

Val Trp Gly Pro Gly Thr Leu Val Thr Val Ser Ser
```

-continued

```
            115                 120

<210> SEQ ID NO 265
<211> LENGTH: 114
<212> TYPE: PRT
<213> ORGANISM: Artificial Sequence
<220> FEATURE:
<223> OTHER INFORMATION: an artificially synthesized sequence

<400> SEQUENCE: 265

Ala Asp Val Val Met Thr Gln Thr Pro Ala Ser Val Glu Ala Ala Val
1               5                   10                  15

Gly Gly Thr Val Thr Ile Asn Cys Gln Ala Ser Gln Asn Ile Tyr Ser
            20                  25                  30

Tyr Leu Ser Trp Tyr Gln Gln Lys Pro Gly Gln Pro Lys Leu Leu
        35                  40                  45

Ile Tyr Arg Thr Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Ala Asp Ala Ala Thr Tyr Tyr Cys Gln Ser Tyr Tyr Ser Ser
                85                  90                  95

Gly Ser Ser Tyr Gly Ala Phe Ala Phe Gly Gly Gly Thr Glu Val Val
            100                 105                 110

Val Lys

<210> SEQ ID NO 266
<211> LENGTH: 114
<212> TYPE: PRT
<213> ORGANISM: Artificial Sequence
<220> FEATURE:
<223> OTHER INFORMATION: an artificially synthesized sequence

<400> SEQUENCE: 266

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Asn Thr Tyr His
            20                  25                  30

Met Ile Trp Val Arg Gln Ala Pro Gly Lys Gly Leu Glu Trp Ile Gly
        35                  40                  45

Ile Val Asp Ser Gly Gly Ser Thr Tyr Tyr Ala Ser Trp Ala Lys Gly
    50                  55                  60

Arg Phe Thr Ile Ser Arg Thr Ser Thr Thr Val Asp Leu Lys Ala Thr
65                  70                  75                  80

Ser Leu Thr Thr Glu Asp Thr Ala Thr Tyr Phe Cys Ala Arg Gly Gly
                85                  90                  95

Ser Trp Asp Gly Phe Asn Ile Trp Gly Pro Gly Thr Leu Val Thr Val
            100                 105                 110

Ser Ser

<210> SEQ ID NO 267
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 267

Asp Val Val Met Thr Gln Thr Pro Ser Ser Val Ser Ala Ala Val Gly
```

-continued

```
               1               5                  10                 15
            Gly Thr Val Thr Ile Asn Cys Gln Ser Ser Gln Ser Val Tyr Asn Ser
                           20                 25                 30

Asp Phe Leu Ala Trp Tyr Gln Gln Lys Pro Gly Gln Pro Pro Lys Leu
                           35                 40                 45

Leu Ile Tyr Ala Ala Ser Thr Leu Ala Ser Gly Val Pro Ser Arg Phe
                50                 55                 60

Lys Gly Ser Gly Ser Gly Thr Gln Phe Thr Leu Thr Ile Ser Asp Leu
            65                 70                 75                 80

Glu Cys Asp Asp Ala Ala Thr Tyr Tyr Cys Gln Gly Thr Tyr Glu Asp
                           85                 90                 95

Val Gly Trp Phe Asn Asp Phe Gly Gly Thr Glu Val Val Val Lys
                          100                105                110

<210> SEQ ID NO 268
<211> LENGTH: 128
<212> TYPE: PRT
<213> ORGANISM: Artificial Sequence
<220> FEATURE:
<223> OTHER INFORMATION: an artificially synthesized sequence

<400> SEQUENCE: 268

Gln Glu Gln Leu Val Glu Ser Gly Gly Gly Leu Val Gln Pro Gly Ala
            1               5                  10                 15

Ser Leu Thr Leu Thr Cys Lys Ala Ser Gly Phe Asp Phe Thr Ser Asn
                           20                 25                 30

Ala Met Cys Trp Val Arg Gln Ala Pro Gly Lys Gly Pro Glu Trp Ile
                           35                 40                 45

Ala Cys Ile Tyr Asn Asp Asp Gly Ser Ala Tyr Ser Ala Ser Trp Ala
                50                 55                 60

Lys Gly Arg Phe Thr Val Ser Lys Thr Ser Ser Thr Ala Val Thr Leu
            65                 70                 75                 80

Gln Val Thr Gly Leu Thr Ala Ala Asp Thr Ala Thr Tyr Phe Cys Ala
                           85                 90                 95

Arg Ser Pro Tyr Tyr Thr Tyr Gly Gly Ala Pro Ser Ala Tyr Ala Ser
                          100                105                110

Gly Tyr Phe Asn Leu Trp Gly Pro Gly Thr Leu Val Thr Val Ser Ser
                          115                120                125

<210> SEQ ID NO 269
<211> LENGTH: 113
<212> TYPE: PRT
<213> ORGANISM: Artificial Sequence
<220> FEATURE:
<223> OTHER INFORMATION: an artificially synthesized sequence

<400> SEQUENCE: 269

Ala Asp Ile Val Met Thr Gln Thr Pro Ala Ser Val Glu Ala Ala Val
            1               5                  10                 15

Gly Gly Thr Val Thr Ile Lys Cys Gln Ala Ser Glu Asn Ile Tyr Asn
                           20                 25                 30

Ser Leu Ala Trp Tyr Gln Gln Lys Pro Gly Gln Pro Pro Lys Leu Leu
                           35                 40                 45

Met His Asp Ala Ser Val Leu Thr Ser Gly Val Pro Ser Arg Phe Ser
                50                 55                 60

Gly Ser Gly Tyr Gly Thr Glu Phe Thr Leu Thr Ile Ser Asp Leu Glu
            65                 70                 75                 80
```

-continued

Cys Ala Asp Ala Ala Thr Tyr Tyr Cys Gln Ser Asp Tyr Tyr Ser Thr
            85                  90                  95

Gly Gly Ser Tyr Gly Phe Ala Phe Gly Gly Thr Glu Val Val Val
        100                 105                 110

Lys

<210> SEQ ID NO 270
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 270

Gln Glu Gln Leu Val Glu Ser Gly Gly Leu Val Gln Pro Gly Ala
1               5                   10                  15

Ser Leu Thr Leu Thr Cys Lys Ala Ser Gly Phe Ser Phe Asn Thr Ser
                20                  25                  30

Tyr Cys Pro Cys Trp Val Arg Gln Val Pro Gly Lys Gly Pro Glu Trp
            35                  40                  45

Ile Ala Cys Ile Asp Ala Gly Tyr Ser Gly Ala Thr Trp Tyr Ala Asn
50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Gly Ala Asp Thr Ala Thr Tyr Phe
                85                  90                  95

Cys Val Arg Cys Asp Ala Ala Gly Ser Gly Ala Phe Asn Leu Trp Gly
            100                 105                 110

Pro Gly Thr Leu Val Thr Val Ser Ser
        115                 120

<210> SEQ ID NO 271
<211> LENGTH: 110
<212> TYPE: PRT
<213> ORGANISM: Artificial Sequence
<220> FEATURE:
<223> OTHER INFORMATION: an artificially synthesized sequence

<400> SEQUENCE: 271

Ala Tyr Asp Met Thr Gln Thr Pro Ala Ser Val Glu Val Pro Val Gly
1               5                   10                  15

Gly Thr Val Thr Ile Lys Cys Gln Ala Ser Gln Ser Ile Tyr Ser Tyr
                20                  25                  30

Leu Ser Trp Tyr Gln Gln Lys Pro Gly Gln Pro Pro Lys Leu Leu Ile
            35                  40                  45

Tyr Glu Ala Ser Lys Leu Thr Ser Gly Val Pro Ser Arg Phe Ser Gly
50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Gln Gly Ser Gly Tyr Met Asp
                85                  90                  95

Val Asp Asn Val Phe Gly Gly Gly Thr Glu Val Val Val Lys
            100                 105                 110

<210> SEQ ID NO 272
<211> LENGTH: 123
<212> TYPE: PRT
<213> ORGANISM: Artificial Sequence
<220> FEATURE:

<223> OTHER INFORMATION: an artificially synthesized sequence

<400> SEQUENCE: 272

| | | | | | | | | | | | | | | |
|---|---|---|---|---|---|---|---|---|---|---|---|---|---|---|
|Gln|Glu|Gln|Leu|Val|Glu|Ser|Gly|Gly|Gly|Leu|Val|Gln|Pro|Glu|Gly|
|1| | | |5| | | | |10| | | | |15| |

Ser Leu Thr Leu Thr Cys Thr Ala Ser Gly Phe Ser Phe Ser Ser
          20                   25                  30

Gly Tyr Met Cys Trp Val Arg Gln Ala Pro Gly Lys Gly Leu Glu Trp
            35                  40                  45

Ile Ala Cys Ile Ser Gly Gly Ser Ser Gly Asp Thr Asp Tyr Ala Asn
 50                  55                  60

Trp Ala Lys Gly Arg Phe Ser Ile Ser Lys Thr Ser Thr Thr Val
65                  70                  75                  80

Thr Leu Gln Met Thr Ser Leu Thr Val Ala Asp Thr Ala Thr Tyr Phe
                85                  90                  95

Cys Ala Arg Asp Val Tyr Ile Asp Ser Thr Ile Phe Asn Phe Asn Leu
            100                 105                 110

Trp Gly Pro Gly Thr Leu Val Thr Val Ser Ser
        115                 120

<210> SEQ ID NO 273
<211> LENGTH: 111
<212> TYPE: PRT
<213> ORGANISM: Artificial Sequence
<220> FEATURE:
<223> OTHER INFORMATION: an artificially synthesized sequence

<400> SEQUENCE: 273

Gln Val Leu Thr Gln Thr Pro Ser Pro Val Ser Ala Ala Val Gly Gly
1               5                   10                  15

Thr Val Thr Ile Ser Cys Gln Ala Ser Gln Ser Val Tyr Asn Asn Asn
            20                  25                  30

Asn Leu Ala Trp Tyr Gln Gln Lys Pro Gly Gln Pro Pro Lys Leu Leu
        35                  40                  45

Ile Tyr Ala Ala Ser Ser Leu Ala Ser Gly Val Pro Ser Arg Phe Lys
 50                 55                  60

Gly Ser Gly Ala Gly Thr Gln Phe Thr Leu Thr Ile Ser Asp Leu Glu
65                  70                  75                  80

Cys Asp Asp Ala Ala Thr Tyr Tyr Cys Gln Gly Thr Tyr Tyr Ser Ser
                85                  90                  95

Gly Trp Tyr Ser Thr Phe Gly Gly Gly Thr Glu Val Val Val Lys
            100                 105                 110

<210> SEQ ID NO 274
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 274

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser
          20                  25                  30

Tyr Asp Met Cys Trp Val Arg Gln Ala Pro Gly Lys Gly Pro Glu Trp
            35                  40                  45

Ile Ala Cys Ile Tyr Thr Gly Asp Gly Ser Thr Asp Tyr Ala Ser Trp

```
                     50                  55                  60
Ala Lys Gly Arg Phe Thr Val Ser Lys Ala Ser Ser Thr Thr Val Thr
 65                  70                  75                  80

Leu Gln Met Thr Ser Leu Ala Val Ala Asp Thr Ala Thr Tyr Phe Cys
                 85                  90                  95

Ala Arg Asn Ser Gly Tyr Gly Tyr Phe Gly Leu Trp Gly Pro Gly Thr
            100                 105                 110

Leu Val Thr Val Ser Ser
            115

<210> SEQ ID NO 275
<211> LENGTH: 109
<212> TYPE: PRT
<213> ORGANISM: Artificial Sequence
<220> FEATURE:
<223> OTHER INFORMATION: an artificially synthesized sequence

<400> SEQUENCE: 275

Gln Val Leu Thr Gln Thr Pro Ser Pro Val Ser Ala Ala Val Gly Gly
  1               5                  10                  15

Thr Val Thr Ile Ser Cys Gln Ser Thr Glu Ser Val Tyr Gly Ser Asp
                 20                  25                  30

Trp Leu Ser Trp Tyr Gln Gln Lys Pro Gly Gln Pro Pro Lys Val Leu
             35                  40                  45

Ile Tyr Gln Ala Ser Asn Leu Glu Ile Gly Val Pro Ser Arg Phe Lys
         50                  55                  60

Gly Ser Gly Ser Gly Thr Gln Phe Thr Leu Thr Ile Ser Gly Ala Gln
 65                  70                  75                  80

Cys Asp Asp Ala Ala Thr Tyr Tyr Cys Gln Gly Tyr Tyr Ser Gly Tyr
                 85                  90                  95

Ile Tyr Ala Phe Gly Gly Gly Thr Glu Val Val Val Lys
            100                 105

<210> SEQ ID NO 276
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 276

Asn Tyr Gly Val Ser
  1               5

<210> SEQ ID NO 277
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 277

Tyr Ile Asp Pro Ala Phe Gly Arg Thr Tyr Tyr Ala Ser Trp Val Asn
  1               5                  10                  15

Gly

<210> SEQ ID NO 278
<211> LENGTH: 15
<212> TYPE: PRT
<213> ORGANISM: Artificial Sequence
<220> FEATURE:
```

<223> OTHER INFORMATION: an artificially synthesized sequence

<400> SEQUENCE: 278

Val Ala Leu Val Val Ala Gly Val Ala Tyr Tyr Gly Met Asp Val
1               5                   10                  15

<210> SEQ ID NO 279
<211> LENGTH: 11
<212> TYPE: PRT
<213> ORGANISM: Artificial Sequence
<220> FEATURE:
<223> OTHER INFORMATION: an artificially synthesized sequence

<400> SEQUENCE: 279

Gln Ala Ser Gln Asn Ile Tyr Ser Tyr Leu Ser
1               5                   10

<210> SEQ ID NO 280
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 280

Arg Thr Ser Thr Leu Ala Ser
1               5

<210> SEQ ID NO 281
<211> LENGTH: 15
<212> TYPE: PRT
<213> ORGANISM: Artificial Sequence
<220> FEATURE:
<223> OTHER INFORMATION: an artificially synthesized sequence

<400> SEQUENCE: 281

Gln Ser Tyr Tyr Tyr Ser Ser Gly Ser Ser Tyr Gly Ala Phe Ala
1               5                   10                  15

<210> SEQ ID NO 282
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 282

Ser Ser Tyr Asp Met Cys
1               5

<210> SEQ ID NO 283
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 283

Cys Ile Tyr Thr Gly Asp Gly Ser Thr Asp Tyr Ala Ser Trp Ala Lys
1               5                   10                  15

Gly

<210> SEQ ID NO 284
<211> LENGTH: 9
<212> TYPE: PRT
<213> ORGANISM: Artificial Sequence

```
<220> FEATURE:
<223> OTHER INFORMATION: an artificially synthesized sequence

<400> SEQUENCE: 284

Asn Ser Gly Tyr Gly Tyr Phe Gly Leu
1               5

<210> SEQ ID NO 285
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 285

Ser Asn Ala Met Cys
1               5

<210> SEQ ID NO 286
<211> LENGTH: 17
<212> TYPE: PRT
<213> ORGANISM: Artificial Sequence
<220> FEATURE:
<223> OTHER INFORMATION: an artificially synthesized sequence

<400> SEQUENCE: 286

Cys Ile Tyr Asn Asp Asp Gly Ser Ala Tyr Ser Ala Ser Trp Ala Lys
1               5                   10                  15

Gly

<210> SEQ ID NO 287
<211> LENGTH: 20
<212> TYPE: PRT
<213> ORGANISM: Artificial Sequence
<220> FEATURE:
<223> OTHER INFORMATION: an artificially synthesized sequence

<400> SEQUENCE: 287

Ser Pro Tyr Tyr Thr Tyr Gly Gly Ala Pro Ser Ala Tyr Ala Ser Gly
1               5                   10                  15

Tyr Phe Asn Leu
            20

<210> SEQ ID NO 288
<211> LENGTH: 11
<212> TYPE: PRT
<213> ORGANISM: Artificial Sequence
<220> FEATURE:
<223> OTHER INFORMATION: an artificially synthesized sequence

<400> SEQUENCE: 288

Gln Ala Ser Glu Asn Ile Tyr Asn Ser Leu Ala
1               5                   10

<210> SEQ ID NO 289
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 289

Asp Ala Ser Val Leu Thr Ser
1               5
```

```
<210> SEQ ID NO 290
<211> LENGTH: 14
<212> TYPE: PRT
<213> ORGANISM: Artificial Sequence
<220> FEATURE:
<223> OTHER INFORMATION: an artificially synthesized sequence

<400> SEQUENCE: 290

Gln Ser Asp Tyr Tyr Ser Thr Gly Gly Ser Tyr Gly Phe Ala
1               5                   10

<210> SEQ ID NO 291
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 291

Ser Ser Gly Tyr Met Cys
1               5

<210> SEQ ID NO 292
<211> LENGTH: 18
<212> TYPE: PRT
<213> ORGANISM: Artificial Sequence
<220> FEATURE:
<223> OTHER INFORMATION: an artificially synthesized sequence

<400> SEQUENCE: 292

Cys Ile Ser Gly Gly Ser Ser Gly Asp Thr Asp Tyr Ala Asn Trp Ala
1               5                   10                  15

Lys Gly

<210> SEQ ID NO 293
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 293

Asp Val Tyr Ile Asp Ser Thr Ile Phe Asn Phe Asn Leu
1               5                   10

<210> SEQ ID NO 294
<211> LENGTH: 13
<212> TYPE: PRT
<213> ORGANISM: Artificial Sequence
<220> FEATURE:
<223> OTHER INFORMATION: an artificially synthesized sequence

<400> SEQUENCE: 294

Gln Ala Ser Gln Ser Val Tyr Asn Asn Asn Leu Ala
1               5                   10

<210> SEQ ID NO 295
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 295

Ala Ala Ser Ser Leu Ala Ser
1               5
```

<210> SEQ ID NO 296
<211> LENGTH: 12
<212> TYPE: PRT
<213> ORGANISM: Artificial Sequence
<220> FEATURE:
<223> OTHER INFORMATION: an artificially synthesized sequence

<400> SEQUENCE: 296

Gln Gly Thr Tyr Tyr Ser Ser Gly Trp Tyr Ser Thr
1               5                   10

<210> SEQ ID NO 297
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 297

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
                20                  25                  30

Tyr Asp Met Gly Trp Val Arg Gln Ala Pro Gly Gln Gly Leu Glu Trp
            35                  40                  45

Met Gly Thr Ile Tyr Thr Gly Asp Tyr Ser Thr Asp Tyr Ala Ser Trp
    50                  55                  60

Ala Lys Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Asn Thr Gly Tyr Gly Tyr Phe Gly Leu Trp Gly Gln Gly
            100                 105                 110

Thr Leu Val Thr Val Ser Ser
        115

<210> SEQ ID NO 298
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 298

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
                20                  25                  30

Tyr Asp Met Gly Trp Val Arg Gln Ala Pro Gly Gln Gly Leu Glu Trp
            35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser

115

<210> SEQ ID NO 299
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 299

Gln Val Thr Leu Arg Glu Ser Gly Pro Ala Leu Val Lys Pro Thr Gln
1               5                   10                  15

Thr Leu Thr Leu Thr Cys Ala Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
            115

<210> SEQ ID NO 300
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 300

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Tyr Asp Met Gly Trp Val Arg Gln Ala Pro Gly Gln Gly Leu Glu Trp
        35                  40                  45

Met Gly Thr Ile Tyr Thr Gly Asp Tyr Ser Thr Asp Tyr Ala Ser Trp
    50                  55                  60

Ala Lys Gly Arg Val Thr Ile Ser Val Asp Ser Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
            115

<210> SEQ ID NO 301
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 301

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
                20                  25                  30

Tyr Asp Met Gly Trp Val Arg Gln Ala Pro Gly Gln Gly Leu Glu Trp
            35                  40                  45

Met Gly Thr Ile Tyr Thr Gly Asp Tyr Ser Asp Tyr Ala Ser Trp
        50                  55                  60

Ala Lys Gly Arg Val Thr Ile Ser Val Asp Lys Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Thr Gly Tyr Gly Tyr Phe Gly Leu Trp Gly Gln Gly
            100                 105                 110

Thr Leu Val Thr Val Ser Ser
            115

<210> SEQ ID NO 302
<211> LENGTH: 110
<212> TYPE: PRT
<213> ORGANISM: Artificial Sequence
<220> FEATURE:
<223> OTHER INFORMATION: an artificially synthesized sequence

<400> SEQUENCE: 302

Asp Ile Gln Leu Thr Gln Ser Pro Ser Phe Leu Ser Ala Ser Val Gly
1               5                   10                  15

Asp Arg Val Thr Ile Thr Cys Gln Ser Thr Glu Ser Val Tyr Gly Ser
                20                  25                  30

Asp Trp Leu Ser Trp Tyr Gln Gln Lys Pro Gly Gln Pro Pro Lys Leu
            35                  40                  45

Leu Ile Tyr Gln Ala Ser Asn Leu Glu Ile Gly Val Pro Ser Arg Phe
        50                  55                  60

Ser Gly Ser Gly Ser Gly Thr Asp Phe Thr Leu Thr Ile Asn Ser Leu
65                  70                  75                  80

Glu Ala Glu Asp Ala Ala Thr Tyr Tyr Cys Gln Gly Tyr Tyr Ser Gly
                85                  90                  95

Tyr Ser Tyr Ala Phe Gly Gly Gly Thr Lys Val Glu Ile Lys
            100                 105                 110

<210> SEQ ID NO 303
<211> LENGTH: 9
<212> TYPE: PRT
<213> ORGANISM: Artificial Sequence
<220> FEATURE:
<223> OTHER INFORMATION: an artificially synthesized sequence

<400> SEQUENCE: 303

Asn Thr Gly Tyr Gly Tyr Phe Gly Leu
1               5

<210> SEQ ID NO 304
<211> LENGTH: 10
<212> TYPE: PRT
<213> ORGANISM: Artificial Sequence
<220> FEATURE:
<223> OTHER INFORMATION: an artificially synthesized sequence

<400> SEQUENCE: 304

```
Gln Gly Tyr Tyr Ser Gly Tyr Ser Tyr Ala
1               5                   10
```

<210> SEQ ID NO 305
<211> LENGTH: 121
<212> TYPE: PRT
<213> ORGANISM: Artificial Sequence
<220> FEATURE:
<223> OTHER INFORMATION: an artificially synthesized sequence

<400> SEQUENCE: 305

```
Gln Val Gln Leu Gln Gln Ser Gly Ala Asp Leu Val Arg Pro Gly Thr
1               5                   10                  15

Ser Val Lys Val Ser Cys Lys Ala Ser Gly Tyr Ala Phe Thr Asn Tyr
                20                  25                  30

Leu Ile Glu Trp Ile Lys Gln Arg Pro Gly Gln Gly Leu Glu Trp Ile
            35                  40                  45

Gly Val Met Asn Pro Gly Ser Gly Gly Thr His Tyr Ser Glu Lys Phe
        50                  55                  60

Arg Gly Lys Ala Thr Leu Thr Ala Asp Lys Ser Ser Ser Thr Ala Tyr
65                  70                  75                  80

Met Gln Leu Ile Ser Leu Thr Ser Asp Asp Ser Ala Val Tyr Phe Cys
                85                  90                  95

Ala Arg Ser Asp Tyr Asp Tyr Val Thr Tyr Ala Met Asp Tyr Trp Gly
                100                 105                 110

Gln Gly Thr Ser Val Thr Val Ser Ser
            115                 120
```

<210> SEQ ID NO 306
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 306

```
Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Thr Phe Thr Asp Tyr
                20                  25                  30

Tyr Met Lys Trp Val Lys Gln Ser His Gly Lys Ser Leu Glu Trp Ile
            35                  40                  45

Gly Asp Ile Asn Pro Asn Asn Gly Asp Thr Phe Tyr Asn Gln Lys Phe
        50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Asp Gly Asn Tyr Ala Tyr Phe Asp Tyr Trp Gly Gln Gly Thr
                100                 105                 110

Thr Leu Thr Val Ser Ser
            115
```

<210> SEQ ID NO 307
<211> LENGTH: 119
<212> TYPE: PRT
<213> ORGANISM: Artificial Sequence
<220> FEATURE:
<223> OTHER INFORMATION: an artificially synthesized sequence

<400> SEQUENCE: 307

Gln Val Gln Leu Gln Gln Ser Gly Gly Asp Leu Met Lys Pro Gly Ala
1               5                   10                  15

Ser Val Lys Ile Ser Cys Lys Ala Ala Gly Tyr Thr Phe Ser Asn Tyr
            20                  25                  30

Tyr Ile Glu Trp Val Lys Gln Arg Pro Gly His Gly Leu Glu Trp Ile
        35                  40                  45

Gly Glu Ile Leu Pro Gly Ser Gly Ser Thr Thr Tyr Asn Glu Lys Phe
    50                  55                  60

Lys Gly Lys Ala Ser Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Ala Arg Glu Pro Gly Phe Pro Tyr Trp Gly Gln Gly
            100                 105                 110

Thr Leu Val Thr Val Ser Ala
        115

<210> SEQ ID NO 308
<211> LENGTH: 123
<212> TYPE: PRT
<213> ORGANISM: Artificial Sequence
<220> FEATURE:
<223> OTHER INFORMATION: an artificially synthesized sequence

<400> SEQUENCE: 308

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Ala Leu Ile Arg Asn Lys Ala Asn Gly Tyr Thr Thr Glu Tyr Asn Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Ser Asp Gly Tyr Tyr Glu Tyr Tyr Phe Asp Tyr
            100                 105                 110

Trp Gly Gln Gly Thr Thr Leu Thr Val Ser Ser
        115                 120

<210> SEQ ID NO 309
<211> LENGTH: 123
<212> TYPE: PRT
<213> ORGANISM: Artificial Sequence
<220> FEATURE:
<223> OTHER INFORMATION: an artificially synthesized sequence

<400> SEQUENCE: 309

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Leu Gly Leu Glu Trp Met
        35                  40                  45

Gly Ile Ile Asn Pro Ser Asp Gly Ser Thr Ser Tyr Ala Gln Lys Phe
            50                  55                  60

Gln Gly Arg Val Thr Met Thr Arg Asp Thr Ser Thr Asn Thr Val Tyr
 65                  70                  75                  80

Met Asp Leu Ser Ser Leu Arg Ser Glu Asp Thr Ala Val Tyr Tyr Cys
                 85                  90                  95

Ala Arg Gly Gly Asn Ser Ala Phe Tyr Ser Tyr Tyr Asp Met Asp Val
            100                 105                 110

Trp Gly Gln Gly Thr Thr Val Thr Val Ser Ser
            115                 120

<210> SEQ ID NO 310
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 310

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Ser Gln Phe Ser Leu
 65                  70                  75                  80

Lys Leu Ser Ser Val Thr Ala Ala Asp Thr Ala Val Tyr Tyr Cys Ala
                85                  90                  95

Ser Ile Ala Val Arg Gly Phe Phe Asp Tyr Trp Gly Gln Gly Thr
            100                 105                 110

Leu Val Thr Val Ser Ser
            115

<210> SEQ ID NO 311
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 311

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

-continued

```
Leu Val Thr Val Ser Ser
        115

<210> SEQ ID NO 312
<211> LENGTH: 118
<212> TYPE: PRT
<213> ORGANISM: Artificial Sequence
<220> FEATURE:
<223> OTHER INFORMATION: an artificially synthesized sequence

<400> SEQUENCE: 312

Gln Val Gln Leu Gln Glu Ser Gly Pro Gly Leu Val Lys Pro Ser Glu
1               5                  10                  15

Thr Leu Ser Leu Thr Cys Thr Val Ser Gly Ala Ser Ile Ser Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Ala Val Ala Gly Phe Phe Asp Tyr Trp Gly Gln Gly Thr
            100                 105                 110

Leu Val Thr Val Ser Ser
        115

<210> SEQ ID NO 313
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 313

Asp Ile Lys Met Thr Gln Ser Pro Ser Ser Met Tyr Ala Ser Leu Gly
1               5                  10                  15

Glu Arg Val Thr Ile Thr Cys Lys Ala Ser Gln Asp Ile Asn Ser Tyr
            20                  25                  30

Leu Ile Trp Phe Gln Gln Lys Pro Gly Lys Ser Pro Lys Thr Leu Ile
        35                  40                  45

Tyr Arg Thr Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Gly Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105

<210> SEQ ID NO 314
<211> LENGTH: 111
<212> TYPE: PRT
<213> ORGANISM: Artificial Sequence
<220> FEATURE:
<223> OTHER INFORMATION: an artificially synthesized sequence

<400> SEQUENCE: 314
```

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Phe Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

His Leu Pro Trp Thr Phe Gly Gly Gly Thr Lys Leu Glu Ile Lys
            100                 105                 110

<210> SEQ ID NO 315
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 315

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105

<210> SEQ ID NO 316
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 316

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Asp Tyr
            20                  25                  30

Leu Ser Trp Leu Gln Gln Lys Pro Asp Gly Thr Ile Lys Arg Leu Ile
        35                  40                  45

Phe Ala Ala Ser Thr Leu Asp Ser Gly Val Pro Lys Arg Phe Ser Gly
    50                  55                  60

Ser Arg Ser Gly Ser Asp Phe Ser Leu Ser Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95
```

```
Thr Phe Gly Ser Gly Thr Lys Leu Glu Ile Lys
            100                 105
```

<210> SEQ ID NO 317
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 317

```
Asp Val Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val Tyr Arg
            20                  25                  30

Asp Gly Asn Thr Tyr Leu Ser Trp Phe Gln Gln Arg Pro Gly Gln Ser
        35                  40                  45

Pro Arg Arg Leu Ile Tyr Lys Val Ser Asn Trp Gln Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Val Glu Ile Lys
            100                 105                 110
```

<210> SEQ ID NO 318
<211> LENGTH: 108
<212> TYPE: PRT
<213> ORGANISM: Artificial Sequence
<220> FEATURE:
<223> OTHER INFORMATION: an artificially synthesized sequence

<400> SEQUENCE: 318

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Leu Thr Phe Gly Gly Gly Thr Lys Val Glu Ile Lys
            100                 105
```

<210> SEQ ID NO 319
<211> LENGTH: 108
<212> TYPE: PRT
<213> ORGANISM: Artificial Sequence
<220> FEATURE:
<223> OTHER INFORMATION: an artificially synthesized sequence

<400> SEQUENCE: 319

```
Glu Ile Val Leu Thr Gln Ser Pro Gly Thr Leu Ser Leu Ser Pro Gly
1               5                   10                  15
```

-continued

```
Glu Arg Val Thr Leu Ser Cys Arg Ala Ser Gln Arg Val Asn Asn Asn
             20                  25                  30

Tyr Leu Ala Trp Tyr Gln Gln Arg Pro Gly Gln Ala Pro Arg Leu Leu
         35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65              70                  75                  80

Pro Glu Asp Phe Ala Val Tyr Tyr Cys Gln Gln Tyr Asp Arg Ser Pro
                 85                  90                  95

Leu Thr Phe Gly Gly Gly Thr Lys Leu Glu Ile Lys
            100                 105

<210> SEQ ID NO 320
<211> LENGTH: 108
<212> TYPE: PRT
<213> ORGANISM: Artificial Sequence
<220> FEATURE:
<223> OTHER INFORMATION: an artificially synthesized sequence

<400> SEQUENCE: 320

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Asn Lys Asn
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65              70                  75                  80

Pro Glu Asp Phe Ala Val Tyr Tyr Cys Gln Gln Tyr Asp Arg Ser Pro
                 85                  90                  95

Leu Thr Phe Gly Gly Gly Thr Lys Val Glu Ile Lys
            100                 105
```

CD3-TARGETING AND DLL3-TARGETING MULTISPECIFIC ANTIGEN-BINDING MOLECULES AND USES THEREOF

CROSS-REFERENCE TO RELATED APPLICATION

This application claims priority to Japanese Application No. 2020-062326, filed on Mar. 31, 2020.

SEQUENCE LISTING

This application contains a Sequence Listing that has been submitted electronically as an ASCII text file named SequenceListing.txt. The ASCII text file, created on Mar. 29, 2021, is 307 kilobytes in size. The material in the ASCII text file is hereby incorporated by reference in its entirety.

TECHNICAL FIELD

The present invention relates to multispecific antigen-binding molecules that comprise a first antigen-binding moiety and a second antigen-binding moiety, each of which is capable of binding to CD3 and CD137, but does not bind to CD3 and CD137 at the same time; and a third antigen-binding moiety that is capable of binding to DLL3. The invention also relates to nucleic acids encoding such antigen-binding molecules; to methods for preparing such antigen-binding molecules; to host cells expressing or capable of expressing such antigen-binding molecules; to compositions comprising such antigen-binding molecules; to uses of such antigen-binding molecules or such compositions, in particular for therapeutic purposes in the field of cancer diseases.

BACKGROUND ART

Cancer is one of the leading causes of death worldwide. With the exception of certain carcinomas, tumors are often inoperable when they are found. Conventional cancer treatments include radiation therapy, chemotherapy, and immunotherapy. These treatments are often not effective enough and eventually cancer recurrence or metastasis occurs after the treatment. Lack of tumor specificity is one of the factors that limit the maximum efficacy; therefore, more tumor-specific molecular targeted therapy has become an additional viable option in cancer treatment.

Antibodies are drawing attention as pharmaceuticals since they are highly stable in plasma and have few side effects. Among multiple therapeutic antibodies, some types of antibodies require effector cells to exert an anti-tumor response. Antibody dependent cell-mediated cytotoxicity (ADCC) is a cytotoxicity exhibited by effector cells against antibody-bound cells via binding of the Fc region of the antibody to Fc receptors present on NK cells and macrophages. To date, multiple therapeutic antibodies that can induce ADCC to exert anti-tumor efficacy have been developed as pharmaceuticals for treating cancer (Non-patent Literature 1). Therapies targeting tumor-specific expressed antigens using conventional therapeutic antibodies show excellent anti-tumor activities, while administration of such antibodies could not always lead to satisfactory outcomes.

In addition to the antibodies that adopt ADCC by recruiting NK cells or macrophages as effector cells, T cell-recruiting antibodies (TR antibodies) that adopt cytotoxicity by recruiting T cells as effector cells have been known since the 1980s (Non-patent Literatures 2 to 4). A TR antibody is a bispecific antibody that recognizes and binds to any one of the subunits forming a T-cell receptor complex on T-cells, in particular the CD3 epsilon chain, and an antigen on cancer cells. Several TR antibodies are currently being developed. Catumaxomab, which is a TR antibody against EpCAM, has been approved in the EU for the treatment of malignant ascites. Furthermore, a type of TR antibody called "bispecific T-cell engager (BiTE)" has been recently found to exhibit a strong anti-tumor activity (Non-patent Literatures 5 and 6). Blinatumomab, which is a BiTE molecule against CD19, received FDA approval first in 2014. Blinatumomab has been proved to exhibit a much stronger cytotoxic activity against CD19/CD20-positive cancer cells in vitro compared with Rituximab, which induces antibody-dependent cell-mediated cytotoxicity (ADCC) and complement-dependent cytotoxicity (CDC) (Non-patent Literature 7).

However, it is known that a trifunctional antibody binds to both a T-cell and a cell such as an NK cell or macrophage at the same time in a cancer antigen-independent manner, and as a result receptors expressed on the cells are cross-linked, and expression of various cytokines is induced in a cancer antigen-independent manner. Systemic administration of a trifunctional antibody is thought to cause cytokine storm-like side effects as a result of such induction of cytokine expression. In fact, it has been reported that, in the phase I clinical trial, a very low dose of 5 micro g/body was the maximum tolerance dose for systemic administration of catumaxomab to patients with non-small cell lung cancer, and that administration of a higher dose causes various severe side effects (Non-patent Literature 8). When administered at such a low dose, catumaxomab can never reach the effective blood level. That is, the expected anti-tumor effect cannot be achieved by administrating catumaxomab at such a low dose.

Meanwhile, unlike catumaxomab, BiTE has no Fc gamma receptor-binding site, and therefore it does not cross-link the receptors expressed on T-cells and cells such as NK cells and macrophages in a cancer antigen-independent manner. Thus, it has been demonstrated that BiTE does not cause cancer antigen-independent cytokine induction which is observed when catumaxomab is administered. However, since BiTE is a modified low-molecular-weight antibody molecule without an Fc region, the problem is that its blood half-life after administration to a patient is significantly shorter than IgG-type antibodies conventionally used as therapeutic antibodies. In fact, the blood half-life of BiTE administered in vivo has been reported to be about several hours (Non-patent Literatures 9 and 10). In the clinical trials of blinatumomab, it is administered by continuous intravenous infusion using a mini pump. This administration method is not only extremely inconvenient for patients but also has the potential risk of medical accidents due to device malfunction or the like. Thus, it cannot be said that such an administration method is desirable.

Delta-like 3 (DLL3) is a type I membrane protein belonging to Notch ligand family members. DLL3 is necessary for normal somite formation and patterning. Mutations in DLL3 cause rib defects or spondylolysis in autosomal recessive spondylocostal dysostosis patients (Non-patent Literatures 11 and 12). There exist previous studies reporting the amplification of the DLL3 gene on chromosome and increased expression of this gene in cancer cell lines (Non-patent Literature 13) and increased DLL3 expression in some glioma cases (Non-patent Literature 14). In addition, DLL3 has been proposed previously in methods to diagnose and treat glioma, in addition to SCLC, using an ADCC enhanced antibody, antibody-drug conjugate (ADC), and T cell-engaging bispecific molecule using BiTE-Fc format (Patent Literatures 1, 2, and 3).

CITATION LIST

Patent Literature

[Patent Literature 1] WO 2011/093097
[Patent Literature 2] WO 2013/126746
[Patent Literature 3] WO 2017/021349

Non-Patent Literature

[Non-patent Literature 1] Clin Cancer Res. 2010 Jan. 1; 16(1):11-20.
[Non-patent Literature 2] Nature. 1985 Apr. 18-24; 314 (6012):628-31.
[Non-patent Literature 3] Int J Cancer. 1988 Apr. 15; 41(4): 609-15.
[Non-patent Literature 4] Proc Natl Acad Sci USA. 1986 March; 83(5):1453-7.
[Non-patent Literature 5] Proc Natl Acad Sci USA. 1995 Jul. 18; 92(15):7021-5.
[Non-patent Literature 6] Drug Discov Today. 2005 Sep. 15; 10(18):1237-44.
[Non-patent Literature 7] Int J Cancer. 2002 Aug. 20; 100(6):690-7.
[Non-patent Literature 8] Cancer Immunol Immunother (2007) 56 (10), 1637-44
[Non-patent Literature 9] Cancer Immunol Immunother. (2006) 55 (5), 503-14
[Non-patent Literature 10] Cancer Immunol Immunother. (2009) 58 (1), 95-109
[Non-patent Literature 11] Bulman, M. P. et al. (2000) Nat Genet 24, 438-441.
[Non-patent Literature 12] Tumpenny, P. D. et al. (2003) J Med Genet 40, 333-339.
[Non-patent Literature 13] Phillips, H. S. (2006) Cancer Cell 9, 157-173.
[Non-patent Literature 14] Mulledndore, M. E. (2009) Clin Cancer Res 15, 2291-2301.

SUMMARY OF INVENTION

Technical Problem

An objective of the present invention is to provide multispecific antigen-binding molecules that enable cancer treatment by recruiting T cells close to DLL3-expressing cells and using the cytotoxicity of T cells against DLL3-expressing cancer cells, methods for producing the multispecific antigen-binding molecules, and therapeutic agents comprising such a multispecific antigen-binding molecule as an active ingredient for inducing cellular cytotoxicity. Another objective of the present invention is to provide pharmaceutical compositions for use in treating or preventing various cancers, which comprise one of the above-mentioned antigen-binding molecules as an active ingredient, and therapeutic methods using the pharmaceutical compositions.

Solution to Problem

The present invention relates to multispecific antigen-binding molecules that comprise a first antigen-binding moiety and a second antigen-binding moiety, each of which is capable of binding to CD3 and CD137, but does not bind to CD3 and CD137 at the same time (i.e. capable of binding to CD3 and CD137 but not simultaneously); and a third antigen-binding moiety that is capable of binding to DLL3, preferably human DLL3, which induce T-cell dependent cytotoxicity more efficiently whilst circumventing adverse toxicity concerns or side effects that other multispecific antigen-binding molecules may have. The present invention provides multispecific antigen-binding molecules and pharmaceutical compositions that can treat various cancers, especially those associated with DLL3 such as DLL3-positive tumors, by comprising the antigen-binding molecule as an active ingredient.

In one aspect, the multispecific antigen-binding molecule of the present invention have very unique structure format(s), which improve or enhance the efficacy of the multispecific antigen-binding molecules. The new antigen-binding molecules with unique structure formats provide the increased number of antigen-binding domains to give the increased valency and/or specificities to respective antigens on effector cells and target cells with the reduced unwanted adverse effects.

In one particular aspect, the present invention relates to multispecific antigen-binding molecules that comprise a first antigen-binding moiety and a second antigen-binding moiety, each of which is capable of binding to CD3 and CD137, but does not bind to CD3 and CD137 at the same time (i.e. capable of binding to CD3 and CD137 but not simultaneously); and a third antigen-binding moiety that is capable of binding to DLL3, preferably human DLL3, which induce T-cell dependent cytotoxicity efficiently whilst circumventing adverse toxicity concerns or side effects which other multispecific antigen-binding molecules may have. In one such aspect, each of the first and second antigen-binding moieties comprises at least one amino acid mutation(s) e.g. cysteine insertion/substitution/mutation which create a disulfide linkage between the first and second antigen-binding moieties to hold them close to each other, and, for example, promote cis-antigen binding to antigen (CD3 and/or CD137) on the same single effector cell as a result of steric hindrance or shorter distance between the two Dual-Fabs, thereby improving the safety profile of the trispecific Ab by preventing undesirable crosslinking of two CD3/CD137-expressing immune cells mediated by the two Dual-Fabs in an DLL3-independent manner. In one specific aspect, said each of the first antigen-binding moiety and the second antigen-binding moiety is a Fab and comprises at least one cysteine residue (via mutation, substitution, or insertion) in the CH1 region, said at least one cysteine residue is capable of forming at least one disulfide bond between the CH1 region of the first antigen-binding moiety and the CH1 region of the second antigen-binding moiety. In another specific aspect, said each of the first antigen-binding moiety and the second antigen-binding moiety comprises one cysteine residue (via mutation, substitution, or insertion) at position 191 according to EU numbering in the CH1 region which is capable of forming one disulfide bond between the CH1 region of the first antigen-binding moiety and the CH1 region of the second antigen-binding moiety.

The antigen-binding molecules having such unique structure formats were surprisingly found to show superior efficacy compared to other multispecific antibody formats (e.g. BiTE) while exhibiting reduced or minimal off-target side-effects attributed by undesired cross-linking among different cells (e.g., effector cells such as T cells).

More specifically, the present disclosure provides the following:

[1] A multispecific antigen-binding molecule comprising:
a first antigen-binding moiety and a second antigen-binding moiety, each of which is capable of binding to CD3 and CD137, but does not bind to CD3 and CD137 at the same time; and
a third antigen-binding moiety that is capable of binding to a third antigen, preferably an antigen expressed on a cancer cell/tissue.

[1A] A multispecific antigen-binding molecule comprising:
a first antigen-binding moiety and a second antigen-binding moiety, each of which is capable of binding to CD3 and CD137, but does not bind to CD3 and CD137 at the same time; and
a third antigen-binding moiety that is capable of binding to DLL3, preferably human DLL3.

[2] The multispecific antigen-binding molecule of any one of [1] to [1A], wherein the first antigen-binding moiety and the second antigen-binding moiety each comprises an antibody variable region comprising any one of (a1) to (a17) below:
- (a1) the heavy chain complementarity determining region (CDR) 1 of SEQ ID NO: 17, the heavy chain CDR 2 of SEQ ID NO: 31, the heavy chain CDR 3 of SEQ ID NO: 45, the light chain CDR 1 of SEQ ID NO: 64, the light chain CDR 2 of SEQ ID NO: 69 and the light chain CDR 3 of SEQ ID NO: 74;
- (a2) the heavy chain complementarity determining region (CDR) 1 of SEQ ID NO: 18, the heavy chain CDR 2 of SEQ ID NO: 32, the heavy chain CDR 3 of SEQ ID NO: 46, the light chain CDR 1 of SEQ ID NO: 63, the light chain CDR 2 of SEQ ID NO: 68 and the light chain CDR 3 of SEQ ID NO: 73;
- (a3) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 63, the light chain CDR 2 of SEQ ID NO: 68 and the light chain CDR 3 of SEQ ID NO: 73;
- (a4) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 65, the light chain CDR 2 of SEQ ID NO: 70 and the light chain CDR 3 of SEQ ID NO: 75;
- (a5) the heavy chain complementarity determining region (CDR) 1 of SEQ ID NO: 20, the heavy chain CDR 2 of SEQ ID NO: 34, the heavy chain CDR 3 of SEQ ID NO: 48, the light chain CDR 1 of SEQ ID NO: 63, the light chain CDR 2 of SEQ ID NO: 68 and the light chain CDR 3 of SEQ ID NO: 73;
- (a6) the heavy chain complementarity determining region (CDR) 1 of SEQ ID NO: 22, the heavy chain CDR 2 of SEQ ID NO: 36, the heavy chain CDR 3 of SEQ ID NO: 50, the light chain CDR 1 of SEQ ID NO: 63, the light chain CDR 2 of SEQ ID NO: 68 and the light chain CDR 3 of SEQ ID NO: 73;
- (a7) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 63, the light chain CDR 2 of SEQ ID NO: 68 and the light chain CDR 3 of SEQ ID NO: 73;
- (a8) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 66, the light chain CDR 2 of SEQ ID NO: 71 and the light chain CDR 3 of SEQ ID NO: 76;
- (a9) the heavy chain complementarity determining region (CDR) 1 of SEQ ID NO: 24, the heavy chain CDR 2 of SEQ ID NO: 38, the heavy chain CDR 3 of SEQ ID NO: 52, the light chain CDR 1 of SEQ ID NO: 63, the light chain CDR 2 of SEQ ID NO: 68 and the light chain CDR 3 of SEQ ID NO: 73;
- (a10) the heavy chain complementarity determining region (CDR) 1 of SEQ ID NO: 25, the heavy chain CDR 2 of SEQ ID NO: 39, the heavy chain CDR 3 of SEQ ID NO: 53, the light chain CDR 1 of SEQ ID NO: 66, the light chain CDR 2 of SEQ ID NO: 71 and the light chain CDR 3 of SEQ ID NO: 76;
- (a11) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 66, the light chain CDR 2 of SEQ ID NO: 71 and the light chain CDR 3 of SEQ ID NO: 76;
- (a12) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 63, the light chain CDR 2 of SEQ ID NO: 68 and the light chain CDR 3 of SEQ ID NO: 73;
- (a13) the heavy chain complementarity determining region (CDR) 1 of SEQ ID NO: 27, the heavy chain CDR 2 of SEQ ID NO: 41, the heavy chain CDR 3 of SEQ ID NO: 55, the light chain CDR 1 of SEQ ID NO: 63, the light chain CDR 2 of SEQ ID NO: 68 and the light chain CDR 3 of SEQ ID NO: 73;
- (a14) the heavy chain complementarity determining region (CDR) 1 of SEQ ID NO: 28, the heavy chain CDR 2 of SEQ ID NO: 42, the heavy chain CDR 3 of SEQ ID NO: 56, the light chain CDR 1 of SEQ ID NO: 63, the light chain CDR 2 of SEQ ID NO: 68 and the light chain CDR 3 of SEQ ID NO: 73;
- (a15) the heavy chain complementarity determining region (CDR) 1 of SEQ ID NO: 82, the heavy chain CDR 2 of SEQ ID NO: 83, the heavy chain CDR 3 of SEQ ID NO: 84, the light chain CDR 1 of SEQ ID NO: 65, the light chain CDR 2 of SEQ ID NO: 70 and the light chain CDR 3 of SEQ ID NO: 75;
- (a16) an antibody variable region that binds to the same epitope of any of the antibody variable region selected from (a1) to (a15); and
- (a17) an antibody variable fragment that competes with the binding of any of the antibody variable fragment selected from (a1) to (a15).

[3] The multispecific antigen-binding molecule of any one of [1] to [2], wherein the first antigen-binding moiety and the second antigen-binding moiety each comprises an antibody variable region comprising any one of (a1) to (a17) below:
(a1) a heavy chain variable region comprising an amino acid sequence of SEQ ID NO: 3, and a light chain variable region comprising an amino acid sequence of SEQ ID NO: 59;
(a2) a heavy chain variable region comprising an amino acid sequence of SEQ ID NO: 4, and a light chain variable region comprising an amino acid sequence of SEQ ID NO: 58;
(a3) a heavy chain variable region comprising an amino acid sequence of SEQ ID NO: 5, and a light chain variable region comprising an amino acid sequence of SEQ ID NO: 58;
(a4) a heavy chain variable region comprising an amino acid sequence of SEQ ID NO: 5, and a light chain variable region comprising an amino acid sequence of SEQ ID NO: 60;
(a5) a heavy chain variable region comprising an amino acid sequence of SEQ ID NO: 6, and a light chain variable region comprising an amino acid sequence of SEQ ID NO: 58;

(a6) a heavy chain variable region comprising an amino acid sequence of SEQ ID NO: 8, and a light chain variable region comprising an amino acid sequence of SEQ ID NO: 58;
(a7) a heavy chain variable region comprising an amino acid sequence of SEQ ID NO: 9, and a light chain variable region comprising an amino acid sequence of SEQ ID NO: 58;
(a8) a heavy chain variable region comprising an amino acid sequence of SEQ ID NO: 9, and a light chain variable region comprising an amino acid sequence of SEQ ID NO: 61;
(a9) a heavy chain variable region comprising an amino acid sequence of SEQ ID NO: 10, and a light chain variable region comprising an amino acid sequence of SEQ ID NO: 58;
(a10) a heavy chain variable region comprising an amino acid sequence of SEQ ID NO: 11, and a light chain variable region comprising an amino acid sequence of SEQ ID NO: 61;
(a11) a heavy chain variable region comprising an amino acid sequence of SEQ ID NO: 12, and a light chain variable region comprising an amino acid sequence of SEQ ID NO: 61;
(a12) a heavy chain variable region comprising an amino acid sequence of SEQ ID NO: 12, and a light chain variable region comprising an amino acid sequence of SEQ ID NO: 58;
(a13) a heavy chain variable region comprising an amino acid sequence of SEQ ID NO: 13, and a light chain variable region comprising an amino acid sequence of SEQ ID NO: 58;
(a14) a heavy chain variable region comprising an amino acid sequence of SEQ ID NO: 14, and a light chain variable region comprising an amino acid sequence of SEQ ID NO: 58;
(a15) a heavy chain variable region comprising an amino acid sequence of SEQ ID NO: 81, and a light chain variable region comprising an amino acid sequence of SEQ ID NO: 60;
(a16) an antibody variable region that binds to the same epitope of any of the antibody variable region selected from (a1) to (a15); and
(a17) an antibody variable fragment that competes with the binding of any of the antibody variable fragment selected from (a1) to (a15).

[4] The multispecific antigen-binding molecule of any one of [1] to [3], wherein each of the first antigen-binding moiety and the second antigen-binding moiety is a Fab molecule and comprises at least one disulfide bond formed between the CH1 region of the first antigen-binding moiety and the CH1 region of the second antigen-binding moiety.

[4A] The multispecific antigen-binding molecule of [4], wherein each of the first antigen-binding moiety and the second antigen-binding moiety is a Fab molecule and comprises one disulfide bond formed between the amino acid residues at position 191 according to EU numbering in the respective CH1 region of the first antigen-binding moiety and the second antigen-binding moiety.

[5] The multispecific antigen-binding molecule of any one of [1] to [4A], wherein the third antigen binding moiety is fused to either one of the first antigen binding moiety or the second antigen binding moiety.

[5A] The multispecific antigen-binding molecule of [5], wherein the third antigen binding moiety is a Fab or scFv.

[6] The multispecific antigen-binding molecule of any one of [5] to [5A], wherein each of the first, second and third antigen binding moiety is a Fab molecule, wherein the third antigen binding moiety is fused at the C-terminus of the Fab heavy chain (CH1) to the N-terminus of the Fab heavy chain of either one of the first antigen binding moiety or the second antigen binding moiety, optionally via a peptide linker.

[6A] The multispecific antigen-binding molecule of any one of [5] to [6], wherein said peptide linker is selected from the group consisting of the amino acid sequence of SEQ ID NO: 248, SEQ ID NO: 249 or SEQ ID NO: 259.

[6B] The multispecific antigen-binding molecule of any one of [1] to [6A], wherein the first antigen binding moiety is identical to the second antigen binding moiety.

[7] The multispecific antigen-binding molecule of any one of [1] to [6B], wherein the third antigen binding moiety is a crossover Fab molecule in which the variable regions of the Fab light chain and the Fab heavy chain are exchanged, and wherein each of the first and second antigen binding moiety is a conventional Fab molecule.

[8] The multispecific antigen-binding molecule of [7], wherein in the constant domain CL of the light chain of each of the first and second antigen binding moiety, the amino acid(s) at position 123 and/or 124 is/are substituted independently by lysine (K), arginine (R) or histidine (H) (numbering according to Kabat), and wherein in the constant domain CH1 of the heavy chain of each of the first and second antigen binding moiety, the amino acid at position 147 and/or the amino acid at position 213 is substituted independently by glutamic acid (E) or aspartic acid (D) (numbering according to Kabat EU index).

[9] The multispecific antigen-binding molecule of [8], wherein in the constant domain CL of the light chain of each of the first and second antigen binding moiety, the amino acids at position 123 and 124 are arginine (R) and lysine (K) respectively (numbering according to Kabat), and wherein in the constant domain CH1 of the heavy chain of each of the first and second antigen binding moiety the amino acids at position 147 and 213 are glutamic acid (E) (numbering according to Kabat EU index).

[10] The multispecific antigen-binding molecule of any one of [1] to [9], wherein the third antigen-binding moiety capable of binding to DLL3 comprises an antibody variable region comprising any one of (a1) to (a5) below:
(a1) the heavy chain complementarity determining region (CDR) 1 of SEQ ID NO: 233, the heavy chain CDR 2 of SEQ ID NO: 234, the heavy chain CDR 3 of SEQ ID NO: 235, the light chain CDR 1 of SEQ ID NO: 237, the light chain CDR 2 of SEQ ID NO: 238 and the light chain CDR 3 of SEQ ID NO: 239;
(a2) the heavy chain complementarity determining region (CDR) 1 of SEQ ID NO: 276, the heavy chain CDR 2 of SEQ ID NO: 277, the heavy chain CDR 3 of SEQ ID NO: 278, the light chain CDR 1 of SEQ ID NO: 279, the light chain CDR 2 of SEQ ID NO: 280 and the light chain CDR 3 of SEQ ID NO: 281;
(a3) the heavy chain complementarity determining region (CDR) 1 of SEQ ID NO: 285, the heavy chain CDR 2 of SEQ ID NO: 286, the heavy chain CDR 3 of SEQ ID NO: 287, the light chain CDR 1 of SEQ ID NO: 288, the light chain CDR 2 of SEQ ID NO: 289 and the light chain CDR 3 of SEQ ID NO: 290;
(a4) an antibody variable region that binds to the same epitope of any of the antibody variable region selected from (a1) to (a3); and
(a5) an antibody variable fragment that competes with the binding of any of the antibody variable fragment selected from (a1) to (a3).

[11] The multispecific antigen-binding molecule of any one of [1] to [10], wherein the third antigen-binding moiety capable of binding to DLL3 comprises an antibody variable region comprising any one of (a1) to (a6) below:

(a1) a heavy chain variable region comprising an amino acid sequence of SEQ ID NO: 232, and a light chain variable region comprising an amino acid sequence of SEQ ID NO: 236;
(a2) a heavy chain variable region comprising an amino acid sequence of SEQ ID NO: 264, and a light chain variable region comprising an amino acid sequence of SEQ ID NO: 265;
(a3) a heavy chain variable region comprising an amino acid sequence of SEQ ID NO: 266, and a light chain variable region comprising an amino acid sequence of SEQ ID NO: 267;
(a4) a heavy chain variable region comprising an amino acid sequence of SEQ ID NO: 268, and a light chain variable region comprising an amino acid sequence of SEQ ID NO: 269;
(a5) an antibody variable region that binds to the same epitope of any of the antibody variable region selected from (a1) to (a4); and
(a6) an antibody variable fragment that competes with the binding of any of the antibody variable fragment selected from (a1) to (a4).

[12] The multispecific antigen-binding molecule of any one of [1] to [11], further comprises a Fc domain.

[12A] The multispecific antigen-binding molecule of [12], wherein the Fc domain composed of a first and a second Fc region subunit capable of stable association, and wherein the Fc domain exhibits reduced binding affinity to human Fc-gamma receptor, as compared to a native human IgG1 Fc domain.

[12B] The multispecific antigen-binding molecule of [12A], wherein the first Fc-region subunit is selected from the group consisting of:
(a1) a Fc region polypeptide comprising Ala at position 234 and Ala at position 235;
(a2) a Fc region polypeptide comprising Ala at position 234, Ala at position 235, and Ala at position 297;
(a3) a Fc region polypeptide comprising Ala at position 234, Ala at position 235, Ala at position 297, Cys at position 354 and Trp at position 366; and wherein the second Fc-region polypeptide is selected from the group consisting of:
(a4) a Fc region polypeptide comprising Ala at position 234 and Ala at position 235;
(a5) a Fc region polypeptide comprising Ala at position 234, Ala at position 235, and Ala at position 297;
(a6) a Fc region polypeptide comprising Ala at position 234, Ala at position 235, Ala at position 297, Cys at position 349, Ser at position 366, Ala at position 368 and Val at position 407; and wherein the amino acid positions are numbered using EU index numbering.

[12C] The multispecific antigen-binding molecule of any one of [12] to [12B], wherein the Fc domain exhibits enhanced FcRn-binding activity under an acidic pH condition (e.g., pH 5.8) as compared to that of an Fc region of a native IgG.

[12D] The multispecific antigen-binding molecule of [12C], wherein the Fc domain comprises Ala at position 434; Glu, Arg, Ser, or Lys at position 438; and Glu, Asp, or Gln at position 440, according to EU numbering.

[12E] The multispecific antigen-binding molecule of [12D], wherein the Fc domain comprises Ala at position 434; Arg or Lys at position 438; and Glu or Asp at position 440, according to EU numbering.

[12F] The multispecific antigen-binding molecule of [12E], wherein the Fc domain further comprises Ile or Leu at position 428; and/or Ile, Leu, Val, Thr, or Phe at position 436, according to EU numbering.

[12G] The multispecific antigen-binding molecule of any one of [12C] to [12F], wherein the Fc domain comprises a combination of amino acid substitutions selected from the group consisting of:
(a) N434A/Q438R/S440E;
(b) N434A/Q438R/S440D;
(c) N434A/Q438K/S440E;
(d) N434A/Q438K/S440D;
(e) N434A/Y436T/Q438R/S440E;
(f) N434A/Y436T/Q438R/S440D;
(g) N434A/Y436T/Q438K/S440E;
(h) N434A/Y436T/Q438K/S440D;
(i) N434A/Y436V/Q438R/S440E;
(j) N434A/Y436V/Q438R/S440D;
(k) N434A/Y436V/Q438K/S440E;
(l) N434A/Y436V/Q438K/S440D;
(m) N434A/R435H/F436T/Q438R/S440E;
(n) N434A/R435H/F436T/Q438R/S440D;
(o) N434A/R435H/F436T/Q438K/S440E;
(p) N434A/R435H/F436T/Q438K/S440D;
(q) N434A/R435H/F436V/Q438R/S440E;
(r) N434A/R435H/F436V/Q438R/S440D;
(s) N434A/R435H/F436V/Q438K/S440E;
(t) N434A/R435H/F436V/Q438K/S440D;
(u) M428L/N434A/Q438R/S440E;
(v) M428L/N434A/Q438R/S440D;
(w) M428L/N434A/Q438K/S440E;
(x) M428L/N434A/Q438K/S440D;
(y) M428L/N434A/Y436T/Q438R/S440E;
(z) M428L/N434A/Y436T/Q438R/S440D;
(aa) M428L/N434A/Y436T/Q438K/S440E;
(ab) M428L/N434A/Y436T/Q438K/S440D;
(ac) M428L/N434A/Y436V/Q438R/S440E;
(ad) M428L/N434A/Y436V/Q438R/S440D;
(ae) M428L/N434A/Y436V/Q438K/S440E;
(af) M428L/N434A/Y436V/Q438K/S440D;
(ag) L235R/G236R/S239K/M428L/N434A/Y436T/Q438R/S440E; and
(ah) L235R/G236R/A327G/A330S/P331S/M428L/N434A/Y436T/Q438R/S440E, according to EU numbering.

[12H] The multispecific antigen-binding molecule of any one of [12C] to [12G], wherein the Fc domain comprises a combination of amino acid substitutions of M428L/N434A/Q438R/S440E.

[12I] The multispecific antigen-binding molecule of any one of [12] to [12H], wherein the Fc domain is a IgG Fc domain, preferably a human IgG Fc domain, more preferably a human IgG1 Fc domain.

[12J] The multispecific antigen-binding molecule of any one of [12] to [12I], wherein the Fc domain comprises any one of:
(a) a first Fc subunit comprising the amino acid sequence shown in SEQ ID NO: 100 and a second Fc subunit comprising the amino acid sequence shown in SEQ ID NO: 111; and
(b) a first Fc subunit comprising the amino acid sequence shown in SEQ ID NO: 99 and a second Fc subunit comprising the amino acid sequence shown in SEQ ID NO: 109.

[12K] The multispecific antigen-binding molecule of any one of [12] to [12J], wherein each of the first and second antigen-binding moiety is a Fab, wherein the first antigen-binding moiety is fused at the C-terminus of the Fab heavy chain to the N-terminus of the first or second subunit of the Fc domain, and the second antigen-binding moiety is fused at the C-terminus of the Fab heavy chain to the N-terminus of the remaining subunit of the Fc domain.

[12L] The multispecific antigen-binding molecule of [12K], wherein the third antigen binding moiety is fused at the C-terminus to the N-terminus of the Fab heavy chain of either one of the first antigen binding moiety or the second antigen binding moiety, optionally via a peptide linker.

[13] The multispecific antigen-binding molecule of any one of [1] to [12L], comprising five polypeptide chains in any one of the combination selected from (a1) to (a15) below:

(a1) a polypeptide chain comprising the amino acid sequence of SEQ ID NO: 201 (chain 1), a polypeptide chain comprising the amino acid sequence of SEQ ID NO: 206 (chain 2), a polypeptide chain comprising the amino acid sequence of SEQ ID NO: 208 (chain 3) and two polypeptide chains each comprising the amino acid sequence of SEQ ID NO: 214 (chain 4 & chain 5);

(a2) a polypeptide chain comprising the amino acid sequence of SEQ ID NO: 203 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a3) a polypeptide chain comprising the amino acid sequence of SEQ ID NO: 204 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a4) a polypeptide chain comprising the amino acid sequence of SEQ ID NO: 205 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a5) a polypeptide chain comprising the amino acid sequence of SEQ ID NO: 216 (chain 1), a polypeptide chain comprising the amino acid sequence of SEQ ID NO: 206 (chain 2), a polypeptide chain comprising the amino acid sequence of SEQ ID NO: 229 (chain 3) and two polypeptide chains each comprising the amino acid sequence of SEQ ID NO: 214 (chain 4 & chain 5);

(a6) a polypeptide chain comprising the amino acid sequence of SEQ ID NO: 217 (chain 1), a polypeptide chain comprising the amino acid sequence of SEQ ID NO: 206 (chain 2), a polypeptide chain comprising the amino acid sequence of SEQ ID NO: 210 (chain 3) and two polypeptide chains each comprising the amino acid sequence of SEQ ID NO: 214 (chain 4 & chain 5);

(a7) a polypeptide chain comprising the amino acid sequence of SEQ ID NO: 219 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);

(a8) a polypeptide chain comprising the amino acid sequence of SEQ ID NO: 220 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);

(a9) a polypeptide chain comprising the amino acid sequence of SEQ ID NO: 221 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);

(a10) a polypeptide chain comprising the amino acid sequence of SEQ ID NO: 222 (chain 1), a polypeptide chain comprising the amino acid sequence of SEQ ID NO: 206 (chain 2), a polypeptide chain comprising the amino acid sequence of SEQ ID NO: 230 (chain 3) and two polypeptide chains each comprising the amino acid sequence of SEQ ID NO: 214 (chain 4 & chain 5);

(a11) a polypeptide chain comprising the amino acid sequence of SEQ ID NO: 223 (chain 1), a polypeptide chain comprising the amino acid sequence of SEQ ID NO: 206 (chain 2), a polypeptide chain comprising the amino acid sequence of SEQ ID NO: 212 (chain 3) and two polypeptide chains each comprising the amino acid sequence of SEQ ID NO: 215 (chain 4 & chain 5);

(a12) a polypeptide chain comprising the amino acid sequence of SEQ ID NO: 225 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5);

(a13) a polypeptide chain comprising the amino acid sequence of SEQ ID NO: 226 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5);

(a14) a polypeptide chain comprising the amino acid sequence of SEQ ID NO: 227 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5); and (a15) a polypeptide chain comprising the amino acid sequence of SEQ ID NO: 228 (chain 1), a polypeptide chain comprising the amino acid sequence of SEQ ID NO: 206 (chain 2), a polypeptide chain comprising the amino acid sequence of SEQ ID NO: 231 (chain 3) and two polypeptide chains each comprising the amino acid sequence of SEQ ID NO: 215 (chain 4 & chain 5);

and wherein, preferably the five polypeptide chains (chain 1 to chain 5) are connect and/or associate with each other according to the orientation shown in panel (a) of FIG. 1.

[14] An isolated polynucleotide or plurality of polynucleotides encoding the multispecific antigen-binding molecule of any one of [1] to [13].

[15] A vector encoding the polynucleotide or plurality of polynucleotides of [14].

[16] A host cell comprising the polynucleotide or plurality of polynucleotides of [14], or the vector of [15].

[17] A method of producing the multispecific antigen-binding molecule of any one of [1] to [13], comprising the steps of a) culturing the host cell of [16] under conditions suitable for the expression of the antigen-binding molecule and b) recovering the antigen-binding molecule.

[17A] A multispecific antigen-binding molecule produced by the method of [17].

[18] A pharmaceutical composition comprising the multispecific antigen-binding molecule of any one of [1] to [13] and a pharmaceutically acceptable carrier.

[19] The multispecific antigen-binding molecule of any one of [1] to [13] or the pharmaceutical composition of [18], which induces cytotoxicity, preferably T-cell-dependent cytotoxicity.
[20] The multispecific antigen-binding molecule of any one of [1] to [13] or the pharmaceutical composition of [18], for use as a medicament.
[21] The multispecific antigen-binding molecule of any one of [1] to [13] or the pharmaceutical composition of [18], for use in the treatment or prevention of a disease in an individual in need thereof[22] The multispecific antigen-binding molecule or the pharmaceutical composition for use in the treatment/prevention of a disease of [21], wherein the disease is cancer.
[22A] The multispecific antigen-binding molecule or the pharmaceutical composition for use in the treatment/prevention of a disease of [22], wherein the cancer is DLL3-expressing cancer or DLL3-positive cancer.
[22B] The multispecific antigen-binding molecule or the pharmaceutical composition for use in the treatment/prevention of a disease of [22] or [22A], wherein the cancer is lung cancer (including small cell lung cancer) and melanoma.
[23] Use of the multispecific antigen binding molecule of any one of [1] to [13] or the pharmaceutical composition of [18], for the manufacture of a medicament for the treatment or prevention of a disease in an individual in need thereof.
[24] A method of treating a disease in an individual, comprising administering to said individual a therapeutically effective amount of a composition comprising the multispecific antigen binding molecule of any one of [1] to [13] or the pharmaceutical composition of [18].
[25] The use of [23] or the method of [24], wherein said disease is cancer, preferably DLL3-positive cancer or DLL3-expressing cancer.
[25A] The use of or the method of [25], wherein the cancer is DLL3-expressing cancer or DLL3-positive cancer.
[25B] The use of or the method of [25A], wherein the cancer is lung cancer (including small cell lung cancer) or melanoma.
[26] A method for inducing lysis of a target cell, comprising contacting a target cell with the multispecific antigen binding molecule of any one of [1] to [13] or the pharmaceutical composition of [18] in the presence of a T cell.
[27] A kit comprising the composition of [18]; and a package insert comprising instructions for administering to a subject to treat or delay progression of cancer, preferably DLL3-positive cancer or DLL3-expressing cancer.
[27A] The kit of [27], wherein the cancer is lung cancer (including small cell lung cancer) and melanoma.
Another aspect of the present invention relates to:
[28] A multispecific antigen-binding molecule comprising:
an antigen-binding moiety which is capable of binding to CD3 and CD137, but does not bind to CD3 and CD137 at the same time; and
an antigen-binding moiety that is capable of binding to DLL3, preferably human DLL3.
[29] The multispecific antigen-binding molecule of [28], wherein the antigen-binding moiety which is capable of binding to CD3 and CD137, but does not bind to CD3 and CD137 at the same time, comprises an antibody variable region comprising any one of (a1) to (a17) below:
  (a1) the heavy chain complementarity determining region (CDR) 1 of SEQ ID NO: 17, the heavy chain CDR 2 of SEQ ID NO: 31, the heavy chain CDR 3 of SEQ ID NO: 45, the light chain CDR 1 of SEQ ID NO: 64, the light chain CDR 2 of SEQ ID NO: 69 and the light chain CDR 3 of SEQ ID NO: 74;
  (a2) the heavy chain complementarity determining region (CDR) 1 of SEQ ID NO: 18, the heavy chain CDR 2 of SEQ ID NO: 32, the heavy chain CDR 3 of SEQ ID NO: 46, the light chain CDR 1 of SEQ ID NO: 63, the light chain CDR 2 of SEQ ID NO: 68 and the light chain CDR 3 of SEQ ID NO: 73;
  (a3) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 63, the light chain CDR 2 of SEQ ID NO: 68 and the light chain CDR 3 of SEQ ID NO: 73;
  (a4) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 65, the light chain CDR 2 of SEQ ID NO: 70 and the light chain CDR 3 of SEQ ID NO: 75;
  (a5) the heavy chain complementarity determining region (CDR) 1 of SEQ ID NO: 20, the heavy chain CDR 2 of SEQ ID NO: 34, the heavy chain CDR 3 of SEQ ID NO: 48, the light chain CDR 1 of SEQ ID NO: 63, the light chain CDR 2 of SEQ ID NO: 68 and the light chain CDR 3 of SEQ ID NO: 73;
  (a6) the heavy chain complementarity determining region (CDR) 1 of SEQ ID NO: 22, the heavy chain CDR 2 of SEQ ID NO: 36, the heavy chain CDR 3 of SEQ ID NO: 50, the light chain CDR 1 of SEQ ID NO: 63, the light chain CDR 2 of SEQ ID NO: 68 and the light chain CDR 3 of SEQ ID NO: 73;
  (a7) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 63, the light chain CDR 2 of SEQ ID NO: 68 and the light chain CDR 3 of SEQ ID NO: 73;
  (a8) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 66, the light chain CDR 2 of SEQ ID NO: 71 and the light chain CDR 3 of SEQ ID NO: 76;
  (a9) the heavy chain complementarity determining region (CDR) 1 of SEQ ID NO: 24, the heavy chain CDR 2 of SEQ ID NO: 38, the heavy chain CDR 3 of SEQ ID NO: 52, the light chain CDR 1 of SEQ ID NO: 63, the light chain CDR 2 of SEQ ID NO: 68 and the light chain CDR 3 of SEQ ID NO: 73;
  (a10) the heavy chain complementarity determining region (CDR) 1 of SEQ ID NO: 25, the heavy chain CDR 2 of SEQ ID NO: 39, the heavy chain CDR 3 of SEQ ID NO: 53, the light chain CDR 1 of SEQ ID NO: 66, the light chain CDR 2 of SEQ ID NO: 71 and the light chain CDR 3 of SEQ ID NO: 76;
  (a11) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 66, the light chain CDR 2 of SEQ ID NO: 71 and the light chain CDR 3 of SEQ ID NO: 76;
  (a12) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 63, the light chain CDR 2 of SEQ ID NO: 68 and the light chain CDR 3 of SEQ ID NO: 73;

(a13) the heavy chain complementarity determining region (CDR) 1 of SEQ ID NO: 27, the heavy chain CDR 2 of SEQ ID NO: 41, the heavy chain CDR 3 of SEQ ID NO: 55, the light chain CDR 1 of SEQ ID NO: 63, the light chain CDR 2 of SEQ ID NO: 68 and the light chain CDR 3 of SEQ ID NO: 73;

(a14) the heavy chain complementarity determining region (CDR) 1 of SEQ ID NO: 28, the heavy chain CDR 2 of SEQ ID NO: 42, the heavy chain CDR 3 of SEQ ID NO: 56, the light chain CDR 1 of SEQ ID NO: 63, the light chain CDR 2 of SEQ ID NO: 68 and the light chain CDR 3 of SEQ ID NO: 73;

(a15) the heavy chain complementarity determining region (CDR) 1 of SEQ ID NO: 82, the heavy chain CDR 2 of SEQ ID NO: 83, the heavy chain CDR 3 of SEQ ID NO: 84, the light chain CDR 1 of SEQ ID NO: 65, the light chain CDR 2 of SEQ ID NO: 70 and the light chain CDR 3 of SEQ ID NO: 75;

(a16) an antibody variable region that binds to the same epitope of any of the antibody variable region selected from (a1) to (a15); and (a17) an antibody variable fragment that competes with the binding of any of the antibody variable fragment selected from (a1) to (a15).

[30] The multispecific antigen-binding molecule of any one of [28] to [29], wherein the antigen-binding moiety which is capable of binding to CD3 and CD137, but does not bind to CD3 and CD137 at the same time, comprises an antibody variable region comprising any one of (a1) to (a17) below:

(a1) a heavy chain variable region comprising an amino acid sequence of SEQ ID NO: 3, and a light chain variable region comprising an amino acid sequence of SEQ ID NO: 59;

(a2) a heavy chain variable region comprising an amino acid sequence of SEQ ID NO: 4, and a light chain variable region comprising an amino acid sequence of SEQ ID NO: 58;

(a3) a heavy chain variable region comprising an amino acid sequence of SEQ ID NO: 5, and a light chain variable region comprising an amino acid sequence of SEQ ID NO: 58;

(a4) a heavy chain variable region comprising an amino acid sequence of SEQ ID NO: 5, and a light chain variable region comprising an amino acid sequence of SEQ ID NO: 60;

(a5) a heavy chain variable region comprising an amino acid sequence of SEQ ID NO: 6, and a light chain variable region comprising an amino acid sequence of SEQ ID NO: 58;

(a6) a heavy chain variable region comprising an amino acid sequence of SEQ ID NO: 8, and a light chain variable region comprising an amino acid sequence of SEQ ID NO: 58;

(a7) a heavy chain variable region comprising an amino acid sequence of SEQ ID NO: 9, and a light chain variable region comprising an amino acid sequence of SEQ ID NO: 58;

(a8) a heavy chain variable region comprising an amino acid sequence of SEQ ID NO: 9, and a light chain variable region comprising an amino acid sequence of SEQ ID NO: 61;

(a9) a heavy chain variable region comprising an amino acid sequence of SEQ ID NO: 10, and a light chain variable region comprising an amino acid sequence of SEQ ID NO: 58;

(a10) a heavy chain variable region comprising an amino acid sequence of SEQ ID NO: 11, and a light chain variable region comprising an amino acid sequence of SEQ ID NO: 61;

(a11) a heavy chain variable region comprising an amino acid sequence of SEQ ID NO: 12, and a light chain variable region comprising an amino acid sequence of SEQ ID NO: 61;

(a12) a heavy chain variable region comprising an amino acid sequence of SEQ ID NO: 12, and a light chain variable region comprising an amino acid sequence of SEQ ID NO: 58;

(a13) a heavy chain variable region comprising an amino acid sequence of SEQ ID NO: 13, and a light chain variable region comprising an amino acid sequence of SEQ ID NO: 58;

(a14) a heavy chain variable region comprising an amino acid sequence of SEQ ID NO: 14, and a light chain variable region comprising an amino acid sequence of SEQ ID NO: 58;

(a15) a heavy chain variable region comprising an amino acid sequence of SEQ ID NO: 81, and a light chain variable region comprising an amino acid sequence of SEQ ID NO: 60;

(a16) an antibody variable region that binds to the same epitope of any of the antibody variable region selected from (a1) to (a15); and (a17) an antibody variable fragment that competes with the binding of any of the antibody variable fragment selected from (a1) to (a15).

In yet another aspect of the present invention relates to:

[31] A multispecific antigen-binding molecule comprising five polypeptide chains in any one of the combinations selected from (a1) to (a15) below:

(a1) a polypeptide chain comprising the amino acid sequence of SEQ ID NO: 201 (chain 1), a polypeptide chain comprising the amino acid sequence of SEQ ID NO: 206 (chain 2), a polypeptide chain comprising the amino acid sequence of SEQ ID NO: 208 (chain 3) and two polypeptide chains each comprising the amino acid sequence of SEQ ID NO: 214 (chain 4 & chain 5);

(a2) a polypeptide chain comprising the amino acid sequence of SEQ ID NO: 203 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a3) a polypeptide chain comprising the amino acid sequence of SEQ ID NO: 204 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a4) a polypeptide chain comprising the amino acid sequence of SEQ ID NO: 205 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chain 4 & chain 5);

(a5) a polypeptide chain comprising the amino acid sequence of SEQ ID NO: 216 (chain 1), a polypeptide chain comprising the amino acid sequence of SEQ ID NO: 206 (chain 2), a polypeptide chain comprising the amino acid sequence of SEQ ID NO: 229 (chain 3) and two polypeptide chains each comprising the amino acid sequence of SEQ ID NO: 214 (chain 4 & chain 5);

(a6) a polypeptide chain comprising the amino acid sequence of SEQ ID NO: 217 (chain 1), a polypeptide chain comprising the amino acid sequence of SEQ ID NO: 206 (chain 2), a polypeptide chain comprising the amino acid sequence of SEQ ID NO: 210 (chain 3) and two polypeptide chains each comprising the amino acid sequence of SEQ ID NO: 214 (chain 4 & chain 5);
(a7) a polypeptide chain comprising the amino acid sequence of SEQ ID NO: 219 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);
(a8) a polypeptide chain comprising the amino acid sequence of SEQ ID NO: 220 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);
(a9) a polypeptide chain comprising the amino acid sequence of SEQ ID NO: 221 (chain 1), a polypeptide chain comprising the amino acid sequence of SEQ ID NO: 206 (chain 2), a polypeptide chain comprising the amino acid sequence of SEQ ID NO: 211 (chain 3) and two polypeptide chains each comprising the amino acid sequence of SEQ ID NO: 214 (chain 4 & chain 5);
(a10) a polypeptide chain comprising the amino acid sequence of SEQ ID NO: 222 (chain 1), a polypeptide chain comprising the amino acid sequence of SEQ ID NO: 206 (chain 2), a polypeptide chain comprising the amino acid sequence of SEQ ID NO: 230 (chain 3) and two polypeptide chains each comprising the amino acid sequence of SEQ ID NO: 214 (chain 4 & chain 5);
(a11) a polypeptide chain comprising the amino acid sequence of SEQ ID NO: 223 (chain 1), a polypeptide chain comprising the amino acid sequence of SEQ ID NO: 206 (chain 2), a polypeptide chain comprising the amino acid sequence of SEQ ID NO: 212 (chain 3) and two polypeptide chains each comprising the amino acid sequence of SEQ ID NO: 215 (chain 4 & chain 5);
(a12) a polypeptide chain comprising the amino acid sequence of SEQ ID NO: 225 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5);
(a13) a polypeptide chain comprising the amino acid sequence of SEQ ID NO: 226 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5);
(a14) a polypeptide chain comprising the amino acid sequence of SEQ ID NO: 227 (chain 1), a polypeptide chain comprising the amino acid sequence of SEQ ID NO: 206 (chain 2), a polypeptide chain comprising the amino acid sequence of SEQ ID NO: 213 (chain 3) and two polypeptide chains each comprising the amino acid sequence of SEQ ID NO: 215 (chain 4 & chain 5); and
(a15) a polypeptide chain comprising the amino acid sequence of SEQ ID NO: 228 (chain 1), a polypeptide chain comprising the amino acid sequence of SEQ ID NO: 206 (chain 2), a polypeptide chain comprising the amino acid sequence of SEQ ID NO: 231 (chain 3) and two polypeptide chains each comprising the amino acid sequence of SEQ ID NO: 215 (chain 4 & chain 5);

and wherein, preferably the five polypeptide chains (chain 1 to chain 5) connect and/or associate with each other according to the orientation shown in panel (a) of FIG. 1.

Yet another aspect of the present invention relates to:
[32] An antigen binding molecule capable of binding to DLL3, which comprises an antibody variable region comprising any one of (a1) to (a5) below:
 (a1) the heavy chain complementarity determining region (CDR) 1 of SEQ ID NO: 233, the heavy chain CDR 2 of SEQ ID NO: 234, the heavy chain CDR 3 of SEQ ID NO: 235, the light chain CDR 1 of SEQ ID NO: 237, the light chain CDR 2 of SEQ ID NO: 238 and the light chain CDR 3 of SEQ ID NO: 239;
 (a2) the heavy chain complementarity determining region (CDR) 1 of SEQ ID NO: 276, the heavy chain CDR 2 of SEQ ID NO: 277, the heavy chain CDR 3 of SEQ ID NO: 278, the light chain CDR 1 of SEQ ID NO: 279, the light chain CDR 2 of SEQ ID NO: 280 and the light chain CDR 3 of SEQ ID NO: 281;
 (a3) the heavy chain complementarity determining region (CDR) 1 of SEQ ID NO: 285, the heavy chain CDR 2 of SEQ ID NO: 286, the heavy chain CDR 3 of SEQ ID NO: 287, the light chain CDR 1 of SEQ ID NO: 288, the light chain CDR 2 of SEQ ID NO: 289 and the light chain CDR 3 of SEQ ID NO: 290;
 (a4) an antibody variable region that binds to the same epitope of any of the antibody variable region selected from (a1) to (a3); and
 (a5) an antibody variable fragment that competes with the binding of any of the antibody variable fragment selected from (a1) to (a3).

[33] An antigen binding molecule capable of binding to DLL3, which comprises an antibody variable region comprising any one of (a1) to (a6) below:
 (a1) a heavy chain variable region comprising an amino acid sequence of SEQ ID NO: 232, and a light chain variable region comprising an amino acid sequence of SEQ ID NO: 236;
 (a2) a heavy chain variable region comprising an amino acid sequence of SEQ ID NO: 264, and a light chain variable region comprising an amino acid sequence of SEQ ID NO: 265;
 (a3) a heavy chain variable region comprising an amino acid sequence of SEQ ID NO: 266, and a light chain variable region comprising an amino acid sequence of SEQ ID NO: 267;
 (a4) a heavy chain variable region comprising an amino acid sequence of SEQ ID NO: 268, and a light chain variable region comprising an amino acid sequence of SEQ ID NO: 269;
 (a5) an antibody variable region that binds to the same epitope of any of the antibody variable region selected from (a1) to (a4); and
 (a6) an antibody variable fragment that competes with the binding of any of the antibody variable fragment selected from (a1) to (a4).

Yet another aspect of the present invention relates to:
[2-1] A multispecific antigen-binding molecule that comprises:
(a) a first antigen-binding moiety and a second antigen-binding moiety, each of which binds to human CD3 and comprises an antibody variable region that can be the same or different and is independently selected from the group consisting of:
 (a1) an antibody variable region comprising heavy chain complementarity determining region (CDR) 1 of SEQ ID NO: 17, heavy chain CDR 2 of SEQ ID NO: 31, heavy chain CDR 3 of SEQ ID NO: 45, light chain CDR 1 of SEQ ID NO: 64, light chain CDR 2 of SEQ ID NO: 69 and light chain CDR 3 of SEQ ID NO: 74;
(a2) an antibody variable region comprising heavy chain complementarity determining region (CDR) 1 of SEQ ID NO: 18, heavy chain CDR 2 of SEQ ID NO: 32, heavy chain CDR 3 of SEQ ID NO: 46, light chain CDR 1 of SEQ ID NO: 63, light chain CDR 2 of SEQ ID NO: 68 and light chain CDR 3 of SEQ ID NO: 73;
(a3) an antibody variable region comprising the heavy chain complementarity determining region (CDR) 1 of SEQ ID NO: 19, the heavy chain CDR 2 of SEQ ID NO: 33, the heavy chain CDR 3 of SEQ ID NO: 47, light chain CDR 1 of SEQ ID NO: 63, light chain CDR 2 of SEQ ID NO: 68 and light chain CDR 3 of SEQ ID NO: 73;
(a4) an antibody variable region comprising the heavy chain complementarity determining region (CDR) 1 of SEQ ID NO: 19, the heavy chain CDR 2 of SEQ ID NO: 33, the heavy chain CDR 3 of SEQ ID NO: 47, light chain CDR 1 of SEQ ID NO: 65, light chain CDR 2 of SEQ ID NO: 70 and light chain CDR 3 of SEQ ID NO: 75;
(a5) an antibody variable region comprising the heavy chain complementarity determining region (CDR) 1 of SEQ ID NO: 20, the heavy chain CDR 2 of SEQ ID NO: 34, the heavy chain CDR 3 of SEQ ID NO: 48, light chain CDR 1 of SEQ ID NO: 63, light chain CDR 2 of SEQ ID NO: 68 and light chain CDR 3 of SEQ ID NO: 73;
(a6) an antibody variable region comprising the heavy chain complementarity determining region (CDR) 1 of SEQ ID NO: 22, the heavy chain CDR 2 of SEQ ID NO: 36, the heavy chain CDR 3 of SEQ ID NO: 50, light chain CDR 1 of SEQ ID NO: 63, light chain CDR 2 of SEQ ID NO: 68 and light chain CDR 3 of SEQ ID NO: 73;
(a7) an antibody variable region comprising the heavy chain complementarity determining region (CDR) 1 of SEQ ID NO: 23, the heavy chain CDR 2 of SEQ ID NO: 37, the heavy chain CDR 3 of SEQ ID NO: 51, light chain CDR 1 of SEQ ID NO: 63, light chain CDR 2 of SEQ ID NO: 68 and light chain CDR 3 of SEQ ID NO: 73;
(a8) an antibody variable region comprising the heavy chain complementarity determining region (CDR) 1 of SEQ ID NO: 23, the heavy chain CDR 2 of SEQ ID NO: 37, the heavy chain CDR 3 of SEQ ID NO: 51, light chain CDR 1 of SEQ ID NO: 66, light chain CDR 2 of SEQ ID NO: 71 and light chain CDR 3 of SEQ ID NO: 76;
(a9) an antibody variable region comprising the heavy chain complementarity determining region (CDR) 1 of SEQ ID NO: 24, the heavy chain CDR 2 of SEQ ID NO: 38, the heavy chain CDR 3 of SEQ ID NO: 52, light chain CDR 1 of SEQ ID NO: 63, light chain CDR 2 of SEQ ID NO: 68 and light chain CDR 3 of SEQ ID NO: 73;
(a10) an antibody variable region comprising the heavy chain complementarity determining region (CDR) 1 of SEQ ID NO: 25, the heavy chain CDR 2 of SEQ ID NO: 39, the heavy chain CDR 3 of SEQ ID NO: 53, light chain CDR 1 of SEQ ID NO: 66, light chain CDR 2 of SEQ ID NO: 71 and light chain CDR 3 of SEQ ID NO: 76;
(a11) an antibody variable region comprising the heavy chain complementarity determining region (CDR) 1 of SEQ ID NO: 26, the heavy chain CDR 2 of SEQ ID NO: 40, the heavy chain CDR 3 of SEQ ID NO: 54, light chain CDR 1 of SEQ ID NO: 66, light chain CDR 2 of SEQ ID NO: 71 and light chain CDR 3 of SEQ ID NO: 76;
(a12) an antibody variable region comprising the heavy chain complementarity determining region (CDR) 1 of SEQ ID NO: 26, the heavy chain CDR 2 of SEQ ID NO: 40, the heavy chain CDR 3 of SEQ ID NO: 54, light chain CDR 1 of SEQ ID NO: 63, light chain CDR 2 of SEQ ID NO: 68 and light chain CDR 3 of SEQ ID NO: 73;
(a13) an antibody variable region comprising the heavy chain complementarity determining region (CDR) 1 of SEQ ID NO: 27, the heavy chain CDR 2 of SEQ ID NO: 41, the heavy chain CDR 3 of SEQ ID NO: 55, light chain CDR 1 of SEQ ID NO: 63, light chain CDR 2 of SEQ ID NO: 68 and light chain CDR 3 of SEQ ID NO: 73;
(a14) an antibody variable region comprising the heavy chain complementarity determining region (CDR) 1 of SEQ ID NO: 28, the heavy chain CDR 2 of SEQ ID NO: 42, the heavy chain CDR 3 of SEQ ID NO: 56, light chain CDR 1 of SEQ ID NO: 63, light chain CDR 2 of SEQ ID NO: 68 and light chain CDR 3 of SEQ ID NO: 73; and
(a15) an antibody variable region comprising heavy chain complementarity determining region (CDR) 1 of SEQ ID NO: 82, heavy chain CDR 2 of SEQ ID NO: 83, heavy chain CDR 3 of SEQ ID NO: 84, light chain CDR 1 of SEQ ID NO: 65, light chain CDR 2 of SEQ ID NO: 70 and light chain CDR 3 of SEQ ID NO: 75;
and
(b) a third antigen-binding moiety that binds to human Delta-like 3 (DLL3) and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

[2-2] The multispecific antigen-binding molecule of [2-1], wherein each of the first and second antigen-binding moieties comprises an antibody variable region that can be the same or different and is independently selected from the group consisting of:
(a1) a heavy chain variable region comprising an amino acid sequence of SEQ ID NO: 3, and a light chain variable region comprising an amino acid sequence of SEQ ID NO: 59;
(a2) a heavy chain variable region comprising an amino acid sequence of SEQ ID NO: 4, and a light chain variable region comprising an amino acid sequence of SEQ ID NO: 58;
(a3) a heavy chain variable region comprising an amino acid sequence of SEQ ID NO: 5, and a light chain variable region comprising an amino acid sequence of SEQ ID NO: 58;
(a4) a heavy chain variable region comprising an amino acid sequence of SEQ ID NO: 5, and a light chain variable region comprising an amino acid sequence of SEQ ID NO: 60;
(a5) a heavy chain variable region comprising an amino acid sequence of SEQ ID NO: 6, and a light chain variable region comprising an amino acid sequence of SEQ ID NO: 58;

(a6) a heavy chain variable region comprising an amino acid sequence of SEQ ID NO: 8, and a light chain variable region comprising an amino acid sequence of SEQ ID NO: 58;

(a7) a heavy chain variable region comprising an amino acid sequence of SEQ ID NO: 9, and a light chain variable region comprising an amino acid sequence of SEQ ID NO: 58;

(a8) a heavy chain variable region comprising an amino acid sequence of SEQ ID NO: 9, and a light chain variable region comprising an amino acid sequence of SEQ ID NO: 61;

(a9) a heavy chain variable region comprising an amino acid sequence of SEQ ID NO: 10, and a light chain variable region comprising an amino acid sequence of SEQ ID NO: 58;

(a10) a heavy chain variable region comprising an amino acid sequence of SEQ ID NO: 11, and a light chain variable region comprising an amino acid sequence of SEQ ID NO: 61;

(a11) a heavy chain variable region comprising an amino acid sequence of SEQ ID NO: 12, and a light chain variable region comprising an amino acid sequence of SEQ ID NO: 61;

(a12) a heavy chain variable region comprising an amino acid sequence of SEQ ID NO: 12, and a light chain variable region comprising an amino acid sequence of SEQ ID NO: 58;

(a13) a heavy chain variable region comprising an amino acid sequence of SEQ ID NO: 13, and a light chain variable region comprising an amino acid sequence of SEQ ID NO: 58;

(a14) a heavy chain variable region comprising an amino acid sequence of SEQ ID NO: 14, and a light chain variable region comprising an amino acid sequence of SEQ ID NO: 58; and (a15) a heavy chain variable region comprising an amino acid sequence of SEQ ID NO: 81, and a light chain variable region comprising an amino acid sequence of SEQ ID NO: 60.

[2-2A] The multispecific antigen-binding molecule of any one [2-1] to [2-2], wherein the first antigen-binding moiety and the second antigen-binding moiety each comprises an antibody variable region comprising a heavy chain complementarity determining region (CDR) 1 of SEQ ID NO: 20, a heavy chain CDR 2 of SEQ ID NO: 34, a heavy chain CDR 3 of SEQ ID NO: 48, a light chain CDR 1 of SEQ ID NO: 63, a light chain CDR 2 of SEQ ID NO: 68 and a light chain CDR 3 of SEQ ID NO: 73.

[2-2B] The multispecific antigen-binding molecule of [2-2A], wherein the first antigen-binding moiety and the second antigen-binding moiety each comprises an antibody variable region comprising a heavy chain variable region comprising an amino acid sequence of SEQ ID NO: 6, and a light chain variable region comprising an amino acid sequence of SEQ ID NO: 58.

[2-2C] The multispecific antigen-binding molecule of any one of [2-1] to [2-2B], wherein the third antigen-binding moiety comprises an antibody variable region comprising a VH comprising SEQ ID NO: 232 and a VL comprising SEQ ID NO: 236.

[2-3] The multispecific antigen-binding molecule of any one of [2-1] to [2-2C], wherein each of the first and second antigen-binding moieties is a Fab that has a cysteine residue at position 191 (EU numbering), and wherein there is a disulfide bond linking the two cysteine residues.

[2-4] The multispecific antigen-binding molecule of [2-3], wherein each of the first, second and third antigen binding moieties is a Fab comprising a heavy chain comprising a VH and a CH1 domain and a light chain comprising a VL and a light chain constant (CL) domain, and wherein the C-terminus of the heavy chain of the third antigen binding moiety is fused, directly or via a peptide linker, to the N-terminus of the Fab heavy chain of either the first antigen binding moiety or the second antigen binding moiety.

[2-5] The multispecific antigen-binding molecule of [2-4], wherein the C-terminus of the heavy chain of the third antigen binding moiety is fused, via a peptide linker, to the N-terminus of the Fab heavy chain of either the first antigen binding moiety or the second antigen binding moiety, and wherein the peptide linker has an amino acid sequence selected from the group consisting of SEQ ID NO: 248, SEQ ID NO: 249, and SEQ ID NO: 259.

[2-6] The multispecific antigen-binding molecule of [2-5], wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

[2-7] The multispecific antigen-binding molecule of [2-6], further comprising an Fc domain.

[2-8] The multispecific antigen-binding molecule of [2-7], wherein the Fc domain comprises a first and a second Fc region subunit, the first Fc-region subunit is selected from the group comprising:

a Fc region polypeptide comprising alanine at each of positions 234 and 235;

a Fc region polypeptide comprising alanine at each of positions 234, 235, and 297; and a Fc region polypeptide comprising alanine at each of positions 234, 235, and 297, cysteine at position 354, and tryptophan at position 366; and the second Fc-region subunit is selected from the group comprising:

a Fc region polypeptide comprising alanine at each of positions 234 and 235;

a Fc region polypeptide comprising alanine at each of positions 234, 235, and 297; and a Fc region polypeptide comprising alanine at each of positions 234, 235, and 297, cysteine at position 349, serine at position 366, alanine at position 368, and valine at position 407, wherein all positions are by EU numbering.

Yet another aspect of the present invention relates to:

[3-1] A multispecific antigen-binding molecule that comprises:

(a) a first antigen-binding moiety and a second antigen-binding moiety, each of which binds to human CD137 and comprises an antibody variable region that can be the same or different and is independently selected from the group consisting of:

(a1) an antibody variable region comprising heavy chain complementarity determining region (CDR) 1 of SEQ ID NO: 17, heavy chain CDR 2 of SEQ ID NO: 31, heavy chain CDR 3 of SEQ ID NO: 45, light chain CDR 1 of SEQ ID NO: 64, light chain CDR 2 of SEQ ID NO: 69 and light chain CDR 3 of SEQ ID NO: 74;

(a2) an antibody variable region comprising heavy chain complementarity determining region (CDR) 1 of SEQ ID NO: 18, heavy chain CDR 2 of SEQ ID NO: 32, heavy chain CDR 3 of SEQ ID NO: 46, light chain CDR 1 of SEQ ID NO: 63, light chain CDR 2 of SEQ ID NO: 68 and light chain CDR 3 of SEQ ID NO: 73;
(a3) an antibody variable region comprising the heavy chain complementarity determining region (CDR) 1 of SEQ ID NO: 19, the heavy chain CDR 2 of SEQ ID NO: 33, the heavy chain CDR 3 of SEQ ID NO: 47, light chain CDR 1 of SEQ ID NO: 63, light chain CDR 2 of SEQ ID NO: 68 and light chain CDR 3 of SEQ ID NO: 73;
(a4) an antibody variable region comprising the heavy chain complementarity determining region (CDR) 1 of SEQ ID NO: 19, the heavy chain CDR 2 of SEQ ID NO: 33, the heavy chain CDR 3 of SEQ ID NO: 47, light chain CDR 1 of SEQ ID NO: 65, light chain CDR 2 of SEQ ID NO: 70 and light chain CDR 3 of SEQ ID NO: 75;
(a5) an antibody variable region comprising the heavy chain complementarity determining region (CDR) 1 of SEQ ID NO: 20, the heavy chain CDR 2 of SEQ ID NO: 34, the heavy chain CDR 3 of SEQ ID NO: 48, light chain CDR 1 of SEQ ID NO: 63, light chain CDR 2 of SEQ ID NO: 68 and light chain CDR 3 of SEQ ID NO: 73;
(a6) an antibody variable region comprising the heavy chain complementarity determining region (CDR) 1 of SEQ ID NO: 22, the heavy chain CDR 2 of SEQ ID NO: 36, the heavy chain CDR 3 of SEQ ID NO: 50, light chain CDR 1 of SEQ ID NO: 63, light chain CDR 2 of SEQ ID NO: 68 and light chain CDR 3 of SEQ ID NO: 73;
(a7) an antibody variable region comprising the heavy chain complementarity determining region (CDR) 1 of SEQ ID NO: 23, the heavy chain CDR 2 of SEQ ID NO: 37, the heavy chain CDR 3 of SEQ ID NO: 51, light chain CDR 1 of SEQ ID NO: 63, light chain CDR 2 of SEQ ID NO: 68 and light chain CDR 3 of SEQ ID NO: 73;
(a8) an antibody variable region comprising the heavy chain complementarity determining region (CDR) 1 of SEQ ID NO: 23, the heavy chain CDR 2 of SEQ ID NO: 37, the heavy chain CDR 3 of SEQ ID NO: 51, light chain CDR 1 of SEQ ID NO: 66, light chain CDR 2 of SEQ ID NO: 71 and light chain CDR 3 of SEQ ID NO: 76;
(a9) an antibody variable region comprising the heavy chain complementarity determining region (CDR) 1 of SEQ ID NO: 24, the heavy chain CDR 2 of SEQ ID NO: 38, the heavy chain CDR 3 of SEQ ID NO: 52, light chain CDR 1 of SEQ ID NO: 63, light chain CDR 2 of SEQ ID NO: 68 and light chain CDR 3 of SEQ ID NO: 73;
(a10) an antibody variable region comprising the heavy chain complementarity determining region (CDR) 1 of SEQ ID NO: 25, the heavy chain CDR 2 of SEQ ID NO: 39, the heavy chain CDR 3 of SEQ ID NO: 53, light chain CDR 1 of SEQ ID NO: 66, light chain CDR 2 of SEQ ID NO: 71 and light chain CDR 3 of SEQ ID NO: 76;
(a11) an antibody variable region comprising the heavy chain complementarity determining region (CDR) 1 of SEQ ID NO: 26, the heavy chain CDR 2 of SEQ ID NO: 40, the heavy chain CDR 3 of SEQ ID NO: 54, light chain CDR 1 of SEQ ID NO: 66, light chain CDR 2 of SEQ ID NO: 71 and light chain CDR 3 of SEQ ID NO: 76;
(a12) an antibody variable region comprising the heavy chain complementarity determining region (CDR) 1 of SEQ ID NO: 26, the heavy chain CDR 2 of SEQ ID NO: 40, the heavy chain CDR 3 of SEQ ID NO: 54, light chain CDR 1 of SEQ ID NO: 63, light chain CDR 2 of SEQ ID NO: 68 and light chain CDR 3 of SEQ ID NO: 73;
(a13) an antibody variable region comprising the heavy chain complementarity determining region (CDR) 1 of SEQ ID NO: 27, the heavy chain CDR 2 of SEQ ID NO: 41, the heavy chain CDR 3 of SEQ ID NO: 55, light chain CDR 1 of SEQ ID NO: 63, light chain CDR 2 of SEQ ID NO: 68 and light chain CDR 3 of SEQ ID NO: 73;
(a14) an antibody variable region comprising the heavy chain complementarity determining region (CDR) 1 of SEQ ID NO: 28, the heavy chain CDR 2 of SEQ ID NO: 42, the heavy chain CDR 3 of SEQ ID NO: 56, light chain CDR 1 of SEQ ID NO: 63, light chain CDR 2 of SEQ ID NO: 68 and light chain CDR 3 of SEQ ID NO: 73; and
(a15) an antibody variable region comprising heavy chain complementarity determining region (CDR) 1 of SEQ ID NO: 82, heavy chain CDR 2 of SEQ ID NO: 83, heavy chain CDR 3 of SEQ ID NO: 84, light chain CDR 1 of SEQ ID NO: 65, light chain CDR 2 of SEQ ID NO: 70 and light chain CDR 3 of SEQ ID NO: 75; and (b) a third antigen-binding moiety that binds to human Delta-like 3 (DLL3) and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

[3-2] The multispecific antigen-binding molecule of [3-1], wherein each of the first and second antigen-binding moieties comprises an antibody variable region that can be the same or different and is independently selected from the group consisting of:
(a1) a heavy chain variable region comprising an amino acid sequence of SEQ ID NO: 3, and a light chain variable region comprising an amino acid sequence of SEQ ID NO: 59;
(a2) a heavy chain variable region comprising an amino acid sequence of SEQ ID NO: 4, and a light chain variable region comprising an amino acid sequence of SEQ ID NO: 58;
(a3) a heavy chain variable region comprising an amino acid sequence of SEQ ID NO: 5, and a light chain variable region comprising an amino acid sequence of SEQ ID NO: 58;
(a4) a heavy chain variable region comprising an amino acid sequence of SEQ ID NO: 5, and a light chain variable region comprising an amino acid sequence of SEQ ID NO: 60;
(a5) a heavy chain variable region comprising an amino acid sequence of SEQ ID NO: 6, and a light chain variable region comprising an amino acid sequence of SEQ ID NO: 58;
(a6) a heavy chain variable region comprising an amino acid sequence of SEQ ID NO: 8, and a light chain variable region comprising an amino acid sequence of SEQ ID NO: 58;
(a7) a heavy chain variable region comprising an amino acid sequence of SEQ ID NO: 9, and a light chain variable region comprising an amino acid sequence of SEQ ID NO: 58;

(a8) a heavy chain variable region comprising an amino acid sequence of SEQ ID NO: 9, and a light chain variable region comprising an amino acid sequence of SEQ ID NO: 61;
(a9) a heavy chain variable region comprising an amino acid sequence of SEQ ID NO: 10, and a light chain variable region comprising an amino acid sequence of SEQ ID NO: 58;
(a10) a heavy chain variable region comprising an amino acid sequence of SEQ ID NO: 11, and a light chain variable region comprising an amino acid sequence of SEQ ID NO: 61;
(a11) a heavy chain variable region comprising an amino acid sequence of SEQ ID NO: 12, and a light chain variable region comprising an amino acid sequence of SEQ ID NO: 61;
(a12) a heavy chain variable region comprising an amino acid sequence of SEQ ID NO: 12, and a light chain variable region comprising an amino acid sequence of SEQ ID NO: 58;
(a13) a heavy chain variable region comprising an amino acid sequence of SEQ ID NO: 13, and a light chain variable region comprising an amino acid sequence of SEQ ID NO: 58;
(a14) a heavy chain variable region comprising an amino acid sequence of SEQ ID NO: 14, and a light chain variable region comprising an amino acid sequence of SEQ ID NO: 58; and
(a15) a heavy chain variable region comprising an amino acid sequence of SEQ ID NO: 81, and a light chain variable region comprising an amino acid sequence of SEQ ID NO: 60.

[3-2A] The multispecific antigen-binding molecule of any one [3-1] to [3-2], wherein the first antigen-binding moiety and the second antigen-binding moiety each comprises an antibody variable region comprising a heavy chain complementarity determining region (CDR) 1 of SEQ ID NO: 20, a heavy chain CDR 2 of SEQ ID NO: 34, a heavy chain CDR 3 of SEQ ID NO: 48, a light chain CDR 1 of SEQ ID NO: 63, a light chain CDR 2 of SEQ ID NO: 68 and a light chain CDR 3 of SEQ ID NO: 73.

[3-2B] The multispecific antigen-binding molecule of [3-2A], wherein the first antigen-binding moiety and the second antigen-binding moiety each comprises an antibody variable region comprising a heavy chain variable region comprising an amino acid sequence of SEQ ID NO: 6, and a light chain variable region comprising an amino acid sequence of SEQ ID NO: 58.

[3-2C] The multispecific antigen-binding molecule of any one of [3-1] to [3-2B], wherein the third antigen-binding moiety comprises an antibody variable region comprising a VH comprising SEQ ID NO: 232 and a VL comprising SEQ ID NO: 236.

[3-3] The multispecific antigen-binding molecule of any one of [3-1] to [3-2C], wherein each of the first and second antigen-binding moieties is a Fab that has a cysteine residue at position 191 (EU numbering), and wherein there is a disulfide bond linking the two cysteine residues.

[3-4] The multispecific antigen-binding molecule of [3-3], wherein each of the first, second and third antigen binding moieties is a Fab comprising a heavy chain comprising a VH and a CH1 domain and a light chain comprising a VL and a light chain constant (CL) domain, and wherein the C-terminus of the heavy chain of the third antigen binding moiety is fused, directly or via a peptide linker, to the N-terminus of the Fab heavy chain of either the first antigen binding moiety or the second antigen binding moiety.

[3-5] The multispecific antigen-binding molecule of [3-4], wherein the C-terminus of the heavy chain of the third antigen binding moiety is fused, via a peptide linker, to the N-terminus of the Fab heavy chain of either the first antigen binding moiety or the second antigen binding moiety, and wherein the peptide linker has an amino acid sequence selected from the group consisting of SEQ ID NO: 248, SEQ ID NO: 249, and SEQ ID NO: 259.

[3-6] The multispecific antigen-binding molecule of [3-5], wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

[3-7] The multispecific antigen-binding molecule of [3-6], further comprising an Fc domain.

[3-8] The multispecific antigen-binding molecule of [3-7], wherein the Fc domain comprises a first and a second Fc region subunit, the first Fc-region subunit is selected from the group comprising:
  a Fc region polypeptide comprising alanine at each of positions 234 and 235;
  a Fc region polypeptide comprising alanine at each of positions 234, 235, and 297; and
  a Fc region polypeptide comprising alanine at each of positions 234, 235, and 297, cysteine at position 354, and tryptophan at position 366; and
the second Fc-region subunit is selected from the group comprising:
  a Fc region polypeptide comprising alanine at each of positions 234 and 235;
  a Fc region polypeptide comprising alanine at each of positions 234, 235, and 297; and
  a Fc region polypeptide comprising alanine at each of positions 234, 235, and 297, cysteine at position 349, serine at position 366, alanine at position 368, and valine at position 407,
wherein all positions are by EU numbering.

Yet another aspect of the present invention relates to:
[4-1] A multispecific antigen-binding molecule that comprises:
(a) a first antigen-binding moiety and a second antigen-binding moiety, each of which binds to human CD3 and comprises an antibody variable region that can be the same or different and is independently selected from the group consisting of (a1) to (a15):
(a1) an antibody variable region comprising a heavy chain complementarity determining region (CDR) 1 comprising SEQ ID NO: 17, a heavy chain CDR 2 comprising SEQ ID NO: 31, a heavy chain CDR 3 comprising SEQ ID NO: 45, a light chain CDR 1 comprising SEQ ID NO: 64, a light chain CDR 2 comprising SEQ ID NO: 69, and a light chain CDR 3 comprising SEQ ID NO: 74;
(a2) an antibody variable region comprising a heavy chain CDR 1 comprising SEQ ID NO: 18, a heavy chain CDR 2 comprising SEQ ID NO: 32, a heavy chain CDR 3 comprising SEQ ID NO: 46, a light chain CDR 1 comprising SEQ ID NO: 63, a light chain CDR 2 comprising SEQ ID NO: 68, and a light chain CDR 3 comprising SEQ ID NO: 73;
(a3) an antibody variable region comprising a heavy chain CDR 1 comprising SEQ ID NO: 19, a heavy chain CDR 2 comprising SEQ ID NO: 33, a heavy chain CDR 3 comprising SEQ ID NO: 47, a light chain CDR 1 comprising SEQ ID NO: 63, a light chain CDR 2 comprising SEQ ID NO: 68, and a light chain CDR 3 comprising SEQ ID NO: 73;

(a4) an antibody variable region comprising a heavy chain CDR 1 comprising SEQ ID NO: 19, a heavy chain CDR 2 comprising SEQ ID NO: 33, a heavy chain CDR 3 comprising SEQ ID NO: 47, a light chain CDR 1 comprising SEQ ID NO: 65, a light chain CDR 2 comprising SEQ ID NO: 70, and a light chain CDR 3 comprising SEQ ID NO: 75;

(a5) an antibody variable region comprising a heavy chain CDR 1 comprising SEQ ID NO: 20, a heavy chain CDR 2 comprising SEQ ID NO: 34, a heavy chain CDR 3 comprising SEQ ID NO: 48, a light chain CDR 1 comprising SEQ ID NO: 63, a light chain CDR 2 comprising SEQ ID NO: 68, and a light chain CDR 3 comprising SEQ ID NO: 73;

(a6) an antibody variable region comprising a heavy chain CDR 1 comprising SEQ ID NO: 22, a heavy chain CDR 2 comprising SEQ ID NO: 36, a heavy chain CDR 3 comprising SEQ ID NO: 50, a light chain CDR 1 comprising SEQ ID NO: 63, a light chain CDR 2 comprising SEQ ID NO: 68, and a light chain CDR 3 comprising SEQ ID NO: 73;

(a7) an antibody variable region comprising a heavy chain CDR 1 comprising SEQ ID NO: 23, a heavy chain CDR 2 comprising SEQ ID NO: 37, a heavy chain CDR 3 comprising SEQ ID NO: 51, a light chain CDR 1 comprising SEQ ID NO: 63, a light chain CDR 2 comprising SEQ ID NO: 68, and a light chain CDR 3 comprising SEQ ID NO: 73;

(a8) an antibody variable region comprising a heavy chain CDR 1 comprising SEQ ID NO: 23, a heavy chain CDR 2 comprising SEQ ID NO: 37, a heavy chain CDR 3 comprising SEQ ID NO: 51, a light chain CDR 1 comprising SEQ ID NO: 66, a light chain CDR 2 comprising SEQ ID NO: 71, and a light chain CDR 3 comprising SEQ ID NO: 76;

(a9) an antibody variable region comprising a heavy chain CDR 1 comprising SEQ ID NO: 24, a heavy chain CDR 2 comprising SEQ ID NO: 38, a heavy chain CDR 3 comprising SEQ ID NO: 52, a light chain CDR 1 comprising SEQ ID NO: 63, a light chain CDR 2 comprising SEQ ID NO: 68, and a light chain CDR 3 comprising SEQ ID NO: 73;

(a10) an antibody variable region comprising a heavy chain CDR 1 comprising SEQ ID NO: 25, a heavy chain CDR 2 comprising SEQ ID NO: 39, a heavy chain CDR 3 comprising SEQ ID NO: 53, a light chain CDR 1 comprising SEQ ID NO: 66, a light chain CDR 2 comprising SEQ ID NO: 71, and a light chain CDR 3 comprising SEQ ID NO: 76;

(a11) an antibody variable region comprising a heavy chain CDR 1 comprising SEQ ID NO: 26, a heavy chain CDR 2 comprising SEQ ID NO: 40, a heavy chain CDR 3 comprising SEQ ID NO: 54, a light chain CDR 1 comprising SEQ ID NO: 66, a light chain CDR 2 comprising SEQ ID NO: 71, and a light chain CDR 3 comprising SEQ ID NO: 76;

(a12) an antibody variable region comprising a heavy chain CDR 1 comprising SEQ ID NO: 26, a heavy chain CDR 2 comprising SEQ ID NO: 40, a heavy chain CDR 3 comprising SEQ ID NO: 54, a light chain CDR 1 comprising SEQ ID NO: 63, a light chain CDR 2 comprising SEQ ID NO: 68, and a light chain CDR 3 comprising SEQ ID NO: 73;

(a13) an antibody variable region comprising a heavy chain CDR 1 comprising SEQ ID NO: 27, a heavy chain CDR 2 comprising SEQ ID NO: 41, a heavy chain CDR 3 comprising SEQ ID NO: 55, a light chain CDR 1 comprising SEQ ID NO: 63, a light chain CDR 2 comprising SEQ ID NO: 68, and a light chain CDR 3 comprising SEQ ID NO: 73;

(a14) an antibody variable region comprising a heavy chain CDR 1 comprising SEQ ID NO: 28, a heavy chain CDR 2 comprising SEQ ID NO: 42, a heavy chain CDR 3 comprising SEQ ID NO: 56, a light chain CDR 1 comprising SEQ ID NO: 63, a light chain CDR 2 comprising SEQ ID NO: 68, and a light chain CDR 3 comprising SEQ ID NO: 73; and (a15) an antibody variable region comprising a heavy chain CDR 1 comprising SEQ ID NO: 82, a heavy chain CDR 2 comprising SEQ ID NO: 83, a heavy chain CDR 3 comprising SEQ ID NO: 84, a light chain CDR 1 comprising SEQ ID NO: 65, a light chain CDR 2 comprising SEQ ID NO: 70, and a light chain CDR 3 comprising SEQ ID NO: 75;

and (b) a third antigen-binding moiety that binds to human Delta-like 3 (DLL3) and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

[4-2] A multispecific antigen-binding molecule that comprises:

(a) a first antigen-binding moiety and a second antigen-binding moiety, each of which comprises an antibody variable region that can be the same or different and is independently selected from the group consisting of:

(a1) an antibody variable region comprising a heavy chain variable region (VH) comprising SEQ ID NO: 3 and a light chain variable region (VL) comprising SEQ ID NO: 59;

(a2) an antibody variable region comprising a VH comprising SEQ ID NO: 4 and a VL comprising SEQ ID NO: 58;

(a3) an antibody variable region comprising a VH comprising SEQ ID NO: 5 and a VL comprising SEQ ID NO:58;

(a4) an antibody variable region comprising a VH comprising SEQ ID NO: 5 and a VL comprising SEQ ID NO: 60;

(a5) an antibody variable region comprising a VH comprising SEQ ID NO: 6 and a VL comprising SEQ ID NO: 58;

(a6) an antibody variable region comprising a VH comprising SEQ ID NO: 8 and a VL comprising SEQ ID NO: 58;

(a7) an antibody variable region comprising a VH comprising SEQ ID NO: 9 and a VL comprising SEQ ID NO: 58;

(a8) an antibody variable region comprising a VH comprising SEQ ID NO: 9 and a VL comprising SEQ ID NO: 61;

(a9) an antibody variable region comprising a VH comprising SEQ ID NO: 10 and a VL comprising SEQ ID NO: 58;

(a10) an antibody variable region comprising a VH comprising SEQ ID NO: 11 and a VL comprising SEQ ID NO: 61;

(a11) an antibody variable region comprising a VH comprising SEQ ID NO: 12 and a VL comprising SEQ ID NO: 61;

(a12) an antibody variable region comprising a VH comprising SEQ ID NO: 12 and a VL comprising SEQ ID NO: 58;

(a13) an antibody variable region comprising a VH comprising SEQ ID NO: 13 and a VL comprising SEQ ID NO: 58;

(a14) an antibody variable region comprising a VH comprising SEQ ID NO: 14 and a VL comprising SEQ ID NO: 58; and (a15) an antibody variable region comprising a VH comprising SEQ ID NO: 81 and a VL comprising SEQ ID NO: 60;

and (b) a third antigen-binding moiety comprising an antibody variable region comprising a VH comprising SEQ ID NO: 232 and a VL comprising SEQ ID NO: 236.

[4-3] The multispecific antigen-binding molecule of [4-1], wherein the antibody variable regions of the first and second antigen binding moieties are identical.

[4-4] The multispecific antigen-binding molecule of [4-2], wherein the antibody variable regions of the first and second antigen binding moieties are identical.

[4-5] The multispecific antigen-binding molecule of [4-3], wherein each of the first and second antigen-binding moieties is a Fab that has a cysteine residue at position 191 (EU numbering), and wherein a disulfide bond links these two cysteine residues.

[4-6] The multispecific antigen-binding molecule of [4-4], wherein each of the first and second antigen-binding moieties is a Fab that has a cysteine residue at position 191 (EU numbering), and wherein a disulfide bond links these two cysteine residues.

[4-7] The multispecific antigen-binding molecule of [4-5], wherein each of the first, second and third antigen binding moieties is in the form of a Fab comprising a VH, a VL, a CH1 domain and a light chain constant (CL) domain, and wherein the C-terminus of the CH1 domain of the third antigen-binding moiety is fused, directly or via a peptide linker, to the N-terminus of the VH of either the first antigen binding moiety or the second antigen binding moiety.

[4-8] The multispecific antigen-binding molecule of [4-6], wherein each of the first, second and third antigen binding moieties is in the form of a Fab comprising a CH1 domain and a light chain constant (CL) domain, and wherein the C-terminus of the CH1 domain of the third antigen-binding moiety is fused, directly or via a peptide linker, to the N-terminus of the VH of either the first antigen binding moiety or the second antigen binding moiety.

[4-9] The multispecific antigen-binding molecule of [4-7], wherein the fusion is via a peptide linker that comprises an amino acid sequence selected from the group consisting of SEQ ID NO: 248, SEQ ID NO: 249, and SEQ ID NO: 259.

[4-10] The multispecific antigen-binding molecule of [4-8], wherein the fusion is via a peptide linker that comprises an amino acid sequence selected from the group consisting of SEQ ID NO: 248, SEQ ID NO: 249, and SEQ ID NO: 259.

[4-11] The multispecific antigen-binding molecule of [4-9], wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

[4-12] The multispecific antigen-binding molecule of [4-10], wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

[4-13] The multispecific antigen-binding molecule of [4-11], wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

[4-14] The multispecific antigen-binding molecule of [4-12], wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

[4-15] The multispecific antigen-binding molecule of [4-13], further comprising an Fc domain.

[4-16] The multispecific antigen-binding molecule of [4-14], further comprising an Fc domain.

[4-17] The multispecific antigen-binding molecule of [4-15], wherein the Fc domain comprises a first and a second Fc region subunit, wherein the first Fc-region subunit is selected from the group comprising:

an Fc region polypeptide comprising alanine at each of positions 234 and 235;

an Fc region polypeptide comprising alanine at each of positions 234, 235, and 297; and an Fc region polypeptide comprising alanine at each of positions 234, 235, and 297, cysteine at position 354, and tryptophan at position 366;

wherein the second Fc-region subunit is selected from the group comprising:

an Fc region polypeptide comprising alanine at each of positions 234 and 235;

an Fc region polypeptide comprising alanine at each of positions 234, 235, and 297; and an Fc region polypeptide comprising alanine at each of positions 234, 235, and 297, cysteine at position 349, serine at position 366, alanine at position 368, and valine at position 407; and wherein all positions are by EU numbering.

[4-18] The multispecific antigen-binding molecule of [4-16], wherein the Fc domain comprises a first and a second Fc region subunit, wherein the first Fc-region subunit is selected from the group comprising:

an Fc region polypeptide comprising alanine at each of positions 234 and 235;

an Fc region polypeptide comprising alanine at each of positions 234, 235, and 297; and an Fc region polypeptide comprising alanine at each of positions 234, 235, and 297, cysteine at position 354, and tryptophan at position 366;

wherein the second Fc-region subunit is selected from the group comprising:

an Fc region polypeptide comprising alanine at each of positions 234 and 235;

an Fc region polypeptide comprising alanine at each of positions 234, 235, and 297; and an Fc region polypeptide comprising alanine at each of positions 234, 235, and 297, cysteine at position 349, serine at position 366, alanine at position 368, and valine at position 407; and wherein all positions are by EU numbering.

[4-19] A multispecific antigen-binding molecule that comprises five polypeptide chains in a combination selected from the group consisting of (A) to (0) below:

(A) a polypeptide chain comprising the amino acid sequence of SEQ ID NO: 201 (chain 1), a polypeptide chain comprising the amino acid sequence of SEQ ID NO: 206 (chain 2), a polypeptide chain comprising the amino acid sequence of SEQ ID NO: 208 (chain 3), and two polypeptide chains each comprising the amino acid sequence of SEQ ID NO: 214 (chains 4 and 5);
(B) a polypeptide chain comprising the amino acid sequence of SEQ ID NO: 203 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5);
(C) a polypeptide chain comprising the amino acid sequence of SEQ ID NO: 204 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5);
(D) a polypeptide chain comprising the amino acid sequence of SEQ ID NO: 205 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5);
(E) a polypeptide chain comprising the amino acid sequence of SEQ ID NO: 216 (chain 1), a polypeptide chain comprising the amino acid sequence of SEQ ID NO: 206 (chain 2), a polypeptide chain comprising the amino acid sequence of SEQ ID NO: 229 (chain 3), and two polypeptide chains each comprising the amino acid sequence of SEQ ID NO: 214 (chains 4 and 5);
(F) a polypeptide chain comprising the amino acid sequence of SEQ ID NO: 217 (chain 1), a polypeptide chain comprising the amino acid sequence of SEQ ID NO: 206 (chain 2), a polypeptide chain comprising the amino acid sequence of SEQ ID NO: 210 (chain 3), and two polypeptide chains each comprising the amino acid sequence of SEQ ID NO: 214 (chains 4 and 5);
(G) a polypeptide chain comprising the amino acid sequence of SEQ ID NO: 219 (chain 1), a polypeptide chain comprising the amino acid sequence of SEQ ID NO: 206 (chain 2), a polypeptide chain comprising the amino acid sequence of SEQ ID NO: 211 (chain 3), and two polypeptide chains each comprising the amino acid sequence of SEQ ID NO: 214 (chains 4 and 5);
(H) a polypeptide chain comprising the amino acid sequence of SEQ ID NO: 220 (chain 1), a polypeptide chain comprising the amino acid sequence of SEQ ID NO: 206 (chain 2), a polypeptide chain comprising the amino acid sequence of SEQ ID NO: 211 (chain 3), and two polypeptide chains each comprising the amino acid sequence of SEQ ID NO: 214 (chains 4 and 5);
(I) a polypeptide chain comprising the amino acid sequence of SEQ ID NO: 221 (chain 1), a polypeptide chain comprising the amino acid sequence of SEQ ID NO: 206 (chain 2), a polypeptide chain comprising the amino acid sequence of SEQ ID NO: 211 (chain 3), and two polypeptide chains each comprising the amino acid sequence of SEQ ID NO: 214 (chains 4 and 5);
(J) a polypeptide chain comprising the amino acid sequence of SEQ ID NO: 222 (chain 1), a polypeptide chain comprising the amino acid sequence of SEQ ID NO: 206 (chain 2), a polypeptide chain comprising the amino acid sequence of SEQ ID NO: 230 (chain 3), and two polypeptide chains each comprising the amino acid sequence of SEQ ID NO: 214 (chains 4 and 5);
(K) a polypeptide chain comprising the amino acid sequence of SEQ ID NO: 223 (chain 1), a polypeptide chain comprising the amino acid sequence of SEQ ID NO: 206 (chain 2), a polypeptide chain comprising the amino acid sequence of SEQ ID NO: 212 (chain 3), and two polypeptide chains each comprising the amino acid sequence of SEQ ID NO: 215 (chains 4 and 5);
(L) a polypeptide chain comprising the amino acid sequence of SEQ ID NO: 225 (chain 1), a polypeptide chain comprising the amino acid sequence of SEQ ID NO: 206 (chain 2), a polypeptide chain comprising the amino acid sequence of SEQ ID NO: 213 (chain 3), and two polypeptide chains each comprising the amino acid sequence of SEQ ID NO: 215 (chains 4 and 5);
(M) a polypeptide chain comprising the amino acid sequence of SEQ ID NO: 226 (chain 1), a polypeptide chain comprising the amino acid sequence of SEQ ID NO: 206 (chain 2), a polypeptide chain comprising the amino acid sequence of SEQ ID NO: 213 (chain 3), and two polypeptide chains each comprising the amino acid sequence of SEQ ID NO: 215 (chains 4 and 5);
(N) a polypeptide chain comprising the amino acid sequence of SEQ ID NO: 227 (chain 1), a polypeptide chain comprising the amino acid sequence of SEQ ID NO: 206 (chain 2), a polypeptide chain comprising the amino acid sequence of SEQ ID NO: 213 (chain 3), and two polypeptide chains each comprising the amino acid sequence of SEQ ID NO: 215 (chains 4 and 5); and
(O) a polypeptide chain comprising the amino acid sequence of SEQ ID NO: 228 (chain 1), a polypeptide chain comprising the amino acid sequence of SEQ ID NO: 206 (chain 2), a polypeptide chain comprising the amino acid sequence of SEQ ID NO: 231 (chain 3), and two polypeptide chains each comprising the amino acid sequence of SEQ ID NO: 215 (chains 4 and 5).

[4-20] The multispecific antigen-binding molecule of [4-19], which comprises a polypeptide chain comprising the amino acid sequence of SEQ ID NO: 203 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5).

[4-21] The multispecific antigen-binding molecule of [4-19], which comprises a polypeptide chain comprising the amino acid sequence of SEQ ID NO: 204 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5).

[4-22] The multispecific antigen-binding molecule of [4-19], which comprises a polypeptide chain comprising the amino acid sequence of SEQ ID NO: 205 (chain 1), a polypeptide chain comprising the amino acid sequence of SEQ ID NO: 206 (chain 2), a polypeptide chain comprising the amino acid sequence of SEQ ID NO: 209 (chain 3) and two polypeptide chains each comprising the amino acid sequence of SEQ ID NO: 214 (chains 4 and 5).

[4-23] A multispecific antigen-binding molecule that comprises:
(a) a first antigen-binding moiety and a second antigen-binding moiety, each of which binds to human CD3 and comprises an antibody variable region comprising a heavy chain CDR 1 comprising SEQ ID NO: 20, a heavy chain CDR 2 comprising SEQ ID NO: 34, a heavy chain CDR 3 comprising SEQ ID NO: 48, a light chain CDR 1 comprising SEQ ID NO: 63, a light chain CDR 2 comprising SEQ ID NO: 68, and a light chain CDR 3 comprising SEQ ID NO: 73;
and
(b) a third antigen-binding moiety that binds to human DLL3 and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

[4-24] The multispecific antigen-binding molecule of [4-23], wherein the antibody variable region of each of the first and second antigen-binding moieties comprises a VH comprising SEQ ID NO: 6 and a VL comprising SEQ ID NO: 58; and the antibody variable region of the third antigen-binding moiety comprises a VH comprising SEQ ID NO: 232 and a VL comprising SEQ ID NO: 236.

[4-25] The multispecific antigen-binding molecule of [4-24], wherein each of the first and second antigen-binding moieties is a Fab that has a cysteine residue at position 191 (EU numbering), and wherein a disulfide bond links these two cysteine residues.

[4-26] The multispecific antigen-binding molecule of [4-25], wherein each of the first, second and third antigen binding moieties is in the form of a Fab comprising a VH, a VL, a CH1 domain and a CL domain, and wherein the C-terminus of the CH1 domain of the third antigen-binding moiety is fused, directly or via a peptide linker, to the N-terminus of the VH of either the first antigen binding moiety or the second antigen binding moiety.

[4-27] The multispecific antigen-binding molecule of [4-26], wherein the fusion is via a peptide linker that comprises an amino acid sequence selected from the group consisting of SEQ ID NO: 248, SEQ ID NO: 249, and SEQ ID NO: 259.

[4-28] The multispecific antigen-binding molecule of [4-27], wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

[4-29] The multispecific antigen-binding molecule of [4-28], wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

[4-30] The multispecific antigen-binding molecule of [4-29], further comprising an Fc domain.

[4-31] The multispecific antigen-binding molecule of [4-30], wherein the Fc domain comprises a first and a second Fc region subunit,
wherein the first Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 354, and tryptophan at position 366;
wherein the second Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 349, serine at position 366, alanine at position 368, and valine at position 407; and
wherein all positions are by EU numbering.

BRIEF DESCRIPTION OF DRAWINGS

FIG. 1 shows design and naming rule of a) Trivalent Ab in DUAL/LINC (1+2) format, b) Bispecific Ab with conventional Ab format, and c) Bispecific Ab with BiTE format.

FIG. 2 shows TDCC activity of antibodies against SK-MEL30 cell lines. a) TDCC comparison among DUAL/LINC and CD3 bispecific formats. b) Linker length effect on cytotoxicity.

FIG. 3 shows in vivo efficacy of antibodies against NCI-H1436 xenograft in huNOG mice model. Y-axis means the tumor volume (mm$^3$) and X-axis means the days after tumor implantation.

FIG. 4 shows results of analyzing CD8 T cell infiltration. Tumors were harvested at indicated time points after antibody injection and T cell infiltration was analyzed using flow cytometer.

FIG. 5 shows results of analyzing exhaustion markers on CD8 T cells. Tumors were harvested on Day 7 after antibody injection and expression of exhaustion markers was analyzed using flow cytometer.

FIG. 6 is a schematic drawing showing the structures of the full-length human DLL3 and human DLL3 ECD fragment proteins. The epitope recognized by each of the anti-DLL3 antibodies is also shown. The EGF domain has six regions, EGF1 to EGF6 from the N-terminal side to the C-terminal side.

DESCRIPTION OF EMBODIMENTS

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The definitions and detailed description below are provided to facilitate understanding of the present disclosure illustrated herein.

Definitions

Amino Acids

Herein, amino acids are described by one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Alteration of Amino Acids

For amino acid alteration (also described as "amino acid substitution" or "amino acid mutation" within this description) in the amino acid sequence of an antigen-binding molecule, known methods such as site-directed mutagenesis methods (Kunkel et al. (Proc. Natl. Acad. Sci. USA (1985) 82, 488-492)) and overlap extension PCR may be appropriately employed. Furthermore, several known methods may also be employed as amino acid alteration methods for substitution to non-natural amino acids (Annu Rev. Biophys. Biomol. Struct. (2006) 35, 225-249; and Proc. Natl. Acad. Sci. U.S.A. (2003) 100 (11), 6353-6357). For example, it is suitable to use a cell-free translation system (Clover Direct (Protein Express)) containing a tRNA which has a non-natural amino acid bound to a complementary amber suppressor tRNA of one of the stop codons, the UAG codon (amber codon).

In the present specification, the meaning of the term "and/or" when describing the site of amino acid alteration includes every combination where "and" and "or" are suitably combined. Specifically, for example, "the amino acids at positions 33, 55, and/or 96 are substituted" includes the following variation of amino acid alterations: amino acid(s) at (a) position 33, (b) position 55, (c) position 96, (d) positions 33 and 55, (e) positions 33 and 96, (f) positions 55 and 96, and (g) positions 33, 55, and 96.

Furthermore, herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Polypeptides

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide as described herein may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

Percent (%) Amino Acid Sequence Identity

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Recombinant Methods and Compositions

Antibodies and antigen-binding molecules may be produced using recombinant methods and compositions, e.g., as described in U.S. Pat. No. 4,816,567. In one embodiment, isolated nucleic acid encoding an antibody as described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making the multispecific antigen-binding molecule of the present invention is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody described herein, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Recombinant production of an antigen-binding molecule described herein could be done with methods similar to those described above, by using a host cell comprises (e.g., has been transformed with) one or plural vectors comprising nucleic acid that encodes an amino acid sequence comprising the whole antigen-binding molecule or part of the antigen-binding molecule.

Antigen-Binding Molecule and Multispecific Antigen-Binding Molecules

The term "antigen-binding molecule", as used herein, refers to any molecule that comprises an antigen-binding site or any molecule that has binding activity to an antigen, and may further refers to molecules such as a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such. Scaffold molecules comprising known stable conformational structure such as alpha/beta barrel as scaffold, and in which part of the molecule is made into antigen-binding site, is also one embodiment of the antigen binding molecule described herein.

"Multispecific antigen-binding molecules" refers to antigen-binding molecules that bind specifically to more than one antigen. The term "bispecific" means that the antigen binding molecule is able to specifically bind to at least two distinct antigenic determinants. The term "trispecific" means that the antigen binding molecule is able to specifically bind to at least three distinct antigenic determinants. In certain embodiments, the multispecific antigen binding molecule of the present application is a trispecific antigen binding molecule, i.e. it is capable of specifically binding to three different antigen—capable of binding to either one of CD3 or CD137 but does not bind to both antigens simultaneously, and is capable of specifically binding to DLL3.

In a first aspect, the present disclosure provides a multispecific antigen binding molecule comprising: a first antigen-binding moiety and a second antigen-binding moiety, each of which is capable of binding to CD3 and CD137, but does not bind to CD3 and CD137 at the same time; and a third antigen-binding moiety that is capable of binding to a third antigen, preferably an antigen expressed on a cancer cell/tissue. In certain embodiments, the third antigen bound by the third antigen-binding moiety is DLL3, and preferably is human DLL3.

The first antigen-binding moiety and the second antigen-binding moiety can be a "Dual antigen binding moiety" capable of binding to CD3 and CD137, but not at the same time, which will be described in more detail below. The third antigen-binding moiety can be a "DLL3 antigen binding moiety", which also will be described in more detail below.

In some embodiments, each of the first antigen-binding moiety and the second antigen-binding moiety is a Fab molecule and comprises at least one disulfide bond formed between the CH1 region of the first antigen-binding moiety and the CH1 region of the second antigen-binding moiety. The disulfide bond may be formed between the amino acid residues at position 191 according to EU numbering in the respective CH1 region of the first antigen-binding moiety and the second antigen-binding moiety.

In some embodiments, the third antigen binding moiety, which may be a Fab or scFv, is fused to either one of the first antigen binding moiety or the second antigen binding moiety. In the case that each of the first, second, and third antigen binding moiety is a Fab molecule, the third antigen binding moiety may be fused at the C-terminus of the Fab heavy chain (CH1) to the N-terminus of the Fab heavy chain of either one of the first antigen binding moiety or the second antigen binding moiety, optionally via a peptide linker. Representative peptide linkers include those consisting of the amino acid sequence of SEQ ID NO: 248, SEQ ID NO: 249, or SEQ ID NO: 259. In certain embodiments, the first antigen binding moiety is identical to the second antigen binding moiety.

In some embodiments, the third antigen binding moiety is a crossover Fab molecule in which the variable regions of the Fab light chain and the Fab heavy chain are exchanged, and wherein each of the first and second antigen binding moiety is a conventional Fab molecule.

In some embodiments, in the constant domain CL of the light chain of each of the first and second antigen binding moiety, the amino acid(s) at position 123 and/or 124 is/are substituted independently by lysine (K), arginine (R) or histidine (H) (numbering according to Kabat), and wherein in the constant domain CH1 of the heavy chain of each of the first and second antigen binding moiety, the amino acid at position 147 and/or the amino acid at position 213 is substituted independently by glutamic acid (E) or aspartic acid (D) (numbering according to Kabat EU index). In other embodiments, in the constant domain CL of the light chain of each of the first and second antigen binding moiety, the amino acids at position 123 and 124 are arginine (R) and lysine (K) respectively (numbering according to Kabat), and wherein in the constant domain CH1 of the heavy chain of each of the first and second antigen binding moiety the amino acids at position 147 and 213 are glutamic acid (E) (numbering according to Kabat EU index).

The multispecific antigen-binding molecule can further comprise a Fc domain, which will be described in detail below. In the case that each of the first and second antigen-binding moiety is a Fab, the first antigen-binding moiety may be fused at the C-terminus of the Fab heavy chain to the N-terminus of the first or second subunit of the Fc domain, and the second antigen-binding moiety may be fused at the C-terminus of the Fab heavy chain to the N-terminus of the remaining subunit of the Fc domain. In some embodiments, the third antigen binding moiety is fused at the C-terminus to the N-terminus of the Fab heavy chain of either one of the first antigen binding moiety or the second antigen binding moiety, optionally via a peptide linker.

In another aspect of the present invention, the present disclosure provides a multispecific antigen-binding molecule comprising: an antigen-binding moiety which is capable of binding to CD3 and CD137, but does not bind to CD3 and CD137 at the same time; and an antigen-binding moiety that is capable of binding to DLL3, preferably human DLL3. In certain embodiments, the antigen-binding moiety which is capable of binding to CD3 and CD137, but does not bind to CD3 and CD137 at the same time, is a "Dual antigen binding moiety" capable of binding to CD3 and CD137, but not at the same time, described in detail below.

The components of the multispecific antigen binding molecules of the present invention can be fused to each other in a variety of configurations. Exemplary configurations are depicted in panel (a) of FIG. 1 read together with Tables 10-1 to 10-3.

According to any of the above embodiments, components of the multispecific antigen binding molecules (e.g. antigen binding moiety, Fc domain) may be fused directly or through various linkers, particularly peptide linkers comprising one or more amino acids, typically about 2-20 amino acids, that are described herein or are known in the art. Suitable, non-immunogenic peptide linkers include, for example, (G4S)n, (SG4)n, (G4S)n or G4(SG4)n peptide linkers, wherein n is generally a number between 1 and 10, typically between 2 and 4.

Pyroglutamylation

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (Journal of Pharmaceutical Sciences, 2008, Vol. 97, p. 2426-2447).

In some embodiments, the multispecific antigen binding molecules of the present invention also includes posttranslational modification. Examples of posttranslational includes undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, 2006, Vol. 348, p. 24-39).

Antigen Binding Moiety

As used herein, the term "antigen binding moiety" refers to a polypeptide molecule that specifically binds to an antigen. In one embodiment, an antigen binding moiety is able to direct the entity to which it is attached to a target site, for example to a specific type of tumor cell expressing the cancer antigen (DLL3). In another embodiment an antigen binding moiety is able to activate signaling through its target antigen, for example a T cell receptor complex antigen (in particular CD3) and/or a co-stimulatory receptor (CD137). Antigen binding moieties include antibodies and fragments thereof as further defined herein. Particular antigen binding moieties include an antigen binding domain or an antibody variable region of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: alpha, delta, epsilon, gamma, or mu. Useful light chain constant regions include any of the two isotypes: kappa and lambda.

As used herein, the terms "first", "second", and "third" with respect to antigen binding moieties etc., are used for convenience of distinguishing when there is more than one of each type of moiety. Use of these terms is not intended to confer a specific order or orientation of the multispecific antigen binding molecule unless explicitly so stated.

In another aspect, antigen binding moiety of the present invention disclosed herein can be used in novel chimeric antigen receptor (CAR) comprising one or more of the antigen binding moiety disclosed herein. In certain embodiments, a CAR of the invention will comprise a scFv construct, and in a preferred embodiment, will comprise and comprise a heavy and light chain variable region as disclosed herein. In a preferred embodiment, the disclosed chimeric antigen receptors are useful for treating or preventing a proliferative disorder and any recurrence or metastasis thereof.

Antigen-Binding Moiety Capable of Binding to CD3 and CD137 but not at the Same Time The multispecific antigen binding molecule described herein comprises at least one antigen binding moiety capable of binding to CD3 and CD137, but does not bind to CD3 and CD137 at the same time (also referred to herein as "Dual antigen binding moiety" or "first antigen binding moiety" or "Dual-Fab" or Dual-Ig"). In a particular embodiment, the multispecific antigen binding molecule comprises two Dual antigen binding moieties ("first antigen binding moiety" and "second antigen binding moiety", each of which may be called as "Dual-Fab"). In some embodiments, each of the two Dual antigen binding moiety ("first antigen binding moiety" or "second antigen binding moiety" or "Dual-Fab") provides monovalent binding to CD3 or CD137, but does not bind to CD3 and CD137 at the same time. In a particular embodiment, the multispecific antigen binding molecule comprises not more than two of the Dual antigen binding moiety ("first antigen binding moiety" or "second antigen binding moiety" or "Dual-Fab").

In certain embodiments, the Dual antigen binding moiety ("first antigen binding moiety" or "second antigen binding moiety" or "Dual-Fab") is generally a Fab molecule, particularly a conventional Fab molecule. In certain embodiments, the Dual antigen binding moiety ("first antigen binding moiety" or "second antigen binding moiety" or "Dual-Fab") is a domain comprising antibody light-chain and heavy-chain variable regions (VL and VH). Suitable examples of such domains comprising antibody light-chain and heavy-chain variable regions include "single chain Fv (scFv)", "single chain antibody", "Fv", "single chain Fv 2 (scFv2)", "Fab", "F(ab')2", etc.

In certain embodiments, the Dual antigen binding moiety ("first antigen binding moiety" or "second antigen binding moiety" or "Dual-Fab") specifically binds to the whole or a portion of a partial peptide of CD3. In a particular embodiment, CD3 is human CD3 or cynomolgus CD3, most particularly human CD3. In a particular embodiment the first antigen binding moiety is cross-reactive for (i.e. specifically binds to) human and cynomolgus CD3. In some embodiments, the first antigen binding moiety is capable of specific binding to the epsilon subunit of CD3, in particular the human CD3 epsilon subunit of CD3 which is shown in SEQ ID NO: 7 (NP_000724.1) (RefSeq registration numbers are shown within the parentheses). In some embodiments, the Dual antigen binding moiety ("first antigen binding moiety" or "second antigen binding moiety" or "Dual-Fab") is capable of specific binding to the CD3 epsilon chain expressed on the surface of eukaryotic cells. In some embodiments, the Dual antigen binding moiety ("first antigen binding moiety" or "second antigen binding moiety" or "Dual-Fab") binds to the CD3 epsilon chain expressed on the surface of T cells.

In certain embodiments, the CD137 is human CD137. In some embodiments, favorable examples of an antigen-binding molecule of the present invention comprises Dual antigen binding moiety ("first antigen binding moiety" or "second antigen binding moiety" or "Dual-Fab") that binds to the same epitope as the human CD137 epitope bound by the antibody selected from the group consisting of:

antibody that recognize a region comprising the SPCPPNSFSSAGGQRTCD ICRQCKGVFRTRKECSSTSNAECDCTPGFHCLGAGCSMCEQDCKQGQELTKKG C sequence (SEQ ID NO: 21), antibody that recognize a region comprising the DCTPGFHCLGAGCSMCEQDCKQGQELTKKGC sequence (SEQ ID NO: 35), antibody that recognize a region comprising the LQDPCSNCPAGTFCDNNRNQICSPCPPNSFSSAGGQRTCDICRQCKGVFRTRKE CSSTSNAEC sequence (SEQ ID NO: 49), and antibody that recognize a region comprising the LQDPCSNCPAGTFCDNNRNQIC sequence (SEQ ID NO: 105) in the human CD137 protein.

In specific embodiments, the Dual antigen binding moiety ("first antigen binding moiety" or "second antigen binding moiety" or "Dual-Fab") comprises any one of the antibody variable region sequences shown in Table 1 below. In specific embodiments, the Dual antigen binding moiety ("first antigen binding moiety" or "second antigen binding moiety" or "Dual-Fab") comprises any one of the combinations of the heavy chain variable region and light chain variable region shown in Table 1.

TABLE 1

SEQ ID NOs of the variable regions of the Dual antigen binding moiety ("first antigen binding moiety" or "second antigen binding moiety" or "Dual-Fab")

| Name | SEQ ID NOs | |
|---|---|---|
| | Heavy chain variable region (VH) | Light chain variable region (VL) |
| DualAE08 | 3 | 59 |
| DualAE06 | 4 | 58 |
| DualAE17 | 5 | 58 |
| DualAE10 | 5 | 60 |
| DualAE05 | 6 | 58 |
| DualAE19 | 8 | 58 |
| DualAE20 | 9 | 58 |
| DualAE21 | 9 | 61 |
| DualAE22 | 10 | 58 |
| DualAE23 | 11 | 61 |
| DualAE09 | 12 | 61 |
| DualAE18 | 12 | 58 |
| DualAE14 | 13 | 58 |
| DualAE15 | 14 | 58 |
| DualAE16 | 81 | 60 |

TABLE 2

SEQ ID NOs of the HVR (CDR) sequences of the Dual antigen binding moiety ("first antigen binding moiety" or "second antigen binding moiety" or "Dual-Fab")

| Name | SEQ ID NOs | | | | | |
|---|---|---|---|---|---|---|
| | HVR-H1 | HVR-H2 | HVR-H3 | HVR-L1 | HVR-L2 | HVR-L3 |
| DualAE08 | 17 | 31 | 45 | 64 | 69 | 74 |
| DualAE06 | 18 | 32 | 46 | 63 | 68 | 73 |
| DualAE17 | 19 | 33 | 47 | 63 | 68 | 73 |
| DualAE10 | 19 | 33 | 47 | 65 | 70 | 75 |
| DualAE05 | 20 | 34 | 48 | 63 | 68 | 73 |
| DualAE19 | 22 | 36 | 50 | 63 | 68 | 73 |
| DualAE20 | 23 | 37 | 51 | 63 | 68 | 73 |
| DualAE21 | 23 | 37 | 51 | 66 | 71 | 76 |
| DualAE22 | 24 | 38 | 52 | 63 | 68 | 73 |
| DualAE23 | 25 | 39 | 53 | 66 | 71 | 76 |
| DualAE09 | 26 | 40 | 54 | 66 | 71 | 76 |
| DualAE18 | 26 | 40 | 54 | 63 | 68 | 73 |
| DualAE14 | 27 | 41 | 55 | 63 | 68 | 73 |
| DualAE15 | 28 | 42 | 56 | 63 | 68 | 73 |
| DualAE16 | 82 | 83 | 84 | 65 | 70 | 75 |

In one embodiment the Dual antigen binding moiety ("first antigen binding moiety" or "second antigen binding moiety" or "Dual-Fab") comprises a heavy chain variable region sequence that is at least about 95%, 96%, 97%, 98%, 99%, or 100% identical to SEQ ID NO: 6 and a light chain variable region sequence that is at least about 95%, 96%, 97%, 98%, 99%, or 100% identical to SEQ ID NO: 58. In one embodiment the Dual antigen binding moiety ("first antigen binding moiety" or "second antigen binding moiety" or "Dual-Fab") comprises a heavy chain variable region comprising the amino acid sequence of SEQ ID NO: 6 and a light chain variable region comprising the amino acid sequence of SEQ ID NO: 58.

In one embodiment the Dual antigen binding moiety ("first antigen binding moiety" or "second antigen binding moiety" or "Dual-Fab") comprises a heavy chain variable region sequence that is at least about 95%, 96%, 97%, 98%, 99%, or 100% identical to SEQ ID NO: 14 and a light chain variable region sequence that is at least about 95%, 96%, 97%, 98%, 99%, or 100% identical to SEQ ID NO: 58. In one embodiment the Dual antigen binding moiety ("first antigen binding moiety" or "second antigen binding moiety" or "Dual-Fab") comprises a heavy chain variable region comprising the amino acid sequence of SEQ ID NO: 14 and a light chain variable region comprising the amino acid sequence of SEQ ID NO: 58.

In one embodiment the Dual antigen binding moiety ("first antigen binding moiety" or "second antigen binding moiety" or "Dual-Fab") comprises a heavy chain variable region sequence that is at least about 95%, 96%, 97%, 98%, 99%, or 100% identical to SEQ ID NO: 81 and a light chain variable region sequence that is at least about 95%, 96%, 97%, 98%, 99%, or 100% identical to SEQ ID NO: 58. In one embodiment the Dual antigen binding moiety ("first antigen binding moiety" or "second antigen binding moiety" or "Dual-Fab") comprises a heavy chain variable region comprising the amino acid sequence of SEQ ID NO: 81 and a light chain variable region comprising the amino acid sequence of SEQ ID NO: 58.

In specific embodiments, the Dual antigen binding moiety ("first antigen binding moiety" or "second antigen binding moiety" or "Dual-Fab") comprises any one of the combinations of HVR sequences shown in Table 2 below.

In some embodiments, the Dual antigen binding moiety ("first antigen binding moiety" or "second antigen binding moiety" or "Dual-Fab") each comprises antibody variable region comprising any one of (a1) to (a17) below:
 (a1) the heavy chain complementarity determining region (CDR) 1 of SEQ ID NO: 17, the heavy chain CDR 2 of SEQ ID NO: 31, the heavy chain CDR 3 of SEQ ID NO: 45, the light chain CDR 1 of SEQ ID NO: 64, the light chain CDR 2 of SEQ ID NO: 69 and the light chain CDR 3 of SEQ ID NO: 74;
 (a2) the heavy chain complementarity determining region (CDR) 1 of SEQ ID NO: 18, the heavy chain CDR 2 of SEQ ID NO: 32, the heavy chain CDR 3 of SEQ ID NO: 46, the light chain CDR 1 of SEQ ID NO: 63, the light chain CDR 2 of SEQ ID NO: 68 and the light chain CDR 3 of SEQ ID NO: 73;
 (a3) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 63, the light chain CDR 2 of SEQ ID NO: 68 and the light chain CDR 3 of SEQ ID NO: 73;
 (a4) the heavy chain complementarity determining region (CDR) 1 of SEQ ID NO: 19, the heavy chain CDR 2 of SEQ ID NO: 33, the heavy chain CDR 3 of SEQ ID NO: 47, the light chain CDR 1 of SEQ ID NO: 65, the light chain CDR 2 of SEQ ID NO: 70 and the light chain CDR 3 of SEQ ID NO: 75;
 (a5) the heavy chain complementarity determining region (CDR) 1 of SEQ ID NO: 20, the heavy chain CDR 2 of SEQ ID NO: 34, the heavy chain CDR 3 of SEQ ID NO: 48, the light chain CDR 1 of SEQ ID NO: 63, the light chain CDR 2 of SEQ ID NO: 68 and the light chain CDR 3 of SEQ ID NO: 73;
 (a6) the heavy chain complementarity determining region (CDR) 1 of SEQ ID NO: 22, the heavy chain CDR 2 of SEQ ID NO: 36, the heavy chain CDR 3 of SEQ ID NO: 50, the light chain CDR 1 of SEQ ID NO: 63, the light chain CDR 2 of SEQ ID NO: 68 and the light chain CDR 3 of SEQ ID NO: 73;
 (a7) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 63, the light chain CDR 2 of SEQ ID NO: 68 and the light chain CDR 3 of SEQ ID NO: 73;
- (a8) the heavy chain complementarity determining region (CDR) 1 of SEQ ID NO: 23, the heavy chain CDR 2 of SEQ ID NO: 37, the heavy chain CDR 3 of SEQ ID NO: 51, the light chain CDR 1 of SEQ ID NO: 66, the light chain CDR 2 of SEQ ID NO: 71 and the light chain CDR 3 of SEQ ID NO: 76;
- (a9) the heavy chain complementarity determining region (CDR) 1 of SEQ ID NO: 24, the heavy chain CDR 2 of SEQ ID NO: 38, the heavy chain CDR 3 of SEQ ID NO: 52, the light chain CDR 1 of SEQ ID NO: 63, the light chain CDR 2 of SEQ ID NO: 68 and the light chain CDR 3 of SEQ ID NO: 73;
- (a10) the heavy chain complementarity determining region (CDR) 1 of SEQ ID NO: 25, the heavy chain CDR 2 of SEQ ID NO: 39, the heavy chain CDR 3 of SEQ ID NO: 53, the light chain CDR 1 of SEQ ID NO: 66, the light chain CDR 2 of SEQ ID NO: 71 and the light chain CDR 3 of SEQ ID NO: 76;
- (a11) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 66, the light chain CDR 2 of SEQ ID NO: 71 and the light chain CDR 3 of SEQ ID NO: 76;
- (a12) the heavy chain complementarity determining region (CDR) 1 of SEQ ID NO: 26, the heavy chain CDR 2 of SEQ ID NO: 40, the heavy chain CDR 3 of SEQ ID NO: 54, the light chain CDR 1 of SEQ ID NO: 63, the light chain CDR 2 of SEQ ID NO: 68 and the light chain CDR 3 of SEQ ID NO: 73;
- (a13) the heavy chain complementarity determining region (CDR) 1 of SEQ ID NO: 27, the heavy chain CDR 2 of SEQ ID NO: 41, the heavy chain CDR 3 of SEQ ID NO: 55, the light chain CDR 1 of SEQ ID NO: 63, the light chain CDR 2 of SEQ ID NO: 68 and the light chain CDR 3 of SEQ ID NO: 73;
- (a14) the heavy chain complementarity determining region (CDR) 1 of SEQ ID NO: 28, the heavy chain CDR 2 of SEQ ID NO: 42, the heavy chain CDR 3 of SEQ ID NO: 56, the light chain CDR 1 of SEQ ID NO: 63, the light chain CDR 2 of SEQ ID NO: 68 and the light chain CDR 3 of SEQ ID NO: 73;
- (a15) the heavy chain complementarity determining region (CDR) 1 of SEQ ID NO: 82, the heavy chain CDR 2 of SEQ ID NO: 83, the heavy chain CDR 3 of SEQ ID NO: 84, the light chain CDR 1 of SEQ ID NO: 65, the light chain CDR 2 of SEQ ID NO: 70 and the light chain CDR 3 of SEQ ID NO: 75;
- (a16) an antibody variable region that binds to the same epitope of any of the antibody variable region selected from (a1) to (a15); and
- (a17) an antibody variable fragment that competes with the binding of any of the antibody variable fragment selected from (a1) to (a15).

In some embodiments, the multispecific antigen binding molecules or the Dual antigen binding moiety ("first antigen binding moiety" or "second antigen binding moiety" or "Dual-Fab") of the present invention also includes posttranslational modification. Examples of posttranslational includes undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, 2006, Vol. 348, p. 24-39).

Antigen-Binding Moiety Capable of Binding to DLL3

The multispecific antigen binding molecule described herein comprises at least one antigen binding moiety capable of binding to Delta-like 3 (DLL3) (also referred to herein as a "DLL3 antigen binding moiety" or "third antigen binding moiety" or "antigen-binding moiety that binds to DLL3").

In certain embodiments, the multispecific antigen binding molecule comprises one antigen binding moiety capable of binding to DLL3. In certain embodiments, the multispecific antigen binding molecule comprises two antigen binding moieties capable of binding to DLL3 ("DLL3 antigen binding moiety"). In a particular such embodiment, each of these antigen binding moieties specifically binds to the same epitope of DLL3. In an even more particular embodiment, all of these "DLL3 antigen binding moiety" are identical. In one embodiment, the multispecific antigen binding molecule comprises an immunoglobulin molecule capable of specific binding to DLL3 ("DLL3 antigen binding moiety"). In one embodiment the multispecific antigen binding molecule comprises not more than two antigen binding moieties capable of binding to DLL3 ("DLL3 antigen binding moiety").

In certain embodiments, the DLL3 antigen binding moiety is a crossover Fab molecule, i.e. a DLL3 molecule wherein either the variable or the constant regions of the Fab heavy and light chains are exchanged. In certain embodiments, the DLL3 antigen binding moiety is a crossover Fab molecule in which the variable regions of the Fab light chain and the Fab heavy chain are exchanged.

In some embodiments, the DLL3 antigen binding moiety binds specifically to the extracellular domain of DLL3. In some embodiments, the DLL3 antigen binding moiety binds specifically to an epitope within the extracellular domain of DLL3. In some embodiments, the DLL3 antigen binding moiety binds to the DLL3 protein expressed on the surface of eukaryotic cells. In some embodiments, the DLL3 antigen binding moiety binds to the DLL3 protein expressed on the surface of cancer cells.

In some embodiments, the multispecific antigen-binding molecules or the DLL3 antigen binding moiety bind to an epitope within the extracellular domain (ECD), i.e., the domain from the N-terminus to immediately before the TM region, but not to the TM region or the C-terminal intracellular domain. The multispecific antigen-binding molecules or the DLL3 antigen binding moiety may bind to an epitope within any of the above-mentioned domains/regions within the ECD. In preferred embodiments, the multispecific antigen-binding molecules or the DLL3 antigen binding moiety bind to an epitope within the region from EGF6 to immediately before the TM region. More specifically, the multispecific antigen-binding molecules or the DLL3 antigen binding moiety may bind to an epitope within the regions defined in SEQ ID NO: 89 in human DLL3. In some embodiments, the multispecific antigen-binding molecules or the DLL3 antigen binding moiety bind to the EGF1, EGF2, EGF3, EGF4, EGF5, or EGF6 region or a region from EGF6 to immediately before the TM region of human DLL3, or an epitope within the EGF1, EGF2, EGF3, EGF4, EGF5, or EGF6 region or a region from EGF6 to immediately before the TM region of human DLL3. In some embodiments, the multispecific antigen-binding molecules or the DLL3 antigen binding moiety can be derived from previously reported anti-DLL3 antibodies in which the DLL3 epitopes bound have been characterized (e.g. WO2019131988 and WO2011093097).

In specific embodiments, the multispecific antigen-binding molecules or the DLL3 antigen binding moiety comprises any one of the antibody variable region sequences shown in Table 3. In specific embodiments, the multispecific antigen-binding molecules or the DLL3 antigen binding moiety comprises any one of the combinations of the heavy chain variable region and light chain variable region shown in Table 3. In some embodiments, multispecific antigen-binding molecules or the DLL3 antigen binding moiety comprises is a domain that comprises an antibody variable fragment that competes for binding to DLL3 with any one of the antibody variable regions shown in Table 3.

TABLE 3

SEQ ID NOs of the variable regions of the exemplary DLL3 antigen binding moiety

| Name | Heavy chain variable region (VH) | Light chain variable region (VL) |
|---|---|---|
| DL301 | 305 | 313 |
| DL306 | 306 | 314 |
| DL309 | 307 | 315 |
| DL312 | 308 | 316 |
| DLL3-14 | 309 | 317 |
| DLL3-22 | 310 | 318 |
| DLL3-4 | 311 | 319 |
| DLL3-6 | 312 | 320 |
| DLA0106 | 260 | 261 |
| DLA0126 | 262 | 263 |
| DLA0316 | 264 | 265 |
| DLA0379 | 266 | 267 |
| DLA0580 | 268 | 269 |
| DLA0641 | 270 | 271 |
| DLA0769 | 272 | 273 |
| DLA0841 | 274 | 275 |
| D30841AE05 | 297 | 236 |
| D30841AE08 | 298 | 236 |
| D30841AE11 | 298 | 302 |
| D30841AE12 | 299 | 236 |
| D30841AE13 | 232 | 236 |
| D30841AE14 | 300 | 236 |
| D30841AE15 | 301 | 236 |

In one embodiment the DLL3 antigen binding moiety comprises a heavy chain variable region sequence that is at least about 95%, 96%, 97%, 98%, 99% or 100% identical to SEQ ID NO: 232 and a light chain variable region sequence that is at least about 95%, 96%, 97%, 98%, 99% or 100% identical to SEQ ID NO: 236. In one embodiment the DLL3 antigen binding moiety comprises a heavy chain variable region comprising the amino acid sequence of SEQ ID NO: 232 and a light chain variable region comprising the amino acid sequence of SEQ ID NO: 236.

In one embodiment the DLL3 antigen binding moiety comprises a heavy chain variable region sequence that is at least about 95%, 96%, 97%, 98%, 99% or 100% identical to SEQ ID NO: 300 and a light chain variable region sequence that is at least about 95%, 96%, 97%, 98%, 99% or 100% identical to SEQ ID NO: 236. In one embodiment the DLL3 antigen binding moiety comprises a heavy chain variable region comprising the amino acid sequence of SEQ ID NO: 300 and a light chain variable region comprising the amino acid sequence of SEQ ID NO: 236.

In one embodiment the DLL3 antigen binding moiety comprises a heavy chain variable region sequence that is at least about 95%, 96%, 97%, 98%, 99% or 100% identical to SEQ ID NO: 301 and a light chain variable region sequence that is at least about 95%, 96%, 97%, 98%, 99% or 100% identical to SEQ ID NO: 236. In one embodiment the DLL3 antigen binding moiety comprises a heavy chain variable region comprising the amino acid sequence of SEQ ID NO: 301 and a light chain variable region comprising the amino acid sequence of SEQ ID NO: 236.

In one embodiment the DLL3 antigen binding moiety comprises a heavy chain variable region sequence that is at least about 95%, 96%, 97%, 98%, 99% or 100% identical to SEQ ID NO: 274 and a light chain variable region sequence that is at least about 95%, 96%, 97%, 98%, 99% or 100% identical to SEQ ID NO: 275. In one embodiment the DLL3 antigen binding moiety comprises a heavy chain variable region comprising the amino acid sequence of SEQ ID NO: 274 and a light chain variable region comprising the amino acid sequence of SEQ ID NO: 275.

In one embodiment the DLL3 antigen binding moiety comprises a heavy chain variable region sequence that is at least about 95%, 96%, 97%, 98%, 99% or 100% identical to SEQ ID NO: 264 and a light chain variable region sequence that is at least about 95%, 96%, 97%, 98%, 99% or 100% identical to SEQ ID NO: 265. In one embodiment the DLL3 antigen binding moiety comprises a heavy chain variable region comprising the amino acid sequence of SEQ ID NO: 264 and a light chain variable region comprising the amino acid sequence of SEQ ID NO: 265.

In specific embodiments, the DLL3 antigen binding moiety comprises any one of the combinations of HVR sequences shown in Table 4 below. In some embodiments, multispecific antigen-binding molecules or the DLL3 antigen binding moiety comprises is a domain that comprises an antibody variable fragment that competes for binding to DLL3 with any one of the antibody variable regions shown in Table 4, or competes for binding to DLL3 with any antibody variable fragment that comprises the HVR sequence identical with the HVR regions of the antibody variable regions shown in Table 4.

TABLE 4

SEQ ID NOs of the HVR (CDR) sequences of exemplary DLL3 antigen binding moiety

| Name | HVR-H1 | HVR-H2 | HVR-H3 | HVR-L1 | HVR-L2 | HVR-L3 |
|---|---|---|---|---|---|---|
| DLA0316 | 276 | 277 | 278 | 279 | 280 | 281 |
| DLA0580 | 285 | 286 | 287 | 288 | 289 | 290 |
| DLA0769 | 291 | 292 | 293 | 294 | 295 | 296 |
| DLA0841 | 282 | 283 | 284 | 237 | 238 | 239 |
| D30841AE05 | 233 | 234 | 303 | 237 | 238 | 239 |
| D30841AE08 | 233 | 234 | 235 | 237 | 238 | 239 |
| D30841AE11 | 233 | 234 | 235 | 237 | 238 | 304 |
| D30841AE12 | 233 | 234 | 235 | 237 | 238 | 239 |
| D30841AE13 | 233 | 234 | 235 | 237 | 238 | 239 |
| D30841AE14 | 233 | 234 | 235 | 237 | 238 | 239 |
| D30841AE15 | 233 | 234 | 235 | 237 | 238 | 239 |

In some embodiments, the multispecific antigen binding molecules or the DLL3 antigen binding moiety of the present invention comprises an antibody variable region comprising any one of (a1) to (a5) below:
 (a1) the heavy chain complementarity determining region (CDR) 1 of SEQ ID NO: 233, the heavy chain CDR 2 of SEQ ID NO: 234, the heavy chain CDR 3 of SEQ ID NO: 235, the light chain CDR 1 of SEQ ID NO: 237, the light chain CDR 2 of SEQ ID NO: 238 and the light chain CDR 3 of SEQ ID NO: 239;

(a2) the heavy chain complementarity determining region (CDR) 1 of SEQ ID NO: 276, the heavy chain CDR 2 of SEQ ID NO: 277, the heavy chain CDR 3 of SEQ ID NO: 278, the light chain CDR 1 of SEQ ID NO: 279, the light chain CDR 2 of SEQ ID NO: 280 and the light chain CDR 3 of SEQ ID NO: 281;

(a3) the heavy chain complementarity determining region (CDR) 1 of SEQ ID NO: 285, the heavy chain CDR 2 of SEQ ID NO: 286, the heavy chain CDR 3 of SEQ ID NO: 287, the light chain CDR 1 of SEQ ID NO: 288, the light chain CDR 2 of SEQ ID NO: 289 and the light chain CDR 3 of SEQ ID NO: 290;

(a4) an antibody variable region that binds to the same epitope of any of the antibody variable region selected from (a1) to (a3); and (a5) an antibody variable fragment that competes with the binding of any of the antibody variable fragment selected from (a1) to (a3).

In some embodiments, the multispecific antigen binding molecules or the DLL3 antigen binding moiety of the present invention also includes posttranslational modification. Examples of posttranslational includes undergone pyroglutamylation at the N terminal of the heavy chain variable region and/or deletion of lysine at the C terminal of the heavy chain. It is known in the field that such posttranslational modification due to pyroglutamylation at the N terminal and deletion of lysine at the C terminal does not have any influence on the activity of the antibody (Analytical Biochemistry, 2006, Vol. 348, p. 24-39).

In another aspect, the DLL3 antigen binding moiety of the present invention can be used in novel chimeric antigen receptor (CAR) incorporating a DLL3 binding domain (DLL3 CAR). In certain embodiments, a DLL3 binding domain (and DLL3 CAR) of the invention will comprise a scFv construct, and in a preferred embodiment, will comprise a heavy and light chain variable region as disclosed herein. In other preferred embodiments, the DLL3 binding domain (and DLL3 CAR) of the invention will comprise a scFv construct or fragment thereof comprising the heavy and light chain variable regions disclosed herein. In a preferred embodiment, the disclosed chimeric antigen receptors are useful for treating or preventing a proliferative disorder and any recurrence or metastasis thereof.

In certain embodiments, the DLL3 protein is expressed on tumor-initiating cells. DLL3 CAR is expressed on cytotoxic lymphocytes (preferably autologous cytotoxic lymphocytes) via genetic modification (e.g., transduction), resulting in DLL3-sensitive lymphocytes that can be used to target and kill DLL3-positive tumor cells. As will be broadly discussed herein, CARs of the invention typically comprise an extracellular domain, a transmembrane domain, and an intracellular signaling domain comprising a DLL3 binding domain that activates certain lymphocytes and produces immune response of DLL3 positive tumor cells. Selected embodiments of the invention comprise immunologically active host cells which exhibit the disclosed CAR and various polynucleotide sequences and vectors encoding the DLL3 CAR of the invention. Other aspects include methods of enhancing the activity of T lymphocytes or natural killer (NK) cells in an individual by introducing a host cell expressing a DLL3 CAR molecule into an individual suffering from cancer and treating the individual. Such aspects include, inter alia, lung cancer (e.g., small cell lung cancer) and melanoma.

Antigen

As used herein, the term "antigen" refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. CD3, CD137, DLL3) can be any native form the proteins from any vertebrate source, including mammals such as primates (e.g. humans) and rodents (e.g. mice and rats), unless otherwise indicated. In a particular embodiment the antigen is a human CD3, human CD137 or human DLL3. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

In certain embodiments the multispecific antigen binding molecule described herein binds to an epitope of CD3, CD137 or DLL3 that is conserved among the CD3, CD137 or DLL3 from different species. In certain embodiments the multispecific antigen binding molecule of the present application is a trispecific antigen binding molecule, i.e. it is capable of specifically binding to three different antigens— capable of binding to either one of CD3 or CD137 but does not bind to both antigens simultaneously, and is capable of specifically binding to DLL3.

In certain embodiments, the multispecific antigen binding molecule specifically binds to the whole or a portion of a partial peptide of CD3. In a particular embodiment CD3 is human CD3 or cynomolgus CD3, most particularly human CD3. In a particular embodiment the multispecific antigen binding molecule is cross-reactive for (i.e. specifically binds to) human and cynomolgus CD3. In some embodiments, the multispecific antigen binding molecule is capable of specific binding to the epsilon subunit of CD3, in particular the human CD3 epsilon subunit of CD3 which is shown in SEQ ID NOs: 7 (NP_000724.1) (RefSeq registration numbers are shown within the parentheses). In some embodiments, the multispecific antigen binding molecule is capable of specific binding to the CD3 epsilon chain expressed on the surface of eukaryotic cells. In some embodiments, the multispecific antigen binding molecule binds to the CD3 epsilon chain expressed on the surface of T cells.

In certain embodiments, the CD137 is human CD137. In some embodiments, favorable examples of an antigen-binding molecule of the present invention include antigen-binding molecules that bind to the same epitope as the human CD137 epitope bound by the antibody selected from the group consisting of:

antibody that recognize a region comprising the SPCPPNSFSSAGGQRTCDICRQCKGVFRTRKE-CSSTSNAECDCTPGFHCLGAGCS MCEQDCKQGQELTKKGC sequence (SEQ ID NO: 21), antibody that recognize a region comprising the DCTPGFHCLGAGCSMCEQDCKQGQELTKKGC sequence (SEQ ID NO: 35), antibody that recognize a region comprising the LQDPCSNCPAGTFCDNNRNQICSPCPPNSFS-SAGGQRTCDICRQCKGVFRTRKE CSSTSNAEC sequence (SEQ ID NO: 49), and antibody that recognize a region comprising the LQDPCSNCPAGTFCDNNRNQIC sequence (SEQ ID NO: 105) in the human CD137 protein.

The term "DLL3", as used herein, refers to any native DLL3 (Delta-like 3) from any vertebrate source, including mammals such as primates (e.g. humans) and rodents (e.g., mice and rats), unless otherwise indicated. The term encompasses "full-length" unprocessed DLL3 as well as any form of DLL3 that results from processing in the cell. The term also encompasses naturally occurring variants of DLL3, e.g., splice variants or allelic variants. The amino acid sequence of an exemplary human DLL3 is known as NCBI Reference Sequence (RefSeq) NM_016941.3, and the amino acid sequence of an exemplary cynomolgus DLL3 is known as NCBI Reference Sequence XP_005589253.1, and the amino acid sequence of an exemplary mouse DLL3 is known as NCBI Reference Sequence NM_007866.2.

The human DLL3 protein comprises a transmembrane (TM) region and an intracellular domain on the C-terminal side, and a DSL (Notch) domain on the N-terminal side (see, e.g., FIG. 6). In addition, DLL3 has an EGF domain comprising six regions, EGF1 to EGF6 from the N-terminal side to the C-terminal side. In some embodiments, the multispecific antigen-binding molecules or the DLL3 antigen binding moiety of the present invention bind to an epitope within the extracellular domain (ECD), i.e., the domain from the N-terminus to immediately before the TM region, but not to the TM region or the C-terminal intracellular domain. The multispecific antigen-binding molecules or the DLL3 antigen binding moiety of the present invention may bind to an epitope within any of the above-mentioned domains/regions within the ECD. In preferred embodiments, the multispecific antigen-binding molecules or the DLL3 antigen binding moiety of the present invention bind to an epitope within the region from EGF6 to immediately before the TM region. More specifically, the multispecific antigen-binding molecules or the DLL3 antigen binding moiety of the present invention may bind to an epitope within the regions defined in SEQ ID NO: 89 in human DLL3. In some embodiments, the molecules/antibodies of the present invention bind to the EGF1, EGF2, EGF3, EGF4, EGF5, or EGF6 region or a region from EGF6 to immediately before the TM region of human DLL3, or an epitope within the EGF1, EGF2, EGF3, EGF4, EGF5, or EGF6 region or a region from EGF6 to immediately before the TM region of human DLL3.

In human DLL3, the above-mentioned domains/regions have the following amino acid residues (see, e.g., http://www.uniprot.org/uniprot/Q9NYJ7 or WO2013/126746):

Extracellular domain (ECD): amino acid residues at positions 1 to 492;
DSL domain: amino acid residues at positions 176 to 215;
EGF domain: amino acid residues at positions 216 to 465;
EGF1 region: amino acid residues at positions 216 to 249;
EGF2 region: amino acid residues at positions 274 to 310;
EGF3 region: amino acid residues at positions 312 to 351;
EGF4 region: amino acid residues at positions 353 to 389;
EGF5 region: amino acid residues at positions 391 to 427;
EGF6 region: amino acid residues at positions 429 to 465;
The region from EGF6 to immediately before the TM region: amino acid residues at positions 429 to 492;
TM region: amino acid residues at positions 493 to 513; and
C-terminal intracellular domain: amino acid residues at positions 516 to 618 (or 516 to 587 in some isoforms). The amino acid positions mentioned above also refers to the amino acid positions in the amino acid sequence shown in SEQ ID NO: 90. Thus, the multispecific antigen-binding molecules or the DLL3 antigen binding moiety of the present invention may bind to an above-mentioned region/domain having the amino acid residues at the above-mentioned positions in human DLL3. That is, the multispecific antigen-binding molecules or the DLL3 antigen binding moiety of the present invention may bind to an epitope within the above-mentioned region/domain having the amino acid residues at the above-mentioned positions in human DLL3.

The DLL3 protein used in the present invention may be a DLL3 protein having the sequence described above or may be a modified protein having a sequence derived from the sequence described above by the modification of one or more amino acids. Examples of the modified protein having a sequence derived from the sequence described above by the modification of one or more amino acids can include polypeptides having 70% or more, preferably 80% or more, more preferably 90% or more, even more preferably 95% or more identity with to the amino acid sequence described above. Alternatively, partial peptides of these DLL3 proteins may be used.

The DLL3 protein used in the present invention is not limited by its origin and is preferably a human or cynomolgus DLL3 protein.

In some embodiments, for the DLL3 protein, DLL3 ECD fragment proteins (or ECD variants) may be used. Depending on the site of truncation, the fragments/variants may comprise, from the N-terminal side to the C-terminal side, the DSL domain to EGF6, EGF1 to EGF6, EGF2 to EGF6, EGF3 to EGF6, EGF4 to EGF6, EGF5 and EGF6, or EGF6. The fragments/variants may further comprise a region spanning from immediately after the EGF6 region to immediately before the TM region. A Flag tag may be attached to the C terminus of the fragments/variants using a technique well-known in the art.

Antigen Binding Domain

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, the antigen-binding domains contain both the antibody light chain variable region (VL) and antibody heavy chain variable region (VH). Such preferable antigen-binding domains include, for example, "single-chain Fv (scFv)", "single-domain antibody or VHH", "single-chain antibody", "Fv", "single-chain Fv2 (scFv2)", "Fab", and "F (ab')2".

Variable Region

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

HVR or CDR

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Hypervariable regions (HVRs) are also referred to as "complementarity determining regions" (CDRs), and these terms are used herein interchangeably in reference to portions of the variable region that form the antigen binding regions. Generally, antibodies comprise six HVRs: three in the VH (H1, H2, H3), and three in the VL (L1, L2, L3). Exemplary HVRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));
  (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
  (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

HVR-H1, HVR-H2, HVR-H3, HVR-L1, HVR-L2, and HVR-L3 are also mentioned as "H-CDR1", "H-CDR2", "H-CDR3", "L-CDR1", "L-CDR2", and "L-CDR3", respectively.

Capable of Binding to CD3 and CD137 but does not Bind to CD3 and CD137 at the Same Time Whether the antibody variable region of the present invention is "capable of binding to CD3 and CD137" can be determined by a method known in the art.

This can be determined by, for example, an electrochemiluminescence method (ECL method) (BMC Research Notes 2011, 4: 281).

Specifically, for example, a low-molecular antibody composed of a region capable of binding to CD3 and CD137, for example, a Fab region, of a biotin-labeled antigen-binding molecule to be tested, or a monovalent antibody (antibody lacking one of the two Fab regions carried by a usual antibody) thereof is mixed with CD3 or CD137 labeled with sulfo-tag (Ru complex), and the mixture is added onto a streptavidin-immobilized plate. In this operation, the biotin-labeled antigen-binding molecule to be tested binds to streptavidin on the plate. Light is developed from the sulfo-tag, and the luminescence signal can be detected using Sector Imager 600 or 2400 (MSD K.K.) or the like to thereby confirm the binding of the aforementioned region of the antigen-binding molecule to be tested to CD3 or CD137.

Alternatively, this assay may be conducted by ELISA, FACS (fluorescence activated cell sorting), AlphaScreen® (amplified luminescent proximity homogeneous assay screen), the Biacore™ method based on a surface plasmon resonance (SPR) phenomenon, etc. (Proc. Natl. Acad. Sci. USA (2006) 103 (11), 4005-4010).

Specifically, the assay can be conducted using, for example, a Biacore™ interaction analyzer (GE Healthcare Japan Corp.) based on a surface plasmon resonance (SPR) phenomenon. The Biacore™ analyzer includes any model such as a Biacore™ T100 surface plasmon resonance system, a Biacore™ T200 surface plasmon resonance system, a Biacore™ X100 surface plasmon resonance system, a Biacore™ A100 surface plasmon resonance system, a Biacore™ 4000 surface plasmon resonance system, a Biacore™ 3000 surface plasmon resonance system, a Biacore™ 2000 surface plasmon resonance system, a Biacore™ 1000 surface plasmon resonance system, or a Biacore™ C surface plasmon resonance system. Any sensor chip for a Biacore™ surface plasmon resonance system, such as a CM7, CM5, CM4, CM3, C1, SA, NTA, L1, HPA, or Au chip, can be used as a sensor chip. Proteins for capturing the antigen-binding molecule of the present invention, such as protein A, protein G, protein L, anti-human IgG antibodies, anti-human IgG-Fab, anti-human L chain antibodies, anti-human Fc antibodies, antigenic proteins, or antigenic peptides, are immobilized onto the sensor chip by a coupling method such as amine coupling, disulfide coupling, or aldehyde coupling. CD3 or CD137 is injected thereon as an analyte, and the interaction is measured to obtain a sensorgram. In this operation, the concentration of CD3 or CD137 can be selected within the range of a few µM to a few µM according to the interaction strength (e.g., KD) of the assay sample.

Alternatively, CD3 or CD137 may be immobilized instead of the antigen-binding molecule onto the sensor chip, with which the antibody sample to be evaluated is in turn allowed to interact. Whether the antibody variable region of the antigen-binding molecule of the present invention has binding activity against CD3 or CD137 can be confirmed on the basis of a dissociation constant (KD) value calculated from the sensorgram of the interaction or on the basis of the degree of increase in the sensorgram after the action of the antigen-binding molecule sample over the level before the action.

In some embodiments, binding activity or affinity of the antibody variable region of the present invention to the antigen of interest (i.e. CD3 or CD137) are assessed at 37° C. (for CD137) or 25° C. (for CD3) using e.g., Biacore™ T200 surface plasmon resonance system (GE Healthcare) or Biacore™ 8K surface plasmon resonance system (GE Healthcare). Anti-human Fc (e.g., GE Healthcare) is immobilized onto all flow cells of a CM4 sensor chip using amine coupling kit (e.g, GE Healthcare). The antigen binding molecules or antibody variable regions are captured onto the anti-Fc sensor surfaces, then the antigen (CD3 or CD137) is injected over the flow cell. The capture levels of the antigen binding molecules or antibody variable regions may be aimed at 200 resonance unit (RU). Recombinant human CD3 or CD137 may be injected at 2000 to 125 nM prepared by two-fold serial dilution, followed by dissociation. All antigen binding molecules or antibody variable regions and analytes are prepared in ACES pH 7.4 containing 20 mM ACES, 150 mM NaCl, 0.05% Tween 20, 0.005% NaN3. Sensor surface is regenerated each cycle with 3M MgCl2. Binding affinity are determined by processing and fitting the data to 1:1 binding model using e.g., Biacore™ Insight Evaluation software, version 2.0 (GE Healthcare) or Biacore™ 8K Evaluation software (GE Healthcare). The KD values are calculated for assessing the specific binding activity or affinity of the antigen binding domains of the present invention.

The AlphaScreen® is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen having an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore™ system plots on the ordinate the amount of the shift, i.e., change in mass on the sensor chip surface, and displays time-dependent change in mass as assay data (sensorgram). The amount of the analyte bound to the ligand captured on the sensor chip surface (amount of change in response on the sensorgram between before and after the interaction of the analyte) can be determined from the sensorgram. However, since the amount bound also depends on the amount of the ligand, the comparison must be performed under conditions where substantially the same amounts of the ligand are used. Kinetics, i.e., an association rate constant (ka) and a dissociation rate constant (kd), can be determined from the curve of the sensorgram, while affinity (KD) can be determined from the ratio between these constants. Inhibition assay is also preferably used in the Biacore™ method. Examples of the inhibition assay are described in Proc. Natl. Acad. Sci. USA (2006) 103 (11), 4005-4010.

The term "does not bind to CD3 and CD137 (4-1BB) at the same time" or "does not bind to CD3 and CD137 (4-1BB) simultaneously" means that the antigen-binding moiety or antibody variable region of the present invention cannot bind to CD137 in a state bound with CD3 whereas the antigen-binding moiety or antibody variable region cannot bind to CD3 in a state bound with CD137. In this context, the phrase "not bind to CD3 and CD137 at the same time" also includes not cross-linking a cell expressing CD3 to a cell expressing CD137, or not binding to CD3 and CD137 each expressed on a different cell, at the same time. This phrase further includes the case where the variable region is capable of binding to both CD3 and CD137 at the same time when CD3 and CD137 are not expressed on cell membranes, as with soluble proteins, or both reside on the same cell, but cannot bind to CD3 and CD137 each expressed on a different cell, at the same time. Such an antibody variable region is not particularly limited as long as the antibody variable region has these functions. Examples thereof can include variable regions derived from an IgG-type antibody variable region by the alteration of a portion of its amino acids so as to bind to the desired antigen. The amino acid to be altered is selected from, for example, amino acids whose alteration does not cancel the binding to the antigen, in an antibody variable region binding to CD3 or CD137.

In this context, the phrase "expressed on different cells" merely means that the antigens are expressed on separate cells. The combination of such cells may be, for example, the same types of cells such as a T cell and another T cell, or may be different types of cells such as a T cell and an NK cell.

Whether the antigen-binding molecule of the present invention does "not bind to CD3 and CD137 at the same time" can be confirmed by: confirming the antigen-binding molecule to have binding activity against both CD3 and CD137; then allowing either CD3 or CD137 to bind in advance to the antigen-binding molecule comprising the variable region having this binding activity; and then determining the presence or absence of its binding activity against the other one by the method mentioned above. Alternatively, this can also be confirmed by determining whether the binding of the antigen-binding molecule to either CD3 or CD137 immobilized on an ELISA plate or a sensor chip is inhibited by the addition of the other one into the solution. In some embodiments, the binding of the antigen-binding molecule of the present invention to either CD3 or CD137 is inhibited by binding of the antigen-binding molecule to the other by at least 50%, preferably 60% or more, more preferably 70% or more, more preferably 80% or more, further preferably 90% or more, or even more preferably 95% or more.

In one aspect, while one antigen (e.g. CD3) is immobilized, the inhibition of the binding of the antigen-binding molecule to CD3 can be determined in the presence of the other antigen (e.g. CD137) by methods known in prior art (i.e. ELISA, Biacore™ and so on). In another aspect, while CD137 is immobilized, the inhibition of the binding of the antigen-binding molecule to CD137 also can be determined in the presence of CD3. When either one of two aspects mentioned above is conducted, the antigen-binding molecule of the present invention is determined not to bind to CD3 and CD137 at the same time if the binding is inhibited by at least 50%, preferably 60% or more, preferably 70% or more, further preferably 80% or more, further preferably 90% or more, or even more preferably 95% or more.

In some embodiments, the concentration of the antigen injected as an analyte is at least 1-fold, 2-fold, 5-fold, 10-fold, 30-fold, 50-fold, or 100-fold higher than the concentration of the other antigen to be immobilized.

In preferable manner, the concentration of the antigen injected as an analyte is 100-fold higher than the concentration of the other antigen to be immobilized and the binding is inhibited by at least 80%.

In one embodiment, the ratio of the KD value for the CD3 (analyte)-binding activity of the antigen-binding molecule to the CD137 (immobilized)-binding activity of the antigen-binding molecule (KD (CD3)/KD (CD137)) is calculated and the CD3 (analyte) concentration which is 10-fold, 50-fold, 100-fold, or 200-fold of the ratio of the KD value (KD(CD3)/KD(CD137)) higher than the CD137 (immobilized) concentration can be used for the competition measurement above. (e.g. 1-fold, 5-fold, 10-fold, or 20-fold higher concentration can be selected when the ratio of the KD value is 0.1. Furthermore, 100-fold, 500-fold, 1000-fold, or 2000-fold higher concentration can be selected when the ratio of the KD value is 10.)

In one aspect, while one antigen (e.g. CD3) is immobilized, the attenuation of the binding signal of the antigen-binding molecule to CD3 can be determined in the presence of the other antigen (e.g. CD137) by methods known in prior art (i.e. ELISA, ECL and so on). In another aspect, while CD137 is immobilized, the attenuation of the binding signal of the antigen-binding molecule to CD137 also can be determined in the presence of CD3. When either one of two aspects mentioned above is conducted, the antigen-binding molecule of the present invention is determined not to bind to CD3 and CD137 at the same time if the binding signal is attenuated by at least 50%, preferably 60% or more, preferably 70% or more, further preferably 80% or more, further preferably 90% or more, or even more preferably 95% or more.

In some embodiments, the concentration of the antigen injected as an analyte is at least 1-fold, 2-fold, 5-fold, 10-fold, 30-fold, 50-fold, or 100-fold higher than the concentration of the other antigen to be immobilized.

In preferable manner, the concentration of the antigen injected as an analyte is 100-fold higher than the concentration of the other antigen to be immobilized and the binding is inhibited by at least 80%.

In one embodiment, the ratio of the KD value for the CD3 (analyte)-binding activity of the antigen-binding molecule to the CD137 (immobilized)-binding activity of the antigen-binding molecule (KD (CD3)/KD (CD137)) is calculated and the CD3 (analyte) concentration which is 10-fold, 50-fold, 100-fold, or 200-fold of the ratio of the KD value (KD(CD3)/KD(CD137)) higher than the CD137 (immobilized) concentration can be used for the measurement above. (e.g. 1-fold, 5-fold, 10-fold, or 20-fold higher concentration can be selected when the ratio of the KD value is 0.1. Furthermore, 100-fold, 500-fold, 1000-fold, or 2000-fold higher concentration can be selected when the ratio of the KD value is 10.)

Specifically, in the case of using, for example, the ECL method, a biotin-labeled antigen-binding molecule to be tested, CD3 labeled with sulfo-tag (Ru complex), and an unlabeled CD137 are prepared. When the antigen-binding molecule to be tested is capable of binding to CD3 and CD137, but does not bind to CD3 and CD137 at the same time, the luminescence signal of the sulfo-tag is detected in the absence of the unlabeled CD137 by adding the mixture of the antigen-binding molecule to be tested and labeled CD3 onto a streptavidin-immobilized plate, followed by light development. By contrast, the luminescence signal is decreased in the presence of unlabeled CD137. This decrease in luminescence signal can be quantified to determine relative binding activity. This analysis may be similarly conducted using the labeled CD137 and the unlabeled CD3.

In the case of the AlphaScreen® technique, the antigen-binding molecule to be tested interacts with CD3 in the absence of the competing CD137 to generate signals of 520 to 620 nm. The untagged CD137 competes with CD3 for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. CD3 can be tagged with GST by an appropriately adopted method which involves, for example: fusing a polynucleotide encoding CD3 in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis. This analysis may be similarly conducted using the tagged CD137 and the untagged CD3.

Alternatively, a method using fluorescence resonance energy transfer (FRET) may be used. FRET is a phenomenon in which excitation energy is transferred directly between two fluorescent molecules located in proximity to each other by electron resonance. When FRET occurs, the excitation energy of a donor (fluorescent molecule having an excited state) is transferred to an acceptor (another fluorescent molecule located near the donor) so that the fluorescence emitted from the donor disappears (to be precise, the lifetime of the fluorescence is shortened) and instead, the fluorescence is emitted from the acceptor. By use of this phenomenon, whether or not bind to CD3 and CD137 at the same time can be analyzed. For example, when CD3 carrying a fluorescence donor and CD137 carrying a fluorescence acceptor bind to the antigen-binding molecule to be tested at the same time, the fluorescence of the donor disappears while the fluorescence is emitted from the acceptor. Therefore, change in fluorescence wavelength is observed. Such an antibody is confirmed to bind to CD3 and CD137 at the same time. On the other hand, if the mixing of CD3, CD137, and the antigen-binding molecule to be tested does not change the fluorescence wavelength of the fluorescence donor bound with CD3, this antigen-binding molecule to be tested can be regarded as antigen binding domain that is capable of binding to CD3 and CD137, but does not bind to CD3 and CD137 at the same time.

For example, a biotin-labeled antigen-binding molecule to be tested is allowed to bind to streptavidin on the donor bead, while CD3 tagged with glutathione S transferase (GST) is allowed to bind to the acceptor bead. The antigen-binding molecule to be tested interacts with CD3 in the absence of the competing second antigen to generate signals of 520 to 620 nm. The untagged second antigen competes with CD3 for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. CD3 can be tagged with GST by an appropriately adopted method which involves, for example: fusing a polynucleotide encoding CD3 in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis.

The tagging is not limited to the GST tagging and may be carried out with any tag such as, but not limited to, a histidine tag, MBP, CBP, a Flag tag, an HA tag, a V5 tag, or a c-myc tag. The binding of the antigen-binding molecule to be tested to the donor bead is not limited to the binding using biotin-streptavidin reaction. Particularly, when the antigen-binding molecule to be tested comprises Fc, a possible method involves allowing the antigen-binding molecule to be tested to bind via an Fc-recognizing protein such as protein A or protein G on the donor bead.

Also, the case where the variable region is capable of binding to CD3 and CD137 at the same time when CD3 and CD137 are not expressed on cell membranes, as with soluble proteins, or both reside on the same cell, but cannot bind to CD3 and CD137 each expressed on a different cell, at the same time can also be assayed by a method known in the art.

Specifically, the antigen-binding molecule to be tested has been confirmed to be positive in ECL-ELISA for detecting binding to CD3 and CD137 at the same time is also mixed with a cell expressing CD3 and a cell expressing CD137. The antigen-binding molecule to be tested can be shown to be incapable of binding to CD3 and CD137 expressed on different cells, at the same time unless the antigen-binding molecule and these cells bind to each other at the same time. This assay can be conducted by, for example, cell-based ECL-ELISA. The cell expressing CD3 is immobilized onto a plate in advance. After binding of the antigen-binding molecule to be tested thereto, the cell expressing CD137 is added to the plate. A different antigen expressed only on the cell expressing CD137 is detected using a sulfo-tag-labeled antibody against this antigen. A signal is observed when the antigen-binding molecule binds to the two antigens respectively expressed on the two cells, at the same time. No signal is observed when the antigen-binding molecule does not bind to these antigens at the same time.

Alternatively, this assay may be conducted by the AlphaScreen® method. The antigen-binding molecule to be tested is mixed with a cell expressing CD3 bound with the donor bead and a cell expressing CD137 bound with the acceptor bead. A signal is observed when the antigen-binding molecule binds to the two antigens expressed on the two cells respectively, at the same time. No signal is observed when the antigen-binding molecule does not bind to these antigens at the same time.

Alternatively, this assay may also be conducted by an Octet® interaction analysis method. First, a cell expressing CD3 tagged with a peptide tag is allowed to bind to a biosensor that recognizes the peptide tag. A cell expressing CD137 and the antigen-binding molecule to be tested are placed in wells and analyzed for interaction. A large wavelength shift caused by the binding of the antigen-binding molecule to be tested and the cell expressing CD137 to the biosensor is observed when the antigen-binding molecule binds to the two antigens expressed on the two cells respectively, at the same time. A small wavelength shift caused by the binding of only the antigen-binding molecule to be tested to the biosensor is observed when the antigen-binding molecule does not bind to these antigens at the same time.

Instead of these methods based on the binding activity, assay based on biological activity may be conducted. For example, a cell expressing CD3 and a cell expressing CD137 are mixed with the antigen-binding molecule to be tested, and cultured. The two antigens expressed on the two cells respectively are mutually activated via the antigen-binding molecule to be tested when the antigen-binding molecule binds to these two antigens at the same time. Therefore, change in activation signal, such as increase in the respective downstream phosphorylation levels of the antigens, can be detected. Alternatively, cytokine production is induced as a result of the activation. Therefore, the amount of cytokines produced can be measured to thereby confirm whether or not to bind to the two cells at the same time. Alternatively, cytotoxicity against a cell expressing CD137 is induced as a result of the activation. Alternatively, the expression of a reporter gene is induced by a promoter which is activated at the downstream of the signal transduction pathway of CD137 or CD3 as a result of the activation. Therefore, the cytotoxicity or the amount of reporter proteins produced can be measured to thereby confirm whether or not to bind to the two cells at the same time.

At Least One Disulfide Bond

In one aspect of the present invention, each of the first antigen-binding moiety and the second antigen-binding moiety comprises at least one cysteine residue (via mutation, substitution or insertion), preferably in the CH1 region, and said at least one cysteine residue is capable of forming at least one disulfide bond between the first antigen-binding moiety and the second antigen-binding moiety. In certain embodiments, the cysteine residue is present within a CH1 region of an antibody heavy chain constant region, and for example, it is present at a position selected from the group consisting of positions 119, 122, 123, 131, 132, 133, 134, 135, 136, 137, 139, 140, 148, 150, 155, 156, 157, 159, 160, 161, 162, 163, 165, 167, 174, 176, 177, 178, 190, 191, 192, 194, 195, 197, 213, and 214 according to EU numbering in the CH1 region. In one embodiment, each of the first antigen-binding moiety and the second antigen-binding moiety comprises one cysteine residue (via mutation, substitution or insertion) at position 191 according to EU numbering in the CH1 region which is capable of forming one disulfide bond between the CH1 region of the first antigen-binding moiety and the CH1 region of the second antigen-binding moiety.

In an embodiment of the above aspects, "at least one bond" to be formed linking the first antigen-binding moiety and the second antigen-binding moiety as described above can hold the two antigen binding moiety (i.e., the first antigen-binding moiety and the second antigen-binding moiety as described above) spatially close positions. By virtue of the linkage between the first antigen-binding moiety and the second antigen-binding moiety via the disulfide bond(s), the antigen-binding molecule of the present invention is capable of holding two antigen-binding moieties at closer positions than a control antigen-binding molecule, which differs from the antigen-binding molecule of the present invention only in that the control antigen-binding molecule does not have the additional bond(s) introduced between the two antigen-binding moieties. In some embodiments, the term "spatially close positions" or "closer positions" includes the meaning that the first antigen-binding domain and the second antigen-binding domain as described above hold in shortened distance and/or reduced flexibility.

As the results, the two antigen binding moieties (i.e., the first antigen-binding moiety and the second antigen-binding moiety as described above) of the antigen-binding molecule of the present invention binds to the antigens expressed on the same single cell. In other words, the respective two antigen-binding moieties (i.e., the first antigen-binding moiety and the second antigen-binding moiety as described above) of the antigen-binding molecule of the present invention do not bind to antigens expressed on different cells so as to cause a cross-linking the different cells. In the present application, such antigen-binding manner of the antigen-binding molecule of the present invention can be called as "cis-binding", whereas the antigen-binding manner of an antigen-binding molecule which respective two antigen-binding moiety of the antigen-binding molecule bind to antigens expressed on different cells so as to cause a cross-linking the different cells can be called as "trans-binding". In some embodiments, the antigen-binding molecule of the present invention predominantly binds to the antigens expressed on the same single cell in "cis-biding" manner.

In an embodiment of the above aspects, by virtue of the disulfide linkage between the first antigen-binding moiety and the second antigen-binding moiety via the disulfide bond(s) as described above, the antigen-binding molecule of the present invention is capable of reducing and/or preventing unwanted cross-linking and activation of immune cells (e.g., T-cells, NK cells, DC cells, or the like). That is, in some embodiments of the present invention, the first antigen-binding moiety of the antigen-binding molecule of the present invention binds to any signaling molecule expressed on an immune cell such as T-cell (e.g., the first antigen), and the second antigen-binding domain of the antigen-binding molecule of the present invention also binds to any signaling molecule expressed on an immune cell such as T-cell (e.g., the first antigen or the second antigen which is different from the first antigen). Thus, the first antigen-binding domain and the second antigen-binding domain of the antigen binding-molecule of the present invention can bind to either of the first or second signaling molecule expressed on the same single immune cell such as T cell (i.e., cis-binding manner) or on different immune cell such as T cells (i.e., trans-biding manner). When the first antigen-binding domain and the second antigen-binding domain bind to the signaling molecule expressed on different immune cells such as T-cells in trans-binging manner, those different immune cells such as T-cells are cross-linked, and, in certain situation, such cross-linking of immune cells such as T-cells may cause unwanted activation of the immune cells such as T-cells.

On the other hand, in the case of another embodiment of the antigen-binding molecule of the present invention, that is, an antigen-binding molecule comprising the first antigen-binding moiety and the second antigen-binding moiety, which are linked with each other via at least one disulfide bond in the CH1 region (position 191 according to EU numbering), both of the first antigen-binding moiety and the second antigen-binding moiety can binds to the signaling molecules expressed on the same single immune cells such as T cell in "cis-biding" manner, so that the crosslinking of different immune cells such as T-cells via the antigen-binding molecule can be reduced to avoid unwanted activation of immune cells.

In the instant application, the above-described feature, the at least one disulfide bond in the CH1 region (e.g. position 191 according to EU numbering) linking the first antigen-binding moiety and the second antigen-binding moiety may be described with the abbreviated term "LINC". Using this abbreviation, in some embodiments, the above-described antigen-binding molecule of the present invention having said at least one disulfide bond may be indicated as, e.g., "LINC format", "Dual/LINC" or "DLL3-Dual/LINC" or the like. Likewise, antigen-binding molecules of which the first antigen-binding moiety and the second antigen-binding moiety that are not linked/yet to be linked with each other via at least one disulfide bond in the CH1 region (e.g. position 191 according to EU numbering) may be described with the abbreviated term "UnLINC".

Fab Molecule

A "Fab molecule" refers to a protein consisting of the VH and CH1 domain of the heavy chain (the "Fab heavy chain") and the VL and CL domain of the light chain (the "Fab light chain") of an immunoglobulin.

Fused

By "fused" is meant that the components (e.g. a Fab molecule and an Fc domain subunit) are linked by peptide bonds, either directly or via one or more peptide linkers.

"Crossover" Fab

By a "crossover" Fab molecule (also termed "Crossfab") is meant a Fab molecule wherein either the variable regions or the constant regions of the Fab heavy and light chain are exchanged, i.e. the crossover Fab molecule comprises a peptide chain composed of the light chain variable region and the heavy chain constant region, and a peptide chain composed of the heavy chain variable region and the light chain constant region. For clarity, in a crossover Fab molecule wherein the variable regions of the Fab light chain and the Fab heavy chain are exchanged, the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged, the peptide chain comprising the heavy chain variable region is referred to herein as the "heavy chain" of the crossover Fab molecule.

"Conventional" Fab

In contrast thereto, by a "conventional" Fab molecule is meant a Fab molecule in its natural format, i.e. comprising a heavy chain composed of the heavy chain variable and constant regions (VH-CH1), and a light chain composed of the light chain variable and constant regions (VL-CL). The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called alpha (IgA), delta (IgD), epsilon (IgE), gamma (IgG), or mu (IgM), some of which may be further divided into subtypes, e.g. gamma1 (IgG1), gamma2 (IgG2), gamma3 (IgG3), gamma4 (IgG4), alpha1 (IgA1) and alpha2 (IgA2). The light chain of an immunoglobulin may be assigned to one of two types, called kappa and lambda, based on the amino acid sequence of its constant domain. An immunoglobulin essentially consists of two Fab molecules and an Fc domain, linked via the immunoglobulin hinge region.

Affinity

"Affinity" refers to the strength of the sum total of noncovalent interactions between a single binding site of a molecule (e.g., an antigen-binding molecule or antibody) and its binding partner (e.g., an antigen). Unless indicated otherwise, as used herein, "binding affinity" refers to intrinsic binding affinity which reflects a 1:1 interaction between members of a binding pair (e.g., antigen-binding molecule and antigen, or antibody and antigen). The affinity of a molecule X for its partner Y can generally be represented by the dissociation constant (KD), which is the ratio of dissociation and association rate constants (koff and kon, respectively). Thus, equivalent affinities may comprise different rate constants, as long as the ratio of the rate constants remains the same. Affinity can be measured by well-established methods known in the art, including those described herein. A particular method for measuring affinity is Surface Plasmon Resonance (SPR).

Methods to Determine Affinity

In certain embodiments, the antigen-binding molecule or antibody provided herein has a dissociation constant (KD) of 1 micro M or less, 120 nM or less, 100 nM or less, 80 nM or less, 70 nM or less, 50 nM or less, 40 nM or less, 30 nM or less, 20 nM or less, 10 nM or less, 2 nM or less, 1 nM or less, 0.1 nM or less, 0.01 nM or less, or 0.001 nM or less (e.g., $10^{-8}$ M or less, $10^{-8}$ M to $10^{-13}$M, $10^{-9}$M to $10^{-13}$ M) for its antigen. In certain embodiments, the KD value of the antibody/antigen-binding molecule for CD3, CD137 or DLL3 falls within the range of 1-40, 1-50, 1-70, 1-80, 30-50, 30-70, 30-80, 40-70, 40-80, or 60-80 nM.

In one embodiment, KD is measured by a radiolabeled antigen-binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, Microtiter™ multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C. In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (Tween-20™) in PBS. When the plates have dried, 150 micro l/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a Biacore™ surface plasmon resonance assay. For example, an assay using a Biacore™ 2000 surface plasmon resonance system or a Biacore™ 3000 surface plasmon resonance system (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 micro l/min. Association rates ($k_{on}$) and dissociation rates ($k_{off}$) are calculated using a simple one-to-one Langmuir binding model (Biacore™) Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

According to the methods for measuring the affinity of the antigen-binding molecule or the antibody described above, persons skilled in art can carry out affinity measurement for other antigen-binding molecules or antibodies, towards various kind of antigens.

Antibody

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody Fragment

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

Class of Antibody

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively.

Unless otherwise indicated, amino acid residues in the light chain constant region are numbered herein according to Kabat et al., and numbering of amino acid residues in the heavy chain constant region is according to the EU numbering system, also called the EU index, as described in Kabat et al., *Sequences of Proteins of Immunological Interest*, 5th Ed. Public Health Service, National Institutes of Health, Bethesda, Md., 1991.

Framework

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3 (L3)-FR4.

Human Consensus Framework

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

Chimeric Antibody

The term "chimeric" antibody refers to an antibody in which a portion of the heavy and/or light chain is derived from a particular source or species, while the remainder of the heavy and/or light chain is derived from a different source or species. Similarly, the term "chimeric antibody variable domain" refers to an antibody variable region in which a portion of the heavy and/or light chain variable region is derived from a particular source or species, while the remainder of the heavy and/or light chain variable region is derived from a different source or species.

Humanized Antibody

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. A "humanized antibody variable region" refers to the variable region of a humanized antibody.

Human Antibody

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. A "human antibody variable region" refers to the variable region of a human antibody.

Polynucleotide (Nucleic Acid)

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Isolated (Nucleic Acid)

An "isolated" nucleic acid molecule is one which has been separated from a component of its natural environment. An isolated nucleic acid molecule further includes a nucleic acid molecule contained in cells that ordinarily contain the nucleic acid molecule, but the nucleic acid molecule is present extrachromosomally or at a chromosomal location that is different from its natural chromosomal location.

Vector

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Vectors could be introduced into host cells using virus or electroporation. However, introduction of vectors is not limited to in vitro method. For example, vectors could also be introduced into a subject using in vivo method directly.

In another aspects of the present invention, the vectors comprising nucleic acid molecule encodes the antigen-binding moiety capable of binding to CD3 and CD137 but not at the same time, antigen-binding moiety capable of binding to DLL3, antigen-binding molecules or antibodies of the present disclosure may be introduced to subjects, to express the antigen-binding moieties, antigen-binding molecules or antibodies of the present disclosure directly within the subject. An example of vectors that is possible to be used is adenovirus, but not limited to. It is also possible to administer the nucleic acid molecule encoding the antigen-binding moieties, antigen-binding molecules or antibodies of the present disclosure directly into a subject, or transfer the nucleic acid molecule encodes the antigen-binding moieties, antigen-binding molecules or antibodies of the present disclosure via electroporation to a subject, or administer cells comprises nucleic acid molecule encodes the antigen-binding moieties, antigen-binding molecules or antibodies of the present disclosure to be expressed and secreted into a subject, to express and secrete the antigen-binding moieties, antigen-binding molecules or antibodies of the present disclosure in the subject continuously.

Host Cell

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

Specificity

"Specific" means that a molecule that binds specifically to one or more binding partners does not show any significant binding to molecules other than the partners. Furthermore, "specific" is also used when an antigen-binding site is specific to a particular epitope of multiple epitopes contained in an antigen. If an antigen-binding molecule binds specifically to an antigen, it is also described as "the antigen-binding molecule has/shows specificity to/towards the antigen". When an epitope bound by an antigen-binding site is contained in multiple different antigens, an antigen-binding molecule containing the antigen-binding site can bind to various antigens that have the epitope.

Antibody Fragment

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

Variable Fragment (Fv)

Herein, the term "variable fragment (Fv)" refers to the minimum unit of an antibody-derived antigen-binding site that is composed of a pair of the antibody light chain variable region (VL) and antibody heavy chain variable region (VH). In 1988, Skerra and Pluckthun found that homogeneous and active antibodies can be prepared from the E. coli periplasm fraction by inserting an antibody gene downstream of a bacterial signal sequence and inducing expression of the gene in E. coli (Science (1988) 240(4855), 1038-1041). In the Fv prepared from the periplasm fraction, VH associates with VL in a manner so as to bind to an antigen.

scFv, Single-Chain Antibody, and Sc(Fv)$_2$

Herein, the terms "scFv", "single-chain antibody", and "sc(Fv)$_2$" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen-binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an single chain low molecule weight antibody in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)$_2$ is a single chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)$_2$ preferably includes, for example, a bispecific sc(Fv)$_2$ that recognizes two epitopes present in a single antigen as disclosed in the Journal of Immunology (1994) 152(11), 5368-5374. sc(Fv)$_2$ can be produced by methods known to those skilled in the art. For example, sc(Fv)$_2$ can be produced by linking scFv by a linker such as a peptide linker.

Herein, an sc(Fv)$_2$ includes two VH units and two VL units which are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Examples of the form are listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)$_2$ is also described in detail in WO 2006/132352.

According to these descriptions, those skilled in the art can appropriately prepare desired sc(Fv)$_2$ to produce the polypeptide complexes disclosed herein.

Furthermore, the antigen-binding molecules or antibodies of the present disclosure may be conjugated with a carrier polymer such as PEG or an organic compound such as an anticancer agent. Alternatively, a sugar chain addition sequence is preferably inserted into the antigen-binding molecules or antibodies such that the sugar chain produces a desired effect.

The linkers to be used for linking the variable regions of an antibody comprise arbitrary peptide linkers that can be introduced by genetic engineering, synthetic linkers, and linkers disclosed in, for example, Protein Engineering, 9(3), 299-305, 1996. However, peptide linkers are preferred in the present disclosure. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)$_2$ contains three peptide linkers, their length may be all the same or different.

For example, such peptide linkers include:

```
Ser,

Gly-Ser,

Gly-Gly-Ser,

Ser-Gly-Gly,
                                       (SEQ ID NO: 91)
Gly-Gly-Gly-Ser,
                                       (SEQ ID NO: 92)
Ser-Gly-Gly-Gly,
                                       (SEQ ID NO: 93)
Gly-Gly-Gly-Gly-Ser,
                                       (SEQ ID NO: 94)
Ser-Gly-Gly-Gly-Gly,
                                       (SEQ ID NO: 95)
Gly-Gly-Gly-Gly-Gly-Ser,
                                       (SEQ ID NO: 96)
Ser-Gly-Gly-Gly-Gly-Gly,
                                       (SEQ ID NO: 97)
Gly-Gly-Gly-Gly-Gly-Gly-Ser,
                                       (SEQ ID NO: 98)
Ser-Gly-Gly-Gly-Gly-Gly-Gly,
                                       (SEQ ID NO: 93)
(Gly-Gly-Gly-Gly-Ser)n,
and
                                       (SEQ ID NO: 94)
(Ser-Gly-Gly-Gly-Gly)n,
``` where n is an integer of 1 or larger. The length or sequences of peptide linkers can be selected accordingly by those skilled in the art depending on the purpose.

Synthetic linkers (chemical crosslinking agents) are routinely used to crosslink peptides, and examples include:
N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES), and
bis[2-(sulfosuccinimidoxycarbonyloxy)ethyl] sulfone (sulfo-BSOCOES). These crosslinking agents are commercially available.

In general, three linkers are required to link four antibody variable regions together. The linkers to be used may be of the same type or different types.

Fab, F(ab')$_2$, and Fab'

"Fab" consists of a single light chain, and a CH1 domain and variable region from a single heavy chain. The heavy chain of Fab molecule cannot form disulfide bonds with another heavy chain molecule.

"F(ab')$_2$" or "Fab" is produced by treating an immunoglobulin (monoclonal antibody) with a protease such as pepsin and papain, and refers to an antibody fragment generated by digesting an immunoglobulin (monoclonal antibody) near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CH gamma 1 (gamma 1 region in an H-chain constant region) via a disulfide bond at their C-terminal regions. Each of these two homologous antibody fragments is called Fab'.

"F(ab')$_2$" consists of two light chains and two heavy chains comprising the constant region of a CH1 domain and a portion of CH2 domains so that disulfide bonds are formed between the two heavy chains. The F(ab')$_2$ disclosed herein can be preferably produced as follows. A whole monoclonal antibody or such comprising a desired antigen-binding site is partially digested with a protease such as pepsin; and Fc fragments are removed by adsorption onto a Protein A column. The protease is not particularly limited, as long as it can cleave the whole antibody in a selective manner to produce F(ab')2 under an appropriate setup enzyme reaction condition such as pH. Such proteases include, for example, pepsin and ficin.

Single-Domain Antibody

In the present specification, the term "single-domain antibody" is not limited by its structure as long as the domain can exert antigen binding activity by itself. It is known that a general antibody, for example, an IgG antibody, exhibits antigen binding activity in a state where a variable region is formed by the pairing of VH and VL, whereas the own domain structure of the single-domain antibody can exert antigen binding activity by itself without pairing with another domain. Usually, the single-domain antibody has a relatively low molecular weight and exists in the form of a monomer.

Examples of the single-domain antibody include, but are not limited to, antigen binding molecules congenitally lacking a light chain, such as VHH of an animal of the family Camelidae and shark VNAR, and antibody fragments containing the whole or a portion of an antibody VH domain or the whole or a portion of an antibody VL domain. Examples of the single-domain antibody which is an antibody fragment containing the whole or a portion of an antibody VH or VL domain include, but are not limited to, artificially prepared single-domain antibodies originating from human antibody VH or human antibody VL as described in U.S. Pat. No. 6,248,516 B1, etc. In some embodiments of the present invention, one single-domain antibody has three CDRs (CDR1, CDR2 and CDR3).

The single-domain antibody can be obtained from an animal capable of producing the single-domain antibody or by the immunization of the animal capable of producing the single-domain antibody. Examples of the animal capable of producing the single-domain antibody include, but are not limited to, animals of the family Camelidae, and transgenic animals harboring a gene capable of raising the single-domain antibody. The animals of the family Camelidae include camels, lamas, alpacas, one-hump camels and guanacos, etc. Examples of the transgenic animals harboring a gene capable of raising the single-domain antibody include, but are not limited to, transgenic animals described in International Publication No. WO2015/143414 and U.S.

Patent Publication No. US2011/0123527 A1. The framework sequences of the single-domain antibody obtained from the animal may be converted to human germline sequences or sequences similar thereto to obtain a humanized single-domain antibody. The humanized single-domain antibody (e.g., humanized WM) is also one embodiment of the single-domain antibody of the present invention.

Alternatively, the single-domain antibody can be obtained by ELISA, panning, or the like from a polypeptide library containing single-domain antibodies. Examples of the polypeptide library containing single-domain antibodies include, but are not limited to, naive antibody libraries obtained from various animals or humans (e.g., Methods in Molecular Biology 2012 911 (65-78); and Biochimica et Biophysica Acta—Proteins and Proteomics 2006 1764: 8 (1307-1319)), antibody libraries obtained by the immunization of various animals (e.g., Journal of Applied Microbiology 2014 117: 2 (528-536)), and synthetic antibody libraries prepared from antibody genes of various animals or humans (e.g., Journal of Biomolecular Screening 2016 21: 1 (35-43); Journal of Biological Chemistry 2016 291:24 (12641-12657); and AIDS 2016 30: 11 (1691-1701)).

Fc Region

The term "Fc region" or "Fc domain" refers to a region comprising a fragment consisting of a hinge or a portion thereof and CH2 and CH3 domains in an antibody molecule. The Fc region of IgG class means, but is not limited to, a region from, for example, cysteine 226 (EU numbering (also referred to as EU index herein)) to the C terminus or proline 230 (EU numbering) to the C terminus. The Fc region can be preferably obtained by the partial digestion of, for example, an IgG1, IgG2, IgG3, or IgG4 monoclonal antibody with a proteolytic enzyme such as pepsin followed by the re-elution of a fraction adsorbed on a protein A column or a protein G column. Such a proteolytic enzyme is not particularly limited as long as the enzyme is capable of digesting a whole antibody to restrictively form Fab or F(ab')2 under appropriately set reaction conditions (e.g., pH) of the enzyme. Examples thereof can include pepsin and papain.

An Fc region derived from, for example, naturally occurring IgG can be used as the "Fc region" of the present invention. In this context, the naturally occurring IgG means a polypeptide that contains an amino acid sequence identical to that of IgG found in nature and belongs to a class of an antibody substantially encoded by an immunoglobulin gamma gene. The naturally occurring human IgG means, for example, naturally occurring human IgG1, naturally occurring human IgG2, naturally occurring human IgG3, or naturally occurring human IgG4. The naturally occurring IgG also includes variants or the like spontaneously derived therefrom. A plurality of allotype sequences based on gene polymorphism are described as the constant regions of human IgG1, human IgG2, human IgG3, and human IgG4 antibodies in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

In some embodiments, the Fc domain of the multispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the multispecific antigen binding molecule described herein comprises not more than one Fc domain.

In one embodiment described herein, the Fc domain of the multispecific antigen binding molecule is an IgG Fc domain. In a particular embodiment the Fc domain is an IgG1 Fc domain. In a further particular embodiment the Fc domain is a human IgG1 Fc region.

In certain embodiments, the Fc domain of the multispecific antigen binding molecule is composed of a first and a second Fc region subunit capable of stable association, and the Fc domain exhibits reduced binding affinity to human Fc gamma receptor, as compared to a native human IgG1 Fc domain.

In certain embodiments, the Fc domain of the multispecific antigen binding molecule described herein comprises a modification promoting the association of the first and the second subunit of the Fc domain. In a specific embodiment said modification is a so-called "knob-into-hole" modification, comprising a "knob" modification in one of the two subunits of the Fc domain and a "hole" modification in the other one of the two subunits of the Fc domain, which will be described in more detail below.

In a specific embodiment, in the Fc domain composed of a first and a second Fc region subunit capable of stable association and exhibiting reduced binding affinity to human Fc-gamma receptor as compared to a native human IgG1 Fc domain, the first Fc-region subunit is selected from the group consisting of:

(a1) a Fc region polypeptide comprising the mutations L234A, L235A;

(a2) a Fc region polypeptide comprising the mutations L234A, L235A, N297A;

(a3) a Fc region polypeptide comprising the mutations L234A, L235A, N297A, S354C, T366W; and the second Fc-region polypeptide is selected from the group consisting of:

(a4) a Fc region polypeptide comprising the mutations L234A, L235A;

(a5) a Fc region polypeptide comprising the mutations L234A, L235A, N297A; and (a6) a Fc region polypeptide comprising the mutations L234A, L235A, N297A, Y349C, T366S, L368A, Y407V (the amino acid positions are numbered using EU index numbering).

In certain embodiments, the Fc domain of the multispecific antigen binding molecule described herein exhibits enhanced FcRn-binding activity under an acidic pH condition (e.g., pH 5.8) as compared to that of an Fc region of a native IgG. Such Fc domain comprises, for example, Ala at position 434; Glu, Arg, Ser, or Lys at position 438; and Glu, Asp, or Gln at position 440, according to EU numbering. In some embodiments, the Fc domain comprises Ala at position 434; Arg or Lys at position 438; and Glu or Asp at position 440, according to EU numbering. In some embodiments, the Fc domain further comprises Ile or Leu at position 428; and/or Ile, Leu, Val, Thr, or Phe at position 436, according to EU numbering. In some embodiments, the Fc domain comprises a combination of amino acid substitutions selected from the group consisting of:

(a) N434A/Q438R/S440E;
(b) N434A/Q438R/S440D;
(c) N434A/Q438K/S440E;
(d) N434A/Q438K/S440D;
(e) N434A/Y436T/Q438R/S440E;
(f) N434A/Y436T/Q438R/S440D;
(g) N434A/Y436T/Q438K/S440E;
(h) N434A/Y436T/Q438K/S440D;

(i) N434A/Y436V/Q438R/S440E;
(j) N434A/Y436V/Q438R/S440D;
(k) N434A/Y436V/Q438K/S440E;
(l) N434A/Y436V/Q438K/S440D;
(m) N434A/R435H/F436T/Q438R/S440E;
(n) N434A/R435H/F436T/Q438R/S440D;
(o) N434A/R435H/F436T/Q438K/S440E;
(p) N434A/R435H/F436T/Q438K/S440D;
(q) N434A/R435H/F436V/Q438R/S440E;
(r) N434A/R435H/F436V/Q438R/S440D;
(s) N434A/R435H/F436V/Q438K/S440E;
(t) N434A/R435H/F436V/Q438K/S440D;
(u) M428L/N434A/Q438R/S440E;
(v) M428L/N434A/Q438R/S440D;
(w) M428L/N434A/Q438K/S440E;
(x) M428L/N434A/Q438K/S440D;
(y) M428L/N434A/Y436T/Q438R/S440E;
(z) M428L/N434A/Y436T/Q438R/S440D;
(aa) M428L/N434A/Y436T/Q438K/S440E;
(ab) M428L/N434A/Y436T/Q438K/S440D;
(ac) M428L/N434A/Y436V/Q438R/S440E;
(ad) M428L/N434A/Y436V/Q438R/S440D;
(ae) M428L/N434A/Y436V/Q438K/S440E;
(af) M428L/N434A/Y436V/Q438K/S440D;
(ag) L235R/G236R/S239K/M428L/N434A/Y436T/Q438R/S440E; and
(ah) L235R/G236R/A327G/A330S/P331S/M428L/N434A/Y436T/Q438R/S440E, according to EU numbering.

In some embodiments, the Fc domain of the multispecific antigen binding molecule comprises a combination of amino acid substitutions of M428L/N434A/Q438R/S440E. In some embodiments, the Fc domain is a IgG Fc domain, preferably a human IgG Fc domain, more preferably a human IgG1 Fc domain. In certain embodiments, the Fc domain of the multispecific antigen binding molecule comprises any of: (a) a first Fc subunit comprising the amino acid sequence shown in SEQ ID NO: 100 and a second Fc subunit comprising the amino acid sequence shown in SEQ ID NO: 111; and (b) a first Fc subunit comprising the amino acid sequence shown in SEQ ID NO: 99 and a second Fc subunit comprising the amino acid sequence shown in SEQ ID NO: 109.

Fc Region with a Reduced Fc Gamma Receptor-Binding Activity

Herein, "a reduced Fc gamma receptor-binding activity" means, for example, that based on the above-described analysis method the competitive activity of a test antigen-binding molecule or antibody is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control antigen-binding molecule or antibody.

Antigen-binding molecules or antibodies comprising the Fc domain of a monoclonal IgG1, IgG2, IgG3, or IgG4 antibody can be appropriately used as control antigen-binding molecules or antibodies. The Fc domain structures are shown in SEQ ID NOs: 85 (A is added to the N terminus of RefSeq accession number AAC82527.1), 86 (A is added to the N terminus of RefSeq accession number AAB59393.1), 87 (A is added to the N terminus of RefSeq accession number CAA27268.1), and 88 (A is added to the N terminus of RefSeq accession number AAB59394.1). Furthermore, when an antigen-binding molecule or antibody comprising an Fc domain mutant of an antibody of a particular isotype is used as a test substance, the effect of the mutation of the mutant on the Fc gamma receptor-binding activity is assessed using as a control an antigen-binding molecule or antibody comprising an Fc domain of the same isotype. As described above, antigen-binding molecules or antibodies comprising an Fc domain mutant whose Fc gamma receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1(1), 47-54); C226S, C229S, E233P, L234V, and L235A (Blood (2007) 109, 1185-1192).

Specifically, the preferred antigen-binding molecules or antibodies include those comprising an Fc domain with a mutation (such as substitution) of at least one amino acid selected from the following amino acid positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering), in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

The preferred antigen-binding molecules or antibodies include, for example, those comprising an Fc domain which has any one of the substitutions shown below, whose positions are specified according to EU numbering (each number represents the position of an amino acid residue in the EU numbering; and the one-letter amino acid symbol before the number represents the amino acid residue before substitution, while the one-letter amino acid symbol after the number represents the amino acid residue after the substitution) in the amino acids forming the Fc domain of IgG1 antibody:
  (a) L234F, L235E, P331S;
  (b) C226S, C229S, P238S;
  (c) C226S, C229S; or
  (d) C226S, C229S, E233P, L234V, L235A;
  as well as those having an Fc domain which has a deletion of the amino acid sequence at positions 231 to 238.

Furthermore, the preferred antigen-binding molecules or antibodies also include those comprising an Fc domain that has any one of the substitutions shown below, whose positions are specified according to EU numbering in the amino acids forming the Fc domain of an IgG2 antibody:
  (e) H268Q, V309L, A330S, and P331S;
  (f) V234A;
  (g) G237A;
  (h) V234A and G237A;
  (i) A235E and G237A; or
  (j) V234A, A235E, and G237A. Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG3 antibody:

(k) F241A;
(l) D265A; or
(m) V264A. Each number represents the position of an amino acid residue in EU numbering; and the one-letter amino acid symbol before the number represents the amino acid residue before substitution, while the one-letter amino acid symbol after the number represents the amino acid residue after the substitution.

Furthermore, the preferred antigen-binding molecules or antibodies also include those comprising an Fc domain that has any one of the substitutions shown below, whose positions are specified according to EU numbering in the amino acids forming the Fc domain of an IgG4 antibody:
(n) L235A, G237A, and E318A;
(o) L235E; or
(p) F234A and L235A. Each number represents the position of an amino acid residue in EU numbering; and the one-letter amino acid symbol before the number represents the amino acid residue before substitution, while the one-letter amino acid symbol after the number represents the amino acid residue after the substitution.

The other preferred antigen-binding molecules or antibodies include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

The preferred antigen-binding molecules or antibodies also include, for example, those comprising an Fc domain in which any one or more of the amino acids at positions 234, 235, and 297 (EU numbering) in the amino acids forming the Fc domain of an IgG1 antibody is substituted with other amino acids. The type of amino acid after substitution is not particularly limited; however, the antigen-binding molecules or antibodies comprising an Fc domain in which any one or more of the amino acids at positions 234, 235, and 297 are substituted with alanine are particularly preferred.

The preferred antigen-binding molecules or antibodies also include, for example, those comprising an Fc domain in which an amino acid at position 265 (EU numbering) in the amino acids forming the Fc domain of an IgG1 antibody is substituted with another amino acid. The type of amino acid after substitution is not particularly limited; however, antigen-binding molecules or antibodies comprising an Fc domain in which an amino acid at position 265 is substituted with alanine are particularly preferred.

Fc Receptor

The term "Fc receptor" or "FcR" refers to a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and plasma half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with increased or decreased binding to FcRs. See also, e.g., Shields et al. *J. Biol. Chem.* 9(2):6591-6604 (2001).

Fc Gamma Receptor

Fc gamma receptor refers to a receptor capable of binding to the Fc domain of monoclonal IgG1, IgG2, IgG3, or IgG4 antibodies, and includes all members belonging to the family of proteins substantially encoded by an Fc gamma receptor gene. In human, the family includes Fc gamma RI (CD64) including isoforms Fc gamma RIa, Fc gamma RIb and Fc gamma RIc; Fc gamma RII (CD32) including isoforms Fc gamma RIIa (including allotype H131 and R131), Fc gamma RIIb (including Fc gamma RIIb-1 and Fc gamma RIIb-2), and Fc gamma RIIc; and Fc gamma RIII (CD16) including isoform Fc gamma RIIIa (including allotype V158 and F158) and Fc gamma RIIIb (including allotype Fc gamma RIIIb-NA1 and Fc gamma RIIIb-NA2); as well as all unidentified human Fc gamma receptors, Fc gamma receptor isoforms, and allotypes thereof. However, Fc gamma receptor is not limited to these examples. Without being limited thereto, Fc gamma receptor includes those derived from humans, mice, rats, rabbits, and monkeys. Fc gamma receptor may be derived from any organisms. Mouse Fc gamma receptor includes, without being limited to, Fc gamma RI (CD64), Fc gamma RII (CD32), Fc gamma RIII (CD16), and Fc gamma RIII-2 (CD16-2), as well as all unidentified mouse Fc gamma receptors, Fc gamma receptor isoforms, and allotypes thereof. Such preferred Fc gamma receptors include, for example, human Fc gamma RI (CD64), Fc gamma RIIA (CD32), Fc gamma RIIB (CD32), Fc gamma RIIIA (CD16), and/or Fc gamma RIIIB (CD16). The polynucleotide sequence and amino acid sequence of Fc gamma RI are shown in RefSeq accession number NM_000566.3 and RefSeq accession number NP_000557.1, respectively; the polynucleotide sequence and amino acid sequence of Fc gamma RIIA are shown in RefSeq accession number BC020823.1 and RefSeq accession number AAH20823.1, respectively; the polynucleotide sequence and amino acid sequence of Fc gamma RIIB are shown in RefSeq accession number BC146678.1 and RefSeq accession number AAI46679.1, respectively; the polynucleotide sequence and amino acid sequence of Fc gamma RIIIA are shown in RefSeq accession number BC033678.1 and RefSeq accession number AAH33678.1, respectively; and the polynucleotide sequence and amino acid sequence of Fc gamma RIIIB are shown in RefSeq accession number BC128562.1 and RefSeq accession number AAI28563.1, respectively. Whether an Fc gamma receptor has binding activity to the Fc domain of a monoclonal IgG1, IgG2, IgG3, or IgG4 antibody can be assessed by ALPHA screen (Amplified Luminescent Proximity Homogeneous Assay), surface plasmon resonance (SPR)-based Biacore™ method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, Fc gamma receptor, Fc alpha receptor, Fc beta receptor, FcRn, C1q, and C3, mannose-binding lectin, mannose receptor, *Staphylococcus* Protein A, *Staphylococcus* Protein G, and viral Fc gamma receptors. The Fc ligands also include Fc receptor homologs (FcRH) (Davis et al., (2002) Immunological Reviews 190, 123-136), which are a family of Fc receptors homologous to Fc gamma receptor. The Fc ligands also include unidentified molecules that bind to Fc.

Fc Gamma Receptor-Binding Activity

The impaired binding activity of Fc domain to any of the Fc gamma receptors Fc gamma RI, Fc gamma RITA, Fc gamma RIIB, Fc gamma RIIIA, and/or Fc gamma RIIIB can be assessed by using the above-described FACS and ELISA formats as well as ALPHA screen (Amplified Luminescent Proximity Homogeneous Assay) and surface plasmon resonance (SPR)-based Biacore™ method (Proc. Natl. Acad. Sci. USA (2006) 103(11), 4005-4010).

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule or antibody is immobilized to the donor beads and glutathione S-transferase (GST)-tagged Fc gamma receptor is immobilized to the acceptor beads. In the absence of an antigen-binding molecule or antibody comprising a competitive mutant Fc domain, Fc gamma receptor interacts with an antigen-binding molecule or antibody comprising a wild-type Fc domain, inducing a signal of 520 to 620 nm as a result. The antigen-binding molecule or antibody having a non-tagged mutant Fc domain competes with the antigen-binding molecule or antibody comprising a wild-type Fc domain for the interaction with Fc gamma receptor. The relative binding affinity can be determined by quantifying the reduction of fluorescence as a result of competition. Methods for biotinylating the antigen-binding molecules or antibodies such as antibodies using Sulfo-NHS-biotin or the like are known. Appropriate methods for adding the GST tag to an Fc gamma receptor include methods that involve fusing polypeptides encoding Fc gamma receptor and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the Biacore™ system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the Biacore™ methods. Examples of such inhibition assay are described in Proc. Natl. Acad. Sci. USA (2006) 103(11), 4005-4010.

Production and Purification of Multispecific Antibodies

Multispecific antigen binding molecules described herein comprise two types of antigen binding moieties having different binding specificities (e.g. the "first antigen binding moiety" and the "second antigen binding moiety" both capable of binding to CD3 and CD137, and the "third antigen-binding moiety" capable of binding to a different antigen), each of which is eventually fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of multispecific antigen binding molecules in recombinant production, it will thus be advantageous to introduce in the Fc domain of the multispecific antigen binding molecule a modification promoting the association of the desired polypeptides.

Accordingly, in particular embodiments the Fc domain of the multispecific antigen binding molecule described herein comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the multi-specific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In other embodiments, other techniques for promoting the association among H chains and between L and H chains having the desired combinations can be applied to the multispecific antigen-binding molecules of the present invention.

For example, techniques for suppressing undesired H-chain association by introducing electrostatic repulsion at the interface of the second constant region or the third constant region of the antibody H chain (CH2 or CH3) can be applied to multispecific antibody association (WO2006/106905).

In the technique of suppressing unintended H-chain association by introducing electrostatic repulsion at the interface of CH2 or CH3, examples of amino acid residues in contact at the interface of the other constant region of the H chain include regions corresponding to the residues at EU numbering positions 356, 439, 357, 370, 399, and 409 in the CH3 region.

More specifically, examples include an antibody comprising two types of H-chain CH3 regions, in which one to three pairs of amino acid residues in the first H-chain CH3 region, selected from the pairs of amino acid residues indicated in (1) to (3) below, carry the same type of charge: (1) amino acid residues comprised in the H chain CH3 region at EU numbering positions 356 and 439; (2) amino acid residues comprised in the H-chain CH3 region at EU numbering positions 357 and 370; and (3) amino acid residues comprised in the H-chain CH3 region at EU numbering positions 399 and 409.

Furthermore, the antibody may be an antibody in which pairs of the amino acid residues in the second H-chain CH3 region which is different from the first H-chain CH3 region mentioned above, are selected from the aforementioned pairs of amino acid residues of (1) to (3), wherein the one to three pairs of amino acid residues that correspond to the aforementioned pairs of amino acid residues of (1) to (3) carrying the same type of charges in the first H-chain CH3 region mentioned above carry opposite charges from the corresponding amino acid residues in the first H-chain CH3 region mentioned above.

Each of the amino acid residues indicated in (1) to (3) above come close to each other during association. Those skilled in the art can find out positions that correspond to the above-mentioned amino acid residues of (1) to (3) in a desired H-chain CH3 region or H-chain constant region by homology modeling and such using commercially available software, and amino acid residues of these positions can be appropriately subjected to modification.

In the antibodies mentioned above, "charged amino acid residues" are preferably selected, for example, from amino acid residues included in either one of the following groups:

(a) glutamic acid (E) and aspartic acid (D); and
(b) lysine (K), arginine (R), and histidine (H).

In the above-mentioned antibodies, the phrase "carrying the same charge" means, for example, that all of the two or more amino acid residues are selected from the amino acid residues included in either one of groups (a) and (b) mentioned above. The phrase "carrying opposite charges" means, for example, that when at least one of the amino acid residues among two or more amino acid residues is selected from the amino acid residues included in either one of groups (a) and (b) mentioned above, the remaining amino acid residues are selected from the amino acid residues included in the other group.

In a preferred embodiment, the antibodies mentioned above may have their first H-chain CH3 region and second H-chain CH3 region crosslinked by disulfide bonds.

In the present invention, amino acid residues subjected to modification are not limited to the above-mentioned amino acid residues of the antibody variable regions or the antibody constant regions. Those skilled in the art can identify the amino acid residues that form an interface in mutant polypeptides or heteromultimers by homology modeling and such using commercially available software; and amino acid residues of these positions can then be subjected to modification so as to regulate the association.

In addition, other known techniques can also be used for formation of multispecific antibodies of the present invention. Association of polypeptides having different sequences can be induced efficiently by complementary association of CH3 using a strand-exchange engineered domain CH3 produced by changing part of one of the H-chain CH3s of an antibody to a corresponding IgA-derived sequence and introducing a corresponding IgA-derived sequence into the complementary portion of the other H-chain CH3 (Protein Engineering Design & Selection, 23; 195-202, 2010). This known technique can also be used to efficiently form multispecific antibodies of interest.

In addition, technologies for antibody production using association of antibody CH1 and CL and association of VH and VL as described in WO 2011/028952, WO2014/018572, and Nat Biotechnol. 2014 February; 32(2):191-8; technologies for producing bispecific antibodies using separately prepared monoclonal antibodies in combination (Fab Arm Exchange) as described in WO2008/119353 and WO2011/131746; technologies for regulating association between antibody heavy-chain CH3s as described in WO2012/058768 and WO2013/063702; technologies for producing multispecific antibodies composed of two types of light chains and one type of heavy chain as described in WO2012/023053; technologies for producing multispecific antibodies using two bacterial cell strains that individually express one of the chains of an antibody comprising a single H chain and a single L chain as described by Christoph et al. (Nature Biotechnology Vol. 31, p 753-758 (2013)); and such may be used for the formation of multispecific antibodies.

Alternatively, even when a multispecific antibody of interest cannot be formed efficiently, a multispecific antibody of the present invention can be obtained by separating and purifying the multispecific antibody of interest from the produced antibodies. For example, a method for enabling purification of two types of homomeric forms and the heteromeric antibody of interest by ion-exchange chromatography by imparting a difference in isoelectric points by introducing amino acid substitutions into the variable regions of the two types of H chains has been reported (WO2007114325). To date, as a method for purifying heteromeric antibodies, methods using Protein A to purify a heterodimeric antibody comprising a mouse IgG2a H chain that binds to Protein A and a rat IgG2b H chain that does not bind to Protein A have been reported (WO98050431 and WO95033844). Furthermore, a heterodimeric antibody can be purified efficiently on its own by using H chains comprising substitution of amino acid residues at EU numbering positions 435 and 436, which is the IgG-Protein A binding site, with Tyr, His, or such which are amino acids that yield a different Protein A affinity, or using H chains with a different protein A affinity, to change the interaction of each of the H chains with Protein A, and then using a Protein A column.

Furthermore, an Fc region whose Fc region C-terminal heterogeneity has been improved can be appropriately used as an Fc region of the present invention. More specifically, the present invention provides Fc regions produced by deleting glycine at position 446 and lysine at position 447 as specified by EU numbering from the amino acid sequences of two polypeptides constituting an Fc region derived from IgG1, IgG2, IgG3, or IgG4.

Multispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the multispecific antigen binding molecule binds. For example, for affinity chromatography purification of multispecific antigen binding molecules of the invention, a matrix with protein A or protein G may be used. Sequential Protein A or G affinity chromatography and size exclusion chromatography can be used to isolate a multispecific antigen binding molecule. The purity of the multispecific antigen binding molecule can be determined by any of a variety of well known analytical methods including gel electrophoresis, high pressure liquid chromatography, and the like.

Antibody-Dependent Cell-Mediated Cytotoxicity

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express Fc gamma RIII only, whereas monocytes express Fc gamma RI, Fc gamma RII, and Fc gamma RIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998).

Complement Dependent Cytotoxicity

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

T Cell Dependent Cellular Cytotoxicity

"T cell dependent cellular cytotoxicity" or "TDCC" refers to a form of cytotoxicity in which an antigen-binding molecule binds to both an antigen expressed on the target cell, and another antigen expressed on T cell, that redirect T cell near to the target cell, as cytotoxicity against the target cell is induced due to the T cell. The method to assess T cell dependent cellular cytotoxicity, an in vitro TDCC assay, is also described in the "Measurement of T cell dependent cellular cytotoxicity" section of this description.

Measurement of T Cell Dependent Cellular Cytotoxicity

In the embodiment that the antigen-binding molecule binds to both DLL3 and CD3/CD137, the methods described below are preferably used as a method for assessing or determining T cell dependent cellular cytotoxicity (TDCC) caused by contacting an antigen-binding molecule of the present disclosure with DLL3-expressing cells to which the antigen-binding site in the antigen-binding molecules of the present disclosure binds. The methods for assessing or determining the cytotoxic activity in vitro include methods for determining the activity of cytotoxic T-cells or the like. Whether an antigen-binding molecule of the present disclosure has the activity of inducing T-cell mediated cellular cytotoxicity can be determined by known methods (see, for example, Current protocols in Immunology, Chapter 7. Immunologic studies in humans, Editor, John E, Coligan et al., John Wiley & Sons, Inc., (1993)). In the cytotoxicity assay, an antigen-binding molecule which is able to bind to an antigen different from DLL3 and which is not expressed in the cells, and CD3/CD137, is used as a control antigen-binding molecule. The control antigen-binding molecule is assayed in the same manner. Then, the activity is assessed by testing whether an antigen-binding molecule of the present disclosure exhibits a stronger cytotoxic activity than that of a control antigen-binding molecule.

Meanwhile, the in vivo anti-tumor efficacy is assessed or determined, for example, by the following procedure. Cells expressing the antigen to which the antigen-binding site in an antigen-binding molecule of the present disclosure binds are transplanted intracutaneously or subcutaneously to a nonhuman animal subject. Then, from the day of transplantation or thereafter, a test antigen-binding molecule is administered into vein or peritoneal cavity every day or at intervals of several days. The tumor size is measured over time. Difference in the change of tumor size can be defined as the cytotoxic activity. As in an in vitro assay, a control antigen-binding molecule is administered. The antigen-binding molecule of the present disclosure can be judged to have cytotoxic activity when the tumor size is smaller in the group administered with the antigen-binding molecule of the present disclosure than in the group administered with the control antigen-binding molecule.

An MTT method and measurement of isotope-labeled thymidine uptake into cells are preferably used to assess or determine the effect of contact with an antigen-binding molecule of the present disclosure to suppress the growth of cells expressing an antigen to which the antigen-binding site in the antigen-binding molecule binds. Meanwhile, the same methods described above for assessing or determining the in vivo cytotoxic activity can be used preferably to assess or determine the activity of suppressing cell growth in vivo.

The TDCC of an antibody or antigen-binding molecule of the disclosure can be evaluated by any suitable method known in the art. For example, TDCC can be measured by lactate dehydrogenase (LDH) release assay. In this assay, target cells (e.g. DLL3-expressing cells) are incubated with T cells (e.g. PBMCs) in the presence of a test antibody or antigen-binding molecule, and the activity of LDH that has been released from target cells killed by T cells is measured using a suitable reagent. Typically, the cytotoxic activity is calculated as a percentage of the LDH activity resulting from the incubation with the antibody or antigen-binding molecule relative to the LDH activity resulting from 100% killing of target cells (e.g. lysed by treatment with Triton-X). If the cytotoxic activity calculated as mentioned above is higher, the test antibody or antigen-binding molecule is determined to have higher TDCC.

Additionally or alternatively, for example, TDCC can also be measured by real-time cell growth inhibition assay. In this assay, target cells (e.g. DLL3-expressing cells) are incubated with T cells (e.g. PBMCs) in the presence of a test antibody or antigen-binding molecule on a 96-well plate, and the growth of the target cells is monitored by methods known in the art, for example, by using a suitable analyzing instrument (e.g. xCELLigence Real-Time Cell Analyzer). The rate of cell growth inhibition (CGI: %) is determined from the cell index value according to the formulation given as CGI (%)=100−(CIAb×100/CINoAb). "CIAb" represents the cell index value of wells with the antibody or antigen-binding molecule on a specific experimental time and "CINoAb" represents the average cell index value of wells without the antibody or antigen-binding molecule. If the CGI rate of the antibody or antigen-binding molecule is high, i.e., has a significantly positive value, it can be said that the antibody or antigen-binding molecule has TDCC activity.

In one aspect, an antibody or antigen-binding molecule of the disclosure has T cell activation activity. T cell activation can be assayed by methods known in the art, such as a method using an engineered T cell line that expresses a reporter gene (e.g. luciferase) in response to its activation (e.g. Jurkat/NFAT-RE Reporter Cell Line (T Cell Activation Bioassay, Promega)). In this method, target cells (e.g. DLL3-expressing cells) are cultured with T cells in the presence of a test antibody or antigen-binding molecule, and then the level or activity of the expression product of the reporter gene is measured by appropriate methods as an index of T cell activation. When the reporter gene is a luciferase gene, luminescence arising from reaction between luciferase and its substrate may be measured as an index of T cell activation. If T cell activation measured as described above is higher, the test antibody or antigen-binding molecule is determined to have higher T cell activation activity.

Pharmaceutical Composition

In one aspect, the present disclosure provides a pharmaceutical composition comprising the antigen-binding molecule or antibody of the disclosure. In certain embodiments, the pharmaceutical composition of the disclosure induces T-cell-dependent cytotoxicity, in another word, the pharmaceutical composition of the disclosure is a therapeutic agent for inducing cellular cytotoxicity. In certain embodiments, the pharmaceutical composition of the disclosure is a pharmaceutical composition used for treatment and/or prevention of cancer. In certain embodiments, the pharmaceutical composition of the disclosure is a pharmaceutical composition used for treatment and/or prevention of DLL3-positive or DLL3-expressing cancers including lung cancer (including small cell lung cancer) and melanoma. In certain embodiments, the pharmaceutical composition of the disclosure is cell growth-suppressing agent. In certain embodiments, the pharmaceutical composition of the disclosure is anticancer agent.

A pharmaceutical composition of the present disclosure, a therapeutic agent for inducing cellular cytotoxicity, a cell growth-suppressing agent, or an anticancer agent of the present disclosure may be formulated with different types of antigen-binding molecules or antibodies, if needed. For example, the cytotoxic action against cells expressing an antigen can be enhanced by a cocktail of multiple antigen-binding molecules or antibodies of the disclosure.

Pharmaceutical compositions of an antigen-binding molecule or antibody as described herein are prepared by mixing such antigen-binding molecule or antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (Hylenex®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

If necessary, the antigen-binding molecules or antibodies of the present disclosure may be encapsulated in microcapsules (microcapsules made from hydroxymethylcellulose, gelatin, poly[methylmethacrylate], and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing agents as sustained-release agents are known, and these can be applied to the antigen-binding molecules of the present disclosure (J. Biomed. Mater. Res. (1981) 15, 267-277; Chemtech. (1982) 12, 98-105; U.S. Pat. No. 3,773,719; European Patent Application (EP) Nos. EP58481 and EP133988; Biopolymers (1983) 22, 547-556).

The pharmaceutical compositions, cell growth-suppressing agents, or anticancer agents of the present disclosure may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present disclosure can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present disclosure is not limited to these doses.

Preferably, a pharmaceutical composition of the present disclosure comprises an antigen-binding molecule or antibody as described herein. In one aspect, the composition is a pharmaceutical composition for use in inducing cellular cytotoxicity. In another aspect, the composition is a pharmaceutical composition for use in treating or preventing cancer. Preferably, the cancer is lung cancer (including small cell lung cancer) and melanoma. The pharmaceutical composition of the present disclosure can be used for treating or preventing cancer. Thus, the present disclosure provides a method for treating or preventing cancer, in which the antigen-binding molecule or antibody as described herein is administered to a patient in need thereof.

The present disclosure also provides methods for damaging cells expressing DLL3 or for suppressing the cell growth by contacting the cells expressing DLL3 with an antigen-binding molecule of the present disclosure that binds to DLL3. Cells to which an antigen-binding molecule of the present disclosure binds are not particularly limited, as long as they express DLL3. Specifically, in the present disclosure, the preferred DLL3-expressing cells include lung cancer (including small cell lung cancer) and melanoma.

In the present disclosure, "contact" can be carried out, for example, by adding an antigen-binding molecule of the present disclosure to culture media of cells expressing DLL3 cultured in vitro. In this case, an antigen-binding molecule to be added can be used in an appropriate form, such as a solution or solid prepared by lyophilization or the like. When the antigen-binding molecule of the present disclosure is added as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The added concentration is not particularly limited; however, the final concentration in a culture medium is preferably in a range of 1 pg/ml to 1 g/ml, more preferably 1 ng/ml to 1 mg/ml, and still more preferably 1 micro g/ml to 1 mg/ml.

In another embodiment of the present disclosure, "contact" can also be carried out by administration to nonhuman animals transplanted with DLL3-expressing cells in vivo or to animals having cancer cells expressing DLL3 endogenously. The administration method may be oral or parenteral. Parenteral administration is particularly preferred. Specifically, the parenteral administration method includes injection, nasal administration, pulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell growth-suppressing agents, or anticancer agents of the present disclosure can be administered locally or systemically by injection. Furthermore, an appropriate administration method can be selected according to the age and symptoms of an animal subject. When the antigen-binding molecule is administered as an aqueous solution, the solution may be a pure aqueous solution containing the antigen-binding molecule alone or a solution containing, for example, an above-described surfactant, excipient, coloring agent, flavoring agent, preservative, stabilizer, buffering agent, suspending agent, isotonizing agent, binder, disintegrator, lubricant, fluidity accelerator, and corrigent. The administered dose can be selected, for example, from the range of 0.0001 to 1,000 mg per kg of body weight for each administration. Alternatively, the dose can be selected, for example, from the range of 0.001 to 100,000 mg/body for each patient. However, the dose of an antigen-binding molecule of the present disclosure is not limited to these examples.

The present disclosure also provides kits for use in a method of the present disclosure, which contain an antigen-binding molecule of the present disclosure or an antigen-binding molecule produced by a method of the present disclosure. The kits may be packaged with an additional pharmaceutically acceptable carrier or medium, or instruction manual describing how to use the kits, etc.

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Package Insert

The term "package insert" is used to refer to instructions customarily included in commercial packages of therapeutic products, that contain information about the indications, usage, dosage, administration, combination therapy, contraindications and/or warnings concerning the use of such therapeutic products.

Pharmaceutical Formulation

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

Pharmaceutically Acceptable Carrier

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Treatment

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antigen-binding molecules or antibodies of the present disclosure are used to delay development of a disease or to slow the progression of a disease.

Cancer

The terms "cancer" and "cancerous" refer to or describe the physiological condition in mammals that is typically characterized by unregulated cell growth/proliferation.

In certain embodiments, the cancer is a DLL3-expressing or DLL3-positive cancer which include lung cancer (including small cell lung cancer) and melanoma.

Tumor

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

In preferred embodiments, the cancer is a cancer (including cancer tissues or cells) expressing DLL3. In some embodiments, the cancer is lung cancer, small cell lung cancer (SCLC), or melanoma.

Other Agents and Treatments

The multispecific antigen binding molecules described herein may be administered in combination with one or more other agents in therapy. For instance, a multispecific antigen binding molecules as described herein may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of multispecific antigen binding molecules used, the type of disorder or treatment, and other factors discussed above. The multispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the multispecific antigen binding molecules described herein can occur prior to, simultaneously, and/or following, administration of the additional therapeutic agent and/or adjuvant. Multispecific antigen binding molecules as described herein can also be used in combination with radiation therapy.

All documents cited herein are incorporated herein by reference.

The following are examples of methods and compositions of the present disclosure. It is understood that various other embodiments may be practiced, given the general description provided above.

EXAMPLES

Example 1

Affinity Matured Variant Screening of Parental Dual-Fab H183L072 for Improvement in In Vitro Cytotoxicity on Tumor Cells 1.1 Sequence of Affinity Matured Variants Concept of providing an immunoglobulin variable (Fab) region that binds CD3 and CD137, but does not bind to CD3 and CD137 at same time (Dual-Fab) is disclosed in WO2019111871 (incorporated herein by reference). To increase the binding affinity of parental Dual-Fab H183L072 (Heavy chain: SEQ ID NO: 1; Light chain: SEQ ID NO: 57) disclosed in WO2019111871, more than 1,000 Dual-Fab variants were generated using H183L072 as a template to introduce single or multiple mutations on a variable region. Antibodies were expressed using Expi293™ (Invitrogen) and purified by Protein A purification followed by gel filtration, when gel filtration was necessary. The sequences of 22 representative Dual-Fab variants with multiple mutations are listed in Table 6 and Tables 8-1 to 8-6 and binding affinity and kinetics towards CD3 and CD137 were evaluated at 25° C. and/or 37° C. using Biacore™ T200 surface plasmon resonance system (GE Healthcare) as described below in Example 1.2.2 (Table 9).

1.2. Binding Kinetics Information of Affinity Matured Variants 1.2.1 Expression and Purification of Human CD3 and CD137

The gamma and epsilon subunits of the human CD3 complex (human CD3εγ linker) were linked by a 29-mer linker and a Flag-tag was fused to the C-terminal end of the gamma subunit (SEQ ID NO: 102, Tables 5 and 7). This construct was expressed transiently using FreeStyle™ 293-F human embryonic kidney cell line (Thermo Fisher). Conditioned media expressing human CD3εγ linker was concentrated using a column packed with Q HP resins (GE healthcare) then applied to FLAG-tag affinity chromatography. Fractions containing human CD3εγ linker were collected and subsequently subjected to a Superdex® 200 gel filtration size exclusion chromatography column (GE healthcare) equilibrated with 1×D-PBS. Fractions containing human CD3εγ linker were then pooled. Human CD137 extracellular domain (ECD) (SEQ ID NO: 103, Tables 5 and 7) with hexahistidine (His-tag) and biotin acceptor peptide (BAP) on its C-terminus was expressed transiently using FreeStyle™ 293-F human embryonic kidney cell line (Thermo Fisher). Conditioned media expressing human CD137 ECD was applied to a HisTrap™ HP chromatography column (GE healthcare) and eluted with buffer containing imidazole (Nacalai). Fractions containing human CD137 ECD were collected and subsequently subjected to a Superdex® 200 gel filtration size exclusion chromatography column (GE healthcare) equilibrated with 1×D-PBS. Fractions containing human CD137 ECD were then pooled and stored at −80° C.

1.2.2 Affinity Measurement Towards Human CD3 and CD137

Binding affinity of Dual-Fab antibodies (Dual-Ig) to human CD3 were assessed at 25° C. using Biacore™ 8K surface plasmon resonance system (GE Healthcare). Anti-human Fc (GE Healthcare) was immobilized onto all flow cells of a CM4 sensor chip using amine coupling kit (GE Healthcare). Antibodies were captured onto the anti-Fc sensor surfaces, then recombinant human CD3 or CD137 was injected over the flow cell. All antibodies and analytes were prepared in ACES pH 7.4 containing 20 mM ACES, 150 mM NaCl, 0.05% Tween 20, 0.005% NaN$_3$. Sensor surface was regenerated each cycle with 3M MgCl$_2$. Binding affinity were determined by processing and fitting the data to 1:1 binding model using Biacore™ Insight Evaluation software, version 2.0 (GE Healthcare). CD137 binding affinity assay was conducted in the same conditions except that assay temperature was set at 37° C. Binding affinity of Dual-Fab antibodies to recombinant human CD3 and CD137 are shown in Tables 9-1 and 9-2 (the expression E used to express the K$_{on}$, K$_{off}$, and KD values in the table means "10 to the power of" and, for instance, 3.54E+04=3.54*10$^4$). As illustrated in Tables 9-1 and 9-2, the Dual Fab variants showed different binding kinetics towards CD3 and CD137 as compared H183/L072.

TABLE 5

| SEQ ID NOs for human CD3 and CD137 antigen used for affinity measurement in Table 9 | |
|---|---|
| Antigen name | SEQ List |
| Human CD3eg linker | 102 |
| Human CD137 ECD | 103 |

TABLE 6

Annotation of SEQ ID NOs used in Tables 8-1 to 8-6 (antibody naming and SEQ ID NOs for variable region including CDR 1, 2, and 3)

| DualAE No. | Ab name | VHR name | VLR name | VHR | VHR_CDR1 | VHR_CDR2 | VHR_CDR3 | VLR | VLR_CDR1 | VLR_CDR2 | VLR_CDR3 |
|---|---|---|---|---|---|---|---|---|---|---|---|
| Parent | H183/L072 | dBBDu183H | dBBDu072L | 1 | 15 | 29 | 43 | 57 | 62 | 67 | 72 |
| DualAE01 | H0868L0581 | dBBDu183H0868 | dBBDu072L0581 | 2 | 16 | 30 | 44 | 58 | 63 | 68 | 73 |
| DualAE08 | H1550L0918 | dBBDu183H1550 | dBBDu072L0918 | 3 | 17 | 31 | 45 | 59 | 64 | 69 | 74 |
| DualAE06 | H1571L0581 | dBBDu183H1571 | dBBDu072L0581 | 4 | 18 | 32 | 46 | 58 | 63 | 68 | 73 |
| DualAE17 | H1610L0581 | dBBDu183H1610 | dBBDu072L0581 | 5 | 19 | 33 | 47 | 58 | 63 | 68 | 73 |
| DualAE10 | H1610L0939 | dBBDu183H1610 | dBBDu072L0939 | 5 | 19 | 33 | 47 | 60 | 65 | 70 | 75 |
| DualAE05 | H1643L0581 | dBBDu183H1643 | dBBDu072L0581 | 6 | 20 | 34 | 48 | 58 | 63 | 68 | 73 |
| DualAE19 | H1647L0581 | dBBDu183H1647 | dBBDu072L0581 | 8 | 22 | 36 | 50 | 58 | 63 | 68 | 73 |
| DualAE20 | H1649L0581 | dBBDu183H1649 | dBBDu072L0581 | 9 | 23 | 37 | 51 | 58 | 63 | 68 | 73 |
| DualAE21 | H1649L0943 | dBBDu183H1649 | dBBDu072L0943 | 9 | 23 | 37 | 51 | 61 | 66 | 71 | 76 |
| DualAE22 | H1651L0581 | dBBDu183H1651 | dBBDu072L0581 | 10 | 24 | 38 | 52 | 58 | 63 | 68 | 73 |
| DualAE23 | H1652L0943 | dBBDu183H1652 | dBBDu072L0943 | 11 | 25 | 39 | 53 | 61 | 66 | 71 | 76 |

TABLE 6-continued

Annotation of SEQ ID NOs used in Tables 8-1 to 8-6 (antibody naming and SEQ ID NOs for variable region including CDR 1, 2, and 3)

| DualAE No. | Ab name | VHR name | VLR name | VHR | VHR_CDR1 | VHR_CDR2 | VHR_CDR3 | VLR | VLR_CDR1 | VLR_CDR2 | VLR_CDR3 |
|---|---|---|---|---|---|---|---|---|---|---|---|
| DualAE09 | H1673L0943 | dBBDu183H1673 | dBBDu072L0943 | 12 | 26 | 40 | 54 | 61 | 66 | 71 | 76 |
| DualAE18 | H1673L0581 | dBBDu183H1673 | dBBDu072L0581 | 12 | 26 | 40 | 54 | 58 | 63 | 68 | 73 |
| DualAE14 | H2591L0581 | dBBDu183H2591 | dBBDu072L0581 | 13 | 27 | 41 | 55 | 58 | 63 | 68 | 73 |
| DualAE15 | H2594L0581 | dBBDu183H2594 | dBBDu072L0581 | 14 | 28 | 42 | 56 | 58 | 63 | 68 | 73 |
| DualAE16 | H1644L0939 | dBBDu183H1644 | dBBDu072L0939 | 81 | 82 | 83 | 84 | 60 | 65 | 70 | 75 |
| DualAE02 | H0888L0581 | dBBDu183H0888 | dBBDu072L0581 | 101 | 114 | 127 | 140 | 58 | 63 | 68 | 73 |
| DualAE24 | H1595L0581 | dBBDu183H1595 | dBBDu072L0581 | 104 | 117 | 130 | 143 | 58 | 63 | 68 | 73 |
| DualAE07 | H1573L0581 | dBBDu183H1573 | dBBDu072L0581 | 106 | 119 | 132 | 145 | 58 | 63 | 68 | 73 |
| DualAE25 | H1579L0581 | dBBDu183H1579 | dBBDu072L0581 | 107 | 120 | 133 | 146 | 58 | 63 | 68 | 73 |
| DualAE26 | H1572L0581 | dBBDu183H1572 | dBBDu072L0581 | 110 | 123 | 136 | 149 | 58 | 63 | 68 | 73 |
| DualAE27 | H0883 | dBBDu183H0883 | dBBDu072L | 113 | 126 | 139 | 152 | 57 | 62 | 67 | 72 |
| CD3ε | CD3εVH | CD3εVL | | 77 | | | | 78 | | | |
| CD137 | CD 137 VH | CD137VL | | 79 | | | | 80 | | | |

TABLE 7

Full length amino acid sequence of antigen

| Antigen name | SEQ List | Amino Acid Sequence |
|---|---|---|
| Human CD3eg linker | 102 | QDGNEEMGGITQTPYKVSISGTTVILTCPQYPGSEILWQHNDKNIGGDEDDKNIGSDEDHLSLKEFSELEQSGYYVCYPRGSKPEDANFYLYLRARVGSADDAKKDAAKKDDAKKDDAKKDGSQSIKGNHLVKVYDYQEDGSVLLTCDAEAKNITWFKDGKMIGFLTEDKKKWNLGSNAKDPRGMYQCKGSQNKSKPLQVYYRMDYKDDDDK |
| Human CD137 ECD | 103 | LQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQHHHHHFIGGGGSGLNDIFEAQKIEWHE |

TABLE 8-1

Full length amino acid sequence of variable region of antibody followed by amino acid sequence of CDR 1, 2 and 3 regions as annotated in Table 6

| SEQ. list | SEQ number | Amino Acid Sequence |
|---|---|---|
| dBBDu183H | 1 | QVQLVESGGGLVQPGRSLRLSCAASGFTFSNAWMHWVRQAPGKGLEWVAQIKDKGNAYAAYYAPSVKGRFTISRDDSKNSIYLQMNSLKTEDTAVYYCHYVHYASASTVLPAFGVDAWGQGTTVTVSS |
| dBBDu183H0868 | 2 | QVQLVESGGGLVQPGRSLRLSCAASGFKFSNVWMHWVRQAPGKGLEWVAQIKDKYNAYAAYYAPSVKGRFTISRDDSKNSIYLQMNSLKTEDTAVYYCHYVHYASASTLLPAFGVDAWGQGTTVTVSS |
| dBBDu183H1550 | 3 | QVQLVESGGGLVQPGRSLRLSCAASGFKFSNVWMHWVRQAPGKGLEWVAQIKDKYNAYAAYYAPSVKGRFTISRDDSKNSIYLQMNSLKTEDTAVYYCHYIHYASASTLLPAFGVDAWGQGTTVEVSS |
| dBBDu183H1571 | 4 | QVQLVESGGGLVQPGRSLRLSCAASGFKFSNVWFHWVRQAPGKGLEWVAQIKDKYNAYATYYAPSVKGRFTISRDDSKNSIYLQMNSLKTEDTAVYYCHYVHYASASTLLPAFGVDAWGQGTTVTVSS |
| dBBDu183H1610 | 5 | QVQLVESGGGLVQPGRSLRLSCAASGFVFSNVWMHWVRQAPGKGLEWVAQIKDKWNAYAAYYAPSVKGRFTISRDDSKNSIYLQMNSLKTEDTAVYYCHYIHYASASTLLPAEGIDAWGQGTTVTVSS |
| dBBDu183H1643 | 6 | QVQLVESGGGLVQPGRSLRLSCAASGFKFSNVWFHWVRQAPGKGLEWVAQIKDYYNAYAAYYAPSVKGRFTISRDDSKNSIYLQMNSLKTEDTAVYYCHYVHYASASTLLPAEGVDAWGQGTTVTVSS |
| dBBDu183H1647 | 8 | QVQLVESGGGLVQPGRSLRLSCAASGFKFSNTWFHWVRQAPGKGLEWVAQIKDYYNDYAAYYAPSVKGRFTISRDDSKNSIYLQMNSLKTEDTAVYYCHYVHYASASTLLPAEGVDAWGQGTTVTVSS |
| dBBDu183H1649 | 9 | QVQLVESGGGLVQPGRSLRLSCAASGFVFSNVWFHWVRQAPGKGLEWVAQIKDKYNAYADYYAPSVKERFTISRDDSKNSIYLQMNSLKTEDTAVYYCHYVHYASASTLLPAEGVDAWGQGTTVTVSS |
| dBBDu183H1651 | 10 | QVQLVESGGGLVQPGRSLRLSCAASGFVFSNVWFHWVRQAPGKGLEWVAQIKDKYNAYADYYAPSVEGRFTISRDDSKNSIYLQMNSLKTEDTAVYYCHYVHYASASTLLPAEGVDAWGQGTTVTVSS |
| dBBDu183H1652 | 11 | QVQLVESGGGLVQPGRSLRLSCAASGFVFSNVWFHWVRQAPGKGLEWVAQIKDYYNAYADYYAPSVEGRFTISRDDSKNSIYLQMNSLKTEDTAVYYCHYVHYASASTLLPAEGVDAWGQGTTVTVSS |
| dBBDu183H1673 | 12 | QVQLVESGGGLVQPGRSLRLSCAASGFVFSNVWFHWVRQAPGKGLEWVAQIKDKWNAYADYYAPSVKERFTISRDDSKNSIYLQMNSLKTEDTAVYYCHYIHYASASTLLPAEGIDAWGQGTTVTVSS |

TABLE 8-2

| SEQ list | SEQ number | Amino Acid Sequence |
|---|---|---|
| dBBDu183H2591 | 13 | QVQLVESGGGLVQPGRSLRLSCAASGFKFSNVWFHWVRQAPGKGLEWVAQIKDYYNAYAGYYHPSVKGRFTISRDDSKNSIYLQMNSLKTEDTAVYYCHYVHYAAASTLLPAEGVDAWGQGTIVTVSS |
| dBBDu183H2594 | 14 | QVQLVESGGGLVQPGRSLRLSCAASGFKFSNVWFHWVRQAPGKGLEWVAQ1KDYYNAYAGYYHPSVKGRFTISRDDSKNS1YLQMNSLKTEDTAVYYCHYVHYAAASQLLPAEGVDAWGQGTTVTVSS |
| dBBDu183H_VHR_CDR1 | 15 | NAWMH |
| dBBDu183H0868_VHR_CDR1 | 16 | NVWMH |
| dBBDu183H1550_VHR_CDR1 | 17 | NVWMH |
| dBBDu183H1571_VHR_CDR1 | 18 | NVWFH |
| dBBDu183H1610_VHR_CDR1 | 19 | NVWMH |
| dBBDu183H1643_VHR_CDR1 | 20 | NVWFH |
| dBBDu183H1647_VHR_CDR1 | 22 | NTWFH |
| dBBDu183H1649_VHR_CDR1 | 23 | NVWFH |
| dBBDu183H1651_VHR_CDR1 | 24 | NVWFH |
| dBBDu183H1652_VHR_CDR1 | 25 | NVWFH |
| dBBDu183H1673_VHR_CDR1 | 26 | NVWFH |
| dBaDu183H2591_VHR_CDR1 | 27 | NVWFH |
| dBaDu183H2594_VHR_CDR1 | 28 | NVWFH |
| dBBDu183H_VHR_CDR2 | 29 | QIKDKGNAYAMYAPSVKG |
| dBBDu183H0868_VHR_CDR2 | 30 | QIKDKYNAYAAYYAPSVKG |
| dBBDu183H1550_VHR_CDR2 | 31 | QIKDKYNAYAANYAPSVKG |
| dBBDu183H1571_VHR_CDR2 | 32 | QIKDKYNAYATYYAPSVKG |

TABLE 8-3

| SEQ list | SEQ number | Amino Acid Sequence |
|---|---|---|
| dBBDu183H1610_VHR_CDR2 | 33 | QIKDKWNAYAAYYAPSVKG |
| dBBDu183H1643_VHR_CDR2 | 34 | QIKDYYNAYAAVYAPSVKG |
| dBBDu183H1647_VHR_CDR2 | 36 | QIKDYYNDYAAYYAPSVKG |
| dBBDu183H1649_VHR_CDR2 | 37 | Q1KDKYNAYADYYAPSVKE |
| dBBDu183H1651_VHR_CDR2 | 38 | QIKDKYNAYADYYAPSVEG |
| dBBDu183H1652_VHR_CDR2 | 39 | QIKDYYNAYADYYAPSVEG |
| dBBDu183H1673_VHR_CDR2 | 40 | QIKDKWNAYADYYAPSVKE |
| dBBDu183H2591_VHR_CDR2 | 41 | QIKDYYNAYAGYYHPSVKG |
| dBBDu183H2594_VHR_CDR2 | 42 | QIKDYYNAYAGYMPSVKG |
| dBBDu183H_VHR_CDR3 | 43 | VHYASASTVLPAFGVDA |
| dBBDu183H0868_VHR_CDR3 | 44 | VHYASASTLLPAFGVDA |
| dBBDu183H1550_VHR_CDR3 | 45 | IHYASASTLLPAFGVDA |
| dBBDu183H1571_VHR_CDR3 | 46 | VHYASASTLLPAFGVDA |
| dBBDu183H1610_VHR_CDR3 | 47 | IHYASASTLLPAEGIDA |
| dBBDu183H1643_VHR_CDR3 | 48 | VHYASASTLLPAEGVDA |
| dBBDu183H1647_VHR_CDR3 | 50 | VHYASASTLLPAEGVDA |
| dBBDu183H1649_VHR_CDR3 | 51 | VHYASASTLLPAEGVDA |
| dBBDu183H1651_VHR_CDR3 | 52 | VHYASASTLLPAEGVDA |
| dBBDu183H1652_VHR_CDR3 | 53 | VHYASASTLLPAEGVDA |
| dBBDu183H1673_VHR_CDR3 | 54 | IHYASASTLLPAEGIDA |
| dBBDu183H2591_VHR_CDR3 | 55 | VHYAAASTLLPAEGVDA |
| dBBDu183H2594_VHR_CDR3 | 56 | VHYAAASQLLPAEGVDA |

TABLE 8-4

| SEQ list | SEQ number | Amino Acid Sequence |
| --- | --- | --- |
| dBBDu072L | 57 | DIVMTQSPLSLPVTPGEPASISCQASQELVHMNRNTYLHWYQQKPGQAPRLLIYKVSNRFPGVPDRFSGSGSGTDFTLKISRVEAEDVGVYYCAQGTSVPFTFGQGTKLEIK |
| dBBDu072L0581 | 58 | DIVMTQSPLSLPVTPGEPASISCQPSQEVVHMNRNTYLHWYQQKPGQAPRLLIYKVSNRFPGVPDRFSGSGSGTDFTLKISRVEAEDVGVYYCAQGTSHPFTFGQGTKLEIK |
| dBBDu072L0918 | 59 | DIVMTQSPLSLPVTPGEPASISCQPSQEVVHMNNVVYLHWYQQKPGQAPRLLIYKVSNRFPGVPDRFSGSGSGTDFTLKISRVEAEDVGVYYCAQGTSHPFTFGQGTKLEIK |
| dBBDu072L0939 | 60 | DIVMTQSPLSLPVTPGEPASISCQPSQEVVHMNRNTYLHWYQQKPGQAPRLLIYKVSNVFPGVPDRFSGSGSGTDFTLKISRVEAEDVGVYYCAQGTHHPFTFGQGTKLEIK |
| dBBDu072L0943 | 61 | DIVMTQSPLSLPVTPGEPASISCQPSEEVVHMNRNTYLHWYQQKPGQAPRLLIYKVSNLFPGVPDRFSGSGSGTDFTLKISRVEAEDVGVYYCAQGTHHPFTFGQGTKLEIK |
| dBBDu072L_VLR_CDR1 | 62 | QASQELVHMNRNTYLH |
| dBBDu072L0581_VLR_CDR1 | 63 | QPSQEVVHMNRNTYLH |
| dBBDu072L0948_VLR_CDR1 | 64 | QPSQEVVHMNNVVYLH |
| dBBDu072L0939_VLR_CDR1 | 65 | QPSQEVVHMNRNTYLH |
| dBBDu072L1943_VLR_CDR1 | 66 | QPSEEVVHMNRNTYLH |
| dBBDu072L_VLR_CDR2 | 67 | KVSNRFP |
| dBBDu072L0581_VLR_CDR2 | 68 | KVSNRFP |
| dBBDu072L0918_VLR_CDR2 | 69 | KVSNRFP |
| dBBDu072L0939_VLR_CDR2 | 70 | KVSNVFP |
| dBBDu072L0943_VLR_CDR2 | 71 | KVSNLVP |
| dBBDu072L_VLR_CDR3 | 72 | AQGTSVPFT |
| dBBDu072L0581_VLR_CDR3 | 73 | AQGTSHPFT |
| dBBDu072L0918_VLR_CDR3 | 74 | AQGTSHPFT |
| dBBDu072L0939_VLR_CDR3 | 75 | AQGTHHPFT |
| dBBDu072L0943_VLR_CDR3 | 76 | AQGTHHPFT |

TABLE 8-5

| SEQ list | SEQ number | Amino Acid Sequence |
| --- | --- | --- |
| CD3εVH | 77 | QVQLVESGGGVVQPGGSLRLSCAASGFTFSNAWMHWVRQAPGKGLEWVAQIKDKSQNYATYVAESVKGRFTISRADSKNSIYLQMNSLKTEDTAVYYCRYVHYAAGYGVDIWGQGTTVTVSS |
| CD3εVL | 78 | DIVMTQSPLSLPVTPGEPASISCRSSQPLVHSNRNTYLHWYQQKPGQAPRLLIYKVSNRFSGVPDRFSGSGSGTDFTLKISRVEAEDVGVYYCGQGTQVPYTFGQGTKLEIK |
| CD137VH | 79 | QVQLQQWGAGLLKPSETLSLTCAVYGGSFSGYYWSWIRQSPEKGLEWIGEINHGGYVTYNPSLESRVTISVDTSKNQFSLKLSSVTAADTAVYYCARDYGPGNYDWYFDLWGRGTLVTVSS |
| CD137VL | 80 | EIVLTQSPATLSLSPGERATLSCRASQSVSSYLAWYQQKPGQAPRLLIYDASNRATGIPARFSGSGSGTDFTLTISSLEPEDFAVYYCQQRSNWPPALTFGGGTKVEIK |
| dBBDu183H1644 | 81 | QVLQLVESGGGLVQPGRSLRLSCAASGFVFSNVWFHWVRQAPGKGLEWVAQIKDYYNAYAAYYAPSVKGRFTISRDDSKNSIYLQMNSLKTEDTAVYYCHYVHYASASTLLPAEGVDAWGQGTTVTVSS |

TABLE 8-5-continued

| SEQ list | SEQ number | Amino Acid Sequence |
|---|---|---|
| dBBDu183H1644_VHR_CDR1 | 82 | NVWFH |
| dBBDu183H1644_VHR_CDR2 | 83 | QIKDYYNAYAAYYAPSVKG |
| dBBDu183H1644_VHR_CDR3 | 84 | VHYASASTLLPAEGVDA |
| dBBDu183H0888 | 101 | QVQLVESGGGLVQPGRSLRLSCAASGFKFSNVWMHWVRQAPGKGLEWVAQIKDKWNAYAAYYAPSVKGRFTISRDDSKNSIYLQMNSLKTEDTAVYYCHYIHYASASTLLPAFGIDAWGQGTTVTVSS |
| dBBDu183H1595 | 104 | QVQLVESGGGLVQPGRSLRLSCAASGFKFSNTWMHWVRQAPGKGLEWVAQIKDKYNAYAAYYAPSVKGRFTISRDDSKNSIYLQMNSLKTEDTAVYYCHYIHYASASTLLPAFGVDAWGQGTTVTVSS |
| dBBDu183H1573 | 106 | QVQLVESGGGLVQPGRSLRLSCAASGFKFSNVWFHWVRQAPGKGLEWVAQIKDYYNAYAAYYAPSVKGRFTISRDDSKNSIYLQMNSLKTEDTAVYYCHYVHYASASTLLPAFGVDAWGQGTTVTVSS |
| dBBDu183H1579 | 107 | QVLQVESGGGLVQPGRSLRLSCAASGFKFSHVWFHWVRQAPGKGLEWVAQIKDKYNAYAAYYAPSVKGRFTISRDDSKNSIYLQMNSLKTEDTAVYYCHYVHYASASTLLPAFGVDAWGQGTTVTVSS |
| dBBDu183H1572 | 110 | QVQLVESGGGLVQPGRSLRLSCAASGFKFSNVWFHWVRQAPGKGLEWVAQIKDKYNAYAAYYAPSVKGRFTISRDDSKNWIYLQMNSLKTEDTAVYYCHYVHYASASTLLPAEGVDAWGQGTTVTVSS |
| dBBDu183H0883 | 113 | QVLQVESGGGLVQPGRSLRLSCAASGFTFSNAWMHWVRQAPGKGLEWVAQIKDKGNAYAAYYAPSVKGRFTISRDDSKNSIYLQMNSLKTEDTAVYYCRYVHYASASTLLPAFGVDAWGQGTTVTVSS |

TABLE 8-6

| SEQ list | SEQ number | Amino Acid Sequence |
|---|---|---|
| dBBDu183H0888_VHR_CDR1 | 114 | NVWMH |
| dBBDu183H1595_VHR_CDR1 | 117 | MTWMH |
| dBBDu183H1573_VHR_CDR1 | 119 | MVWFH |
| dBBDu183H1579_VHR_CDR1 | 120 | HVWFH |
| dBBDu183H1572_VHR_CDR1 | 123 | NVWFH |
| dBBDu183H0883_VHR_CDR1 | 126 | NAWMH |
| dBBDu183H0888_VHR_CDR2 | 127 | QIKDKWNAYAAYYAPSVKG |
| dBBDu183H1595_VHR_CDR2 | 130 | QIKDKYNAYAAYYAPSVKG |
| dBBDu183H1573_VHR_CDR2 | 132 | QIKDYYANYAAYYAPSVKG |
| dBBDu183H1579_VHR_CDR2 | 133 | QIKDKYNAYAAYYAPSVKG |
| dBBDu183H1572_VHR_CDR2 | 136 | QIKDKYNAYAAYYAPSVKG |
| dBBDu183H0883_VHR_CDR2 | 139 | QIKDKGNAYAAYYAPSVKG |
| dBBDu183H0888_VHR_CDR3 | 140 | IHYASASTLLPAFGIDA |
| dBBDu183H1575_VHR_CDR3 | 143 | IHYASASTLLPAFGVDA |
| dBBDu183H1573_VHR_CDR3 | 145 | VHYASASTLLPAFGVDA |
| dBBDu183H1579_VHR_CDR3 | 146 | VHYASASTLLPAFGVDA |
| dBBDu183H1572_VHR_CDR3 | 149 | VHYASASTLLPAEGVDA |
| dBBDu183H0883_VHR_CDR3 | 152 | VHYASASTLLPAFGVDA |

TABLE 9-1

Binding kinetics of Dual variants towards human CD3 and human CD137

| | CD3 (25° C.) | | | CD137 (37° C.) | | |
|---|---|---|---|---|---|---|
| Antibody name | ka (M-1s-1) | kd (s-1) | KD (M) | ka (M-1s-1) | kd (s-1) | KD (M) |
| H183L072 | 3.54E+04 | 1.20E−02 | 3.40E−07 | 3.47E+03 | 1.96E−02 | 5.66E−06 |
| H0868L0581 | 1.23E+05 | 1.94E−02 | 1.57E−07 | 1.22E+04 | 1.36E−03 | 1.11E−07 |
| H1550L0918 | 7.20E+04 | 3.16E−03 | 4.38E−08 | 1.09E+04 | 5.79E−03 | 5.30E−07 |
| H1571L0581 | 1.42E+05 | 1.56E−02 | 1.10E−07 | 1.21E+04 | 1.05E−03 | 8.68E−08 |
| H1610L0581 | 6.80E+04 | 1.42E−03 | 2.09E−08 | 1.07E+04 | 1.10E−03 | 1.03E−07 |
| H1610L0939 | 5.00E+04 | 2.53E−03 | 5.07E−08 | 1.30E+04 | 8.01E−04 | 6.18E−08 |
| H1643L0581 | 9.46E+04 | 2.51E−02 | 2.65E−07 | 1.23E+04 | 6.06E−04 | 4.94E−08 |
| H1644L0939 | 5.58E+04 | 8.08E−02 | 1.45E−06 | 1.21E+04 | 4.44E−04 | 3.68E−08 |
| H1647L0581 | 4.43E+04 | 1.01E−01 | 2.28E−06 | 9.98E+03 | 6.47E−04 | 6.48E−08 |

TABLE 9-1-continued

Binding kinetics of Dual variants towards human CD3 and human CD137

| | CD3 (25° C.) | | | CD137 (37° C.) | | |
|---|---|---|---|---|---|---|
| Antibody name | ka (M-1s-1) | kd (s-1) | KD (M) | ka (M-1s-1) | kd (s-1) | KD (M) |
| H1649L0581 | 7.50E+04 | 3.36E−02 | 4.49E−07 | 1.29E+04 | 5.53E−04 | 4.28E−08 |
| H1649L0943 | 6.10E+04 | 4.81E−02 | 7.89E−07 | 1.43E+04 | 4.68E−04 | 3.28E−08 |
| H1651L0581 | 7.18E+04 | 3.71E−02 | 5.17E−07 | 1.40E+04 | 6.03E−04 | 4.32E−08 |
| H1652L0943 | 6.23E+04 | 6.36E−02 | 1.02E−06 | 1.29E+04 | 4.70E−04 | 3.64E−08 |
| H1673L0581 | 7.96E+04 | 1.06E−03 | 1.33E−08 | 1.19E+04 | 9.60E−04 | 8.04E−08 |
| H1673L0943 | 5.50E+04 | 1.16E−03 | 2.10E−08 | 1.22E+04 | 7.22E−04 | 5.91E−08 |
| H2591L0581 | 1.02E+05 | 5.35E−02 | 5.25E−07 | 2.04E+04 | 7.42E−04 | 3.63E−08 |
| H2594L0581 | 9.83E+04 | 5.84E−02 | 5.93E−07 | 2.09E+04 | 1.63E−03 | 7.81E−08 |

TABLE 9-2

Binding kinetics of Dual variants towards human CD3 and human CD137

| | CD3 (25° C.) | | | CD137 (37° C.) | | |
|---|---|---|---|---|---|---|
| Antibody Name | ka (1/Ms) | kd (1/s) | KD (M) | ka (1/Ms) | kd (1/s) | KD (M) |
| H0888L0581 | 9.50E+04 | 1.92E−03 | 2.02E−08 | 1.50E+04 | 3.11E−03 | 2.08E−07 |
| H1595L0581 | 1.16E4-05 | 6.58E−03 | 5.70E−08 | 1.38E+04 | 2.69E−03 | 1.95E−07 |
| H1573L0581 | 1.21E+05 | 1.88E−02 | 1.56F−07 | 1.46E+04 | 1.03E−03 | 7.06E−08 |
| H1579L0581 | 1.24E+05 | 3.40E−02 | 2.73E−07 | 1.48E+04 | 4,06E−03 | 2.75E−07 |
| H1572L0581 | 9.77E+04 | 2.80E−02 | 2.86E−07 | 1.39E+04 | 7.22E−04 | 5.21E−08 |
| H0883 | 9.07E+04 | 9.99E−03 | 1.10E−07 | | n.d. | |

Example 2

Bi-Specific and Tri-Specific Antibody Sequences and Preparation 2.1. Design and Preparation of Bi- or Tri-Specific Ab (1+1) Format To evaluate the efficacy of Dual-Ig variants (DualAE05 etc.) prepared in Example 1, bi-specific and tri-specific antibodies were generated with one arm recognizing tumor antigen DLL3 (from anti-DLL3 antibody D30841AE13) and the other arm recognizing effector cells, predominantly T-cells. DLL3/CD3ε (1+1) and DLL3/DualAE05 (1+1) antibodies were generated by using Fab-arm exchange (FAE) according to the method described in Proc Natl Acad Sci USA. 2013 Mar. 26; 110(13):5145-5150. The (1+1) format is depicted in panel (b) of FIG. 1. The target antigen of each Fv region and naming rule of each binding domain in the bi- and trispecific antibodies in the (1+1) format are shown in Table 10-2 and the SEQ ID NOs are shown in Table 12.

2.2. Design and Preparation of Trivalent Ab (1+2) Format Comprising One Monovalent DLL3-Binding Arm and Two Dual-Fabs Target antigen expression in solid tumors are likely to be highly heterogeneous and regions of tumors with low antigen expression may not provide sufficient cross-linking of CD3 or CD137. In particular, CD137 receptor clustering is critical for efficient agonistic activity (Trends Biochem Sci. 2002 January; 27(1)19-26). To improve cytotoxicity mediated by CD3 binding and activation, a new trivalent trispecific antibody format i.e. DLL3-DUAL/LINC, 1+2) was designed to increase number of binding domains to CD137 molecules. Specifically, the new antibody format is a trivalent tri-specific antibody with "1+2" format which comprises two monovalent Dual-Fabs each capable of binding to one CD3 or CD137 but not simultaneously (FvB and FvC of panel (a) of FIG. 1, and one monovalent DLL3-binding arm (FvA of panel (a) of FIG. 1, wherein one disulfide bond ("LINC") is introduced/engineered between the two Dual-Fabs by introducing a cysteine substitution e.g. at the 191 position (S191C with Kabat numbering) of the CH1 domain of each of the two Dual-Fabs panel (a) of FIG. 1 and Table 10-1). Without wishing to be bound by a theory, we envisioned that such engineered disulfide bond ("LINC") would restrict the antigen (CD3 or CD137) binding orientation of the two Dual-Fabs to cis antigen-binding (i.e. binding to two antigens on the same cell) as a results of steric hindrance or shorter distance between the two Dual-Fabs, thereby improving the safety profile of the trispecific Ab by preventing undesirable crosslinking of two CD3/CD137-expressing immune cells mediated by the two Dual-Fabs in an DLL3-independent manner. Specifically, DLL3-Dual/Dual antibody variants (DLL3-Dual/LINC, 1+2) having monovalent tumor antigen binding ability towards DLL3, bivalent CD3 and bivalent CD137 binding properties attributed to two Dual-Fabs were prepared panel (a) of FIG. 1 and Table 10-1). CrossMab technology (WO2017055539) was also utilized. Fc region was Fc-gamma R silent and deglycosylated. The target antigen of each Fv region and naming rule of each binding domain in the trispecific antibodies are shown in Table 11-1 and 12. As for a negative control, Ctrl (VHR IC17HdK and VLR IC17L) which does not bind to DLL3 was used in place of the monovalent DLL3-binding arm (Table 12). All antibodies were expressed as trivalent form by transient expression in Expi293™ cells (Invitrogen) and purified according to Example 1.1. To improve the purities, antibodies were further purified by passing through an affinity column that specifically binds the UnLINC format (i.e., trivalent 1+2 antibody without the engineered disulfide bond) but not the LINC format (i.e., trivalent 1+2 antibody with the engineered disulfide bond).

2.3. Generation of Bispecific Ab (BiTE)

In order to compare the efficacy of Trivalent Ab (DLL3-DUAL/LINC, 2+1) with other DLL3/CD3 bispecific format antibodies, an antibody with half-life extended BiTE format was generated, named as DLL3CD3BiTE. DLL3CD3BiTE was composed of two single-chain variable fragments (ScFv), one directed against the tumor-associated antigen DLL3 fused to one that is directed against CD3 (panel (c) of FIG. 1). The target antigen of each Fv region in the BiTE format bispecific antibody is shown in Table 10-3, and the SEQ ID NO is shown in Table 11-2 and Table 14.

TABLE 10-2

Bi- and Trispecific Ab (1 + 1)

| Antibody name | Fv A | Fv B |
| --- | --- | --- |
| DLL3/CD3ε | DLL3 | CD3ε |
| DLL3/DualAE05 | DLL3 | DualAE05 |

TABLE 10-3

Bispecific Ab (BiTE)

| Antibody name | Fv A | Fv B |
| --- | --- | --- |
| DLL3CD3BiTE | Anti-DLL3 | Anti-CD3 |

TABLE 10-1

Antibody name, targeted arm and Fc information

| Trivalent Ab (1 + 2 LINC) Antibody Name | Format | Fv A | Linker | Fv B | Fv C | FC | Fc (knob) | Fc (hole) |
| --- | --- | --- | --- | --- | --- | --- | --- | --- |
| DLL3-DualAE05/DualAE05-FF091 | (1 + 2) Dual/LINC | Anti-DLL3 | Long | DualAE05 | DualAE05 | LALA, N297A, Act5 (M428L, N434A, Q438R, S440E) | SG1321kV11Fc | SG1321hV11Fc |
| Ctrl-DualAE05/DualAE05-FF091 | (1 + 2) Dual/LINC | Ctrl | Long | DualAE05 | DualAE05 | LALA, N297A, Act5 (M428L, N434A, Q438R, S440E) | SG1321kV11Fc | SG1321hV11Fc |
| DLL3-DualAE05/DualAE05-FF102 | (1 + 2) Dual/LINC | Anti-DLL3 | Long | DualAE05 | DualAE05 | LALA, N297A, Act5 (M428L, N434A, Q438R, S440E) | SG1372kV11Fc | SG1372hV11Fc |
| DLL3-DualAE05/DualAE05-FF110 | (1 + 2) Dual/LINC | Anti-DLL3 | Mid | DualAE05 | DualAE05 | LALA, N297A, Act5 (M428L, N434A, Q438R, S440E) | SG1372kV11Fc | SG1372hV11Fc |
| DLL3-DualAE05/DualAE05-FF111 | (1 + 2) Dual/LINC | Anti-DLL3 | Short | DualAE05 | DualAE05 | LALA, N297A, Act5 (M428L, N434A, Q438R, S440E) | SG1372kV11Fc | SG1372hV11Fc |
| DLL3-DualAE05/DualAE05-FF056 | (1 + 2) Dual/LINC | Anti-DLL3 | Long | DualAE05 | DualAE05 | L235R, S239K, N297A | SG1176kV11Fc | SG1176hV11Fc |
| DLL3-DualAE15/DualAE15-FF119 | (1 + 2) Dual/LINC | Anti-DLL3 | Long | DualAE15 | DualAE15 | LALA, N297A, Act5 (M428L, N434A, Q438R, S440E) | SG1321kV11Fc | SG1321hV11Fc |
| Ctrl-DualAE15/DualAE15-FF119 | (1 + 2) Dual/LINC | Ctrl | Long | DualAE15 | DualAE15 | LALA, N297A, Act5 (M428L, N434A, Q438R, S440E) | SG1321kV11Fc | SG1321hV11Fc |
| DLL3-DualAE15/DualAE15-FF120 | (1 + 2) Dual/LINC | Anti-DLL3 | Long | DualAE15 | DualAE15 | LALA, N297A, Act5 (M428L, N434A, Q438R, S440E) | SG1372kV11Fc | SG1372hV11Fc |
| DLL3-DualAE15/DualAE15-FF121 | (1 + 2) Dual/LINC | Anti-DLL3 | Mid | DualAE15 | DualAE15 | LALA, N297A, Act5 (M428L, N434A, Q438R, S440E) | SG1372kV11Fc | SG1372hV11Fc |
| DLL3-DualAE15/DualAE15-FF122 | (1 + 2) Dual/LINC | Anti-DLL3 | Short | DualAE15 | DualAE15 | LALA, N297A, Act5 (M428L, N434A, Q438R, S440E) | SG1372kV11Fc | SG1372hV11Fc |
| DLL3-DualAE15/DualAE15-FF123 | (1 + 2) Dual/LINC | Anti-DLL3 | Long | DualAE15 | DualAE15 | L235 R, S239K, N297A | SG1176kV11Fc | SG1176hV11Fc |
| DLL3-DualAE16/DualAE16-FF124 | (1 + 2) Dual/LINC | Anti-DLL3 | Long | DualAE16 | DualAE16 | LALA, N297A, Act5 (M428L, N434A, Q438R, 5440E) | SG1321kV11Fc | SG1321hV11Fc |
| Ctrl-DualAE16/DualAE16-FF124 | (1 + 2) Dual/LINC | Ctrl | Long | DualAE16 | DualAE16 | LALA, N297A, Act5 (M428L, N434A, Q438R, 5440E) | SG1321kV11Fc | SG1321hV11Fc |
| DLL3-DualAE16/DualAE16-FF125 | (1 + 2) Dual/LINC | Anti-DLL3 | Long | DualAE16 | DualAE16 | LALA, N297A, Act5 (M428L, N434A, Q438R, S440E) | SG1372kV11Fc | SG1372hV11Fc |
| DLL3-DualAE16/DualAE16-FF126 | (1 + 2) Dual/LINC | Anti-DLL3 | Mid | DualAE16 | DualAE16 | LALA, N297A, Act5 (M428L, N434A, Q438R, S440E) | SG1372kV11Fc | SG1372hV11Fc |
| DLL3-DualAE16/DualAE16-FF127 | (1 + 2) Dual/LINC | Anti-DLL3 | Short | DualAE16 | DualAE16 | LALA, N297A, Act5 (M428L, N434A, Q438R, 5440E) | SG1372kV11Fc | SG1372hV11Fc |
| DLL3-DualAE16/DualAE16-FF128 | (1 + 2) Dual/LINC | Anti-DLL3 | Long | DualAE16 | DualAE16 | L235 R, S239K, N297A | SG1176kV11Fc | SG1176hV11Fc |

TABLE 11-1

Antibody chain number and SEQ ID NO

| Variant name | Linker | Chain 1 | Chain 2 | Chain 3 | Chain 4 or Chain 5 |
|---|---|---|---|---|---|
| DLL3-DualAE05/DualAE05-FF091 | 249 | 201 | 206 | 208 | 214 |
| Ctrl-DualAE05/DualAE05-FF091 | 249 | 202 | 207 | 208 | 214 |
| DLL3-DualAE05/DualAE05-FF102 | 249 | 203 | 206 | 209 | 214 |
| DLL3-DualAE05/DualAE05-FF110 | 248 | 204 | 206 | 209 | 214 |
| DLL3-DualAE05/DualAE05-FF111 | 259 | 205 | 206 | 209 | 214 |
| DLL3-DualAE05/DualAE05-FF056 | 249 | 216 | 206 | 229 | 214 |
| DLL3-DualAE15/DualAE15-FF119 | 249 | 217 | 206 | 210 | 214 |
| Ctrl-DualAE15/DualAE15-FF119 | 249 | 218 | 207 | 210 | 214 |
| DLL3-DualAE15/DualAE15-FF120 | 249 | 219 | 206 | 211 | 214 |
| DLL3-DualAE15/DualAE15-FF121 | 248 | 220 | 206 | 211 | 214 |
| DLL3-DualAE15/DualAE15-FF122 | 259 | 221 | 206 | 211 | 214 |
| DLL3-DualAE15/DualAE15-FF123 | 249 | 222 | 206 | 230 | 214 |
| DLL3-DualAE16/DualAE16-FF124 | 249 | 223 | 206 | 212 | 215 |
| Ctrl-DualAE16/DualAE16-FF124 | 249 | 224 | 207 | 212 | 215 |
| DLL3-DualAE16/DualAE16-FF125 | 249 | 225 | 206 | 213 | 215 |
| DLL3-DualAE16/DualAE16-FF126 | 248 | 226 | 206 | 213 | 215 |
| DLL3-DualAE16/DualAE16-FF127 | 259 | 227 | 206 | 213 | 215 |
| DLL3-DualAE16/DualAE16-FF128 | 249 | 228 | 206 | 231 | 215 |

TABLE 11-2

Antibody chain number and SEQ ID NO

| Antibody name | Chain 1 |
|---|---|
| DLL3CD3BiTE | 250 |

TABLE 12

Variable region and their CDR 1-3 SEQ ID NO

| VR name | VHR name | VLR name | VHR | VHR_CDR1 | VHR_CDR2 | VHR_CDR3 | VLR | VLR_CDR1 | VLR_CDR2 | VLR_CDR3 |
|---|---|---|---|---|---|---|---|---|---|---|
| DLL3 (D30841AE13) | D08410053H0118 | D084101L0000 | 232 | 233 | 234 | 235 | 236 | 237 | 238 | 239 |
| DualAE05 | dBBDu183H1643 | dBBDu072L0581 | 6 | 20 | 34 | 48 | 58 | 63 | 68 | 73 |
| DualAE15 | dBBDu183H2594 | dBBDu072L0581 | 14 | 28 | 42 | 56 | 58 | 63 | 68 | 73 |
| DualAE16 | dBBDu183H1644 | dBBDu072L0939 | 81 | 82 | 83 | 84 | 60 | 65 | 70 | 75 |
| CD3ε | CD3εVH | CD3εVL | 251 | 252 | 253 | 254 | 255 | 256 | 257 | 258 |
| Ctrl | IC17HdK | IC17L | 240 | 241 | 242 | 243 | 244 | 245 | 246 | 247 |

TABLE 13

SEQ ID NO of Fc regions in Table 14

| Fc Name | SED ID NO |
|---|---|
| SG1321kV11Fc | 99 |
| SG1372kV11Fc | 100 |
| SG1176kV11Fc | 108 |
| SG1321hV11Fc | 109 |
| SG1372hV11Fc | 111 |
| SG1176hV11Fc | 112 |

TABLE 14-1

| Sequence Name | SEQ ID NOs | Amino Acid Sequence |
|---|---|---|
|  | 201 | DIQLTQSPSFLSASVGDRVTITCQSTESVYGSDWLSWYQQKPGQPPKLLIYQASNLEIGVPSRFSGSGSG TDFTLTINSLEAEDAATYYCQGYYSGYIYAFGGGTKVEIKSSASTKGPSVFPLAPSSRSTSESTAALGCL VKDYFPEPVTVSWNSGALTSGVHTFPAVLQSSGLYSLSSVVTVPSSSGLTKTYTCNVDHKPSNTKVDKRV EPKSCGGGGSGGGGSQVQLVESGGGLVQPGRSLRLSCAASGFKFSNVWFHWVRQAPGKGLEWVAQIKDYY NAYAAYYAPSVKGRFTISRDDSKNSIYLQMNSLKTEDTAVYYCHYVHYASASTLLPAEGVDAWGQGTTVT VSSASTKGPSVFPLAPSSKSTSGGTAALGCLVEDYFPEPVTVSWNSGALTSGVHTFPAVLQSSGLYSLSS |

TABLE 14-1-continued

| Sequence Name | SEQ ID NOs | Amino Acid Sequence |
|---|---|---|
| | | VVTVPSCSLGTQTYICNVNHKPSNTKVDEKVEPKSCDKTHTCPPCPAPEAAGGPSVFLFPPKPKDTLMIS RTPEVTCVVVDVSHEDPEVKFNWYVDGVEVHNAKTKPREEQYASTYRVVSVLTVLHQDWLNGKEYKCKVS NKALPAPIEKTISKAKGQPREPQVYTLPPCRDELTKNQVSLWCLVKGFYPSDIAVEWESNGQPENNYKTT PPVLDSDGSFFLYSKLTVDKSRWQEGNVFSCSVLHEALHAHYTRKELSLSP |
| | 202 | DIQMTQSSSSFSVSLGDRVTITCKASEDIYNRLAWYQQKPGNAPRLLISGATSLETGVPSRFSGSGSGKD YTLSITSLQTEDVATYYCQQYWSTPYTFGGGTKLEVKSSASTKGPSVFPLAPSSRSTSESTAALGCLVKD YFPEPVTVSWNSGALTSGVHTFPAVLQSSGLYSLSSVVTVPSSSLGTKTYTCNVDHKPSNTKVDKRVEPK SCGGGGSGGGGSQVQLVESGGGLVQPGRSLRLSCAASGFKFSNVWFHWVRQAPGKGLEWVAQIKDYYNAY AAYYAPSVKGRFTISRDDSKNSIYLQMNSLKTEDTAVYYCHYVHYASASTLLPAEGVDAWGQGTTVTVSS ASTKGPSVFPLAPSSKSTSGGTAALGCLVEDYFPEPVTVSWNSGALTSGVHTFPAVLQSSGLYSLSSVVT VPSCSLGTQTYICNVNHKPSNTKVDEKVEPKSCDKTHTCPPCPAPEAAGGPSVFLFPPKPKDTLMISRTP EVTCVVVDVSHEDPEVKFNWYVDGVEVHNAKTKPREEQYASTYRVVSVLTVLHQDWLNGKEYKCKVSNKA LPAPIEKTISKAKGQPREPQVYTLPPCRDELTKNQVSLWCLVKGFYPSDIAVEWESNGQPENNYKTTPPVL DSDGSFFLYSKLTVDKSRWQEGNVFSCSVLHEALHAHYTRKELSLSP |
| | 203 | DIQLTQSPSFLSASVGDRVTITCQSTESVYGSDWLSWYQQKPGQPPKLLIYQASNLEIGVPSRFSGSGSG TDFTLTINSLEAEDAATYYCQGYYSGYIYAFGGGTKVEIKSSASTKGPSVFPLAPSSRSTSESTAALGCL VKDYFPEPVTVSWNSGALTSGVHTFPAVLQSSGLYSLSSVVTVPSSSLGTKTYTCNVDHKPSNTKVDKRV EPKSCGGGGSGGGGSQVQLVESGGGLVQPGRSLRLSCAASGFKFSNVWFHWVRQAPGKGLEWVAQIKDYY NAYAAYYAPSVKGRFTISRDDSKNSIYLQMNSLKTEDTAVYYCHYVHYASASTLLPAEGVDAWGQGTTVT VSSASTKGPSVFPLAPSSKSTSGGTAALGCLVEDYFPEPVTVSWNSGALTSGVHTFPAVLQSSGLYSLSS VVTVPSCSLGTQTYICNVNHKPSNTKVDEKVEPKSCDKTHTCPPCPAPEAAGGPSVFLFPPKPKDTLMIS RTPEVTCVVVDVSHEDPEVKFNWYVDGVEVHNAKTKPREEQYASTYRVVSVLTVLHQDWLNGKEYKCKVS NKALPAPIEKTISKAKGQPREPQVYTLPPCRDELTKNQVSLWCLVKGFYPSDIAVEWESNGQPENNYKTT PPVLDSDGSFFLYSKLTVDKSRWQQGNVFSCSVLHEALHAHYTRKELSLSP |

TABLE 14-2

| Sequence Name | SEQ ID NOs | Amino Acid Sequence |
|---|---|---|
| | 204 | DIQLTQSPSFLSASVGDRVTITCQSTESVYGSDWLSWYQQKPGQPPKLLIYQASNLEIGVPSRFSGSG SGTDFTLTINSLEAEDAATYYCQGYYSGYIYAFGGGTKVEIKSSASTKGPSVFPLAPSSRSTSESTAA LGCLVKDYFPEPVTVSWNSGALTSGVHTFPAVLQSSGLYSLSSVVTVPSSSLGTKTYTCNVDHKPSNT KVDKRVEPKSCGGGGSQVQLVESGGGLVQPGRSLRLSCAASGFKFSNVWFHWVRQAPGKGLEWVAQIK DYYNAYAAYYAPSVKGRFTISRDDSKNSIYLQMNSLKTEDTAVYYCHYVHYASASTLLPAEGVDAWGQ GTTVTVSSASTKGPSVFPLAPSSKSTSGGTAALGCLVEDYFPEPVTVSWNSGALTSGVHTFPAVLQSS GLYSLSSVVTVPSCSLGTQTYICNVNHKPSNTKVDEKVEPKSCDKTHTCPPCPAPEAAGGPSVFLFPP KPKDTLMISRTPEVTCVVVDVSHEDPEVKFNWYVDGVEVHNAKTKPREEQYASTYRVVSVLTVLHQDW LNGKEYKCKVSNKALPAPIEKTISKAKGQPREPQVYTLPPCRDELTKNQVSLWCLVKGFYPSDIAVEW ESNGQPENNYKTTPPVLDSDGSFFLYSKLTVDKSRWQQGNVFSCSVLHEALHAHYTRKELSLSP |
| | 205 | DIQLTQSPSFLSASVGDRVTITCQSTESVYGSDWLSWYQQKPGQPPKLLIYQASNLEIGVPSRFSGSG SGTDFTLTINSLEAEDAATYYCQGYYSGYIYAFGGGTKVEIKSSASTKGPSVFPLAPSSRSTSESTAA LGCLVKDYFPEPVTVSWNSGALTSGVHTFPAVLQSSGLYSLSSVVTVPSSSLGTKTYTCNVDHKPSNT KVDKRVEPKSCQVQLVESGGGLVQPGRSLRLSCAASGFKFSNVWFHWVRQAPGKGLEWVAQIKDYYNA YAAYYAPSVKGRFTISRDDSKNSIYLQMNSLKTEDTAVYYCHYVHYASASTLLPAEGVDAWGQGTTVT VSSASTKGPSVFPLAPSSKSTSGGTAALGCLVEDYFPEPVTVSWNSGALTSGVHTFPAVLQSSGLYSL SSVVTVPSCSLGTQTYICNVNHKPSNTKVDEKVEPKSCDKTHTCPPCPAPEAAGGPSVFLFPPKPKDT LMISRTPEVTCVVVDVSHEDPEVKFNWYVDGVEVHNAKTKPREEQYASTYRVVSVLTVLHQDWLNGKE YKCKVSNKALPAPIEKTISKAKGQPREPQVYTLPPCRDELTKNQVSLWCLVKGFYPSDIAVEWESNGQ PENNYKTTPPVLDSDGSFFLYSKLTVDKSRWQQGNVFSCSVLHEALHAHYTRKELSLSP |
| | 206 | QVTLRESGPALVKPTQTLTLTCTFSGFSLSSSYDMGWVRQAPGQGLEWMGTIYTGDYSTDYASWAKGR VTISVDRSKNQFSLKLSSVTAADTAVYYCARHTGYGYFPGLWGQGTLVTVSSASVVAAPSVFIFPPSDEQ LKSGTASVVCLLNNFYPREAKVQWKVDNALQSGNSQESVTEQDSKDSTYSLSSTLTLSKADYEKHKVY ACEVTHQGLSSPVTKSFNRGEC |
| | 207 | QVQLQQSGPQLVRPGASVKISCKASGYSFTSYWMHWVNQRPGQGLEWIGMIDPSYSETRLNQKFKDKA TLTVDKSSSTAYMQLSSPTSEDSAVYYCALYGNYFDYWGQGTTLTVSSASVAAPSVFIFPPSDEQLKS GTASVVCLLNNFYPREAKVQWKVDNALQSGNSQESVTEQDSKDSTYSLSSTLTLSKADYEKHKVYACE VTHQGLSSPVTKSFNRGEC |
| | 208 | QVQLVESGGGLVQPGRSLRLSCAASGFKFSNVWFHWVRQAPGKGLEWVAQIKDYYNAYAAYYAPSVKG RFTISRDDSKNSIYLQMNSLKTEDTAVYYCHYVHYASASTLLPAEGVDAWGQGTTVTVSSASTKGPSV FPLAPSSKSTSGGTAALGCLVEDYFPEPVTVSWNSGALTSGVHTFPAVLQSSGLYSLSSVVTVPSCSL GTQTYICNVNHKPSNTKVDEKVEPKSCDKTHTCPPCPAPEAAGGPSVFLFPPKPKDTLMISRTPEVTC VVVDVSHEDPEVKFNWYVDGVEVHNAKTKPREEQYASTYRVVSVLTVLHQDWLNGKEYKCKVSNKALP APIEKTISKAKGQPREPQVCTLPPSRDELTKNQVSLSCAVKGFYPSDIAVEWESNGQPENNYKTTPPV LDSDGSFFLVSKLTVDKSRWQEGNVFSCSVLHEALHAHYTRKELSLSP |

TABLE 14-3

| Sequence Name | SEQ ID NOs | Amino Acid Sequence |
|---|---|---|
| | 209 | QVQLVESGGGLVQPGRSLRLSCAASGFKFSNVWFHWVRQAPGKGLEWVAQIKDYYNAYAAYYAPSVKG<br>RFTISRDDSKNSIYLQMNSLKTEDTAVYYCHYVHYASASTLLPAEGVDAWGQGTTVTVSSASTKGPSV<br>FPLAPSSKSTSGGTAALGCLVEDYFPEPVTVSWNSGALTSGVHTFPAVLQSSGLYSLSSVVTVPSCSL<br>GTQTYICNVNHKPSNTKVDEKVEPKSCDKTHTCPPCPAPEAAGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNKALP<br>APIEKTISKAKGQPREPQVCTLPPSRDELTKNQVSLSCAVKGFYPSDIAVEWESNGQPENNYKTTPPV<br>LDSDGSFFLVSKLTVDKSRWQQGNVFSCSVLHEALHAHYTRKELSLSP |
| | 210 | QVQLVESGGGLVQPGRSLRLSCAASGFKFSNVWFHWVRQAPGKGLEWVAQIKDYYNAYAGYYHPSVKG<br>RFTISRDDSKNSIYLQMNSLKTEDTAVYYCHYVHYAAASQLLPAEGVDAWGQGTTVTVSSASTKGPSV<br>FPLAPSSKSTSGGTAALGCLVEDYFPEPVTVSWNSGALTSGVHTFPAVLQSSGLYSLSSVVTVPSCSL<br>GTQTYICNVNHKPSNTKVDEKVEPKSCDKTHTCPPCPAPEAAGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNKALP<br>APIEKTISKAKGQPREPQVCTLPPSRDELTKNQVSLSCAVKGFYPSDIAVEWESNGQPENNYKTTPPV<br>LDSDGSFFLVSKLTVDKSRWQEGNVFSCSVLHEALHAHYTRKELSLSP |
| | 211 | QVQLVESGGGLVQPGRSLRLSCAASGFKFSNVWFHWVRQAPGKGLEWVAQIKDYYNAYAGYYHPSVKG<br>RFTISRDDSKNSIYLQMNSLKTEDTAVYYCHYVHYAAASQLLPAEGVDAWGQGTTVTVSSASTKGPSV<br>FPLAPSSKSTSGGTAALGCLVEDYFPEPVTVSWNSGALTSGVHTFPAVLQSSGLYSLSSVVTVPSCSL<br>GTQTYICNVNHKPSNTKVDEKVEPKSCDKTHTCPPCPAPEAAGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNKALP<br>APIEKTISKAKGQPREPQVCTLPPSRDELTKNQVSLSCAVKGFYPSDIAVEWESNGQPENNYKTTPPV<br>LDSDGSFFLVSKLTVDKSRWQQGNVFSCSVLHEALHAHYTRKELSLSP |
| | 212 | QVQLVESGGGLVQPGRSLRLSCAASGFVFSNVWFHWVRQAPGKGLEWVAQIKDYYNAYAAYYAPSVKG<br>RFTISRDDSKNSIYLQMNSLKTEDTAVYYCHYVHYASASTLLPAEGVDAWGQGTTVTVSSASTKGPSV<br>FPLAPSSKSTSGGTAALGCLVEDYFPEPVTVSWNSGALTSGVHTFPAVLQSSGLYSLSSVVTVPSCSL<br>GTQTYICNVNHKPSNTKVDEKVEPKSCDKTHTCPPCPAPEAAGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNKALP<br>APIEKTISKAKGQPREPQVCTLPPSRDELTKNQVSLSCAVKGFYPSDIAVEWESNGQPENNYKTTPPV<br>LDSDGSFFLVSKLTVDKSRWQEGNVFSCSVLHEALHAHYTRKELSLSP |
| | 213 | QVQLVESGGGLVQPGRSLRLSCAASGFVFSNVWFHWVRQAPGKGLEWVAQIKDYYNAYAAYYAPSVKG<br>RFTISRDDSKNSIYLQMNSLKTEDTAVYYCHYVHYASASTLLPAEGVDAWGQGTTVTVSSASTKGPSV<br>FPLAPSSKSTSGGTAALGCLVEDYFPEPVTVSWNSGALTSGVHTFPAVLQSSGLYSLSSVVTVPSCSL<br>GTQTYICNVNHKPSNTKVDEKVEPKSCDKTHTCPPCPAPEAAGGPSVFLFPPKPKDTLMISRTPEVTC<br>VVVDVSHEDPEVKFNWYVDGVEVHNAKTKPREEQYASTYRVVSVLTVLHQDWLNGKEYKCKVSNKALP<br>APIEKTISKAKGQPREPQVCTLPPSRDELTKNQVSLSCAVKGFYPSDIAVEWESNGQPENNYKTTPPV<br>LDSDGSFFLVSKLTVDKSRWQQGNVFSCSVLHEALHAHYTRKELSLSP |

TABLE 14-4

| Sequence Name | SEQ ID NOs | Amino Acid Sequence |
|---|---|---|
| | 214 | DIVMTQSPLSLPVTPGEPASISCQPSQEVVHMNRNTYLHWYQQKPGQAPRLLIYKVSNRFPGVPDRFS<br>GSGSGTDFTLKISRVEAEDVGVYYCAQGTSHPFTFGQGTKLEIKRTVAAPSVFIFPPSDRKLKSGTAS<br>VVCLLNNFYPREAKVQWKVDNALQSGNSQESVTEQDSKDSTYSLSSTLTLSKADYEKHKVYACEVTHQ<br>GLSSPVTKSFNRGEC |
| | 215 | DIVMTQSPLSLPVTPGEPASISCQPSQEVVHMNRNTYLHWYQQKPGQAPRLLIYKVSNVFPGVPDRFS<br>GSGSGTDFTLKISRVEAEDVGVYYCAQGTHHPFTFGQGTKLEIKRTVAAPSVFIFPPSDRKLKSGTAS<br>VVCLLNNFYPREAKVQWKVDNALQSGNSQESVTEQDSKDSTYSLSSTLTLSKADYEKHKVYACEVTHQ<br>GLSSPVTKSFNRGEC |
| | 216 | DIQLTQSPSFLSASVGDRVTITCQSTESVYGSDWLSWYQQKPGQPPKLLIYQASNLEIGVPSRFSGSG<br>SGTDFTLTINSLEAEDAATYYCQGYYSGYIYAFGGGTKVEIKSSASTKGPSVFPLAPSSRSTSESTAA<br>LGCLVKDYFPEPVTVSWNSGALTSGVHTFPAVLQSSGLYSLSSVVTVPSSSLGTKTYTCNVDHKPSNT<br>KVDKRVEPKSCGGGGSGGGGSQVQLVESGGGLVQPGRSLRLSCAASGFKFSNVWFHWVRQAPGKGLEW<br>VAQIKDYYNAYAAYYAPSVKGRFTISRDDSKNSIYLQMNSLKTEDTAVYYCHYVHYASASTLLPAEGV<br>DAWGQGTTVTVSSASTKGPSVFPLAPSSKSTSGGTAALGCLVEDYFPEPVTVSWNSGALTSGVHTFPA<br>VLQSSGLYSLSSVVTVPSCSLGTQTYICNVNHKPSNTKVDEKVEPKSCDKTHTCPPCPAPELRGGPKV<br>FLFPPKPKDTLMISRTPEVTCVVVDVSHEDPEVKFNWYVDGVEVHNAKTKPREEQYASTYRVVSVLTV<br>LHQDWLNGKEYKCKVSNKALPAPIEKTISKAKGQPREPQVYTLPPCREEMTKNQVSLWCLVKGFYPSD<br>IAVEWESNGQPENNYKTTPPVLDSDGSFFLYSKLTVDKSRWQEGNVFSCSVMHEALHNHYTQKSLSLS<br>P |
| | 217 | DIQLTQSPSFLSASVGDRVTITCQSTESVYGSDWLSWYQQKPGQPPKLLIYQASNLEIGVPSRFSGSG<br>SGTDFTLTINSLEAEDAATYYCQGYYSGYIYAFGGGTKVEIKSSASTKGPSVFPLAPSSRSTSESTAA<br>LGCLVKDYFPEPVTVSWNSGALTSGVHTFPAVLQSSGLYSLSSVVTVPSSSLGTKTYTCNVDHKPSNT<br>KVDKRVEPKSCGGGGSGGGGSQVQLVESGGGLVQPGRSLRLSCAASGFKFSNVWFHWVRQAPGKGLEW<br>VAQIKDYYNAYAGYYHPSVKGRFTISRDDSKNSIYLQMNSLKTEDTAVYYCHYVHYAAASQLLPAEGV<br>DAWGQGTTVTVSSASTKGPSVFPLAPSSKSTSGGTAALGCLVEDYFPEPVTVSWNSGALTSGVHTFPA |

TABLE 14-4-continued

| Sequence Name | SEQ ID NOs | Amino Acid Sequence |
|---|---|---|
| | | VLQSSGLYSLSSVVTVPSCSLGTQTYICNVNHKPSNTKVDEKVEPKSCDKTHTCPPCPAPEAAGGPSV FLFPPKPKDTLMISRTPEVTCVVVDVSHEDPEVKFNWYVDGVEVHNAKTKPREEQYASTYRVVSVLTV LHQDWLNGKEYKCKVSNKALPAPIEKTISKAKGQPREPQVYTLPPCRDELTKNQVSLWCLVKGFYPSD IAVEWESNGQPENNYKTTPPVLDSDGSFFLYSKLTVDKSRWQEGNVFSCSVLHEALHAHYTRKELSLS P |
| | 218 | DIQMTQSSSSFSVSLGDRVTITCKASEDIYNRLAWYQQKPGNAPRLLISGATSLETGVPSRFSGSGSG KDYTLSITSLQTEDVATYYCQQYWSTPYTFGGGTKLEVKSSASTKGPSVFPLAPSSRSTSESTAALGC LVKDYFPEPVTVSWNSGALTSGVHTFPAVLQSSGLYSLSSVVTVPSSSLGTKTYTCNVDHKPSNTKVD KRVEPKSCGGGGSGGGGSQVQLVESGGGLVQPGRSLRLSCAASGFKFSNVWFHWVRQAPGKGLEWVAQ IKDYYNAYAGYYHPSVKGRFTISRDDSKNSIYLQMNSLKTEDTAVYYCHYVHYAAASQLLPAEGVDAW GQGTTVTVSSASTKGPSVFPLAPSSKSTSGGTAALGCLVEDYFPEPVTVSWNSGALTSGVHTFPAVLQ SSGLYSLSSVVTVPSCSLGTQTYICNVNHKPSNTKVDEKVEPKSCDKTHTCPPCPAPEAAGGPSVFLF PPKPKDTLMISRTPEVTCVVVDVSHEDPEVKFNWYVDGVEVHNAKTKPREEQYASTYRVVSVLTVLHQ DWLNGKEYKCKVSNKALPAPIEKTISKAKGQPREPQVYTLPPCRDELTKNQVSLWCLVKGFYPSDIAV EWESNGQPENNYKTTPPVLDSDGSFFLYSKLTVDKSRWQEGNVFSCSVLHEALHAHYTRKELSLSP |

TABLE 14-5

| Sequence Name | SEQ ID NOs | Amino Acid Sequence |
|---|---|---|
| | 219 | DIQLTQSPSFLSASVGDRVTITCQSTESVYGSDWLSWYQQKPGQPPKLLIYQASNLEIGVPSRFS GSGSGTDFTLTINSLEAEDAATYYCQGYYSGYIYAFGGGTKVEIKSSASTKGPSVFPLAPSSRST SESTAALGCLVKDYFPEPVTVSWNSGALTSGVHTFPAVLQSSGLYSLSSVVTVPSSSLGTKTYTC NVDHKPSNTKVDKRVEPKSCGGGGSGGGGSQVQLVESGGGLVQPGRSLRLSCAASGFKFSNVWFH WVRQAPGKGLEWVAQIKDYYNAYAGYYHPSVKGRFTISRDDSKNSIYLQMNSLKTEDTAVYYCHY VHYAAASQLLPAEGVDAWGQGTTVTVSSASTKGPSVFPLAPSSKSTSGGTAALGCLVEDYFPEPV TVSWNSGALTSGVHTFPAVLQSSGLYSLSSVVTVPSCSLGTQTYICNVNHKPSNTKVDEKVEPKS CDKTHTCPPCPAPEAAGGPSVFLFPPKPKDTLMISRTPEVTCVVVDVSHEDPEVKFNWYVDGVEV HNAKTKPREEQYASTYRVVSVLTVLHQDWLNGKEYKCKVSNKALPAPIEKTISKAKGQPREPQVY TLPPCRDELTKNQVSLWCLVKGFYPSDIAVEWESNGQPENNYKTTPPVLDSDGSFFLYSKLTVDK SRWQQGNVFSCSVLHEALHAHYTRKELSLSP |
| | 220 | DIQLTQSPSFLSASVGDRVTITCQSTESVYGSDWLSWYQQKPGQPPKLLIYQASNLEIGVPSRFS GSGSGTDFTLTINSLEAEDAATYYCQGYYSGYIYAFGGGTKVEIKSSASTKGPSVFPLAPSSRST SESTAALGCLVKDYFPEPVTVSWNSGALTSGVHTFPAVLQSSGLYSLSSVVTVPSSSLGTKTYTC NVDHKPSNTKVDKRVEPKSCGGGGSQVQLVESGGGLVQPGRSLRLSCAASGFKFSNVWFHWVRQA PGKGLEWVAQIKDYYNAYAGYYHPSVKGRFTISRDDSKNSIYLQMNSLKTEDTAVYYCHYVHYAA ASQLLPAEGVDAWGQGTTVTVSSASTKGPSVFPLAPSSKSTSGGTAALGCLVEDYFPEPVTVSWN SGALTSGVHTFPAVLQSSGLYSLSSVVTVPSCSLGTQTYICNVNHKPSNTKVDEKVEPKSCDKTH TCPPCPAPEAAGGPSVFLFPPKPKDTLMISRTPEVTCVVVDVSHEDPEVKFNWYVDGVEVHNAKT KPREEQYASTYRVVSVLTVLHQDWLNGKEYKCKVSNKALPAPIEKTISKAKGQPREPQVYTLPPC RDELTKNQVSLWCLVKGFYPSDIAVEWESNGQPENNYKTTPPVLDSDGSFFLYSKLTVDKSRWQQ GNVFSCSVLHEALHAHYTRKELSLSP |
| | 221 | DIQLTQSPSFLSASVGDRVTITCQSTESVYGSDWLSWYQQKPGQPPKLLIYQASNLEIGVPSRFS GSGSGTDFTLTINSLEAEDAATYYCQGYYSGYIYAFGGGTKVEIKSSASTKGPSVFPLAPSSRST SESTAALGCLVKDYFPEPVTVSWNSGALTSGVHTFPAVLQSSGLYSLSSVVTVPSSSLGTKTYTC NVDHKPSNTKVDKRVEPKSCQVQLVESGGGLVQPGRSLRLSCAASGFKFSNVWFHWVRQAPGKGL EWVAQIKDYYNAYAGYYHPSVKGRFTISRDDSKNSIYLQMNSLKTEDTAVYYCHYVHYAAASQLL PAEGVDAWGQGTTVTVSSASTKGPSVFPLAPSSKSTSGGTAALGCLVEDYFPEPVTVSWNSGALT SGVHTFPAVLQSSGLYSLSSVVTVPSCSLGTQTYICNVNHKPSNTKVDEKVEPKSCDKTHTCPPC PAPEAAGGPSVFLFPPKPKDTLMISRTPEVTCVVVDVSHEDPEVKFNWYVDGVEVHNAKTKPREE QYASTYRVVSVLTVLHQDWLNGKEYKCKVSNKALPAPIEKTISKAKGQPREPQVYTLPPCRDELT KNQVSLWCLVKGFYPSDIAVEWESNGQPENNYKTTPPVLDSDGSFFLYSKLTVDKSRWQQGNVFS CSVLHEALHAHYTRKELSLSP |

TABLE 14-6

| Sequence Name | SEQ ID NOs | Amino Acid Sequence |
|---|---|---|
| | 222 | DIQLTQSPSFLSASVGDRVTITCQSTESVYGSDWLSWYQQKPGQPPKLLIYQASNLEIGVPSRF SGSGSGTDFTLTINSLEAEDAATYYCQGYYSGYIYAFGGGTKVEIKSSASTKGPSVFPLAPSSR STSESTAALGCLVKDYFPEPVTVSWNSGALTSGVHTFPAVLQSSGLYSLSSVVTVPSSSLGTKT YTCNVDHKPSNTKVDKRVEPKSCGGGGSGGGGSQVQLVESGGGLVQPGRSLRLSCAASGFKFSN VWFHWVRQAPGKGLEWVAQIKDYYNAYAGYYHPSVKGRFTISRDDSKNSIYLQMNSLKTEDTAV |

TABLE 14-6-continued

| Sequence Name | SEQ ID NOs | Amino Acid Sequence |
|---|---|---|
| | | YYCHYVHYAAASQLLPAEGVDAWGQGTTVTVSSASTKGPSVFPLAPSSKSTSGGTAALGCLVED YFPEPVTVSWNSGALTSGVHTFPAVLQSSGLYSLSSVVTVPSCSLGTQTYICNVNHKPSNTKVD EKVEPKSCDKTHTCPPCPAPELRGGPKVFLFPPKPKDTLMISRTPEVTCVVVDVSHEDPEVKFN WYVDGVEVHNAKTKPREEQYASTYRVVSVLTVLHQDWLNGKEYKCKVSNKALPAPIEKTISKAK GQPREPQVYTLPPCREEMTKNQVSLWCLVKGFYPSDIAVEWESNGQPENNYKTTPPVLDSDGSF FLYSKLTVDKSRWQEGNVFSCSVMHEALHNHYTQKSLSLSP |
| | 223 | DIQLTQSPSFLSASVGDRVTITCQSTESVYGSDWLSWYQQKPGQPPKLLIYQASNLEIGVPSRF SGSGSGTDFTLTINSLEAEDAATYYCQGYYSGYIYAFGGGTKVEIKSSASTKGPSVFPLAPSSR STSESTAALGCLVKDYFPEPVTVSWNSGALTSGVHTFPAVLQSSGLYSLSSVVTVPSSSLGTKT YTCNVDHKPSNTKVDKRVEPKSCGGGGSGGGGSQVQLVESGGGLVQPGRSLRLSCAASGFVFSN VWFHWVRQAPGKGLEWVAQIKDYYNAYAAYYAPSVKGRFTISRDDSKNSIYLQMNSLKTEDTAV YYCHYVHYASASTLLPAEGVDAWGQGTTVTVSSASTKGPSVFPLAPSSKSTSGGTAALGCLVED YFPEPVTVSWNSGALTSGVHTFPAVLQSSGLYSLSSVVTVPSCSLGTQTYICNVNHKPSNTKVD EKVEPKSCDKTHTCPPCPAPEAAGGPSVFLFPPKPKDTLMISRTPEVTCVVVDVSHEDPEVKFN WYVDGVEVHNAKTKPREEQYASTYRVVSVLTVLHQDWLNGKEYKCKVSNKALPAPIEKTISKAK GQPREPQVYTLPPCRDELTKNQVSL223WCLVKGFYPSDIAVEWESNGQPENNYKTTPPVLDSD GSFFLYSKLTVDKSRWQEGNVFSCSVLHEALHAHYTRKELSLSP |
| | 224 | DIQMTQSSSSFSVSLGDRVTITCKASEDIYNRLAWYQQKPGNAPRLLISGATSLETGVPSRFSG SGSGKDYTLSITSLQTEDVATYYCQQYWSTPYTFGGGTKLEVKSSASTKGPSVFPLAPSSRSTS ESTAALGCLVKDYFPEPVTVSWNSGALTSGVHTFPAVLQSSGLYSLSSVVTVPSSSLGTKTYTC NVDHKPSNTKVDKRVEPKSCGGGGSGGGGSQVQLVESGGGLVQPGRSLRLSCAASGFVFSNVWF HWVRQAPGKGLEWVAQIKDYYNAYAAYYAPSVKGRFTISRDDSKNSIYLQMNSLKTEDTAVYYC HYVHYASASTLLPAEGVDAWGQGTTVTVSSASTKGPSVFPLAPSSKSTSGGTAALGCLVEDYFP EPVTVSWNSGALTSGVHTFPAVLQSSGLYSLSSVVTVPSCSLGTQTYICNVNHKPSNTKVDEKV EPKSCDKTHTCPPCPAPEAAGGPSVFLFPPKPKDTLMISRTPEVTCVVVDVSHEDPEVKFNWYV DGVEVHNAKTKPREEQYASTYRVVSVLTVLHQDWLNGKEYKCKVSNKALPAPIEKTISKAKGQP REPQVYTLPPCRDELTKNQVSLWCLVKGFYPSDIAVEWESNGQPENNYKTTPPVLDSDGSFFLY SKLTVDKSRWQEGNVFSCSVLHEALHAHYTRKELSLSP |

TABLE 14-7

| Sequence Name | SEQ ID NOs | Amino Acid Sequence |
|---|---|---|
| | 225 | DIQLTQSPSFLSASVGDRVTITCQSTESVYGSDWLSWYQQKPGQPPKLLIYQASNLEIGVPSRF SGSGSGTDFTLTINSLEAEDAATYYCQGYYSGYIYAFGGGTKVEIKSSASTKGPSVFPLAPSSR STSESTAALGCLVKDYFPEPVTVSWNSGALTSGVHTFPAVLQSSGLYSLSSVVTVPSSSLGTKT YTCNVDHKPSNTKVDKRVEPKSCGGGGSGGGGSQVQLVESGGGLVQPGRSLRLSCAASGFVFSN VWFHWVRQAPGKGLEWVAQIKDYYNAYAAYYAPSVKGRFTISRDDSKNSIYLQMNSLKEDTAVY YCHYVHYASASTLLPAEGVDAWGQGTTVTVSSASTKGPSVFPLAPSSKSTSGGTAALGCLVEDY FPEPVTVSWNSGALTSGVHTFPAVLQSSGLYSLSSVVTVPSCSLGTQTYICNVNHNHKPSNTKVDE KVPEKSCDKTHTCPPCPAPEAAGGPSVFLFPPKPKDTLMISRTPEVTCVVVDVSHEDPEVKFNW YVDGVEVHNAKTKPREEQYASTYRVVSVLTVLHQDWLNGKEYKCKVSNKALPAPIEKTISKAKG QPREPQVYTLPPCRDELTKNQVSLWCLVKGFYPSDIAVEWESNGQPENNYKTTPPVLDSDGSFF LYSKLTVDKSRWQQGVNFSCSVLHEALHAHYTRKELSLSP |
| | 226 | DIQLTQSPSFLSASVGDRVTITCQSTESVYGSDWLSWYQQKPGQPPKLLIYQASNLEIGVPSRF SGSGSGTDFTLTINSLEAEDAATYVCQYGYYSGYIYAFGGGTKVEIKSSASTKGPSVFPLAPSS RSTSESTAALGCLVKDYFPEPVTVSWNSGALTSGVHTFPAVLQSSGLYSLSSVVTVPSSSLGTK THTCNVDHKPSNTKVDKRVEPKSCGGGGSQVQLVESGGGLVQPGRSLRLSCAASGFVFSNVWFH WVRQAPGKGLEWVAQIKDYYNAYAAYYAPSVKGRFTISRDDSKNSIYLQMNSLKTEDTAVYYCH YVHYASASTLLPAEGVDAWGQGTTVTVSSASTKGPSVFPLAPSSKSTSGGTAALGCLVEDYFPE PVTVSWNSGALTSGVHTFPAVLQSSGLYSLSSVVTVPSCSLGTQTYICNVNHKPSNTKVDEKVE PKSCDKTHTCPPCPAPEAAGGPSVFLFPPKPKDTLMISRTPEVTCVVVDVSHEDPEVKFNWYVD GVEVHNAKTKPREEQYASTYRVVSVLTVLHQDWLNGKEYKCKVSNKALPAPIEKTISKAKGQPR EPQVYTLPPCRDELTKNQVSLWCLVKGFYPSDIAVEWESNGQEPNNYKTTPPVLDSDGSFFLYS KLTVDKSRWQQGNVFSCSVLHEAHLHAYTRKELSLSP |
| | 227 | DIQLTQSPSFLSASVGDRVTITCQSTESVYGSDWLSWYQQKPGQPPKLLIYQASNLEIGVPSRF SGSGSGTDFTLTINSLEAEDAATYYCQGYYSGYIYAFGGGTKVEIKSSASTKGPSVFPLAPSSR STSESTAALGCLVKDYFPEPVTVSWNSGALTSGVHTFPAVLQSSGLYSLSSVVTVPSSSLGTKT YTCNVDHKPSNTKVDKRVEPKSCQVQLVESGGGLVQPGRSLRLSCAASGFVFSNVWFHWVRQAP GKGLEWVAQIKDYYNAYAAYYAPSVKGRFTISRDDSKNSIYLQMNSLKTEDTAVYYCHYVHYAS ASTLLPAEGVDAWGQGTTVTVSSASTKGPSVFPLAPSSKSTSGGTAALGCLVEDYFPEPVTVSW NSGALTSGVHTFPAVLQSSGLYSLSSVVTVPSCSLGTQTYICNVNHKPSNTKVDEKVEPKSCDK THTCPPCPAPEAAGGPSVFLFPPKPKDTLMISRTPEVTCVVVDVSHEDPEVKFNWYVDGVEVHN AKTKPREEQYASTYRVVSVLTVLHQDWLNGKEYKCKVSNKALPAPIEKTISKAKAGQPREPQVYT LPPCRDELTKNQVSLWCLVKGFYPSDIAVEWESNGQPENNYKTTPPVLDSDGSFFLYSKLTVDK SRWQQGNVFSCSVLHEALHAHYTRKELSLSP |

TABLE 14-8

| Sequence Name | SEQ ID NOs | Amino Acid Sequence |
|---|---|---|
| | 228 | DIQLTQSPSFLSASVGDRVTITCQSTESVYGSDWLSWYQQKPGQPPKLLIYQASNLEIGVPS RFSGSGSGTDFTLTINSLEAEDAATYYCQGYYSGYIYAFGGGTKVEIKSSASTKGPSVFPLA PSSSRSTSESTAALGCLVKDYFPEPVTVSWNSGALTSGVHTFPAVLQSSGLYSLSSVVTVPSS SLGTKTYTCNVDHKPSNTKVDKRVEPKSCGGGGSGGGGSQVQLVESGGGLVQPGRSLRLSCA ASGFVFSNVWFHWVRQAPGKGLEWVAQIKDYYNAYAAYYAPSVKGRFTISRDDSKNSIYLQM NSLKTEDTAVYYCHYVHYASASTLLPAEGVDAWGQGTTVTVSSASTKGPSVFPLAPSSKSTS GGTAALGCLVEDYFPEPVTVSWNSGALTSGVHTFPAVLQSSGLYSLSSVVTVPSCSLGTQTY ICNVNHKPSNTKVDEKVEPKSCDKTHTCPPCPAPELRGGPKVFLFPPKPKDTLMISRTPEVT CVVVDVSHEDPEVKFNWYVDGVEVHNAKTKPREEQYASTYRVVSVLTVLHQDWLNGKEYKCK VSNKALPAPIEKTISKAKGQPREPQVYTLPPCREEMTKNQVSLWCLVKGFYPSDIAVEWESN GQPENNYKTTPPVLDSDGSFFLYSKLTVDKSRWQEGNVFSCSVMHEALHNHYTQKSLSLSP |
| | 229 | QVQLVESGGGLVQPGRSLRLSCAASGFKFSNVWFHWVRQAPGKGLEWVAQIKDYYNAYAAYY APSVKGRFTISRDDSKNSIYLQMNSLKTEDTAVYYCHYVHYASASTLLPAEGVDAWGQGTTV TVSSASTKGPSVFPLAPSSKSTSGGTAALGCLVEDYFPEPVTVSWNSGALTSGVHTFPAVLQ SSGLYSLSSVVTVPSCSLGTQTYICNVNHKPSNTKVDEKVEPKSCDKTHTCPPCPAPELRGG PKVFLFPPKPKDTLMISRTPEVTCVVVDVSHEDPEVKFNWYVDGVEVHNAKTKPREEQYAST YRVVSVLTVLHQDWLNGKEYKCKVSNKALPAPIEKTISKAKGQPREPQVCTLPPSREEMTKN QVSLSCAVKGFYPSDIAVEWESNGQPENNYKTTPPVLDSDGSFFLVSKLTVDKSRWQEGNVF SCSVMHEALHNHYTQKSLSLSP |
| | 230 | QVQLVESGGGLVQPGRSLRLSCAASGFKFSNVWFHWVRQAPGKGLEWVAQIKDYYNAYAGYY HPSVKGRFTISRDDSKNSIYLQMNSLKTEDTAVYYCHYVHYAAASQLLPAEGVDAWGQGTTV TVSSASTKGPSVFPLAPSSKSTSGGTAALGCLVEDYFPEPVTVSWNSGALTSGVHTFPAVLQ SSGLYSLSSVVTVPSCSLGTQTYICNVNHKPSNTKVDEKVEPKSCDKTHTCPPCPAPELRGG PKVFLFPPKPKDTLMISRTPEVTCVVVDVSHEDPEVKFNWYVDGVEVHNAKTKPREEQYAST YRVVSVLTVLHQDWLNGKEYKCKVSNKALPAPIEKTISKAKGQPREPQVCTLPPSREEMTKN QVSLSCAVKGFYPSDIAVEWESNGQPENNYKTTPPVLDSDGSFFLVSKLTVDKSRWQEGNVF SCSVMHEALHNHYTQKSLSLSP |
| | 231 | QVQLVESGGGLVQPGRSLRLSCAASGFVFSNVWFHWVRQAPGKGLEWVAQIKDYYNAYAAYY APSVKGRFTISRDDSKNSIYLQMNSLKTEDTAVYYCHYVHYASASTLLPAEGVDAWGQGTTV TVSSASTKGPSVFPLAPSSKSTSGGTAALGCLVEDYFPEPVTVSWNSGALTSGVHTFPAVLQ SSGLYSLSSVVTVPSCSLGTQTYICNVNHKPSNTKVDEKVEPKSCDKTHTCPPCPAPELRGG PKVFLFPPKPKDTLMISRTPEVTCVVVDVSHEDPEVKFNWYVDGVEVHNAKTKPREEQYAST YRVVSVLTVLHQDWLNGKEYKCKVSNKALPAPIEKTISKAKGQPREPQVCTLPPSREEMTKN QVSLSCAVKGFYPSDIAVEWESNGQPENNYKTTPPVLDSDGSFFLVSKLTVDKSRWQEGNVF SCSVMHEALHNHYTQKSLSLSP |

TABLE 14-9

| Sequence Name | SEQ ID NOs | Amino Acid Sequence |
|---|---|---|
| d08410053h0118 | 232 | QVLTRESGPALVKPTQTLTLTCTFSGFSLSSSYDMGWVRQAPGQGLEWMGTIY TGDYSTDYASWAKGRVTISVDRSKNQFSLKLSSVTAADTAVYYCARHTGYGYF GLWGQGTLVTVSS |
| D08410053H0118_VH4_CDR1 | 233 | SSYDMG |
| D08410053H0118_VH4_CDR2 | 234 | TIYTGDYSTDYASWAKG |
| D08410053H0118_VH4_CDR3 | 235 | HTGYGYFGL |
| D084101L0000 | 236 | DIQLTQSPSFLSASVGDRVTITCQSTESVYGSDWLSWYQQKPGQPPKLLIYQA SNLEIGVPSRFSGSGSGTDFTLTINSLEAEDAATYYCQGYYSGYIYAFGGGTK VEIK |
| D084101L0000_VLR_CDR1 | 237 | QSTESVYGSDWLS |
| D084101L0000_VLR_CDR2 | 238 | QASNLEI |
| D084101L0000_VLR_CDR3 | 239 | QGYYSGYIYA |
| IC17HdK | 240 | QVQLQQSGPQLVRPGASVKISCKASGYSFTSYWMHWVNQRPGQGLEWIGMIDP SYSETRLNQKFKDKATLTVDKSSSTAYMQLSSPTSEDSAVYYCALYGNYFDYW GQGTTLVTVSS |
| IC17HdK_VHR_CDR1 | 241 | SYWMH |
| IC17HdK_VHR_CDR2 | 242 | MIDPSYSETRLNQKFKD |

TABLE 14-9-continued

| Sequence Name | SEQ ID NOs | Amino Acid Sequence |
|---|---|---|
| IC17HdK_VHR_CDR3 | 243 | YGNYFDY |
| IC17L | 244 | DIQMTQSSSSFSVSLGDRVTITCKASEDIYNRLAWYQQKPGNAPRLLISGATSLETGVPSRFSGSGSGKDYTLSITSLQTEDVATYYCQQYWSTPYTFGGGTKLEVK |
| IC17L_VLR_CDR1 | 245 | KASEDIYNRLA |
| IC17L_VLR_CDR2 | 246 | GATSLET |
| IC17L_VLR_CDR3 | 247 | QQYWSTPYT |
|  | 248 | VEPKSCGGGGS |
|  | 249 | VEPKSCGGGGSGGGGS |

TABLE 14-10

| Sequence Name | SEQ ID NOs | Amino Acid Sequence |
|---|---|---|
| DLL3CD3BiTE | 250 | QVQLQESGPGLVKPSETLSLTCTVSGGSISSYYWSWIRQPPGKGLEWIGYVYYSGTTNYNPSLKSRVTISVDTSKNQFSLKLSSVTAADTAVYYCASIAVTGFYFDYWGQGTLVTVSSGGGGSGGGGSGGGGSEIVLTQSPGTLSLSPGERVTLSCRASQRVNNNYLAWYQQRPGQAPRLLIYGASSRATGIPDRFSGSGSGTDFTLTISRLEPEDFAVYYCQQYDRSPLTFGGGTKLEIKSGGGGSEVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSSTGAVTSGNYPNWVQQKPGQAPRGLIGGTKFLAPGTPARFSGSLLGGKAALTLSGVQPEDEAEYYCVLWYSNRWVFGGGTKLTVLGGGGDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKGGGGSGGGGSGGGGSGGGGSGGGGSGGGGSDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CD3εVH | 251 | QVQLVESGGGVVQPGGSLRLSCAASGFTFSNAWMHWVRQAPGKGLEWVAQIKDKSQNYATVAESVKGRFTISRADSKNSIYLQMNSLKTEDTAVYYCRYVHYAAGYGVDIWGQGTTVTVSS |
| CD3εVH_VHR_CDR1 | 252 | NAWMH |
| CD3εVH_VHR_CDR2 | 253 | QIKDKSQNYATVAESVKG |
| CD3εVH_VHR_CDR3 | 254 | VHYAAGYGVDI |
| CD3εVL | 255 | DIVMTQSPLSLPVTPGEPASISCRSSQPLVHSNRNTYLHWYQQKPGQAPRLLIYKVSNRFSGVPDRFSGSGSGTDFTLKISRVEAEDVGVYYCGQGTQVPYTFGQGTKLEIK |
| CD3εVL_VLR_CDR1 | 256 | RSSQPLVHSNRNTYLH |
| CD3εVL_VLR_CDR2 | 257 | KVSNRFS |
| CD3εVL_VLR_CDR3 | 258 | GQGTQVPYT |
|  | 259 | VEPKSC |

TABLE 14-11

| Sequence Name | SEQ ID NOs | Amino Acid Sequence |
|---|---|---|
| SG1321kV11Fc | 99 | CPPCPAPEAAGGPSVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVYTLPPCRDELTKNQVSLW<br>CLVKGFYPSDIAVEWESNGQPENNYKTTPPVLDSDGSFFLYSKLTVD<br>KSRWQEGNVFSCSVLHEALHAHYTRKELSLSP |
| SG1372kV11Fc | 100 | CPPCPAPEAAGGPSVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVYTLPPCRDELTKNQVSLW<br>CLVKGFYPSDIAVEWESNGQPENNYKTTPPVLDSDGSFFLYSKLTVD<br>KSRWQQGNVFSCSVLHEALHAHYTRKELSLSP |
| SG1176kV11Fc | 108 | CPPCPAPELRGGPKVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVYTLPPCREEMTKNQVSLW<br>CLVKGFYPSDIAVEWESNGQPENNYKTTPPVLDSDGSFFLYSKLTVD<br>KSRWQEGNVFSCSVMHEALHNHYTQKSLSLSP |
| SG1321hV11Fc | 109 | CPPCPAPEAAGGPSVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVCTLPPSRDELTKNQVSLS<br>CAVKGFYPSDIAVEWESNGQPENNYKTTPPVLDSDGSFFLVSKLTVD<br>KSRWQEGNVFSCSVLHEALHAHYTRKELSLSP |
| SG1372hV11Fc | 111 | CPPCPAPEAAGGPSVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVCTLPPSRDELTKNQVSLS<br>CAVKGFYPSDIAVEWESNGQPENNYKTTPPVLDSDGSFFLVSKLTVD<br>KSRWQQGNVFSCSVLHEALHAHYTRKELSLSP |
| SG1176hV11Fc | 112 | CPPCPAPELRGGPKVFLFPPKPKDTLMISRTPEVTCVVVDVSHEDPE<br>VKFNWYVDGVEVHNAKTKPREEQYASTYRVVSVLTVLHQDWLNGKEY<br>KCKVSNKALPAPIEKTISKAKGQPREPQVCTLPPSREEMTKNQVSLS<br>CAVKGFYPSDIAVEWESNGQPENNYKTTPPVLDSDGSFFLVSKLTVD<br>KSRWQEGNVFSCSVMHEALHNHYTQKSLSLSP |

Example 3

In Vitro Efficacy of DLL3-Dual-LINC Antibody Towards DLL3 Expression Cell Lines 3.1. Measurement of TDCC Activity Using Anti-DLL3/Dual-Linc (1+2) Antibody, Dual (1+1) Antibody, DLL3CD3BiTE, and DLL3/CD3ε (1+1) Antibody Cytotoxic activity was assessed by observing the rate of tumor cell growth inhibition using xCELLigence™ Real-Time Cell Analyzer (Roche Diagnostics) in the presence of PBMCs. FIG. 2 shows the TDCC activity of anti-DLL3/Dual-Linc antibody (DLL3-DualAE05/DualAE05, 1+2), Dual (1+1) antibody (DLL3/DualAE05), DLL3CD3BiTE, and DLL3/CD3ε (1+1) antibody prepared according to Tables 10-13. SK-MEL30 cell line was used as target cells. Target cells were detached from the dish and cells were plated into E-plate 96 (Roche Diagnostics) in aliquots of 100 micro L/well by adjusting the cells to $5 \times 10^3$ cells/well, and measurement of cell growth was initiated using the xCELLigence™ Real-Time Cell Analyzer. 24 hours later, the plate was removed and 50 micro L of the respective antibodies prepared at each concentration (5-fold serial dilutions starting from 10 nM i.e., 0.25, 1.25, 2.5, 5, and 10 nM) were added to the plate. After 15 minutes of reaction at room temperature, 50 micro L of the fresh human PBMC solution was added in effector:target ratio of 2 (i.e. $1 \times 10^4$ cells/well) and measurement of cell growth was resumed using xCELLigence™ Real-Time Cell Analyzer. The reaction was carried out under the conditions of 5% carbon dioxide gas at 37° C. As CD137 signaling enhances T-cell survival and prevents activation induced cell death, TDCC assay was conducted at a low E:T ratio. An extended period of time may be required to observe superior cytotoxicity contributed by CD137 activation. As such, approximately 68 hours after the addition of PBMCs, Cell Growth Inhibition (CGI) rate (%) was determined using the equation below. The Cell Index Value obtained from xCELLigence™ Real-Time Cell Analyzer used in the calculation was a normalized value where the Cell Index value immediately at the time point before antibody addition was defined as 1.

Cell Growth Inhibition rate (%)=$(A-B) \times 100/(A-1)$

A represents the mean value of Cell Index values in wells without antibody addition (containing only target cells and human PBMCs), and B represents the mean value of the Cell Index values of target wells. The examinations were performed in duplicates.

As shown in panel (a) of FIG. 2, anti-DLL3/Dual-Linc antibody (DLL3-DualAE05/DualAE05, 1+2) showed stronger TDCC activity than those of Dual (1+1) antibody (DLL3/DualAE05) and DLL3/CD3ε (1+1) antibody. This suggests that Dual-Linc molecular format contributes to improved cytotoxicity. In addition, at these antibody concentrations, TDCC activity of anti-DLL3/Dual-Linc antibody are comparable to DLL3/CD3BiTE.

3.2. Evaluation of Linker Length Effect for Cytotoxicity

To improve cytotoxicity against tumor cells, the closer proximity and more rigid binding between tumor cells and effector cells would be critical. This means that the shorter distance may help to bring the T cell and tumor cell in close proximity, which may help for the TDCC. Therefore, we generated three anti-DLL3/Dual-Linc antibody variants which have linkers of different lengths. The linker length of DLL3-DualAE05/DualAE05-FF110 (mid linker) and DLL3-DualAE05/DualAE05-FF111 (short linker) are shorter than that of DLL3-DualAE05/DualAE05-FF091

(long linker) (herein below these variants may be abbreviated as DLL3-AE05/AE05-FF110, DLL3-AE05/AE05-FF111, and DLL3-AE05/AE05-FF091, respectively). To evaluate the linker length effect for cytotoxicity, TDCC measurement was conducted as described in Example 3.1 using 0.2, 1, and 5 nM of antibodies.

As shown in panel (b) of FIG. 2, DLL3-AE05/AE05-FF110 (mid linker) and DLL3-AE05/AE05-FF111 (short linker) showed stronger TDCC activity than that of DLL3-AE05/AE05-FF091 (long linker) at 0.2 nM. DLL3-AE05/AE05-FF110 (mid linker) showed the strongest TDCC activity. These results suggest that the linker length is important for TDCC activity and the mid-length linker is most appropriate for in vitro TDCC activity.

Example 4

Assessment of In Vivo Efficacy of DLL3-DualAE05/DualAE05-FF091 Tri-Specific Antibody when Compared to DLL3CD3BiTE.

The anti-tumor activity of DLL3-DualAE05/DualAE05-FF091 antibody and DLL3CD3BiTE prepared in Example 2 were tested in a human small cell lung cancer NCI-H1436 cancer model. NCI-H1436 cells were subcutaneously transplanted to NOG humanized mice. NOG female mice were purchased from In-Vivo Science. For humanization, mice were sub lethally irradiated followed 1 day later by injection of 100,000 human cord blood cells (ALLCELLS). After humanization, NCI-H1436 ($5\times10^6$ cells) were mixed with Matrigel Basement Membrane Matrix (Corning) and transplanted to the right flank of humanized NOG mice. The day of transplantation was defined as day 0. On day 11, the mice were randomized on the basis of tumor volume and body weight. On the following day, mice were injected i.v. with either vehicle (PBS containing 0.05% Tween), 6.5 mg/kg DLL3-DualAE05/DualAE05-FF091, or 3.5 mg/kg DLL3CD3BiTE.

For T cell infiltration analysis, the xenografted tumors on the mice were harvested at indicated time points after the antibody administration. The tumors were weighed, minced by using human Tumor Dissociation Kit (Miltenyi) according to the manufacturer's protocol and CountBright™ Absolute Counting Beads (ThermoFisher scientific) was added after dissociation. Intratumor CD8+ T cell number was evaluated using LSRFortessa™ X20 cell analyzer (BD).

For T cell exhaustion analysis, the xenografted tumors on the mice were harvested on day 7 after the antibody administration. The tumors were minced by human Tumor Dissociation Kit (Miltenyi) according to the manufacturer's protocol and the intratumor T cells were evaluated for the expression of T cell exhaustion markers, Tim-3, PD-1, and Lag-3.

As a result, DLL3-DualAE05/DualAE05-FF091 showed stronger efficacy and higher T cell infiltration than DLL3CD3BiTE (FIG. 3 and FIG. 4). Furthermore, T cells of DLL3-DualAE05/DualAE05-FF091-treated group had lower expression of PD-1, Tim-3, and LAG3 (FIG. 5), suggesting that DLL3-DualAE05/DualAE05-FF091 induces less T cell exhaustion.

INDUSTRIAL APPLICABILITY

The present invention provides multispecific antigen-binding molecules capable of binding to CD3 and CD137 (4-1BB) but not binding to CD3 and CD137 at the same time, and capable of binding to DLL3. The antigen-binding molecules of the present invention exhibit enhanced T-cell dependent cytotoxic activity in a DLL3-dependent manner through binding to the CD3/CD37 and DLL3. The antigen-binding molecules and pharmaceutical compositions thereof can be used for targeting cells expressing DLL3, for use in immunotherapy for treating various cancers, especially those associated with DLL3 such as DLL3-positive cancers.

The invention claimed is:

1. A multispecific antigen-binding molecule that comprises:
  (a) a first antigen-binding moiety and a second antigen-binding moiety, at least one of which binds to human CD3 and comprises
    an antibody variable region comprising a heavy chain CDR 1 comprising SEQ ID NO: 20, a heavy chain CDR 2 comprising SEQ ID NO: 34, a heavy chain CDR 3 comprising SEQ ID NO: 48, a light chain CDR 1 comprising SEQ ID NO: 63, a light chain CDR 2 comprising SEQ ID NO: 68, and a light chain CDR 3 comprising SEQ ID NO: 73;
  and
  (b) a third antigen-binding moiety that binds to human Delta-like 3 (DLL3) and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

2. The multispecific antigen-binding molecule of claim 1, wherein
  (i) the first antigen-binding moiety binds to human CD3 and comprises an antibody variable region comprising a heavy chain CDR 1 comprising SEQ ID NO: 20, a heavy chain CDR 2 comprising SEQ ID NO: 34, a heavy chain CDR 3 comprising SEQ ID NO: 48, a light chain CDR 1 comprising SEQ ID NO: 63, a light chain CDR 2 comprising SEQ ID NO: 68, and a light chain CDR 3 comprising SEQ ID NO: 73; and
  (ii) the second antigen-binding moiety binds to human CD3 and comprises an antibody variable region selected from the group consisting of (I) to (XIV):
    (I) an antibody variable region comprising a heavy chain complementarity determining region (CDR) 1 comprising SEQ ID NO: 17, a heavy chain CDR 2 comprising SEQ ID NO: 31, a heavy chain CDR 3 comprising SEQ ID NO: 45, a light chain CDR 1 comprising SEQ ID NO: 64, a light chain CDR 2 comprising SEQ ID NO: 69, and a light chain CDR 3 comprising SEQ ID NO: 74;
    (II) an antibody variable region comprising a heavy chain CDR 1 comprising SEQ ID NO: 18, a heavy chain CDR 2 comprising SEQ ID NO: 32, a heavy chain CDR 3 comprising SEQ ID NO: 46, a light chain CDR 1 comprising SEQ ID NO: 63, a light chain CDR 2 comprising SEQ ID NO: 68, and a light chain CDR 3 comprising SEQ ID NO: 73;

(III) an antibody variable region comprising a heavy chain CDR 1 comprising SEQ ID NO: 19, a heavy chain CDR 2 comprising SEQ ID NO: 33, a heavy chain CDR 3 comprising SEQ ID NO: 47, a light chain CDR 1 comprising SEQ ID NO: 63, a light chain CDR 2 comprising SEQ ID NO: 68, and a light chain CDR 3 comprising SEQ ID NO: 73;

(IV) an antibody variable region comprising a heavy chain CDR 1 comprising SEQ ID NO: 19, a heavy chain CDR 2 comprising SEQ ID NO: 33, a heavy chain CDR 3 comprising SEQ ID NO: 47, a light chain CDR 1 comprising SEQ ID NO: 65, a light chain CDR 2 comprising SEQ ID NO: 70, and a light chain CDR 3 comprising SEQ ID NO: 75;

(V) an antibody variable region comprising a heavy chain CDR 1 comprising SEQ ID NO: 22, a heavy chain CDR 2 comprising SEQ ID NO: 36, a heavy chain CDR 3 comprising SEQ ID NO: 50, a light chain CDR 1 comprising SEQ ID NO: 63, a light chain CDR 2 comprising SEQ ID NO: 68, and a light chain CDR 3 comprising SEQ ID NO: 73;

(VI) an antibody variable region comprising a heavy chain CDR 1 comprising SEQ ID NO: 23, a heavy chain CDR 2 comprising SEQ ID NO: 37, a heavy chain CDR 3 comprising SEQ ID NO: 51, a light chain CDR 1 comprising SEQ ID NO: 63, a light chain CDR 2 comprising SEQ ID NO: 68, and a light chain CDR 3 comprising SEQ ID NO: 73;

(VII) an antibody variable region comprising a heavy chain CDR 1 comprising SEQ ID NO: 23, a heavy chain CDR 2 comprising SEQ ID NO: 37, a heavy chain CDR 3 comprising SEQ ID NO: 51, a light chain CDR 1 comprising SEQ ID NO: 66, a light chain CDR 2 comprising SEQ ID NO: 71, and a light chain CDR 3 comprising SEQ ID NO: 76;

(VIII) an antibody variable region comprising a heavy chain CDR 1 comprising SEQ ID NO: 24, a heavy chain CDR 2 comprising SEQ ID NO: 38, a heavy chain CDR 3 comprising SEQ ID NO: 52, a light chain CDR 1 comprising SEQ ID NO: 63, a light chain CDR 2 comprising SEQ ID NO: 68, and a light chain CDR 3 comprising SEQ ID NO: 73;

(IX) an antibody variable region comprising a heavy chain CDR 1 comprising SEQ ID NO: 25, a heavy chain CDR 2 comprising SEQ ID NO: 39, a heavy chain CDR 3 comprising SEQ ID NO: 53, a light chain CDR 1 comprising SEQ ID NO: 66, a light chain CDR 2 comprising SEQ ID NO: 71, and a light chain CDR 3 comprising SEQ ID NO: 76;

(X) an antibody variable region comprising a heavy chain CDR 1 comprising SEQ ID NO: 26, a heavy chain CDR 2 comprising SEQ ID NO: 40, a heavy chain CDR 3 comprising SEQ ID NO: 54, a light chain CDR 1 comprising SEQ ID NO: 66, a light chain CDR 2 comprising SEQ ID NO: 71, and a light chain CDR 3 comprising SEQ ID NO: 76;

(XI) an antibody variable region comprising a heavy chain CDR 1 comprising SEQ ID NO: 26, a heavy chain CDR 2 comprising SEQ ID NO: 40, a heavy chain CDR 3 comprising SEQ ID NO: 54, a light chain CDR 1 comprising SEQ ID NO: 63, a light chain CDR 2 comprising SEQ ID NO: 68, and a light chain CDR 3 comprising SEQ ID NO: 73;

(XII) an antibody variable region comprising a heavy chain CDR 1 comprising SEQ ID NO: 27, a heavy chain CDR 2 comprising SEQ ID NO: 41, a heavy chain CDR 3 comprising SEQ ID NO: 55, a light chain CDR 1 comprising SEQ ID NO: 63, a light chain CDR 2 comprising SEQ ID NO: 68, and a light chain CDR 3 comprising SEQ ID NO: 73;

(XIII) an antibody variable region comprising a heavy chain CDR 1 comprising SEQ ID NO: 28, a heavy chain CDR 2 comprising SEQ ID NO: 42, a heavy chain CDR 3 comprising SEQ ID NO: 56, a light chain CDR 1 comprising SEQ ID NO: 63, a light chain CDR 2 comprising SEQ ID NO: 68, and a light chain CDR 3 comprising SEQ ID NO: 73; and (XIV) an antibody variable region comprising a heavy chain CDR 1 comprising SEQ ID NO: 82, a heavy chain CDR 2 comprising SEQ ID NO: 83, a heavy chain CDR 3 comprising SEQ ID NO: 84, a light chain CDR 1 comprising SEQ ID NO: 65, a light chain CDR 2 comprising SEQ ID NO: 70, and a light chain CDR 3 comprising SEQ ID NO: 75.

3. A multispecific antigen-binding molecule that comprises:

(a) a first antigen-binding moiety and a second antigen-binding moiety, at least one of which binds to human CD3 and comprises
an antibody variable region comprising a VH comprising SEQ ID NO: 6 and a VL comprising SEQ ID NO: 58;
and (b) a third antigen-binding moiety comprising an antibody variable region comprising a VH comprising SEQ ID NO: 232 and a VL comprising SEQ ID NO: 236.

4. The multispecific antigen-binding molecule of claim 1, wherein the antibody variable regions of the first and second antigen binding moieties are identical.

5. The multispecific antigen-binding molecule of claim 3, wherein the antibody variable regions of the first and second antigen binding moieties are identical.

6. The multispecific antigen-binding molecule of claim 4, wherein each of the first and second antigen-binding moieties is a Fab that has a cysteine residue at EU numbering position 191, and wherein a disulfide bond links these two cysteine residues.

7. The multispecific antigen-binding molecule of claim 5, wherein each of the first and second antigen-binding moieties is a Fab that has a cysteine residue at EU numbering position 191, and wherein a disulfide bond links these two cysteine residues.

8. The multispecific antigen-binding molecule of claim 6, wherein each of the first, second and third antigen binding moieties is in the form of a Fab comprising a VH, a VL, a CH1 domain and a light chain constant (CL) domain, and wherein the C-terminus of the CH1 domain of the third antigen-binding moiety is fused, directly or via a peptide linker, to the N-terminus of the VH of either the first antigen binding moiety or the second antigen binding moiety.

9. The multispecific antigen-binding molecule of claim 7, wherein each of the first, second and third antigen binding moieties is in the form of a Fab comprising a CH1 domain and a light chain constant (CL) domain, and wherein the C-terminus of the CH1 domain of the third antigen-binding moiety is fused, directly or via a peptide linker, to the N-terminus of the VH of either the first antigen binding moiety or the second antigen binding moiety.

10. The multispecific antigen-binding molecule of claim 8, wherein the fusion is via a peptide linker that comprises an amino acid sequence selected from the group consisting of SEQ ID NO: 248, SEQ ID NO: 249, and SEQ ID NO: 259.

11. The multispecific antigen-binding molecule of claim 9, wherein the fusion is via a peptide linker that comprises an amino acid sequence selected from the group consisting of SEQ ID NO: 248, SEQ ID NO: 249, and SEQ ID NO: 259.

12. The multispecific antigen-binding molecule of claim 10, wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

13. The multispecific antigen-binding molecule of claim 11, wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

14. The multispecific antigen-binding molecule of claim 12, wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

15. The multispecific antigen-binding molecule of claim 13, wherein, in the CL domain of each of the first and second antigen binding moieties, the amino acids at positions 123 and 124 (Kabat numbering) are arginine and lysine, respectively; and wherein, in the CH1 domain of each of the first and second antigen binding moieties, the amino acid at each of positions 147 and 213 (EU numbering) is glutamic acid.

16. The multispecific antigen-binding molecule of claim 14, further comprising an Fc domain.

17. The multispecific antigen-binding molecule of claim 15, further comprising an Fc domain.

18. The multispecific antigen-binding molecule of claim 16,
wherein the Fc domain comprises a first and a second Fc region subunit,
wherein the first Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 354, and tryptophan at position 366;
wherein the second Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 349, serine at position 366, alanine at position 368, and valine at position 407; and
wherein all positions are by EU numbering.

19. The multispecific antigen-binding molecule of claim 17,
wherein the Fc domain comprises a first and a second Fc region subunit,
wherein the first Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 354, and tryptophan at position 366;
wherein the second Fc-region subunit is selected from the group comprising:
an Fc region polypeptide comprising alanine at each of positions 234 and 235;
an Fc region polypeptide comprising alanine at each of positions 234, 235, and 297; and
an Fc region polypeptide comprising alanine at each of positions 234, 235, and 297, cysteine at position 349, serine at position 366, alanine at position 368, and valine at position 407; and
wherein all positions are by EU numbering.

20. A multispecific antigen-binding molecule that comprises a set of five polypeptide chains, wherein the set is one of (A) to (E) below:
(A) a polypeptide chain comprising the amino acid sequence of SEQ ID NO: 201 (chain 1), a polypeptide chain comprising the amino acid sequence of SEQ ID NO: 206 (chain 2), a polypeptide chain comprising the amino acid sequence of SEQ ID NO: 208 (chain 3), and two polypeptide chains each comprising the amino acid sequence of SEQ ID NO: 214 (chains 4 and 5);
(B) a polypeptide chain comprising the amino acid sequence of SEQ ID NO: 203 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5);
(C) a polypeptide chain comprising the amino acid sequence of SEQ ID NO: 204 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5);
(D) a polypeptide chain comprising the amino acid sequence of SEQ ID NO: 205 (chain 1), a polypeptide chain comprising the amino acid sequence of SEQ ID NO: 206 (chain 2), a polypeptide chain comprising the amino acid sequence of SEQ ID NO: 209 (chain 3), and two polypeptide chains each comprising the amino acid sequence of SEQ ID NO: 214 (chains 4 and 5); or
(E) a polypeptide chain comprising the amino acid sequence of SEQ ID NO: 216 (chain 1), a polypeptide chain comprising the amino acid sequence of SEQ ID NO: 206 (chain 2), a polypeptide chain comprising the amino acid sequence of SEQ ID NO: 229 (chain 3), and two polypeptide chains each comprising the amino acid sequence of SEQ ID NO: 214 (chains 4 and 5).

21. A multispecific antigen-binding molecule that comprises:
(a) a first antigen-binding moiety and a second antigen-binding moiety, each of which binds to human CD3 and comprises an antibody variable region comprising a heavy chain CDR 1 comprising SEQ ID NO: 20, a heavy chain CDR 2 comprising SEQ ID NO: 13, a heavy chain CDR 3 comprising SEQ ID NO: 48, a light chain CDR 1 comprising SEQ ID NO: 63, a light chain CDR 2 comprising SEQ ID NO: 68, and a light chain CDR 3 comprising SEQ ID NO: 73; and (b) a third antigen-binding moiety that binds to human DLL3 and comprises an antibody variable region comprising a heavy chain CDR1 comprising SEQ ID NO: 233, a heavy chain CDR 2 comprising SEQ ID NO: 234, a heavy chain CDR 3 comprising SEQ ID NO: 235, a light chain CDR 1 comprising SEQ ID NO: 237, a light chain CDR 2 comprising SEQ ID NO: 238, and a light chain CDR 3 comprising SEQ ID NO: 239.

22. The multispecific antigen-binding molecule of claim 21, wherein the antibody variable region of each of the first and second antigen-binding moieties comprises a VH comprising SEQ ID NO: 6 and a VL comprising SEQ ID NO: 58; and the antibody variable region of the third antigen-binding moiety comprises a VH comprising SEQ ID NO: 232 and a VL comprising SEQ ID NO: 236.

23. The multispecific antigen-binding molecule of claim 22, wherein each of the first and second antigen-binding moieties is a Fab that has a cysteine residue at EU numbering position 191, and wherein a disulfide bond links these two cysteine residues.

24. The multispecific antigen-binding molecule of claim 23, wherein each of the first, second and third antigen binding moieties is in the form of a Fab comprising a VH, a VL, a CH1 domain and a CL domain, and wherein the C-terminus of the CH1 domain of the third antigen-binding moiety is fused, directly or via a peptide linker, to the N-terminus of the VH of either the first antigen binding moiety or the second antigen binding moiety.

25. The multispecific antigen-binding molecule of claim 24, wherein the fusion is via a peptide linker that comprises an amino acid sequence selected from the group consisting of SEQ ID NO: 248, SEQ ID NO: 249, and SEQ ID NO: 259.

26. The multispecific antigen-binding molecule of claim 25, wherein the third antigen binding moiety is a crossover Fab in which the VH is linked to the CL domain and the VL is linked to the CH1 domain, and wherein each of the first and second antigen binding moieties is a conventional Fab in which the VH is linked to the CH1 domain and the VL is linked to the CL domain.

27. The multispecific antigen-binding molecule of claim 26, wherein, in the CL domain of each of the first and second antigen binding moieties, the amino acids at Kabat numbering positions 123 and 124 are arginine and lysine, respectively; and wherein, in the CH1 domain of each of the first and second antigen binding moieties, the amino acid at each of EU numbering positions 147 and 213 is glutamic acid.

28. The multispecific antigen-binding molecule of claim 27, further comprising an Fc domain.

* * * * *

UNITED STATES PATENT AND TRADEMARK OFFICE
CERTIFICATE OF CORRECTION

PATENT NO. : 11,274,151 B2
APPLICATION NO. : 17/216981
DATED : March 15, 2022
INVENTOR(S) : Sotaro Naoi et al.

It is certified that error appears in the above-identified patent and that said Letters Patent is hereby corrected as shown below:

In the Specification

Column 93, Table 8-3, Line 45, in the Amino Acid Sequence for SEQ number 34, delete "QIKDYYNAYAAVYAPSVKG" and replace it with -- QIKDYYNAYAAYYAPSVKG --.

In the Claims

Column 363, Line 2 (Claim 21): Delete "SEQ ID NO: 13" and replace it with -- SEQ ID NO: 34 --.

Signed and Sealed this
Twelfth Day of July, 2022

Katherine Kelly Vidal
*Director of the United States Patent and Trademark Office*